(12) United States Patent
Remenar et al.

(10) Patent No.: US 12,180,164 B2
(45) Date of Patent: Dec. 31, 2024

(54) HETEROCYCLIC COMPOUNDS FOR THE TREATMENT OF NEUROLOGICAL AND PSYCHOLOGICAL DISORDERS

(71) Applicant: Alkermes Pharma Ireland Limited, Dublin (IE)

(72) Inventors: Julius F. Remenar, Framingham, MA (US); Laura Cook Blumberg, Lincoln, MA (US); Tarek A. Zeidan, Watertown, MA (US)

(73) Assignee: Alkermes Pharma Ireland Limited, Dublin (IE)

( * ) Notice: Subject to any disclaimer, the term of this patent is extended or adjusted under 35 U.S.C. 154(b) by 0 days.

(21) Appl. No.: 18/051,216

(22) Filed: Oct. 31, 2022

(65) Prior Publication Data
US 2023/0150941 A1   May 18, 2023

Related U.S. Application Data

(63) Continuation of application No. 17/020,499, filed on Sep. 14, 2020, now Pat. No. 11,518,745, which is a continuation of application No. 16/425,119, filed on May 29, 2019, now Pat. No. 10,822,306, which is a continuation of application No. 16/131,773, filed on Sep. 14, 2018, now Pat. No. 10,351,529, which is a continuation of application No. 15/875,478, filed on Jan. 19, 2018, now Pat. No. 10,112,903, which is a continuation of application No. 15/147,021, filed on May 5, 2016, now Pat. No. 10,023,537, which is a continuation of application No. 14/677,333, filed on Apr. 2, 2015, now abandoned, which is a continuation of application No. 14/297,195, filed on Jun. 5, 2014, now abandoned, which is a continuation of application No. 13/607,066, filed on Sep. 7, 2012, now Pat. No. 8,796,276, which is a continuation of application No. 12/823,007, filed on Jun. 24, 2010, now Pat. No. 8,431,576.

(60) Provisional application No. 61/293,087, filed on Jan. 7, 2010, provisional application No. 61/220,480, filed on Jun. 25, 2009.

(51) Int. Cl.
| | |
|---|---|
| *C07D 215/227* | (2006.01) |
| *A61K 31/496* | (2006.01) |
| *A61K 31/497* | (2006.01) |
| *C07D 215/22* | (2006.01) |
| *C07D 263/58* | (2006.01) |
| *C07D 401/12* | (2006.01) |
| *C07D 401/14* | (2006.01) |
| *C07D 413/10* | (2006.01) |
| *C07D 413/14* | (2006.01) |
| *C07D 417/12* | (2006.01) |
| *C07D 417/14* | (2006.01) |
| *C07D 471/04* | (2006.01) |
| *C07F 9/6558* | (2006.01) |
| *C07D 241/04* | (2006.01) |

(52) U.S. Cl.
CPC ........ *C07D 215/227* (2013.01); *A61K 31/496* (2013.01); *A61K 31/497* (2013.01); *C07D 215/22* (2013.01); *C07D 263/58* (2013.01); *C07D 401/12* (2013.01); *C07D 401/14* (2013.01); *C07D 413/10* (2013.01); *C07D 413/14* (2013.01); *C07D 417/12* (2013.01); *C07D 417/14* (2013.01); *C07D 471/04* (2013.01); *C07F 9/6558* (2013.01); *C07F 9/65583* (2013.01); *C07D 241/04* (2013.01)

(58) Field of Classification Search
CPC .................................................. C07D 215/227
See application file for complete search history.

(56) References Cited

U.S. PATENT DOCUMENTS

| | | |
|---|---|---|
| 2,418,499 A | 4/1947 | Burke |
| 3,523,121 A | 8/1970 | Lewis et al. |
| 3,573,308 A | 3/1971 | Ning et al. |
| 3,957,808 A | 5/1976 | Miller et al. |
| 4,160,099 A | 7/1979 | Bodor |
| 4,204,065 A | 5/1980 | Bodor |
| 4,234,584 A | 11/1980 | Lattrell et al. |
| 4,260,769 A | 4/1981 | Stella et al. |

(Continued)

FOREIGN PATENT DOCUMENTS

| | | |
|---|---|---|
| CN | 102260290 A | 11/2011 |
| DE | 1070760 B | 11/1955 |

(Continued)

OTHER PUBLICATIONS

U.S. Appl. No. 12/823,007 / 2011/0015156 A1 / U.S. Pat. No. 8,431,576, filed Jun. 24, 2010 / Jan. 20, 2011 / Apr. 30, 2013, Julius F. Remenar.
U.S. Appl. No. 13/607,066 / 2013/0096089 A1 / U.S. Pat. No. 8,796,276, filed Sep. 7, 2012 / Apr. 18, 2013 / Aug. 5, 2014, Julius F. Remenar.
U.S. Appl. No. 14/297,195 / 2014/0350254 A1, filed Jun. 5, 2014 / Nov. 27, 2014, Julius F. Remenar.

(Continued)

*Primary Examiner* — Paul V Ward
(74) *Attorney, Agent, or Firm* — Lathrop GPM LLP; Brian Trinque; Nicole Sassu

(57) ABSTRACT

Lactam compounds of Formula I and their use for the treatment of neurological and psychiatric disorders including schizophrenia, bipolar disorder, anxiety disorder and insomnia is disclosed.

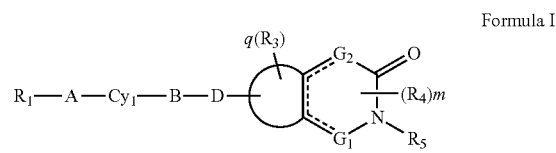

Formula I

5 Claims, 9 Drawing Sheets

(56) References Cited

U.S. PATENT DOCUMENTS

| | | |
|---|---|---|
| 4,267,326 A | 5/1981 | Ozaki et al. |
| 4,428,935 A | 1/1984 | Myers |
| 4,443,464 A | 4/1984 | Biedermann et al. |
| 4,594,190 A | 6/1986 | Giani et al. |
| 4,734,416 A | 3/1988 | Banno et al. |
| 4,760,057 A | 7/1988 | Alexander |
| 4,831,031 A | 5/1989 | Lowe, III et al. |
| 4,837,337 A | 6/1989 | Murao et al. |
| 4,914,094 A | 4/1990 | Oshiro et al. |
| 4,992,550 A | 2/1991 | Hughes |
| 5,006,528 A | 4/1991 | Oshiro et al. |
| 5,206,386 A | 4/1993 | Narayanan et al. |
| 5,236,927 A | 8/1993 | Jones et al. |
| 5,350,747 A | 9/1994 | Howard |
| 5,462,934 A | 10/1995 | Goto et al. |
| 5,700,946 A | 12/1997 | Shimasaki et al. |
| 5,719,303 A | 2/1998 | Yoshida et al. |
| 5,783,589 A | 7/1998 | Latimer et al. |
| 5,985,856 A | 11/1999 | Stella et al. |
| 6,127,357 A | 10/2000 | Cliffe et al. |
| 6,133,248 A | 10/2000 | Stella |
| 6,180,095 B1 | 1/2001 | Greenwald et al. |
| 6,444,668 B1 | 9/2002 | Grubb et al. |
| 6,608,084 B1 | 8/2003 | Bourzat et al. |
| 6,653,312 B1 | 11/2003 | Auvin et al. |
| 6,656,932 B2 | 12/2003 | Picard et al. |
| 7,112,603 B2 | 9/2006 | Moon et al. |
| 7,115,587 B2 | 10/2006 | Nerurkar et al. |
| 7,160,888 B2 | 1/2007 | Johnson et al. |
| 7,538,121 B2 | 5/2009 | MacDonald et al. |
| 8,247,420 B2 | 8/2012 | Bhat et al. |
| 8,536,328 B2 | 9/2013 | Remenar et al. |
| 8,592,427 B2 | 11/2013 | Blumberg et al. |
| 8,669,281 B1 | 3/2014 | Zeidan et al. |
| 8,686,009 B2 | 4/2014 | Blumberg et al. |
| 9,072,788 B2 | 7/2015 | Blumberg et al. |
| 9,090,558 B2 | 7/2015 | Zeidan et al. |
| 9,102,618 B2 | 8/2015 | Blumberg et al. |
| 9,351,976 B2 | 5/2016 | Perry et al. |
| 9,452,131 B2 | 9/2016 | Hickey et al. |
| 9,526,726 B2 | 12/2016 | Hickey et al. |
| 9,585,965 B2 | 3/2017 | Blumberg et al. |
| 9,650,341 B2 | 5/2017 | Remenar et al. |
| 9,861,699 B2 | 1/2018 | Perry et al. |
| 9,993,556 B2 | 6/2018 | Perry et al. |
| 9,999,670 B2 | 6/2018 | Perry et al. |
| 10,023,537 B2 | 7/2018 | Remenar et al. |
| 10,040,787 B2 | 8/2018 | Blumberg et al. |
| 10,085,980 B2 | 10/2018 | Hickey et al. |
| 11,518,745 B2 * | 12/2022 | Remenar ............. C07D 401/14 |
| 2004/0138230 A1 | 7/2004 | Andreana et al. |
| 2005/0203089 A1 | 9/2005 | Starrett, Jr. et al. |
| 2005/0282821 A1 | 12/2005 | Lesur et al. |
| 2006/0142333 A1 | 6/2006 | MacDonald et al. |
| 2007/0031513 A1 | 2/2007 | Kikuchi et al. |
| 2008/0085888 A1 | 4/2008 | Breining et al. |
| 2008/0143403 A1 | 6/2008 | Huang et al. |
| 2008/0186971 A1 | 8/2008 | Carmichael et al. |
| 2008/0261954 A1 | 10/2008 | Maelicke |
| 2008/0312199 A1 | 12/2008 | Glinsky |
| 2008/0318905 A1 | 12/2008 | Muhammad et al. |
| 2009/0053329 A1 | 2/2009 | Peters et al. |
| 2009/0068290 A1 | 3/2009 | Bourin et al. |
| 2009/0143403 A1 | 6/2009 | Brown |
| 2010/0292316 A1 | 11/2010 | Sanders et al. |
| 2011/0003828 A1 | 1/2011 | Blumberg et al. |
| 2011/0166128 A1 | 7/2011 | Remenar et al. |
| 2011/0166156 A1 | 7/2011 | Blumberg et al. |
| 2011/0166194 A1 | 7/2011 | Blumberg et al. |
| 2011/0178068 A1 | 7/2011 | Almarsson et al. |
| 2011/0275803 A1 | 11/2011 | Remenar et al. |
| 2011/0319422 A1 | 12/2011 | Blumberg et al. |
| 2012/0004165 A1 | 1/2012 | Keil et al. |
| 2012/0015866 A1 | 1/2012 | Blumberg et al. |
| 2012/0202823 A1 | 8/2012 | Zeidan et al. |
| 2012/0238552 A1 | 9/2012 | Perry et al. |
| 2013/0096089 A1 | 4/2013 | Remenar et al. |
| 2013/0184265 A1 | 7/2013 | Blumberg et al. |
| 2013/0267503 A1 | 10/2013 | Perry et al. |
| 2013/0267504 A1 | 10/2013 | Perry et al. |
| 2013/0267505 A1 | 10/2013 | Perry et al. |
| 2014/0051853 A1 | 2/2014 | Bürger et al. |
| 2014/0088115 A1 | 3/2014 | Perry et al. |
| 2014/0094472 A1 | 4/2014 | Blumberg et al. |
| 2014/0221653 A1 | 8/2014 | Blumberg et al. |
| 2014/0275048 A1 | 9/2014 | Zeidan et al. |
| 2014/0350254 A1 | 11/2014 | Remenar et al. |
| 2015/0274670 A1 | 10/2015 | Remenar et al. |
| 2015/0376143 A1 | 12/2015 | Blumberg et al. |
| 2017/0015659 A1 | 1/2017 | Blumberg et al. |

FOREIGN PATENT DOCUMENTS

| | | |
|---|---|---|
| DE | 1273533 B | 7/1968 |
| DE | 4439493 A1 | 5/1996 |
| EP | 0 339 976 A1 | 11/1989 |
| EP | 0 367 141 A2 | 5/1990 |
| EP | 0 409 435 A1 | 1/1991 |
| GB | 849541 A | 9/1960 |
| JP | S61-171467 A | 8/1986 |
| JP | S61-267580 A | 11/1986 |
| JP | S62-061979 A | 3/1987 |
| JP | S63-301861 A | 12/1988 |
| JP | H02-191256 A | 7/1990 |
| JP | H08-281115 A | 10/1996 |
| WO | WO 1990/008128 A1 | 7/1990 |
| WO | WO 1990/014080 A1 | 11/1990 |
| WO | WO 1991/000863 A1 | 1/1991 |
| WO | WO 1992/006089 A1 | 4/1992 |
| WO | WO 1993/025197 A1 | 12/1993 |
| WO | WO 1996/012725 A1 | 5/1996 |
| WO | WO 1997/036893 A1 | 10/1997 |
| WO | WO 1997/041132 A1 | 11/1997 |
| WO | WO 1997/043284 A1 | 11/1997 |
| WO | WO 1998/049157 A1 | 11/1998 |
| WO | WO 1999/033846 A2 | 7/1999 |
| WO | WO 2000/066571 A1 | 11/2000 |
| WO | WO 2001/090103 A2 | 11/2001 |
| WO | WO 2002/096351 A2 | 12/2002 |
| WO | WO 2003/080047 A1 | 10/2003 |
| WO | WO 2004/026864 A1 | 4/2004 |
| WO | WO 2004/037819 A1 | 5/2004 |
| WO | WO 2004/067546 A1 | 8/2004 |
| WO | WO 2004/089925 A1 | 10/2004 |
| WO | WO 2005/016262 A2 | 2/2005 |
| WO | WO 2005/019215 A1 | 3/2005 |
| WO | WO 2005/066165 A1 | 7/2005 |
| WO | WO 2005/079807 A1 | 9/2005 |
| WO | WO 2005/090357 A1 | 9/2005 |
| WO | WO 2006/037090 A2 | 4/2006 |
| WO | WO 2006/090273 A2 | 8/2006 |
| WO | WO 2007/052104 A2 | 5/2007 |
| WO | WO 2007/059111 A2 | 5/2007 |
| WO | WO 2007/082907 A1 | 7/2007 |
| WO | WO 2007/084391 A2 | 7/2007 |
| WO | WO 2008/025781 A1 | 3/2008 |
| WO | WO 2009/003136 A1 | 12/2008 |
| WO | WO 2009/037172 A1 | 3/2009 |
| WO | WO 2009/052467 A1 | 4/2009 |
| WO | WO 2010/085684 A1 | 7/2010 |
| WO | WO 2010/149755 A1 | 12/2010 |
| WO | WO 2011/084848 A2 | 7/2011 |
| WO | WO 2011/161030 A1 | 12/2011 |

OTHER PUBLICATIONS

U.S. Appl. No. 14/677,333 / 2015/0274670 A1, filed Apr. 2, 2015 / Oct. 1, 2015, Julius F. Remenar.

U.S. Appl. No. 15/147,021 / 2016/0318869 A1 / U.S. Pat. No. 10,023,537, filed May 5, 2016 / Nov. 3, 2016 / Jul. 17, 2018, Julius F. Remenar.

(56) References Cited

OTHER PUBLICATIONS

U.S. Appl. No. 15/875,478 / 2018/0162816 A1 / U.S. Pat. No. 10,112,903, filed Jan. 19, 2018 / Jun. 14, 2018 / Oct. 30, 2018, Julius F. Remenar.
U.S. Appl. No. 16/131,773 2019/0084937 A1 / U.S. Pat. No. 10,351,529, filed Sep. 14, 2018 / Mar. 21, 2019 / Jul. 16, 2019, Julius F. Remenar.
U.S. Appl. No. 16/425,119 / 2019/0276406 A1 / U.S. Pat. No. 10,822,306, filed May 29, 2019 / Sep. 12, 2019 / Nov. 3, 2020, Julius F. Remenar.
U.S. Appl. No. 17/020,499 / 2020/0407320 A1 / U.S. Pat. No. 11,518,745, filed Sep. 14, 2020 / Dec. 31, 2020 / Dec. 6, 2022, Julius F. Remenar.
U.S. Appl. No. 18/051,216, filed Oct. 31, 2022, Julius F. Remenar.
U.S. Appl. No. 12/823,102 / 2011/0003828 A1 / U.S. Pat. No. 8,686,009, filed Jun. 24, 2010 / Jan. 6, 2011 / Apr. 1, 2014, Laura Cook Blumberg.
U.S. Appl. No. 14/172,391 / 2014/0221653 A1 / U.S. Pat. No. 9,102,618, filed Feb. 4, 2014 / Aug. 7, 2014 / Aug. 11, 2015, Laura Cook Blumberg.
U.S. Appl. No. 14/755,412 / 2015/0376143 A1, filed Jun. 30, 2015 / Dec. 31, 2015, Laura Cook.
U.S. Appl. No. 15/227,117 / 2017/0015659 A1 / U.S. Pat. No. 10,040,787, filed Aug. 3, 2016 / Jan. 19, 2017 / Aug. 7, 2018, Laura Cook Blumberg.
U.S. Appl. No. 16/023,887 / 2019/0031648 A1 / U.S. Pat. No. 10,428,058, filed Jun. 29, 2018 / Jan. 31, 2019 / Oct. 1, 2019, Laura Cook Blumberg.
U.S. Appl. No. 16/540,802 / 2019/0367501 A1 / U.S. Pat. No. 10,723,728, filed Aug. 14, 2019 / Dec. 5, 2019 / Jul. 28, 2020, Laura Cook Blumberg.
Altamura et al., "Intramuscular Preparations of Antipsychotics, Uses and Relevance in Clinical Practice", *Drugs* 63:493-512 (2003).
Alvarez et al., "Pancreatic lipase-catalyzed hydrolysis of esters of hydroxymethyl phenytoin dissolved in various metabolizable vehicles, dispersed in micellar systems, and in aqueous suspensions", *Pharmaceutical Research* 6(7):555-563 (1989).
Barnes et al., "Long Term Depot Antipsychotics: A Risk-Benefit Assessment", *Drug Safety* 10:464-479 (1994).
Bender et al., "Cyclopropanecarboxylic Acid Esters as Potential Prodrugs with Enhanced Hydrolytic Stability", *Organic Letters* 10(3):509-511 (2008).
Berman et al., "The efficacy and safety of aripiprazole as adjunctive therapy in major depressive disorder: a multicenter, randomized, double-blind, placebo-controlled study", *The Journal of Clinical Psychiatry* 68(6):843-53 (2007).
Böhme et al., "Zur Kenntnis der N-[α-Alkoxy-alkyl]-carbonsäureamide und der durch ihre thermische Spaltung entstehenden Enamide", *Chemische Berichte* 99(7):2127-2135 (1966)—Drawings.
Borthwick et al., "Design and Synthesis of Pyrrolidine-5,5-trans-lactams (5-Oxohexahydropyrrolo[3,2-b]pyrroles) as Novel Mechanism-Based Inhibitors of Human Cytomegalovirus Protease. 2. Potency and Chirality", *Journal of Medicinal Chemistry* 45(1):1-18 (2002).
Bristol Myers Squibb "Abilify Patient information leaflet FDA" 2005.
British National Formulary RPS Publishing & BMJ Group, London 2008, 56, 192-197 and 200-201.
Bundgaard, "Design of Prodrugs: Bioreversible Derivatives for various functional groups and chemical entities", Ch. 1 in; Design of Prodrugs. Elsevier Science Ltd., pp. 2-92 (1985).
Collins et al., "Novel pyrrole-containing progesterone receptor modulators", *Bioorganic & Medicinal Chemistry Letters* 14:2185-2189 (2004).
Collins et al., "Design and Development of Signal Transduction Inhibitors for Cancer Treatment: Experience and Challenges with Kinase Targets", *Current Signal Transduction Therapy* 1(1):13-23 (2006).
Dezi, "Modeling of 5-HT2A and 5-HT2C receptors and of theirs complexes with actual and potential antipsychotic drugs", PhD Thesis. Pompeu Fabra University, Barcelona, Spain, pp. 1-239 (2007).
Doshi et al., "In vivo pharmacokinetic studies of prodrugs of ibuprofen", *Indian Journal of Pharmaceutical Sciences* 69(6):824-827 (2009).
European Search Report for EP Application No. 17176623.1, dated Jan. 30, 2023, 11 pages.
Extended European Search Report for EP Application No. 22195630.3, dated Dec. 13, 2022, 12 pages.
Fensome et al., "Design, synthesis, and SAR of new pyrrole-oxindole progesterone receptor modulators leading to 5-(7-fluoro-3,3-dimethyl-2-oxo-dihydro-1H-indol-5-yl)-1-methyl-1H-pyrrole-2-carbonitrile (WAY-255348)", *Journal of Medicinal Chemistry* 51(6):1861-1873 (2008).
Girouard et al., "Neurovascular coupling in the normal brain and in hypertension, stroke, and Alzheimer disease", *Journal of Applied Physiology* 100(1):328-335 (2006).
Glick et al., "Treatment with atypical antipsychotics: new indications and new populations", *Journal of Psychiatric Research* 35(3):187-191 (2001).
Hartung et al., "A Simple and Efficient Preparation of Novel Formaldehyde Derivatives", *Synthesis* 3:495-501 (2009).
Harvey et al., "Ziprasidone: efficacy, tolerability, and emerging data on wide-ranging effectiveness", *Expert Opinion on Pharmacotherapy* 6(2):337-346 (2005).
Hutchings et al., "An Oxazoline-Mediated Synthesis of the Pyrrolophenanthridine Alkaloids and Some Novel Derivatives", *The Journal of Organic Chemistry* 61(3):1004-1013 (1996).
International Search Report with Written Opinion corresponding to International Patent Application No. PCT/US2010/039855, mailed Aug. 23, 2010.
Johansen et al., "Prodrugs as Drug Delivery Systems. XVI. Novel Water-soluble Prodrug Types of Chlorzoxazone by Esterification of the N-Hydroxymethyl Derivatives", *Arch. Pharm. Chem. Sci. Ed.* 8:43-54 (1981).
Kearney, "Prodrugs and targeted drug delivery", *Advanced Drug Delivery Reviews* 19(2):225-239 (1996).
Keck et al., "Aripiprazole monotherapy in the treatment of acute bipolar I mania: a randomized, double-blind, placebo- and lithium-controlled study", *Journal of Affective Disorders* 112(1-3):36-49 (2009).
Kong et al., "Simultaneous determination of 3'-azido-2',3'-dideoxyuridine and novel prodrugs in rat plasma by liquid chromatography", *Journal of Chromatography B Analytical Technologies in the Biomedical and Life Sciences* 795(2):371-376 (2003).
Krise et al., "Novel Prodrug Approach for Tertiary Amines: Synthesis and Preliminary Evaluation of N-Phosphonooxymethyl Prodrugs", *Journal of Medicinal Chemistry* 42(16):3094-3100 (1999).
Lin et al., "Diazonamide Support Studies: Stereoselective Formation of the C10 Chiral Center in both the CDFG and AEFG Fragments", *Organic Letters* 10(18):3969-3972 (2008).
Link et al., "Regioselective imide reduction: An issue in the total synthesis of staurosporine", *Tetrahedron Letters* 35(49):9135-9138 (1994).
Link et al., "First Total Synthesis of Staurosporine and ent-Staurosporine", *Journal of the American Chemical Society* 117(1):552-553 (1995).
Link et al., "Staurosporine and ent-Staurosporine: The First Total Synthesis, Prospects for a Regioselective Approach, and Activity Profiles", *Journal of the American Chemical Society* 118(12):2825-2842 (1996).
Lozhkin et al., "The first conglomerate in the series of 2,4,5,8,10-pentatricyclo[5.3.1.03,11]undecane-1,5-diones", *Mendeleev Communications* 17(2):85-87 (2007).
McCarron et al., "Incorporation of novel 1-alkylcarbonyloxymethyl prodrugs of 5-fluorouracil into poly(lactide-co-glycolide) nanoparticles", *International Journal of Pharmaceutics* 348(1-2):115-24 (2008).
Miao et al., "Characterization of a novel metabolite intermediate of ziprasidone in hepatic cytosolic fractions of rat, dog, and human by ESI-MS/MS, hydrogen/deuterium exchange, and chemical derivatization", *Drug Metabolism and Disposition* 33(7):879-883 (2005).

(56) References Cited

OTHER PUBLICATIONS

Mizutani et al., "Discovery of Novel Benzoxazinones as Potent and Orally Active Long Chain Fatty Acid Elongase 6 Inhibitors", *Journal of Medicinal Chemistry* 52(22):7289-7300 (2009).

Naber et al., "Aripiprazole: a new atypical antipsychotic with a different pharmacological mechanism", *Progress in Neuro-Psychopharmacology & Biological Psychiatry* 28(8):1213-1219 (2004).

Nagase et al., "The Practice of Medicinal Chemistry", Japan, *Technomic* 2:280-281 (1999).

Niele et al., "Palladium (II) cage compounds based on diphenylglycoluril", *Journal of the American Chemical Society* 110(1):172-177 (1988).

Niele et al., "Rhodium (II) cage compounds based on diphenylglycoluril", *Journal of the American Chemical Society* 111(6):2078-2085 (1989).

Nielsen et al., "Bioreversible quaternary N-acyloxymethyl derivatives of the tertiary amines bupivacaine and lidocaine—synthesis, aqueous solubility and stability in buffer, human plasma and simulated intestinal fluid", *European Journal of Pharmaceutical Sciences* 24(5):433-440 (2005).

Nomura et al., "(3-substituted benzyl) thiazolidine-2,4-diones as structurally new antihyperglycemic agents", *Bioorganic & Medicinal Chemistry Letters* 9(4):533-538 (1999).

O'Brien et al., "Vascular cognitive impairment", *Lancet Neurology* 2(2):89-98 (2003).

Opposition against European Patent No. 2 445 502 mailed Mar. 21, 2018, 13 pages.

Pass et al., "Thrombin inhibitors base on [5,5] trans-fused indane lactams", *Bioorganic & Medicinal Chemistry* 9(12):1657-1662 (1999).

Pitman, "Pro-drugs of am ides, imides, and amines", *Medicinal Research Reviews* 1(2):189-214 (1981).

Rautio et al., "Prodrugs: design and clinical applications", *Nature Reviews Drug Discovery* 7(3):255-270 (2008).

Redden et al., "Acyloxymethyl acidic drug derivatives: in vitro hydrolytic reactivity", *International Journal of Pharmaceutics* 180(2):151-60 (1999).

Rowley et al., "Current and Novel Approaches to the Drug Treatment of Schizophrenia", *Journal of Medicinal Chemistry* 44:477-501 (2001).

Sajatovic, "Treatment for mood and anxiety disorders: Quetiapine and aripiprazole", *Current Psychiatry Reports* 5(4):320-326 (2003).

Schmidt et al., "Ziprasidone: a novel antipsychotic agent with a unique human receptor binding profile", *European Journal of Pharmacology* 425(3):197-201 (2001).

Shah et al., "Current approaches in the treatment of Alzheimer's disease", *Biomedicine & Pharmacotherapy* 62(4):199-207 (2008).

Siegel, "Extended Release Drug Delivery Strategies in Psychiatry: Theory to Practice", *Psychiatry* 2(6):22-31 (2005).

Simplicio et al., "Beta-aminoketones as prodrugs with pH-controlled activation", *International Journal of Pharmaceutics* 336(2):208-214 (2007).

Simplicio et al., "Prodrugs for Amines", *Molecules* 13(3):519-547 (2008).

Skinner et al., "Topical Mosquito Repellents: X: 2-Oxazolidones", *Journal of Pharmaceutical Sciences* 66(4):587-589 (1977).

Stella et al., "Aqueous solubility and dissolution rate does not adequately predict in vivo performance: a probe utilizing some N-acyloxymethyl phenytoin prodrugs", *Journal of Pharmaceutical Sciences* 88(8):775-779 (1999).

Stella et al., "Prodrugs: Challenges and Rewards," Part 1, Springer, New York, Chapter 2.4.1 (2007).

Varia et al., "Phenytoin Prodrugs III: Water-Soluble Prodrugs for Oral and/or Parenteral Use", *Journal of Pharmaceutical Sciences* 73(8):1068-1073 (1984).

Weiler et al., "Isothiazoles VII: N-hydroxyalkylation and mannich reaction of 4-isothiazolin-3-one", *Journal of Heterocyclic Chemistry* 13(5):1097-1098 (1976).

Weitzel et al., "Weitere Tumorhemmende Verbindungsklassen, I Cytostatische Effekte von N-und 5-Hydroxymethyl-Verbindungen", *Hoppe-Seyler's Zeitschrift Fur Physiologische Chemie* 334(1):1-25—Drawings (1963).

Wermuth, "Designing Prodrugs and Bioprecursors: Carrier Prodrugs", *The Practice of Medicinal Chemistry* pp. 680-681 (1996).

Wise et al., "Examination of a Series of 8-[3-[Bis(4-fluorophenyl)amino]propyl]-1-aryl-1,3,8-triazaspiro[4.5]decan-4-ones as Potential Antipsychotic Agents", *Journal of Medicinal Chemistry* 28(12):1811-1817 (1985).

Wong et al., "Unsaturated cyclic ureas as new non-toxic biodegradable transdermal penetration enhancers. II. Evaluation Study", *International Journal of Pharmaceutics* 52(3):191-202 (1989).

Yamada, "Oxidation Products of Hydroxylcoctonam", *Bulletin of the Chemical Society of Japan* 35(4):670-672 (1962).

Yates et al., "1,3-Dipolar Cycloadditions to Oxidopyraziniums", *Heterocycles* 40(1):331-347 (1995).

Yoda et al., "Sml 2-mediated hetero-coupling reaction of lactams with aldehydes; synthesis of indolizidine alkaloids, (−)-δ-coniceine, (+)-5-epiindolizidine 167B and (+)-lentiginosine", *Tetrahedron Letters* 42(13):2509-2512 (2001)—Abstract Provided Only, 2 pages.

Young, "The Neuroleptic Treatment of Schizophrenia: Dosing Strategies, Depot Preparations and Novel Medications", *Jefferson Journal of Psychiatry* 13(1):18-26 (1996).

Zinner et al., "Benzazole, XXIX. [2-Oxo-benzoxazolyl-(3)-methyl]-ester von Carbonsauren und Thiocarbonsauren", *Journal of Practical Chemistry* 317:379-386 (1975)—Drawings.

\* cited by examiner

HETEROCYCLIC COMPOUNDS FOR THE TREATMENT OF NEUROLOGICAL AND PSYCHOLOGICAL DISORDERS

RELATED APPLICATIONS

This application is a continuation of U.S. patent application Ser. No. 16/425,119, filed on May 29, 2019, which is a continuation of U.S. patent application Ser. No. 16/131,773, filed on Sep. 14, 2018, now U.S. Pat. No. 10,351,529, which is a continuation of U.S. patent application Ser. No. 15/875,478, filed on Jan. 19, 2018, now U.S. Pat. No. 10,112,903, which is a continuation of U.S. patent application Ser. No. 15/147,021, filed May 5, 2016, now U.S. Pat. No. 10,023,537, which is a continuation of U.S. patent application Ser. No. 14/677,333, filed Apr. 2, 2015, now abandoned, which is a continuation of U.S. patent application Ser. No. 14/297,195, filed Jun. 5, 2014, now abandoned, which is a continuation of U.S. patent application Ser. No. 13/607,066, filed Sep. 7, 2012, now U.S. Pat. No. 8,796,276, issued Aug. 5, 2014, which is a continuation of U.S. patent application Ser. No. 12/823,007, filed Jun. 24, 2010, now U.S. Pat. No. 8,431,576, issued Apr. 30, 2013 which claims the benefit of U.S. Provisional Patent Application No. 61/293,087, filed Jan. 7, 2010 and U.S. Provisional Patent Application No. 61/220,480, filed Jun. 25, 2009. The entire contents of these applications are incorporated herein by reference in their entirety.

BACKGROUND OF THE INVENTION

Currently there are several drugs in clinical use for the treatment of neurological and psychological disorders including schizophrenia, bipolar disorder, insomnia and anxiety disorders. Examples of these compounds include aripiprazole ziprasidone, and bifeprunox. The chemical structures of these compounds are given below.

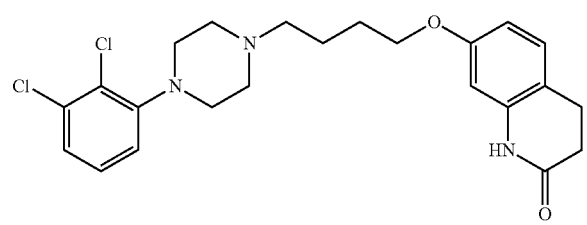

Aripiprazole

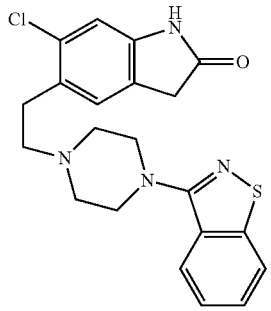

Ziprasidone

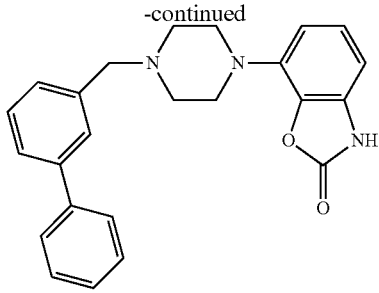

Bifeprunox

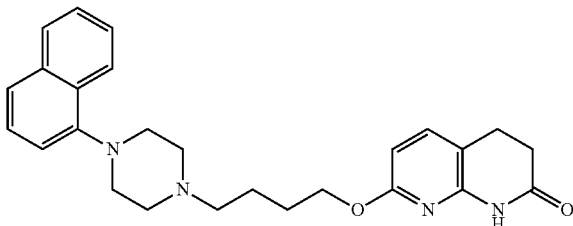

PF-00217830

Aripiprazole is an atypical antipsychotic used for the treatment of schizophrenia and schizoaffective disorder. Mace et al., CNS Drugs, 2009(23), 773-780. Other examples of heterocyclic derivatives that are useful for the treatment of schizophrenia are discussed in U.S. Pat. Nos. 5,350,747, 5,006, 528, 7,160,888, and in U.S. Pat. No. 6,127,357. PF-00217830 is another antipsychotic drug currently undergoing clinical studies for the treatment of schizophrenia. (NCT00580125) Other heterocyclic derivatives that have been stated to be useful as antipsychotic agents are those discussed in WO 93/04684, and European patent application EP 402644. However, many of the current antipsychotic drugs suffer from side effects and other undesirable drawbacks.

Aripiprazole is a dopamine partial agonist antipsychotic that is currently approved for clinical use in the United States and Europe. From the safety perspective it is remarkable that it is not highly sedative and does not impair the metabolic parameters. The advantages of a non-sedative and metabolically neutral antimanic drug are particularly relevant in the long-term, due to their impact on cognition and quality of life. (Vieta et al. *Actas Esp Psiquiatr* 2008:36(3): 158-164). However, Aripiprazole is known to produce injection site reactions. (U.S. Pat. No. 7,115,587). Ziprasidone is an effective acute and long-term maintenance treatment option for patients with schizophrenia, schizoaffective disorder, and schizophric disorder. (Kutcher et al., *Neuropsychiatr Dis Treat.*, 2005 1(2) 89-108). Ziprasidone users also suffer from multiple side effects including somnolence. Bifeprunox is known to improve symptoms in patients with schizophrenia. However, it also suffers from side effects such as weight gain an increase in cholesterol levels. (Barbato et al., WO 08/025781). Other antipsychotic agents also show substantial side effects. For example, paliperidone and riperidone are associated with weight gain in patients. (Nussbaum et al., *Schizophrenia Bulletin* 34(3) 419-422, 2008). Considering the range of side effects associated with current antipsychotic drugs, it is imperative to develop drugs with reduced side effects.

Optimization of a drug's bioavailability has many potential benefits. For patient convenience and enhanced compliance it is generally recognized that less frequent dosing is desirable. By extending the period through which the drug is released, a longer duration of action per dose is expected. This will then lead to an overall improvement of dosing parameters such as taking a drug once a day where it has previously required four times a day dosing or once a week or even less frequently when daily dosing was previously required. Many drugs are presently given at a once a day dosing frequency. Yet, not all of these drugs have pharmacokinetic properties that are suitable for dosing intervals of exactly twenty-four hours. Extending the period through which these drugs are released would also be beneficial.

One of the fundamental considerations in drug therapy involves the relationship between blood levels and therapeutic activity. For most drugs, it is of primary importance that serum levels remain between a minimally effective concentration and a potentially toxic level. In pharmacokinetic terms, the peaks and troughs of a drug's blood levels ideally fit well within the therapeutic window of serum concentrations. For certain therapeutic agents, this window is so narrow that dosage formulation becomes critical.

In an attempt to address the need for improved bioavailability, several drug release modulation technologies have been developed. Enteric coatings have been used as a protector of pharmaceuticals in the stomach and microencapsulating active agents using protenoid microspheres, liposomes or polysaccharides have been effective in abating enzyme degradation of the active agent. Enzyme inhibiting adjuvants have also been used to prevent enzyme degradation.

A wide range of pharmaceutical formulations provide sustained release through microencapsulation of the active agent in amides of dicarboxylic acids, modified amino acids or thermally condensed amino acids. Slow release rendering additives can also be intermixed with a large array of active agents in tablet formulations.

While microencapsulation and enteric coating technologies impart enhanced stability and time-release properties to active agent substances these technologies suffer from several shortcomings. Incorporation of the active agent is often dependent on diffusion into the microencapsulating matrix, which may not be quantitative and may complicate dosage reproducibility. In addition, encapsulated drugs rely on diffusion out of the matrix, degradation of the matrix, or both which is highly dependent the chemical properties and on the water solubility of the active agent. Conversely, water-soluble microspheres swell by an infinite degree and, unfortunately, may release the active agent in bursts with limited active agent available for sustained release. Furthermore, in some technologies, control of the degradation process required for active agent release is unreliable. Several implantable drug delivery systems have utilized polypeptide attachment to drugs. Additionally, other large polymeric carriers incorporating drugs into their matrices are used as implants for the gradual release of drug. Yet another technology combines the advantages of covalent drug attachment with liposome formation where the active ingredient is attached to highly ordered lipid films.

However, there is still a need for an active agent delivery system that is able to deliver certain active agents which have been heretofore not formulated or difficult to formulate in a sustained release formulation for release over a sustained period of time and which is convenient for patient dosing.

Self administered antipsychotic drugs often suffer from poor patient compliance in regular administration. Outpatients with schizophrenia often have problems complying with a regimen of oral antipsychotic medications. Bartko G et al., *Psychiatry Research* 1987 (22) 221-227. Thus, it is particularly useful to develop long acting antipsychotic drugs that can be administered less frequently.

SUMMARY

The instant application relates to compounds of Formula I and their use for the treatment of neurological and psychiatric disorders including schizophrenia, mania, anxiety and bipolar disease. In particular, the instant application relates to compounds of Formula I:

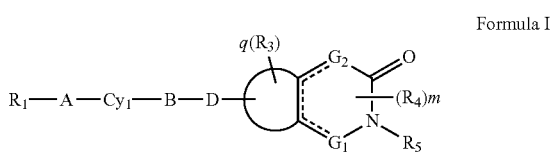

Formula I and the geometric isomers, enantiomers, diastereomers, racemates, pharmaceutically acceptable salts and solvates thereof, wherein ═══ represents a single or double bond;

Semicircle represents an optionally substituted cycloalkyl, cycloalkenyl, heterocyclyl, aryl or heteroaryl containing one, two or three rings;

A is selected from absent, optionally substituted alkyl, optionally substituted alkenyl, optionally substituted alkynyl, —S—, —O—, —S(O)—, —S(O)$_2$—, —S[C(R$_{10}$)(R$_{11}$)]$_u$—, —S(O)[C(R$_{10}$)(R$_{11}$)]$_u$—, —S(O)$_2$[C(R$_{10}$)(R$_{11}$)]$_u$—, —O[C(R$_{10}$)(R$_{11}$)]$_u$—, —N(R$_{10}$)—, —NR$_{(10)}$—[C(R$_{10}$)(R$_{11}$)]$_u$—, —[C(R$_{10}$)(R$_{11}$)]$_u$;

wherein each u is independently 1, 2, 3, 4, 5, 6 or 7;

wherein each R$_{10}$ and R$_{11}$ is independently absent, hydrogen, halogen, aliphatic, substituted aliphatic, aryl or substituted aryl;

Cy$_1$ is an optionally substituted cycloalkyl, optionally substituted cycloalkenyl, optionally substituted heterocyclyl or optionally substituted aryl;

B is a linker or a direct bond;

D is selected from absent, —O—, —NR$_{10}$, —C(R$_{10}$)(R$_{11}$)— and —S—, —S(O)—, —S(O)$_2$—, —C(O)—;

Each G$_1$ and G$_2$ is independently selected from absent, —S—, —O—, —S(O)—, —S(O)$_2$—, —SC(R$_{10}$)(R$_{11}$)—, —S(O) C(R$_{10}$)(R$_{11}$)—, —S(O)$_2$C(R$_{10}$)(R$_{11}$)—, —OC(R$_{10}$)(R$_{11}$)—, —C(R$_{10}$)═C(R$_{11}$)—, —N(R$_{10}$)—C(R$_{10}$)(R$_{11}$)—, —[C(R$_{10}$)(R$_{11}$)]$_t$—;

wherein t is 1, 2 or 3;

Each R$_1$, R$_3$ and R$_4$ is independently selected from absent, hydrogen, halogen, —OR$_{10}$, —SR$_{10}$, —N(R$_{10}$)(R$_{11}$), —S(O)R$_{10}$, —S(O)$_2$R$_{10}$, optionally substituted aliphatic, optionally substituted aryl or optionally substituted heterocyclyl;

Alternatively, two R$_3$ and R$_4$ together form an optionally substituted ring;

R$_5$ is selected from —CH(R$_{10}$)—OR$_{20}$, —CH(R$_{10}$)—OC(O)OR$_{20}$, —CH(R$_{10}$)—OC(O)R$_{20}$, —CH(R$_{10}$)—OC(O)NR$_{20}$R$_{21}$, —(CH(R$_{10}$))—OPO$_3$MY, —(CH(R$_{10}$))—OP(O)(OR$_{20}$)(OR$_{21}$), —[CH(R$_{10}$)O]$_z$—R$_{20}$, —[CH(R$_{10}$)O]$_z$—C(O)OR$_{20}$, —[CH(R$_{10}$)O]$_z$—C(O)R$_{20}$, —[CH(R$_{10}$)O]$_z$—C(O)NR$_{20}$R$_{21}$, —[CH(R$_{10}$)O]z-OPO$_3$MY, —[CH(R$_{10}$)O]$_z$—P(O)$_2$(OR$_{20}$)M and —[CH(R$_{10}$)O]$_z$—P(O)(OR$_{20}$)(OR$_{21}$);

wherein z is 1, 2, 3, 4, 5, 6, or 7;

each $R_{20}$ and $R_{21}$ is independently selected from hydrogen, aliphatic, substituted aliphatic, aryl or substituted aryl; Y and M are the same or different and each is a monovalent cation; or M and Y together is a divalent cation; and n, m and q are independently selected from 0, 1, and 2.

The invention further relates to prodrugs of antipsychotic drugs that become active agents after in vivo administration. The invention further relates to sustained release of antipsychotic drugs.

DETAILED DESCRIPTION OF THE INVENTION

Figure 1:
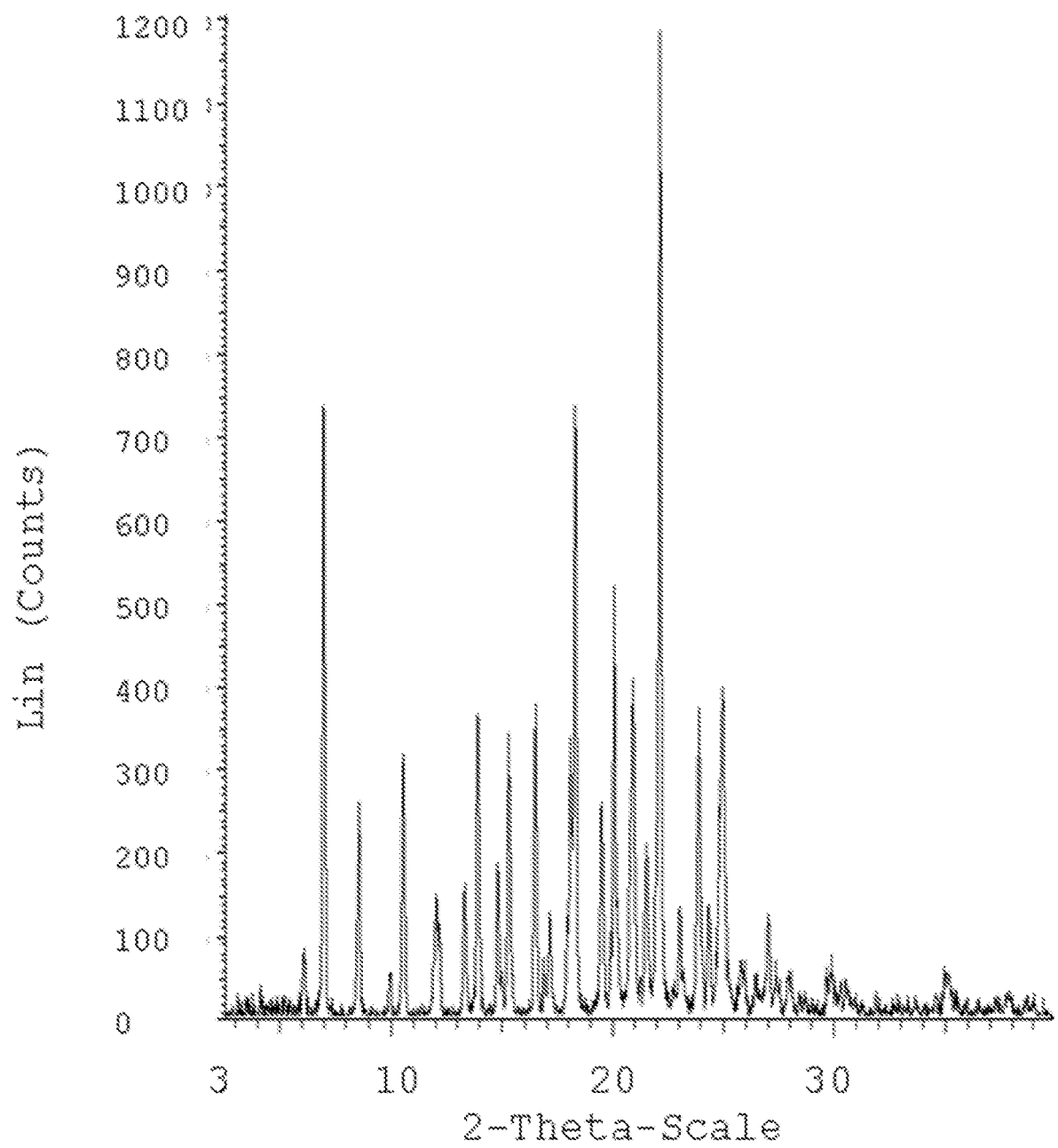
FIG. 1: PXRD spectrum of Compound-7.
Figure 2:
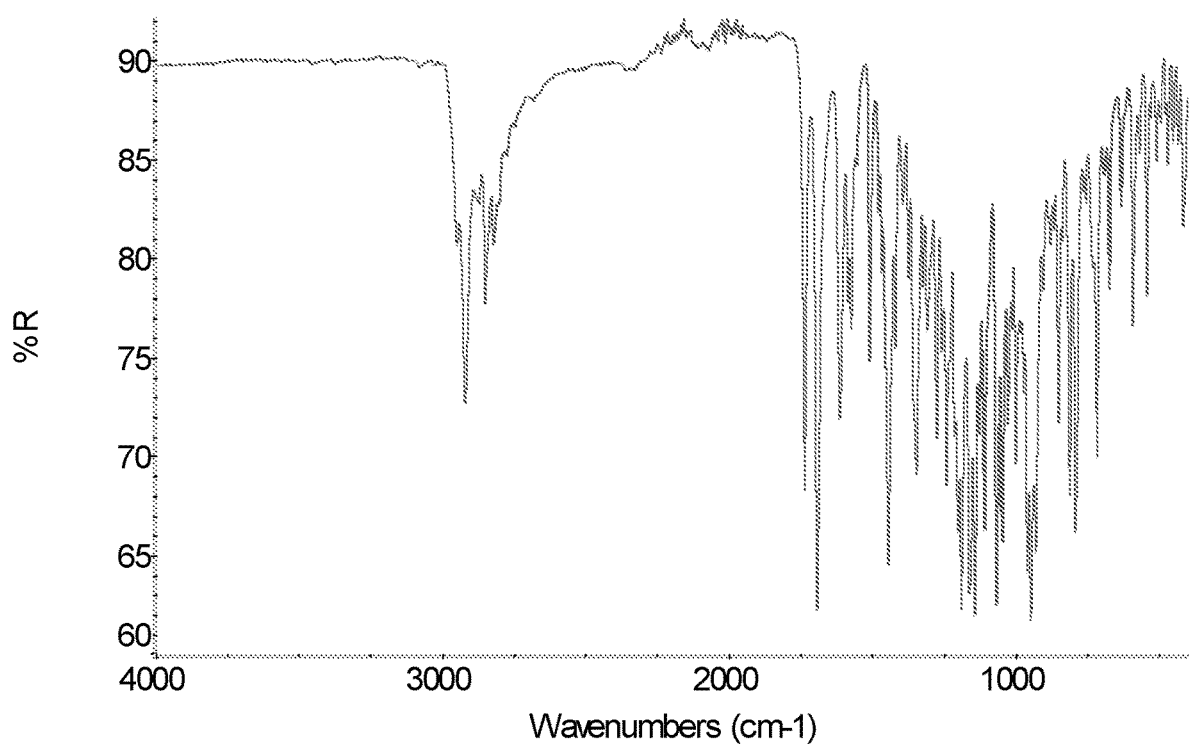
FIG. 2: IR Spectrum of Compound-7.
Figure 3:
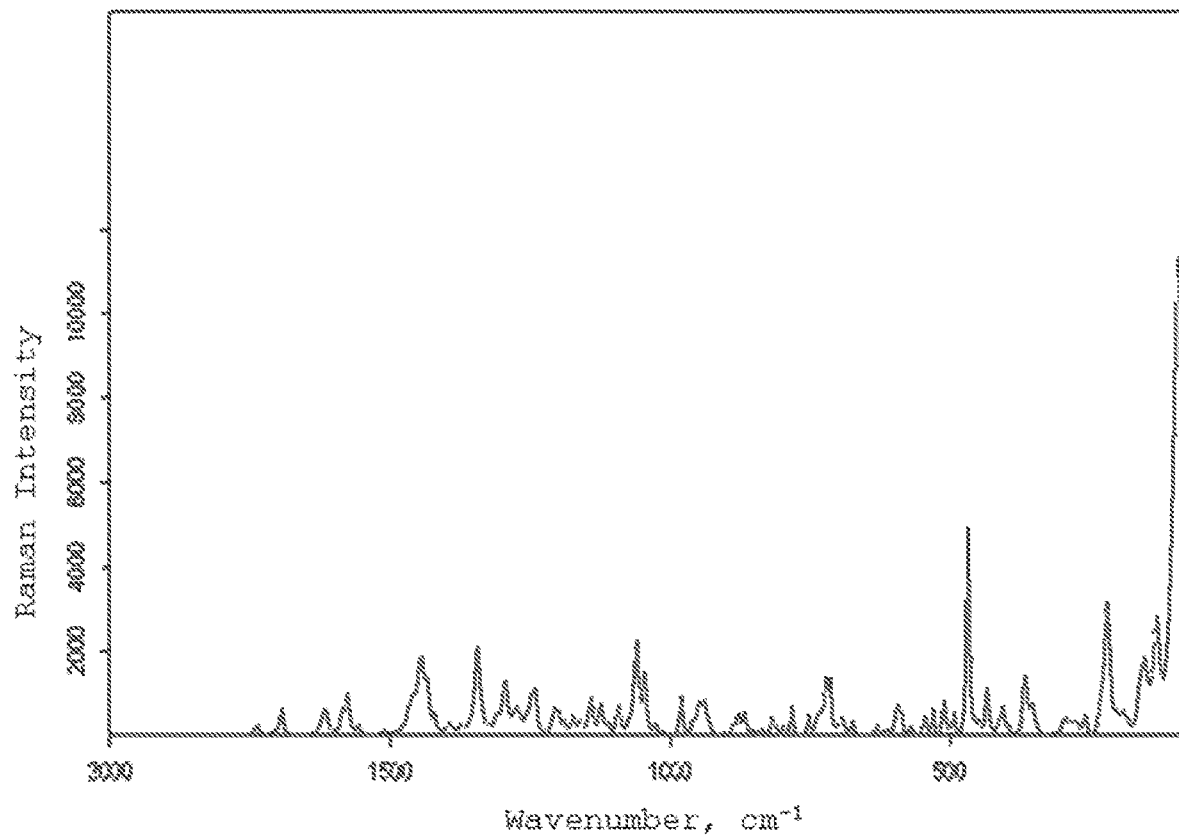
FIG. 3: Raman spectrum of Compound-7.
Figure 4:
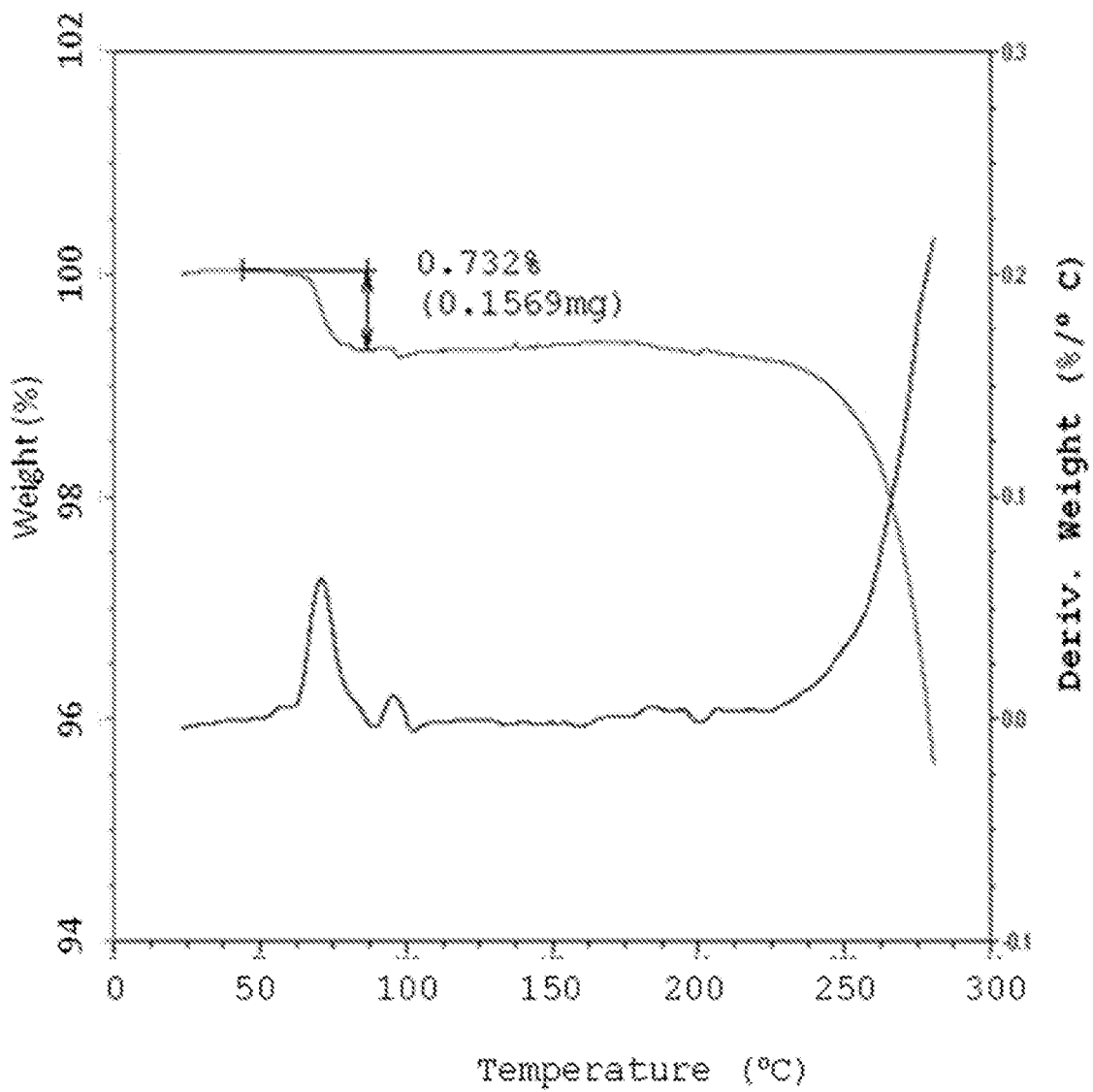
FIG. 4: TGA thermogram of Compound-7.
Figure 5:
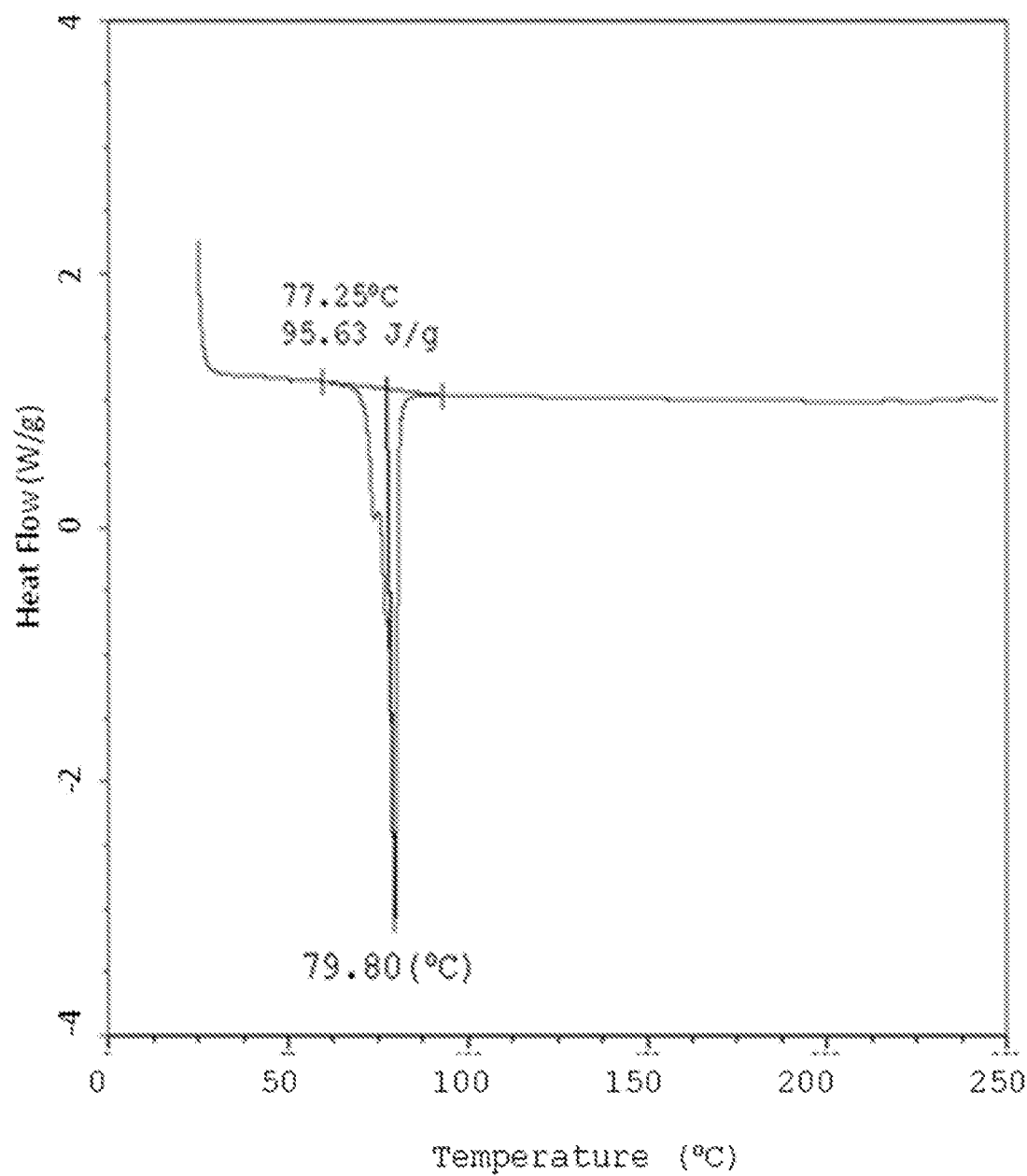
FIG. 5: DSC thermogram of Compound-7.

One aspect of the present invention provides a compound having the general Formula I:

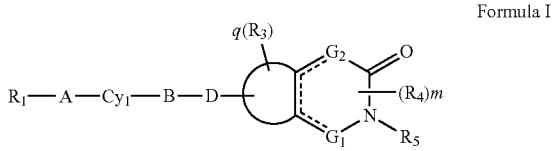

Formula I or its geometric isomers, enantiomers, diastereomers, racemates, pharmaceutically acceptable salts and solvates thereof,
wherein ===== represents a single or double bond;
Semicircle represents an optionally substituted cycloalkyl, cycloalkenyl, heterocyclyl, aryl or heteroaryl containing one, two or three rings;
A is selected from absent, optionally substituted alkyl, optionally substituted alkenyl, optionally substituted alkynyl, —S—, —O—, —S(O)—, —S(O)$_2$—, —[C(R$_{10}$)(R$_{11}$)]$_u$—, —S(O)[C(R$_{10}$)(R$_{11}$)]$_u$—, —S(O)$_2$[C(R$_{10}$)(R$_{11}$)]$_u$—, —O[C(R$_{10}$)(R$_{11}$)]$_u$—, —N(R$_{10}$)—, —N(R$_{10}$)—[C(R$_{10}$)(R$_{11}$)]$_u$—, —[C(R$_{10}$)(R$_{11}$)]$_u$;
wherein each u is independently 1, 2, 3, 4, 5, 6 or 7;
wherein each $R_{10}$ and $R_{11}$ is independently absent, hydrogen, halogen, aliphatic, substituted aliphatic, aryl or substituted aryl;
Cy$_1$ is an optionally substituted cycloalkyl, optionally substituted cycloalkenyl, optionally substituted heterocyclyl or optionally substituted aryl;
B is a linker or a direct bond;
D is selected from absent, —O—, —NR$_{10}$, —C(R$_{10}$)(R$_{11}$)— and —S—, —S(O)—, —S(O)$_2$—, —C(O)—;
Each G$_1$ and G$_2$ is independently selected from absent, —S—, —O—, —S(O)—, —S(O)$_2$—, —SC(R$_{10}$)(R$_{11}$)—, —S(O)C(R$_{10}$)(R$_{11}$)—, —S(O)$_2$C(R$_{10}$)(R$_{11}$)—, —OC(R$_{10}$)(R$_{11}$)—, —C(R$_{10}$)=C(R$_{11}$)—, —N(R$_{10}$)—C(R$_{10}$)(R$_{11}$)—, —[C(R$_{10}$)(R$_{11}$)]$_t$—;

wherein t is 1, 2 or 3;

Each $R_1$, $R_3$ and $R_4$ is independently selected from absent, hydrogen, halogen, —OR$_{10}$, —SR$_{10}$, —N(R$_{10}$)(R$_{11}$), —S(O)R$_{10}$, —S(O)$_2$R$_{10}$, optionally substituted aliphatic, optionally substituted aryl or optionally substituted heterocyclyl;

Alternatively, two $R_3$ and $R_4$ together form an optionally substituted ring;

$R_5$ is selected from —CH(R$_{10}$)—OR$_{20}$, —CH(R$_{10}$)—OC(O)OR$_{20}$, —CH(R$_{10}$)—OC(O)R$_{20}$, —CH(R$_{10}$)—OC(O)NR$_{20}$R$_{21}$, —(CH(R$_{10}$))—OPO$_3$MY, —(CH(R$_{10}$))—OP(O)(OR$_{20}$)(OR$_{21}$), —[CH(R$_{10}$)O]$_z$—R$_{20}$, —[CH(R$_{10}$)O]$_z$—C(O)OR$_{20}$, —[CH(R$_{10}$)O]$_z$—C(O)R$_{20}$, —[CH(R$_{10}$)O]$_z$—C(O)NR$_{20}$R$_{21}$, —[CH(R$_{10}$)O]z—OPO$_3$MY, —[CH(R$_{10}$)O]$_z$—P(O)$_2$(OR$_{20}$)M and —[CH(R$_{10}$)O]$_z$—P(O)(OR$_{20}$)(OR$_{21}$).

wherein z is 1, 2, 3, 4, 5, 6, or 7;

each $R_{20}$ and $R_{21}$ is independently selected from hydrogen, aliphatic, substituted aliphatic, aryl or substituted aryl; Y and M are the same or different and each is a monovalent cation; or M and Y together is a divalent cation; and n, m and q are independently selected from 0, 1, and 2.

Substituents indicated as attached through variable points of attachments can be attached to any available position on the ring structure.

In another embodiment, compounds of the present invention are represented by Formula II as illustrated below, or its geometric isomers, enantiomers, diastereomers, racemates, pharmaceutically acceptable salts and solvates thereof:

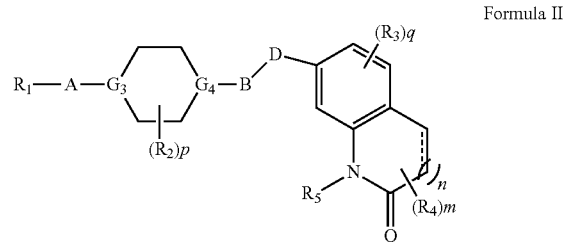

Formula II wherein ===== represents a single or double bond; and,
$R_1$, $R_3$, $R_4$, $R_5$, A, B, D, n, m, p, and q are as defined above;
$R_2$ selected from absent, hydrogen, halogen, —OR$_{10}$, —SR$_{10}$, —N(R$_{10}$)(R$_{11}$), —S(O)R$_{10}$, —S(O)$_1$R$_{10}$, optionally substituted aliphatic, optionally substituted aryl or optionally substituted heterocyclyl;
each G$_3$ and G$_4$ is independently selected from —N—, —C(R$_{10}$)—[C(R$_{10}$)(R$_{11}$)]$_a$—, wherein a is 0, 1 or 2; and,
p is 0, 1, 2, 3 or 4.

In another embodiment, compounds of the present invention are represented by Formula III as illustrated below, or its geometric isomers, enantiomers, diastereomers, racemates, pharmaceutically acceptable salts and solvates thereof:

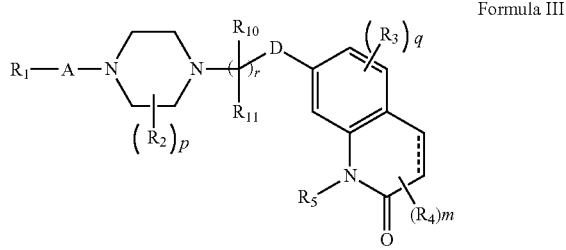

Formula III wherein, $R_1$, $R_2$, $R_3$, $R_4$, $R_5$, $R_{10}$, $R_{11}$, A, D, m, p and q are as defined above; and r is 0, 1, 2, 3, 4, 5, 6, 7, 8, 9, 10 or 11.

In another embodiment, compounds of the present invention are represented by Formula IV as illustrated below, or its geometric isomers, enantiomers, diastereomers, racemates, pharmaceutically acceptable salts and solvates thereof:

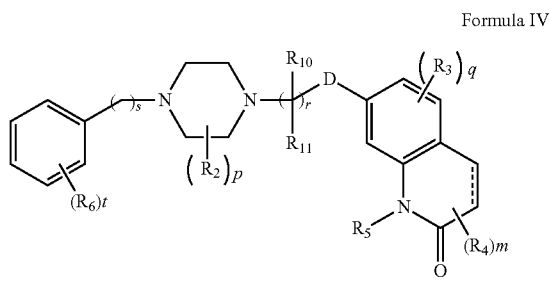

Formula IV wherein $R_2$, $R_3$, $R_4$, $R_5$, $R_{10}$, $R_{11}$, D, m, p, q and r are as defined above;
  each $R_6$ is independently selected from hydrogen, halogen, $OR_{10}$, $SR_{10}$, $NR_{10}R_{11}$, aliphatic, substituted aliphatic, aromatic, substituted aromatic, wherein each $R_{10}$ and $R_{11}$ are independently hydrogen, halogen, aliphatic, substituted aliphatic aryl or substituted aryl; or alternatively two adjacent $R_6$ groups form a second ring; and
  t and s are independently selected from 0, 1, and 2.

In another embodiment, compounds of the present invention are represented by Formula V as illustrated below, or its geometric isomers, enantiomers, diastereomers, racemates, pharmaceutically acceptable salts and solvates thereof:

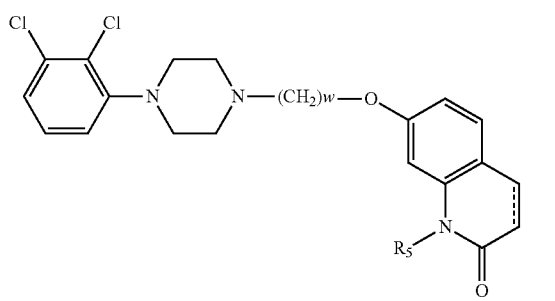

Formula V wherein ═══ represents a single or double bond; $R_5$, is as defined above; and
w is 0, 1, 2, 3, 4, 5, 6, 7, 8, 9, 10 or 11.

In a preferred embodiment, a compound of Formula VI is provided below or its geometric isomers, enantiomers, diastereomers, racemates, pharmaceutically acceptable salts and solvates thereof:

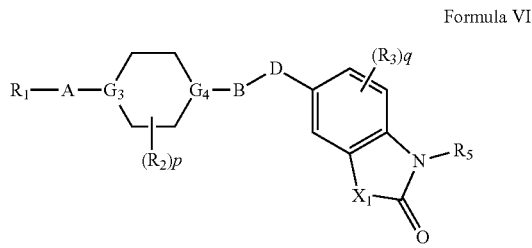

Formula VI wherein, $R_1$, $R_2$, $R_3$, $R_5$, A, B, D, $G_3$, $G_4$, p, q, $R_{10}$ and $R_{11}$ are as defined above; and, $X_1$ is —S—, —O—, —$NR_{10}$— or —$C(R_{10})(R_{11})$—.

In a preferred embodiment, a compound of Formula VII is provided below or its geometric isomers, enantiomers, diastereomers, racemates, pharmaceutically acceptable salts and solvates thereof:

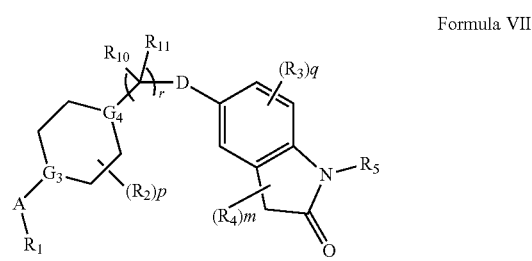

Formula VII wherein, $R_1$, $R_2$, $R_3$, $R_4$, $R_5$, A, D, $G_3$, $G_4$, m, p, q, r, $R_{10}$ and $R_{11}$ are as defined above.

In a preferred embodiment, a compound of Formula VIII is provided below or its geometric isomers, enantiomers, diastereomers, racemates, pharmaceutically acceptable salts and solvates thereof:

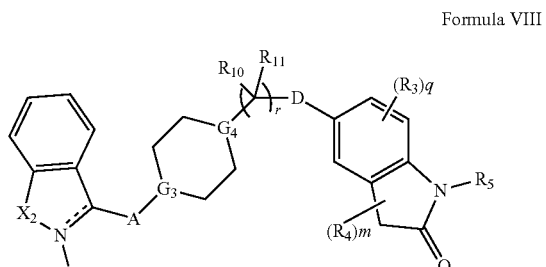

Formula VIII wherein, $R_2$, $R_3$, $R_4$, $R_5$, A, D, $G_3$, $G_4$, m, q, r, $R_{10}$ and $R_{11}$ are as defined above; and, $X_2$ is —S— or —O—.

In a preferred embodiment, a compound of Formula IX is provided below or its geometric isomers, enantiomers, diastereomers, racemates, pharmaceutically acceptable salts and solvates thereof:

Formula IX

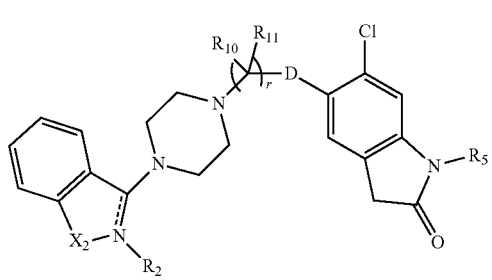

wherein, $X_2$, D, $R_2$, $R_5$, r, $R_{10}$ and $R_{11}$ are as defined above.

In a preferred embodiment, a compound of Formula X is provided below or its geometric isomers, enantiomers, diastereomers, racemates, pharmaceutically acceptable salts and solvates thereof:

Formula X

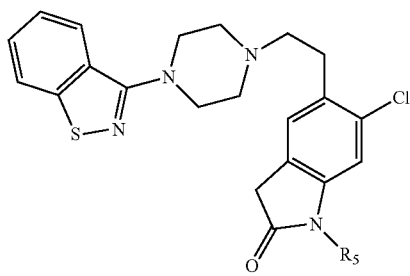

wherein, $R_5$ is as defined above.

In a preferred embodiment, a compound of Formula XI is provided below or its geometric isomers, enantiomers, diastereomers, racemates, pharmaceutically acceptable salts and solvates thereof:

Formula XI

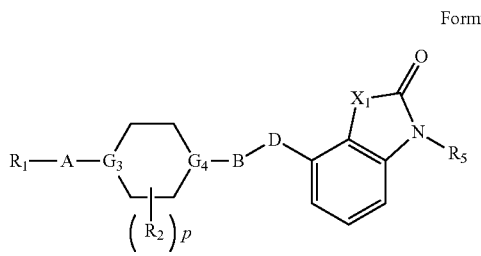

wherein, $R_1$, $R_2$, $R_5$, $G_3$, $G_4$, $X_1$, A, B, D and p are as defined above.

In a preferred embodiment, a compound of Formula XII is provided below or its geometric isomers, enantiomers, diastereomers, racemates, pharmaceutically acceptable salts and solvates thereof:

Formula XII

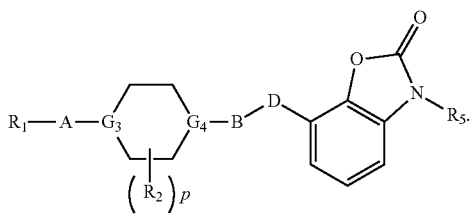

A more preferred embodiment is a compound of Formula XII wherein B is a bond; D is absent; $G_3$ and $G_4$ are N; $R_2$ is H; p is 1; A is alkyl; and $R_1$ is substituted phenyl.

A more preferred embodiment is a compound of Formula XIII below or its geometric isomers, enantiomers, diastereomers, racemates, pharmaceutically acceptable salts and solvates thereof:

Formula XIII

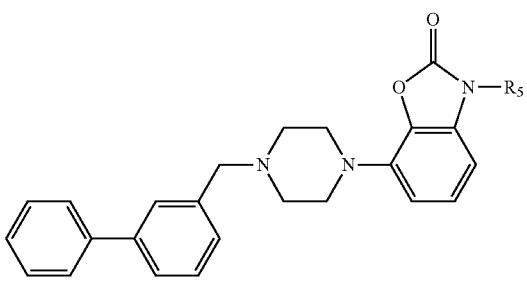

wherein, $R_5$ is as defined above.

A preferred embodiment is a compound of Formula XIV below or its geometric isomers, enantiomers, diastereomers, racemates, pharmaceutically acceptable salts and solvates thereof:

Formula XIV

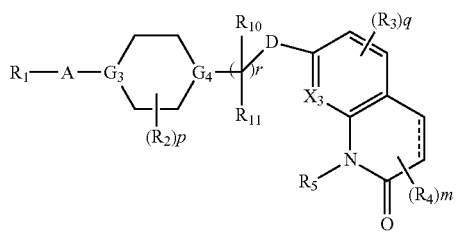

wherein, A, $R_1$, $R_2$, $R_3$, $R_4$, $R_5$, $R_{10}$, $R_{11}$, $G_3$, $G_4$, D, m, p, q, and r as defined above; and, $X_3$ is —CH— or —N—.

A more preferred embodiment is a compound where $G_3$ and $G_3$ is —N—.

A preferred embodiment is a compound of Formula XV below or its geometric isomers, enantiomers, diastereomers, racemates, pharmaceutically acceptable salts and solvates thereof:

Formula XV

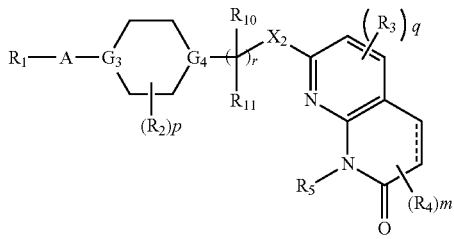

wherein, A, $R_1$, $R_2$, $R_3$, $R_4$, $R_5$, $R_{10}$, $R_{11}$, $G_3$, $G_4$, $X_2$, m, p, q, and r as defined above.

A preferred embodiment is a compound of Formula XVI below or its geometric isomers, enantiomers, diastereomers, racemates, pharmaceutically acceptable salts and solvates thereof:

Formula XVI

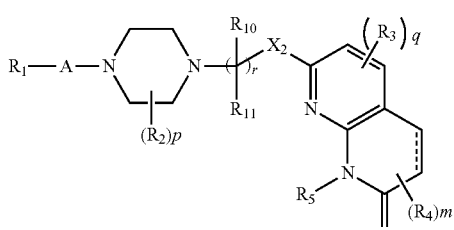

wherein, A, $R_1$, $R_2$, $R_3$, $R_4$, $R_5$, $R_{10}$, $R_{11}$, $X_2$, m, p, q, and r as defined above.

A preferred embodiment is a compound of Formula XVII below or its geometric isomers, enantiomers, diastereomers, racemates, pharmaceutically acceptable salts and solvates thereof:

Formula XVII

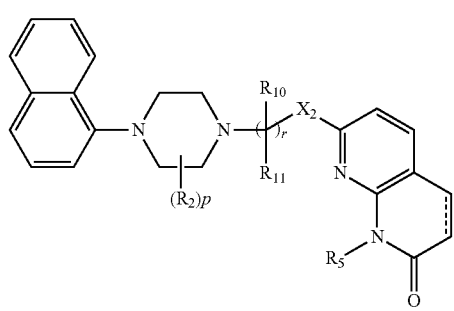

wherein, $R_2$, $R_5$, $R_{10}$, $R_{11}$, $X_2$, p and r as defined above.

A preferred embodiment is a compound of Formula XVIII below or its geometric isomers, enantiomers, diastereomers, racemates, pharmaceutically acceptable salts and solvates thereof:

Formula XVIII

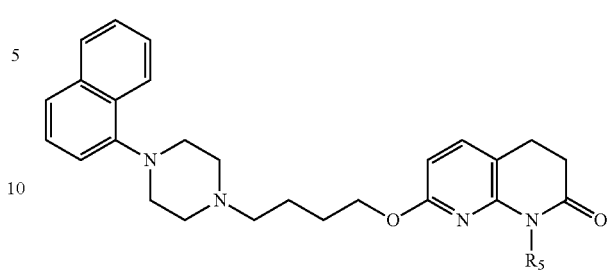

In a preferred embodiment, the $R_1$ moiety is an aryl or heteroaryl group selected from:

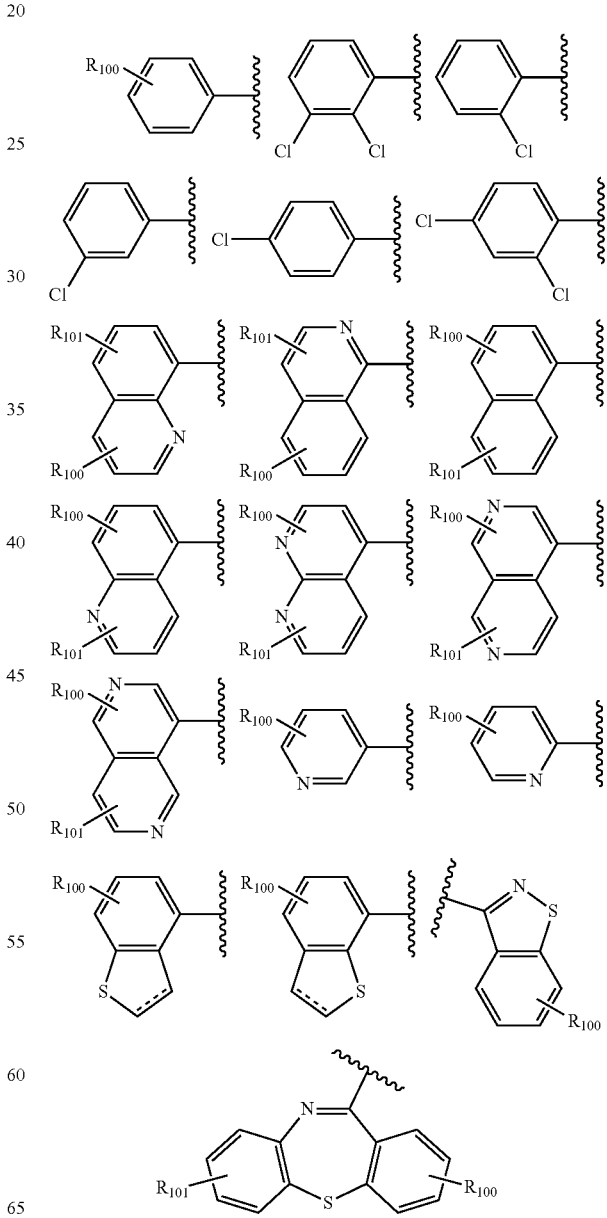

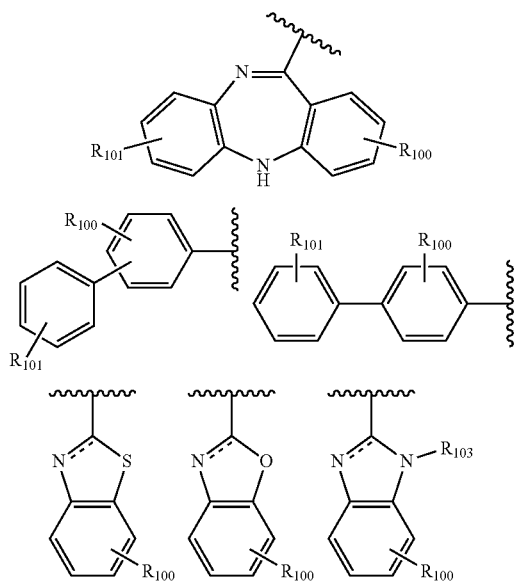

wherein $R_{100}$ $R_{101}$ and $R_{103}$ are independently selected from hydrogen, halogen, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ alkylamino and optionally substituted $C_1$-$C_8$ aryl.

In a preferred embodiment, the $R_5$ moiety is selected from:

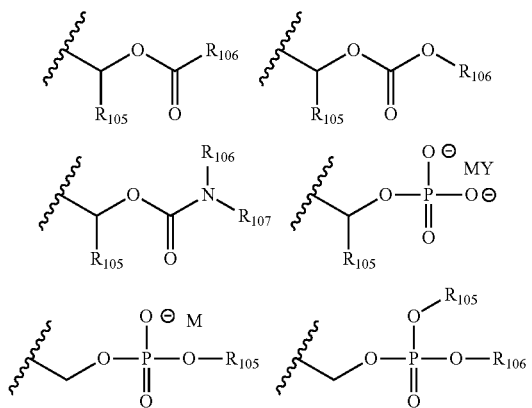

wherein $R_{105}$, $R_{106}$ and $R_{107}$ are independently selected from hydrogen, halogen, optionally substituted $C_1$-$C_{24}$ alkyl, optionally substituted $C_2$-$C_{24}$ alkenyl, optionally substituted $C_2$-$C_{24}$ alkynyl, optionally substituted $C_3$-$C_{24}$ cycloalkyl, optionally substituted $C_1$-$C_{24}$ alkoxy, optionally substituted $C_1$-$C_{24}$ alkylamino and optionally substituted $C_1$-$C_{24}$ aryl.

In a more preferred embodiment, $R_5$ is selected from:

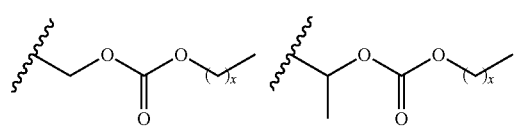

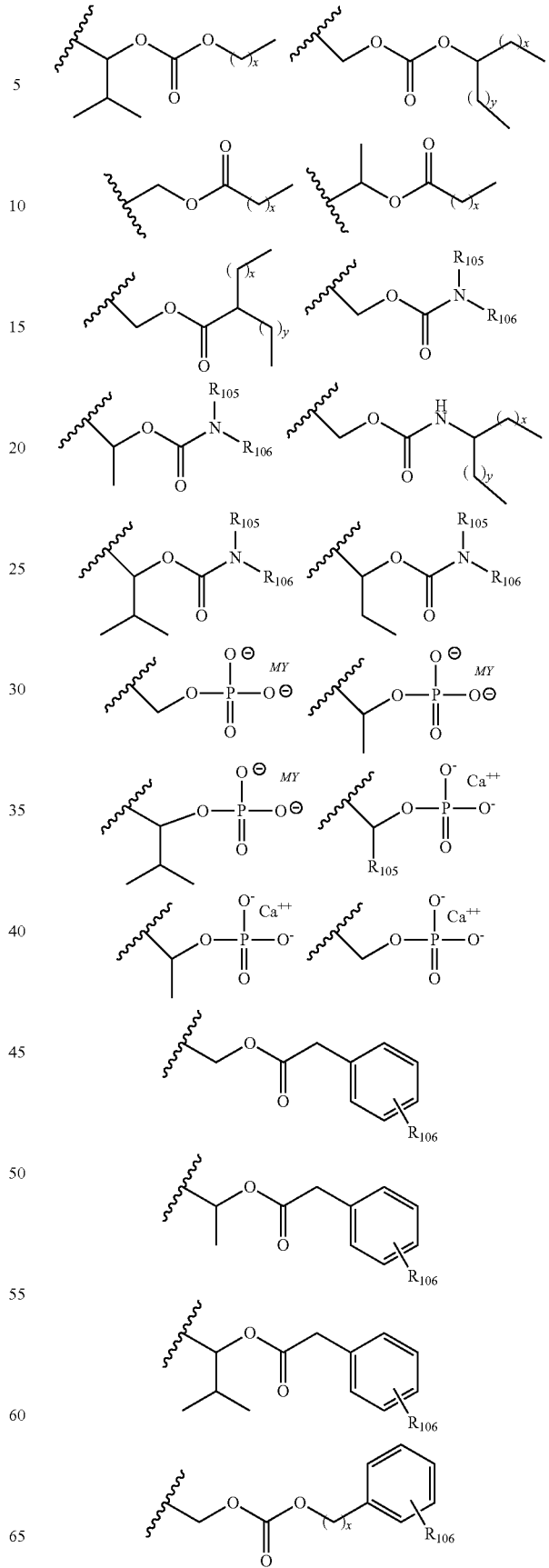

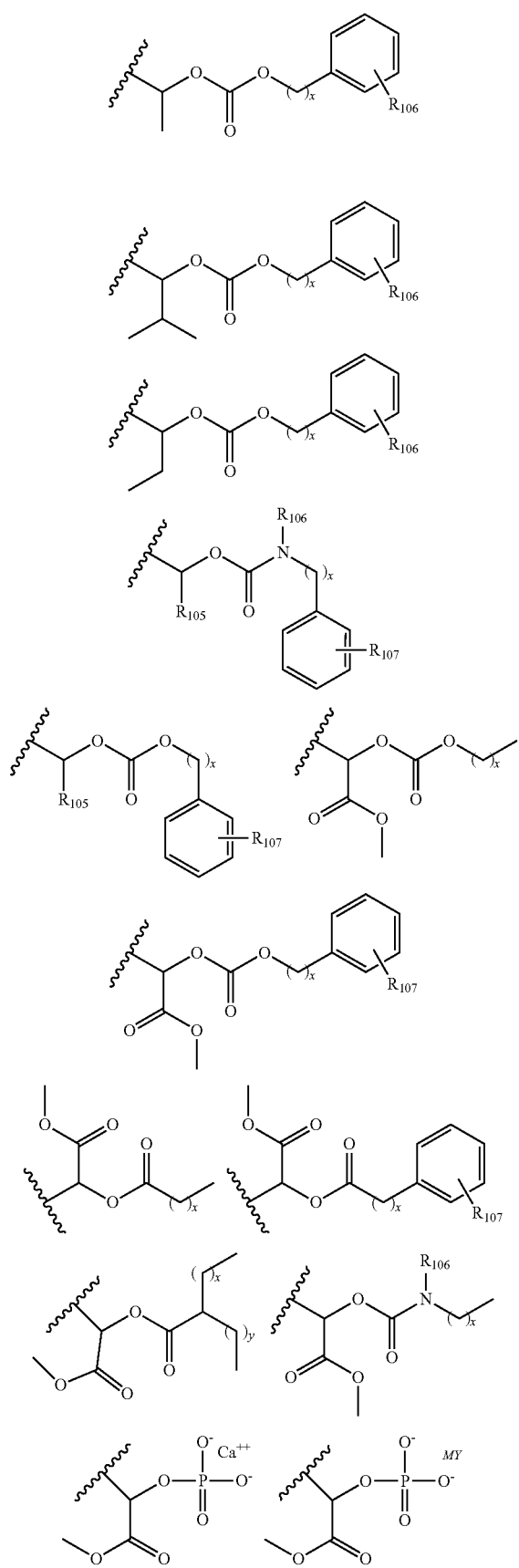
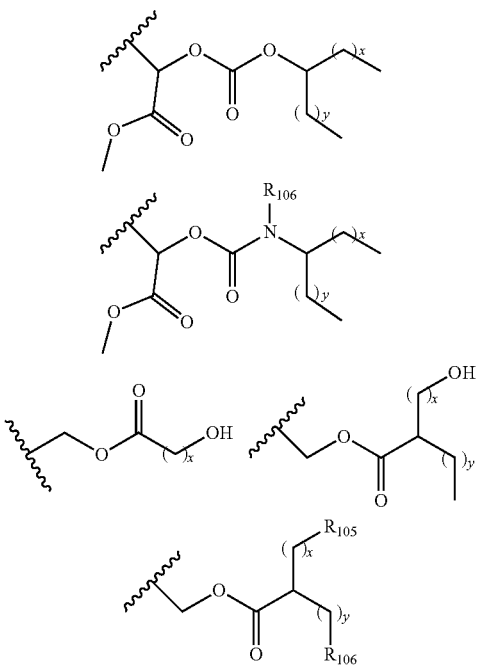
wherein each x and y is independently an integer between 0 and 30, and $R_{105}$, $R_{106}$, and $R_{107}$ are as defined above.
In a more preferred embodiment, x is an integer between 5 and 20.
In a preferred embodiment, Cy1 is selected from:
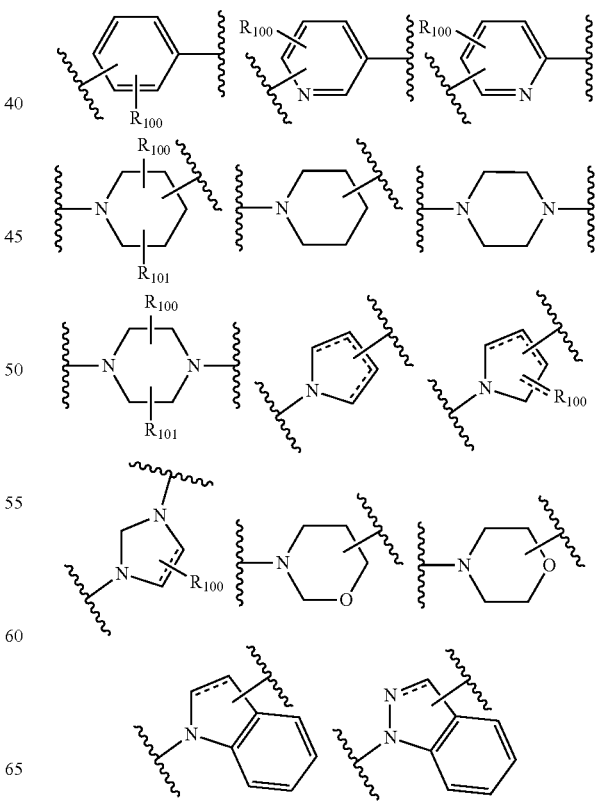

-continued

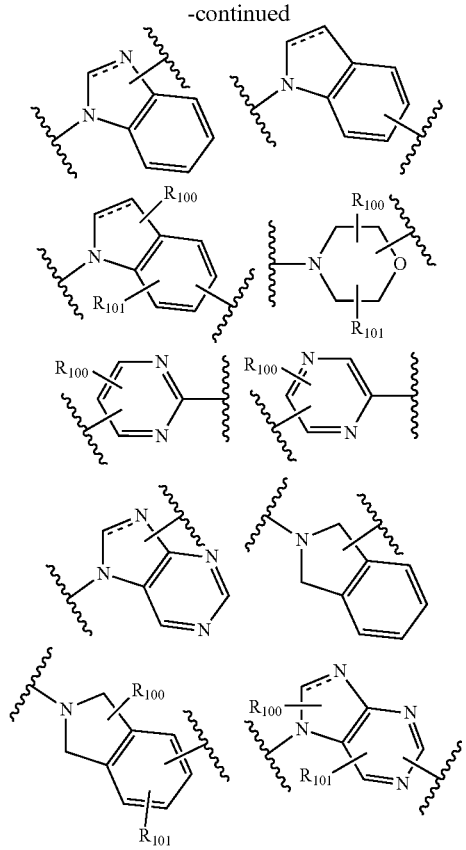

In a preferred embodiment, the bivalent B is a direct bond, a straight chain $C_1$-$C_{10}$ alkyl, $C_1$-$C_{10}$ alkenyl, $C_1$-$C_{10}$ alkynyl, $C_1$-$C_{10}$ alkoxy, alkoxy$C_1$-$C_{10}$alkoxy, $C_1$-$C_{10}$ alkylamino, alkoxy$C_1$-$C_{10}$alkylamino, $C_1$-$C_{10}$ alkylcarbonylamino, $C_1$-$C_{10}$ alkylaminocarbonyl, aryloxy$C_1$-$C_{10}$alkoxy, aryloxy$C_1$-$C_{10}$alkylamino, aryloxy$C_1$-$C_{10}$alkylamino carbonyl, $C_1$-$C_{10}$-alkylaminoalkylaminocarbonyl, $C_1$-$C_{10}$ alkyl(N-alkyl)aminoalkyl-aminocarbonyl, alkylaminoalkylamino, alkylcarbonylaminoalkylamino, alkyl(N-alkyl)aminoalkylamino, (N-alkyl)alkylcarbonylaminoalkylamino, alkylaminoalkyl, alkylaminoalkylaminoalkyl, alkylpiperazinoalkyl, piperazinoalkyl, alkylpiperazino, alkenylaryloxyC1-C10alkoxy, alkenylarylamino$C_1$-$C_{10}$alkoxy, alkenylaryllalkylamino$C_1$-$C_{10}$alkoxy, alkenylaryloxy$C_1$-$C_{10}$alkylamino, alkenylaryloxy$C_1$-$C_{10}$alkylaminocarbonyl, piperazinoalkylaryl, heteroaryl$C_1$-$C_{10}$alkyl, heteroaryl$C_2$-$C_{10}$alkenyl, heteroaryl$C_2$-$C_{10}$alkynyl, heteroaryl$C_1$-$C_{10}$alkylamino, heteroaryl$C_1$-$C_{10}$alkoxy, heteroaryloxy$C_1$-$C_{10}$alkyl, heteroaryloxy$C_2$-$C_{10}$alkenyl, heteroaryloxy$C_2$-$C_{10}$alkynyl, heteroaryloxy$C_1$-$C_{10}$alkylamino and heteroaryloxy$C_1$-$C_{10}$alkoxy.

In one embodiment, variable $R_5$ in Formula I and the geometric isomers, enantiomers, diastereomers, racemates, pharmaceutically acceptable salts or solvates thereof are selected from the group set forth in the table below, where the variables Y and M are the same or different and each is a monovalent cation, or M and Y together are a divalent cation.

In a more preferred embodiment, $R_5$ is selected from Table 1.

TABLE 1

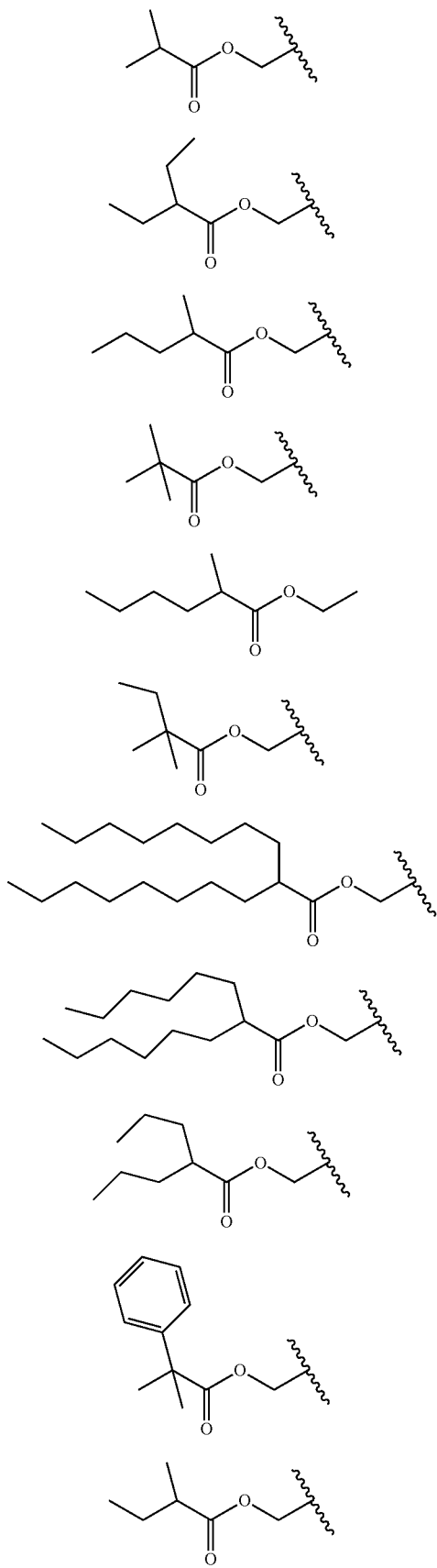

TABLE 1-continued
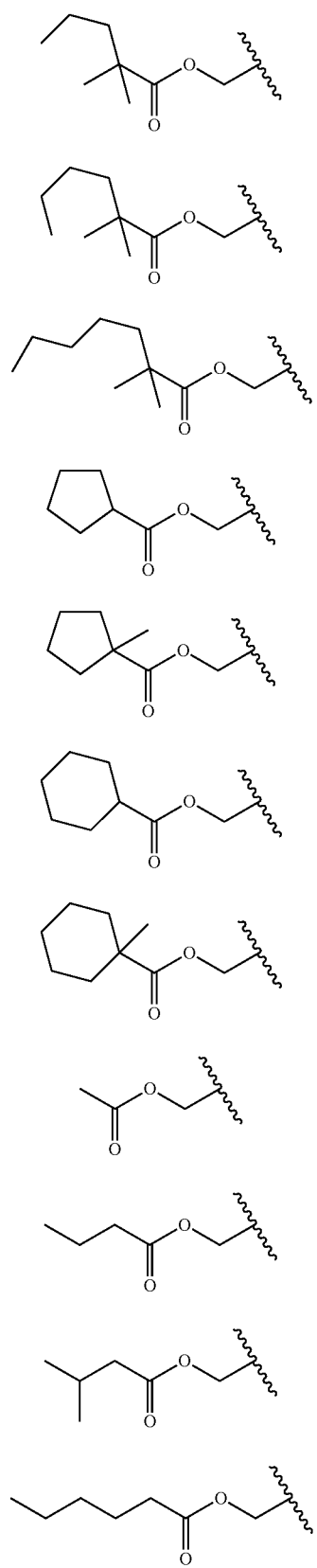
TABLE 1-continued
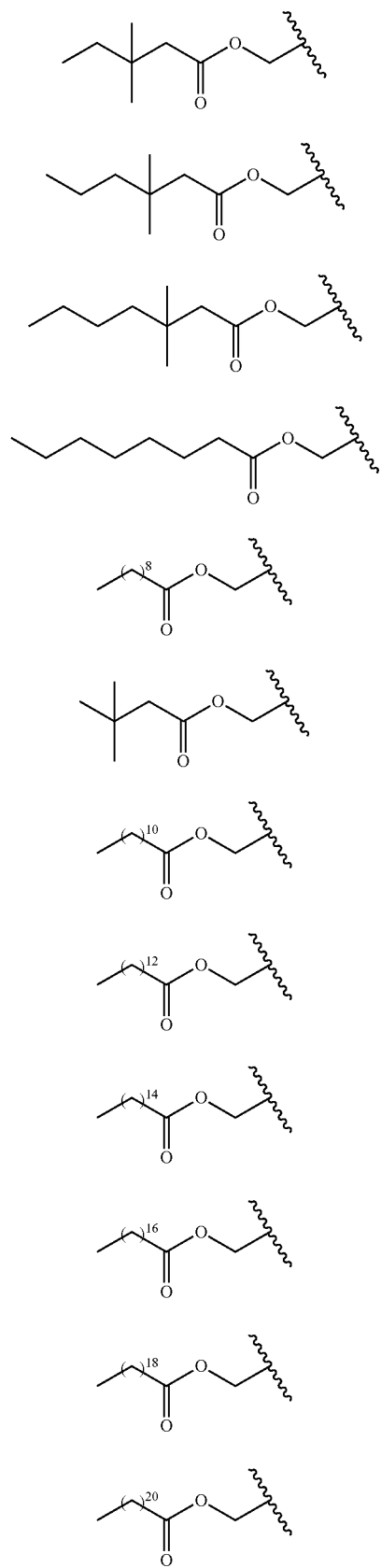

TABLE 1-continued
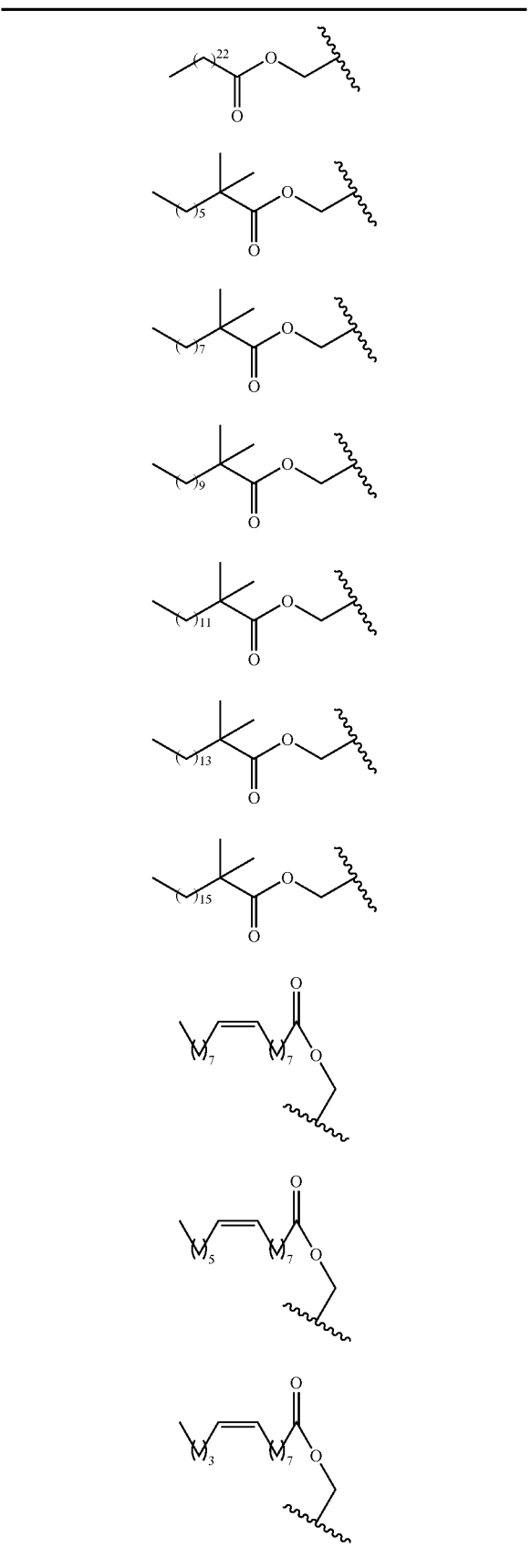
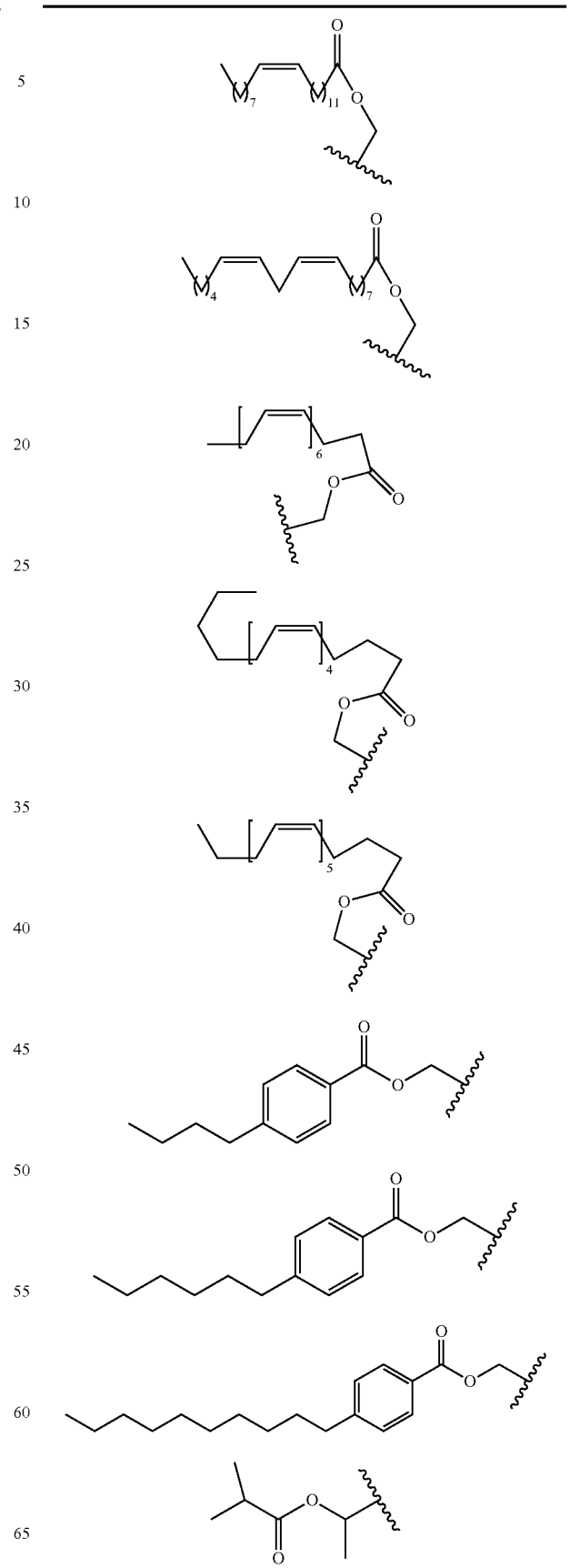

TABLE 1-continued
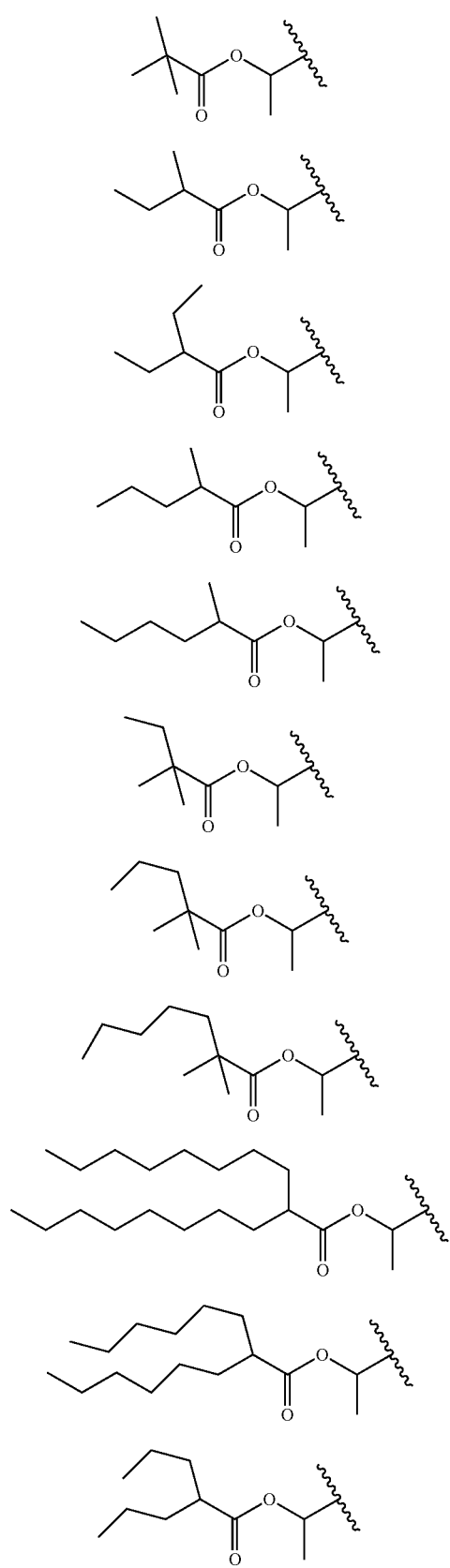
TABLE 1-continued
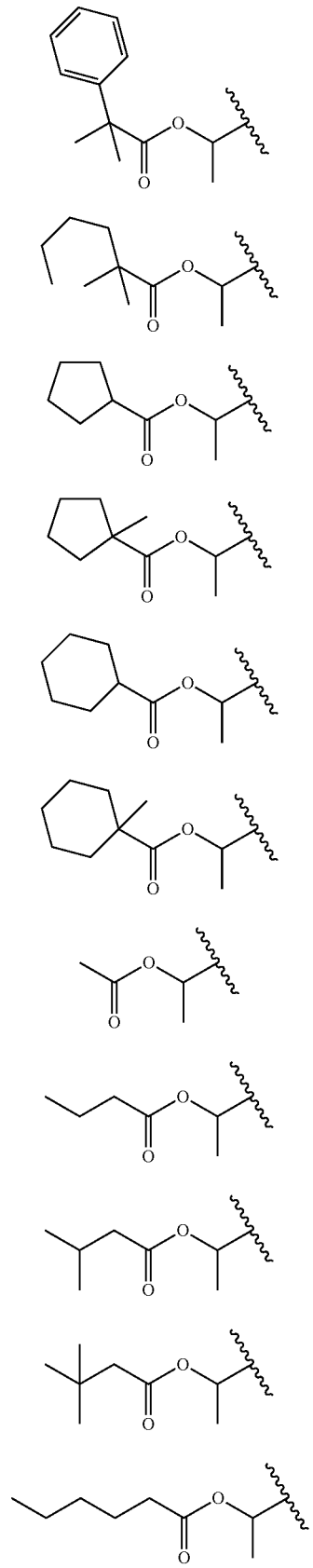

TABLE 1-continued
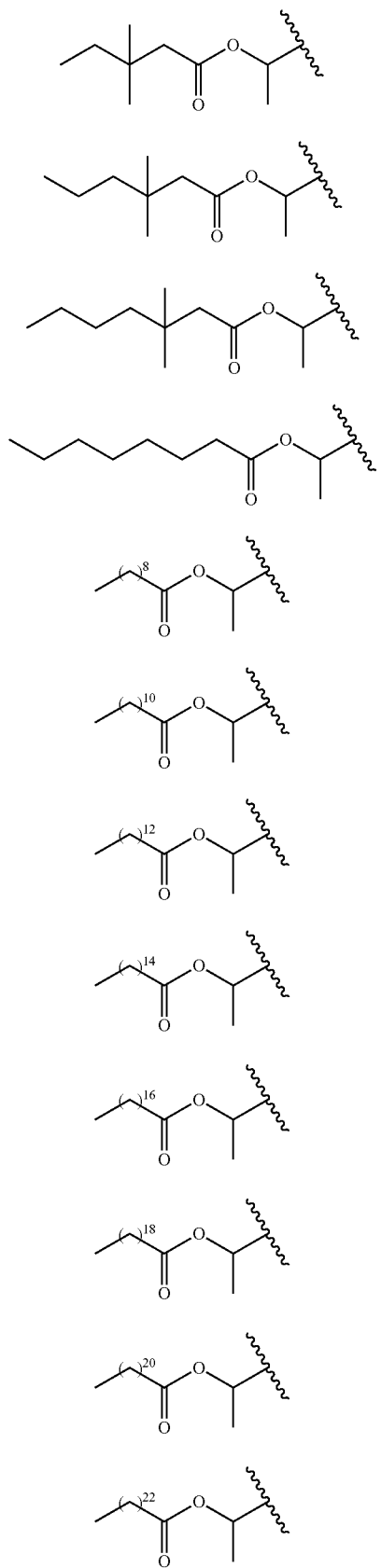
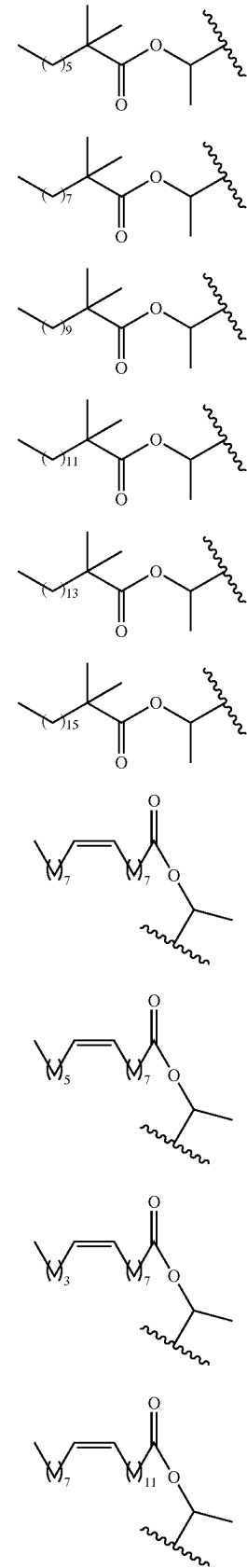

TABLE 1-continued
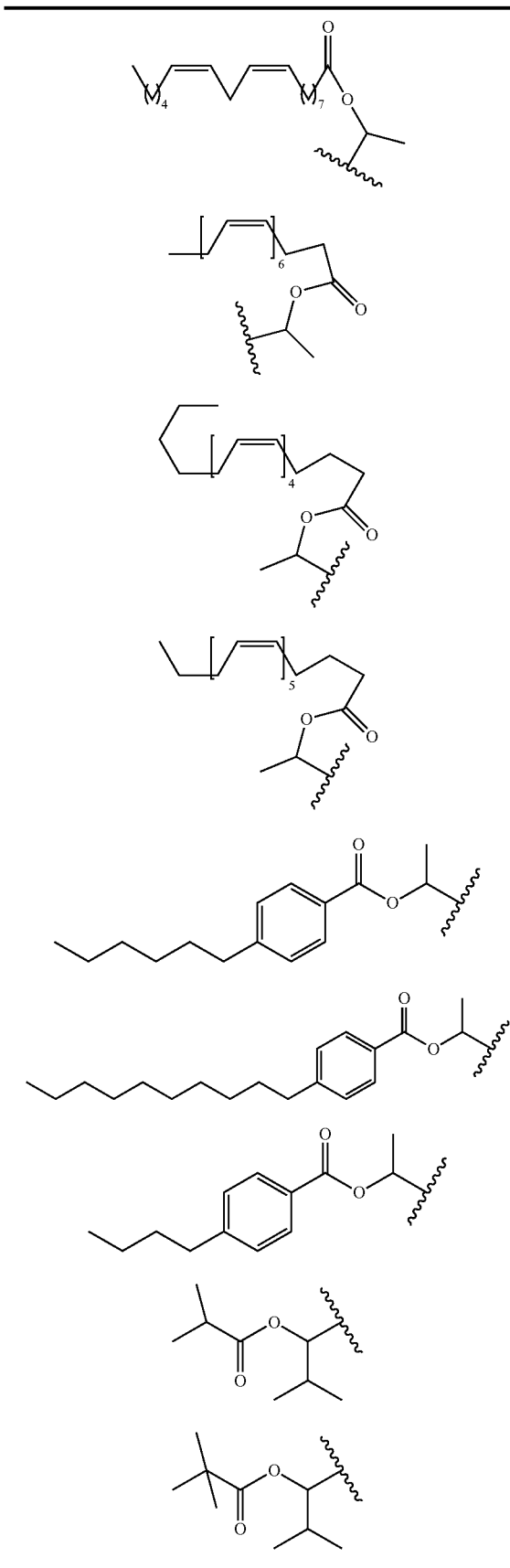
TABLE 1-continued
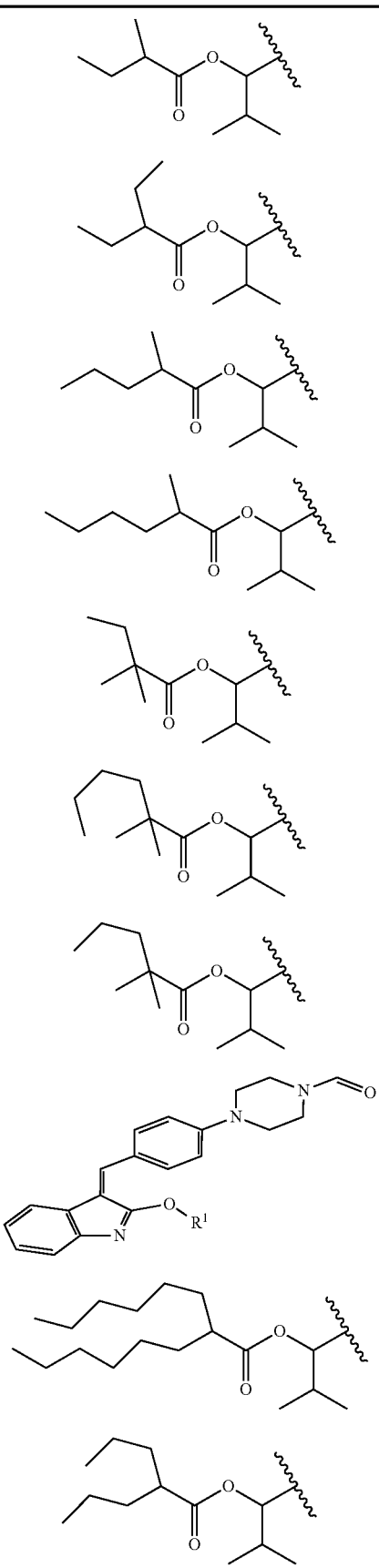

TABLE 1-continued
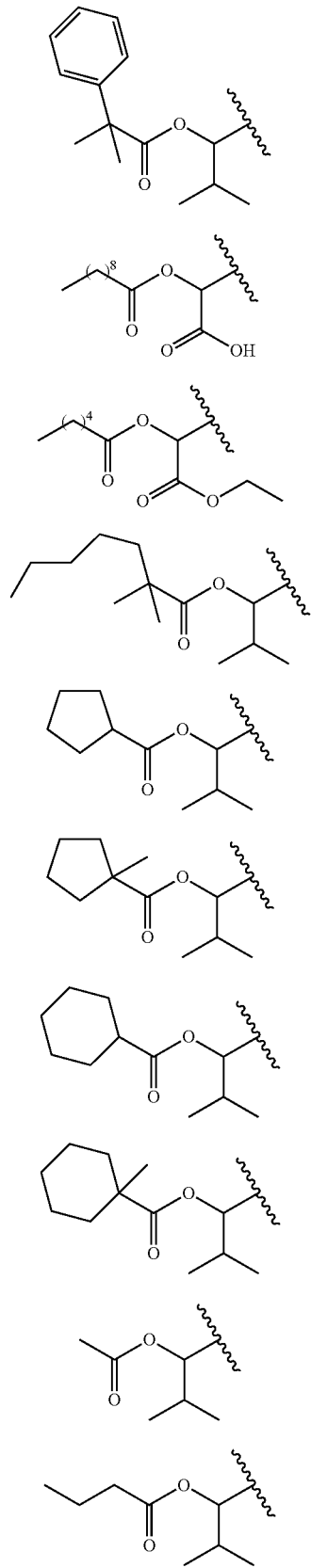
TABLE 1-continued
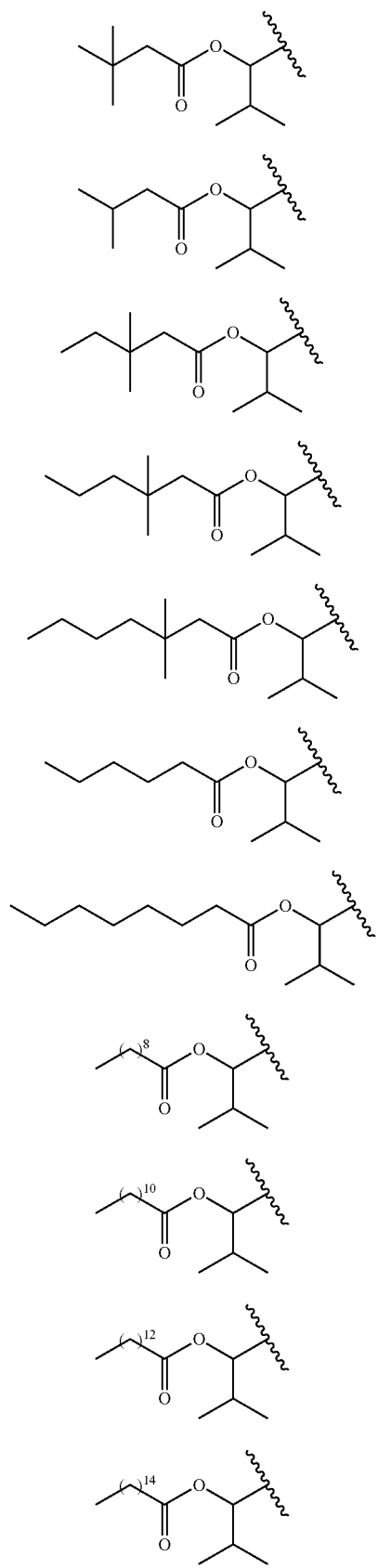

TABLE 1-continued
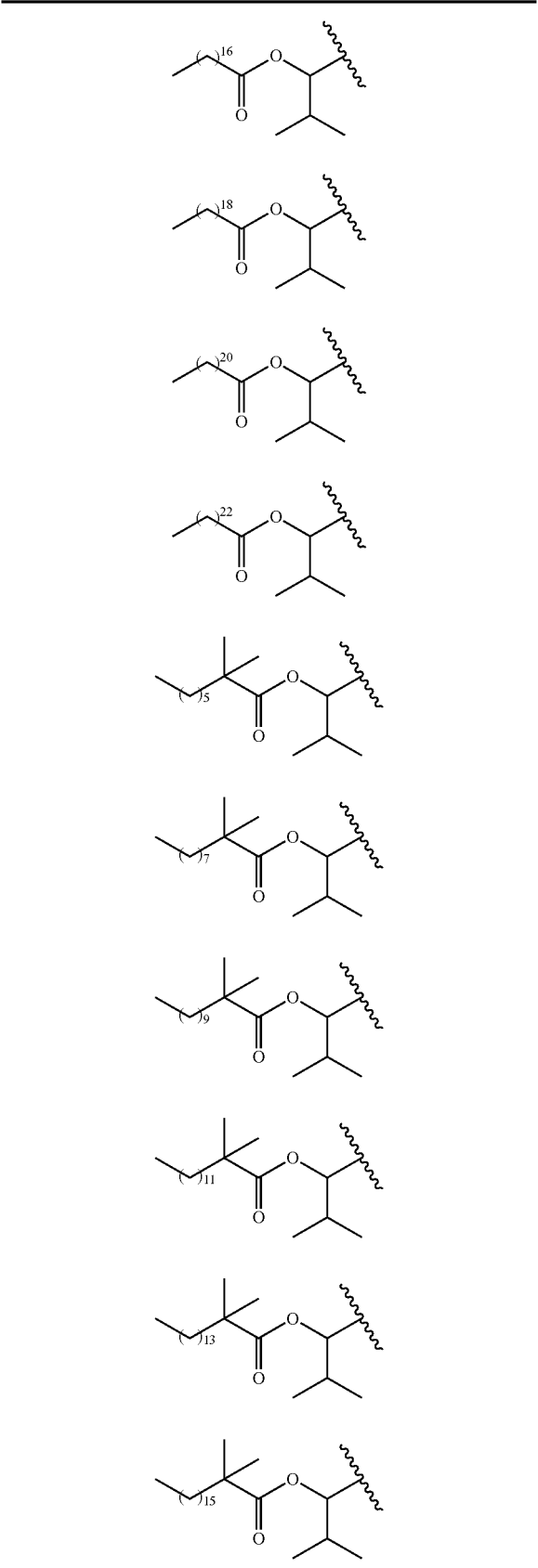
TABLE 1-continued
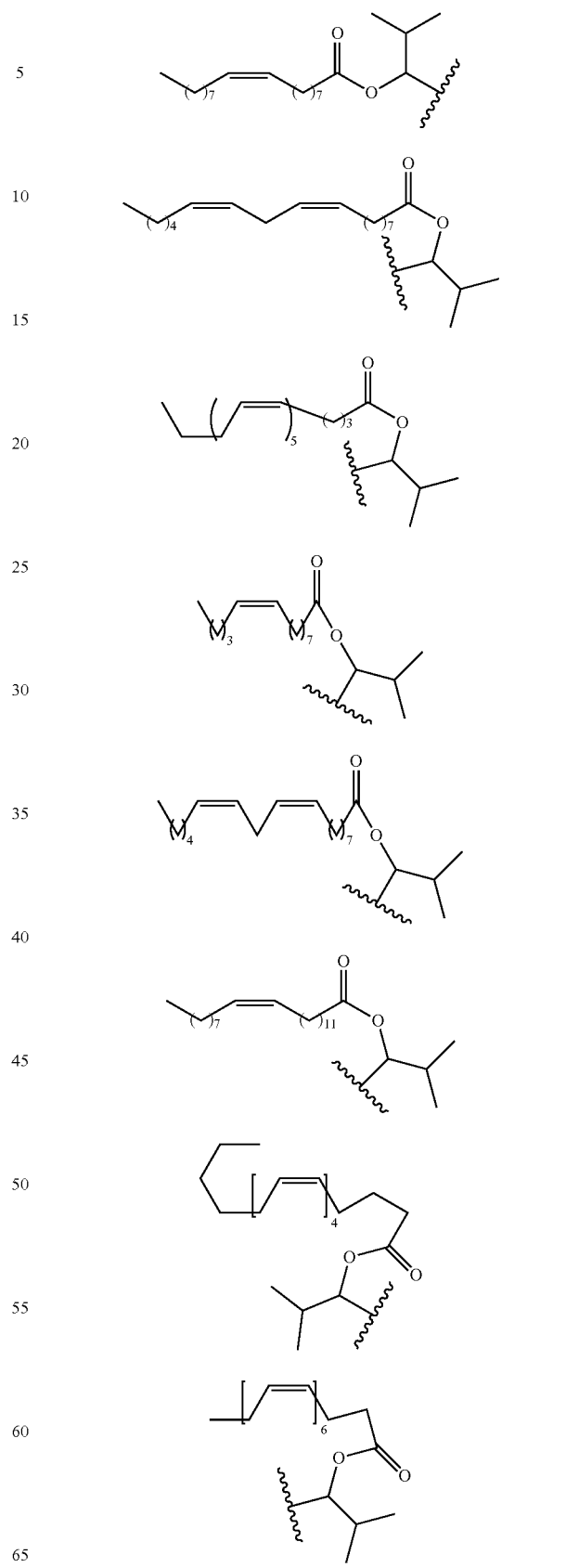

TABLE 1-continued
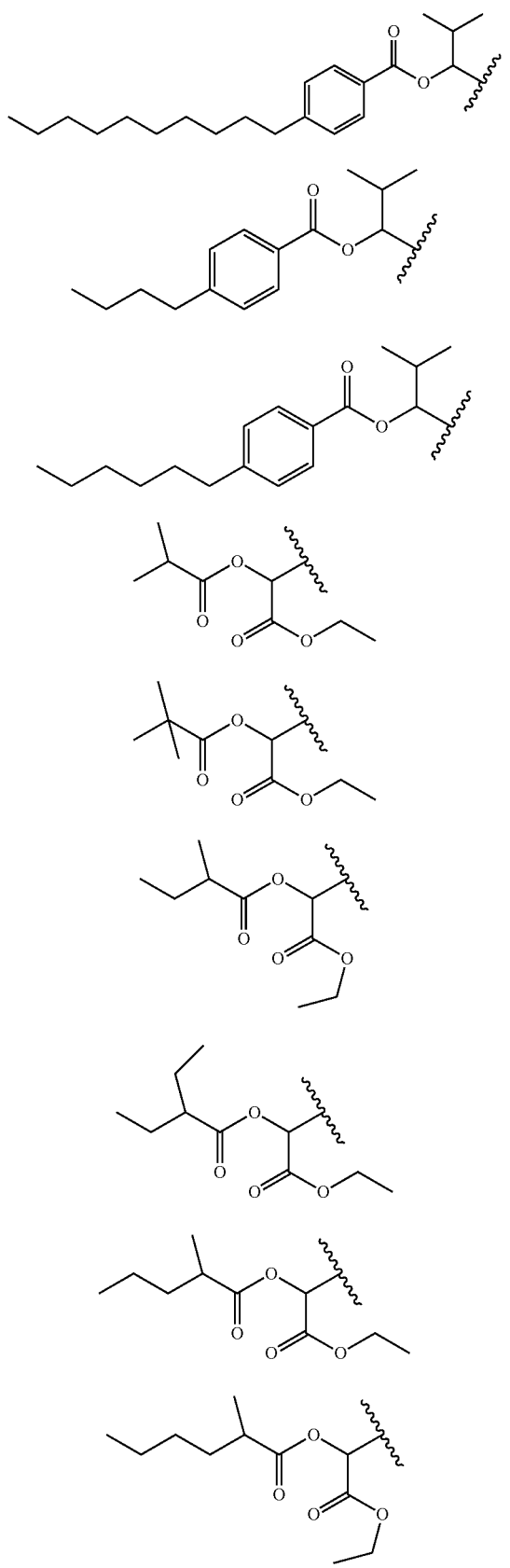
TABLE 1-continued
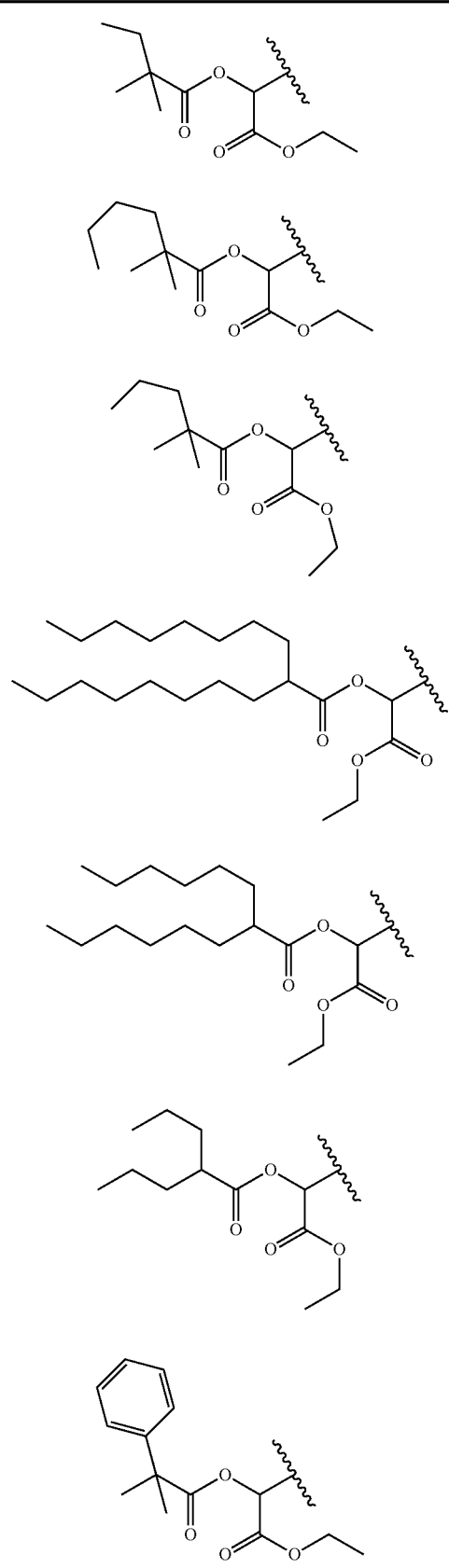

TABLE 1-continued
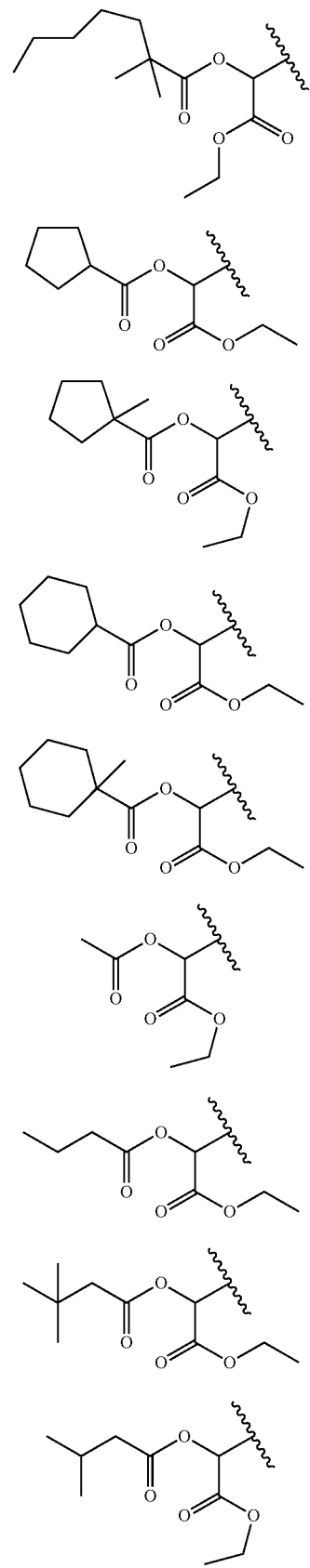
TABLE 1-continued
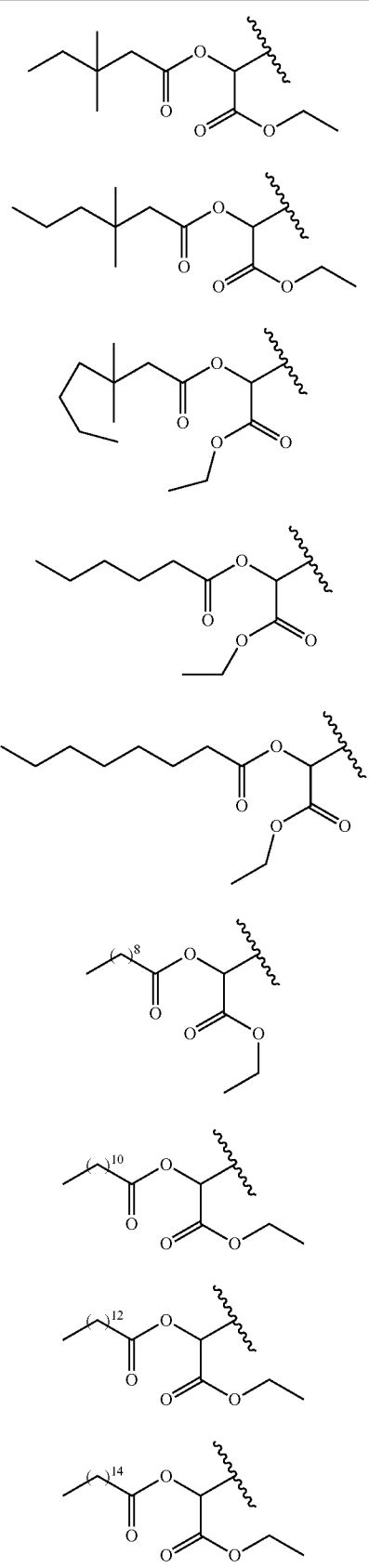

TABLE 1-continued
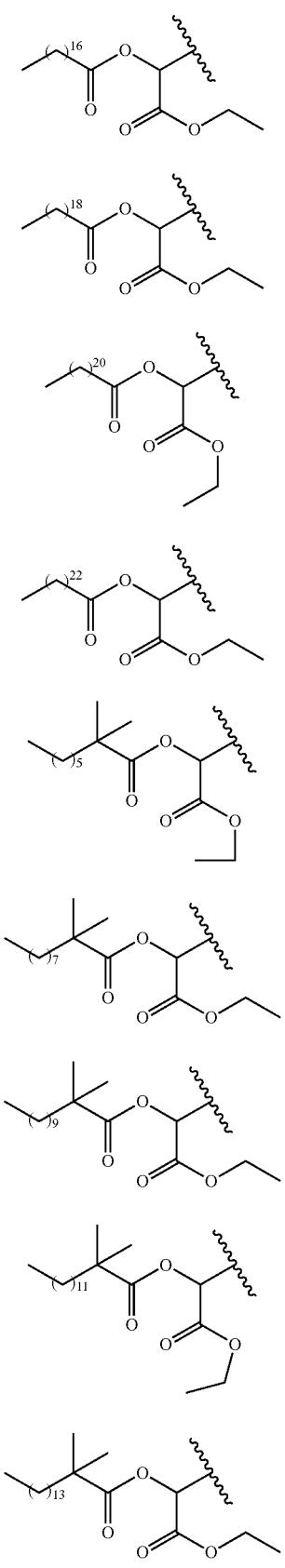
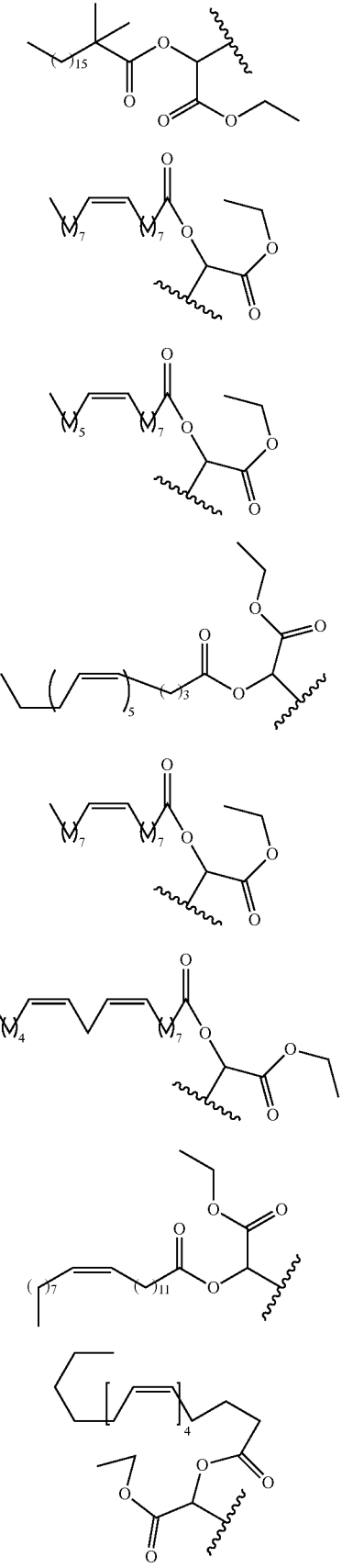

TABLE 1-continued
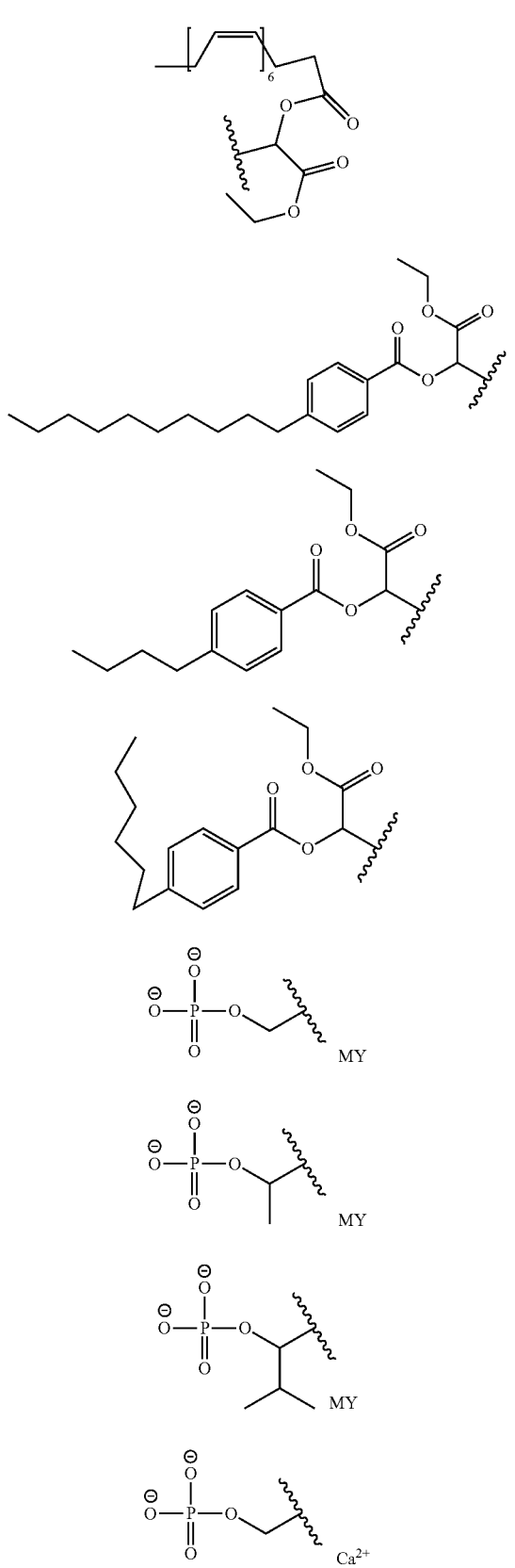
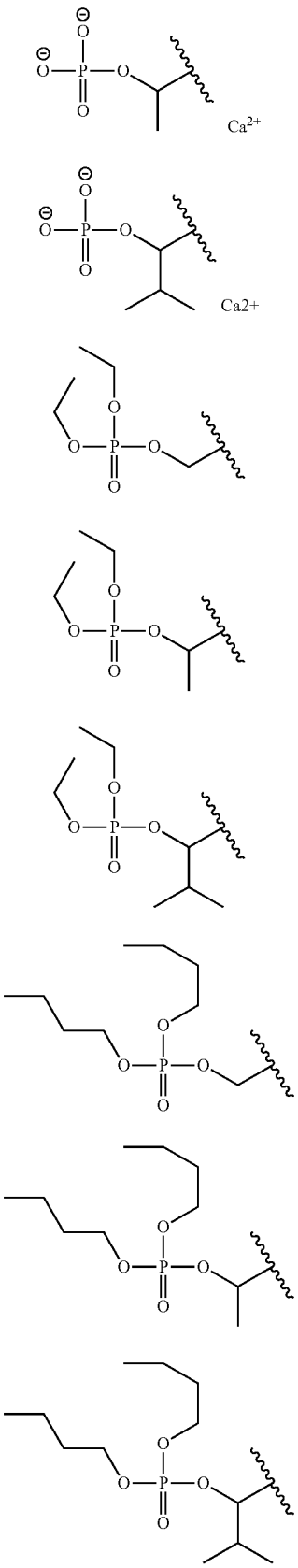

TABLE 1-continued
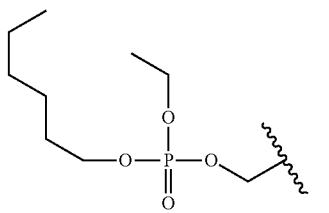 [SMILES: *COP(=O)(OCC)OCCCCCC]
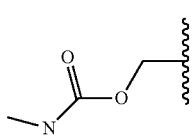
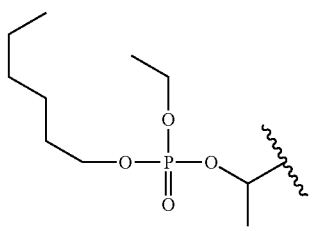 [SMILES: *C(C)OP(=O)(OCC)OCCCCCC]
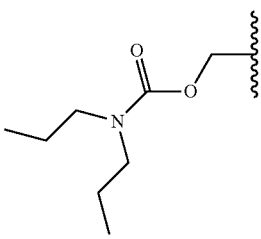
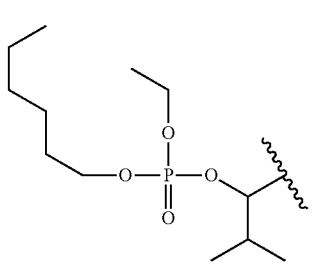 [SMILES: *C(OP(=O)(OCC)OCCCCCC)C(C)C]
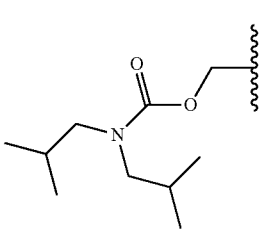
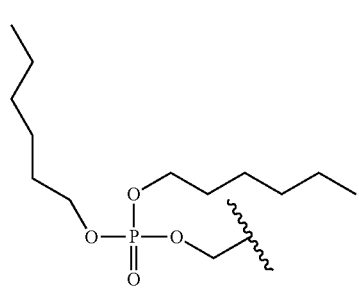 [SMILES: *COP(=O)(OCCCCCC)OCCCCCC]
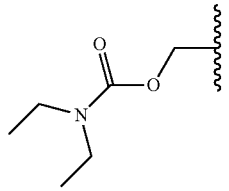
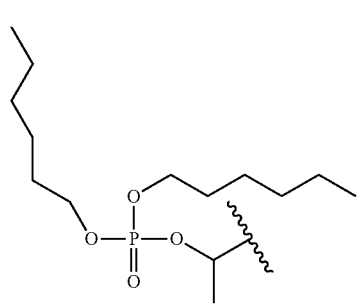 [SMILES: *C(C)OP(=O)(OCCCCCC)OCCCCCC]
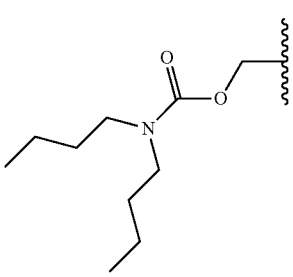 [SMILES: *COC(=O)N(CCCC)CCCC]
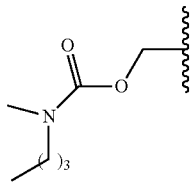
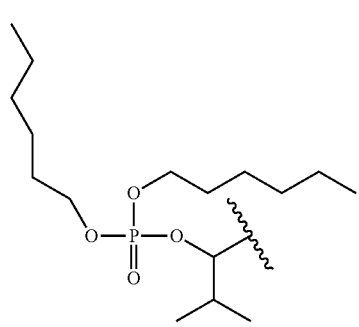
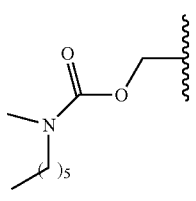

TABLE 1-continued
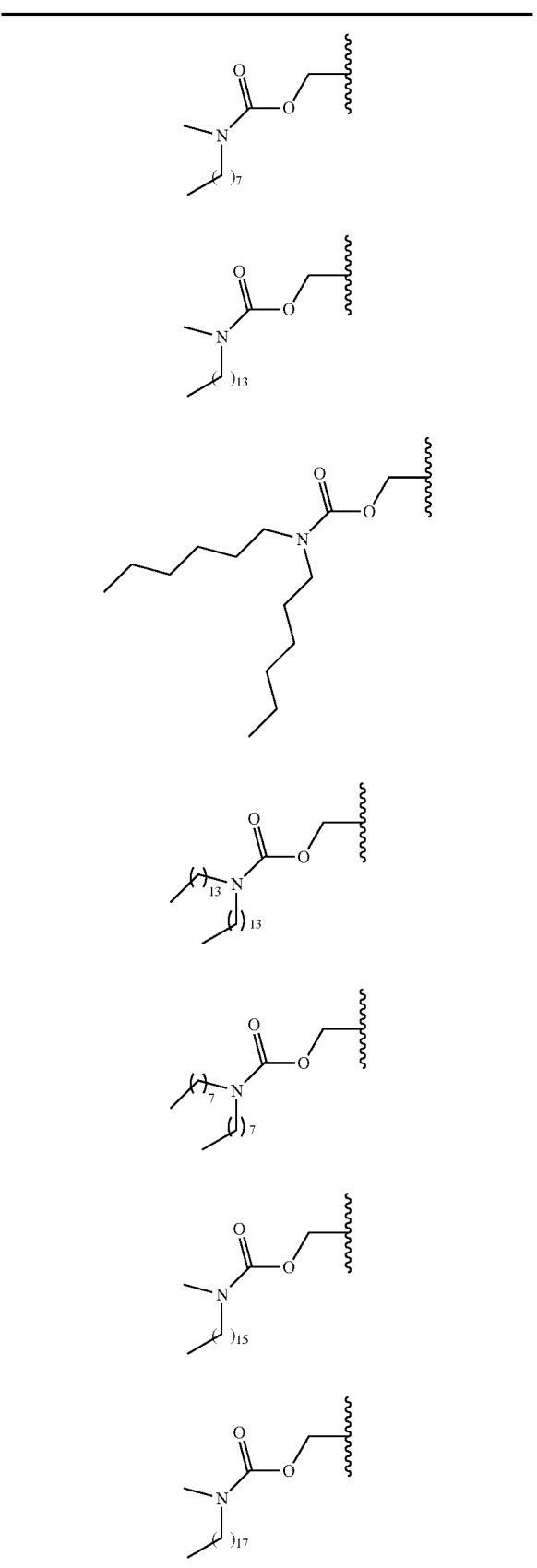
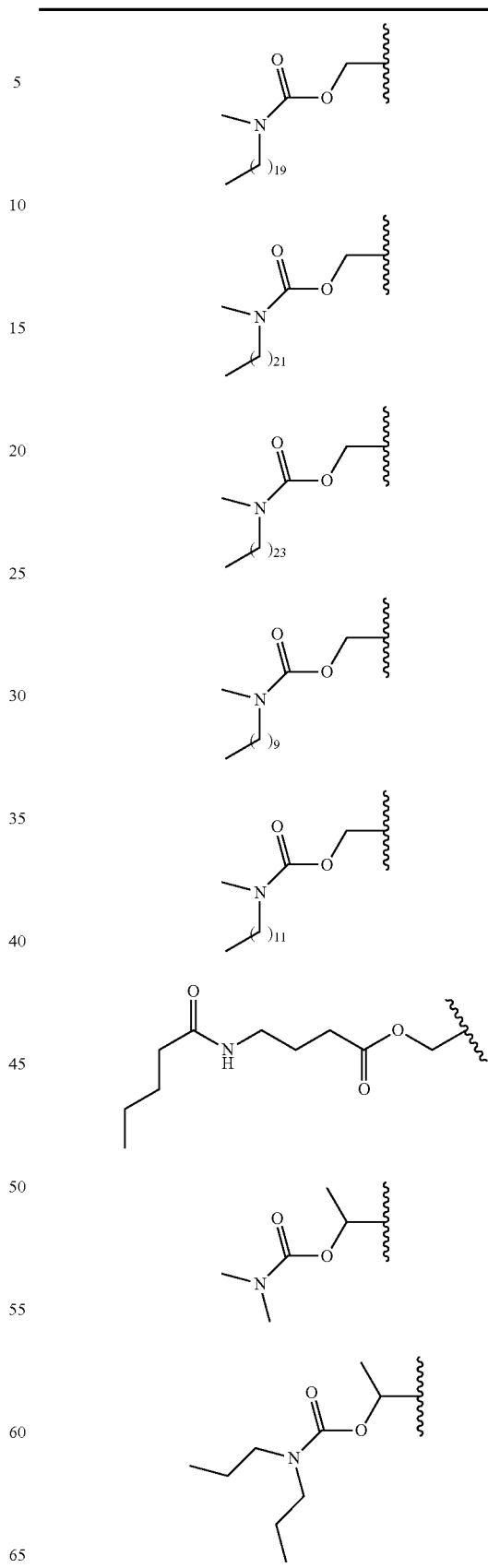

TABLE 1-continued
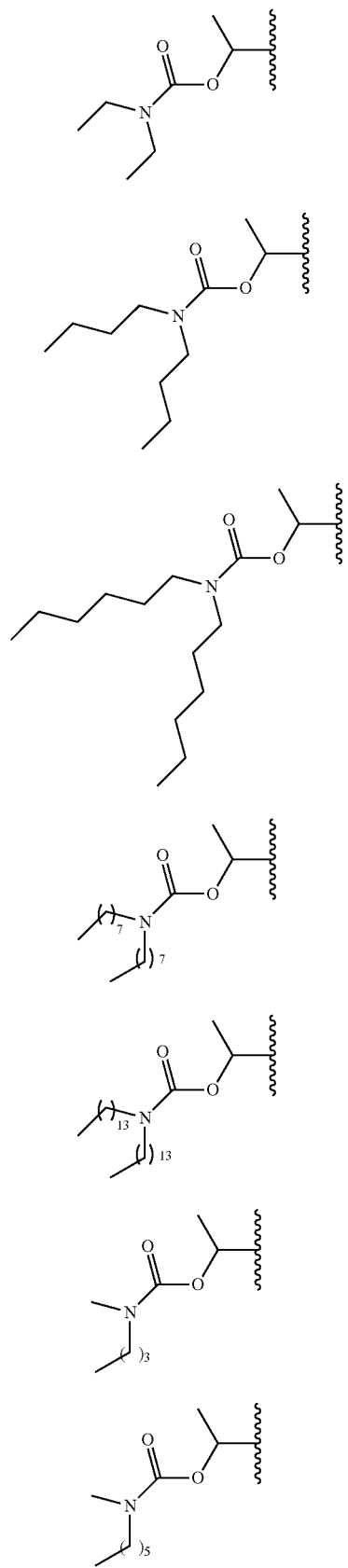
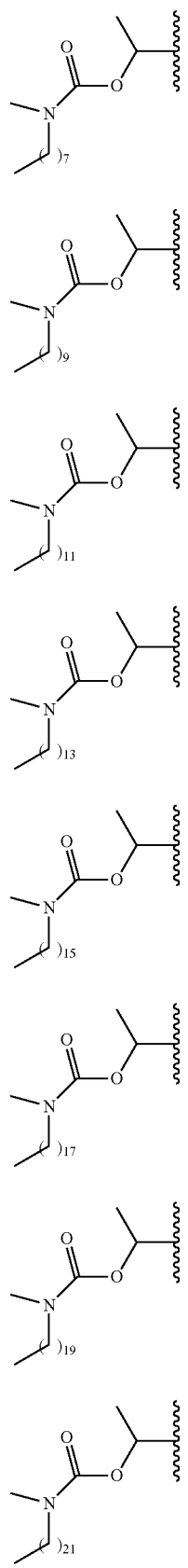

TABLE 1-continued
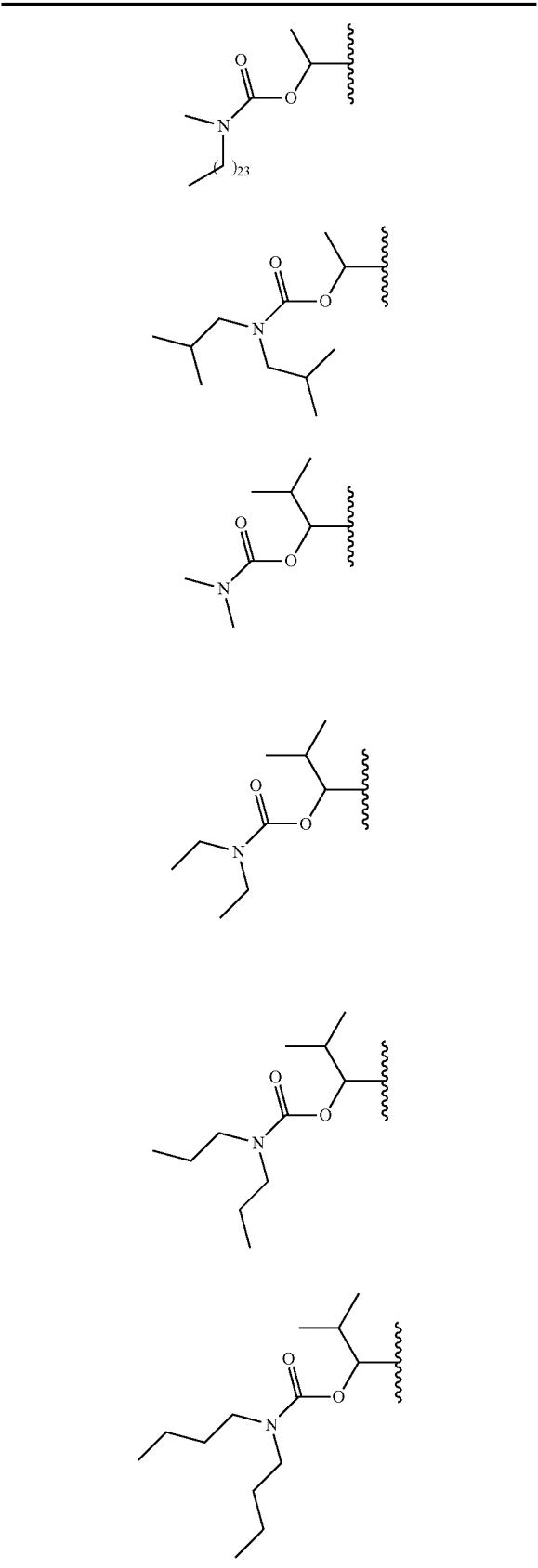
TABLE 1-continued
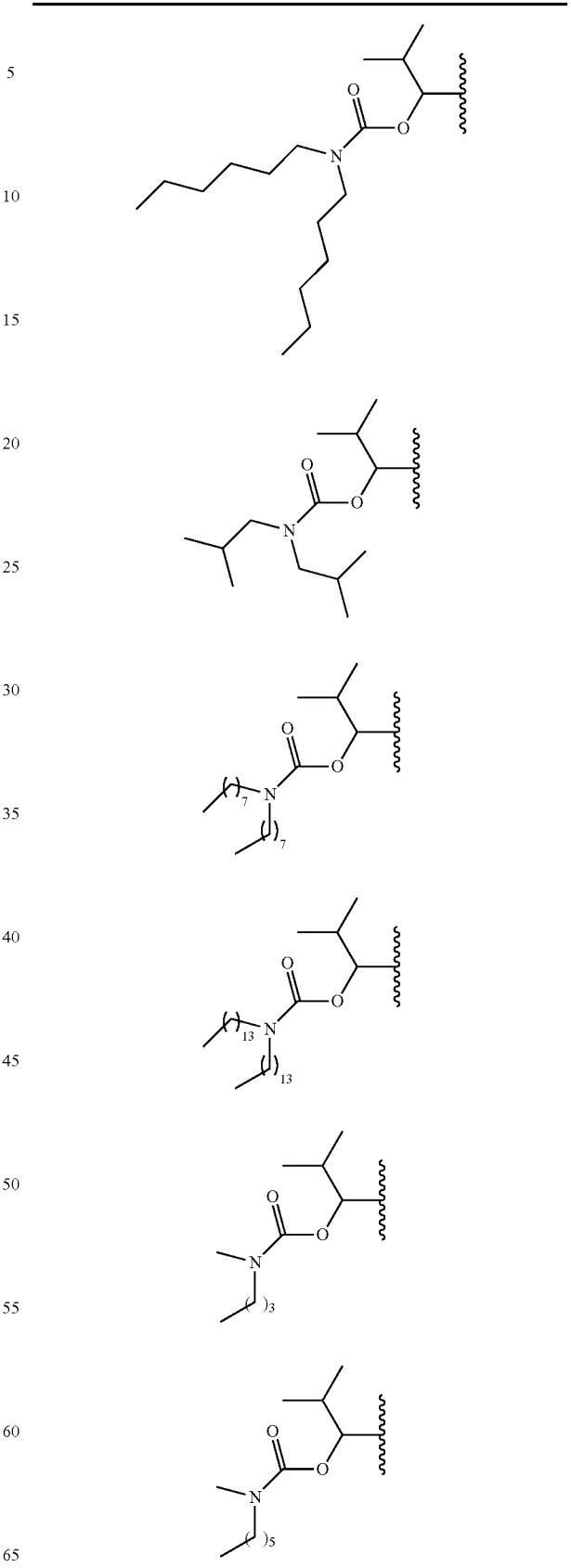

TABLE 1-continued
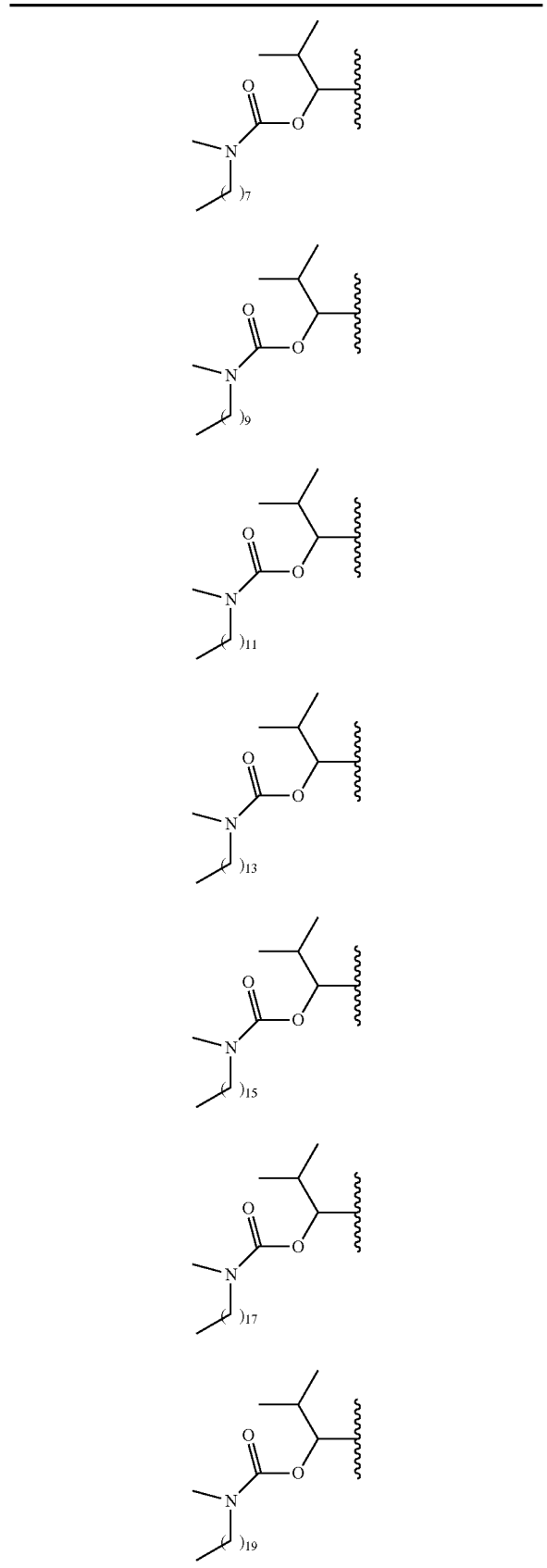
TABLE 1-continued
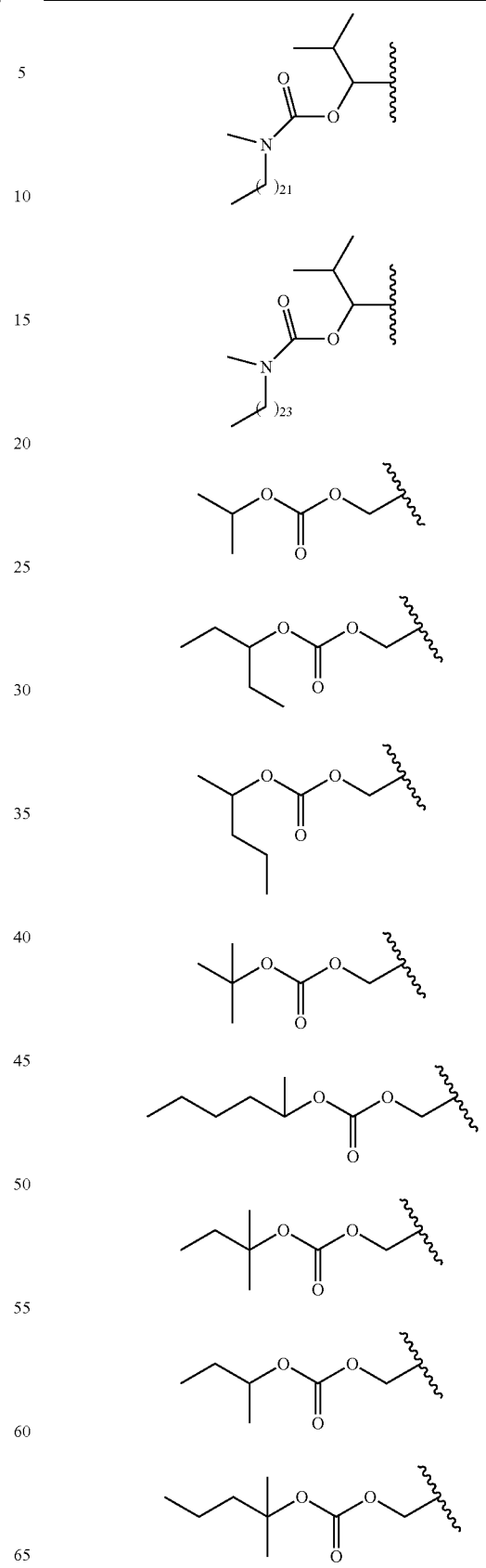

TABLE 1-continued
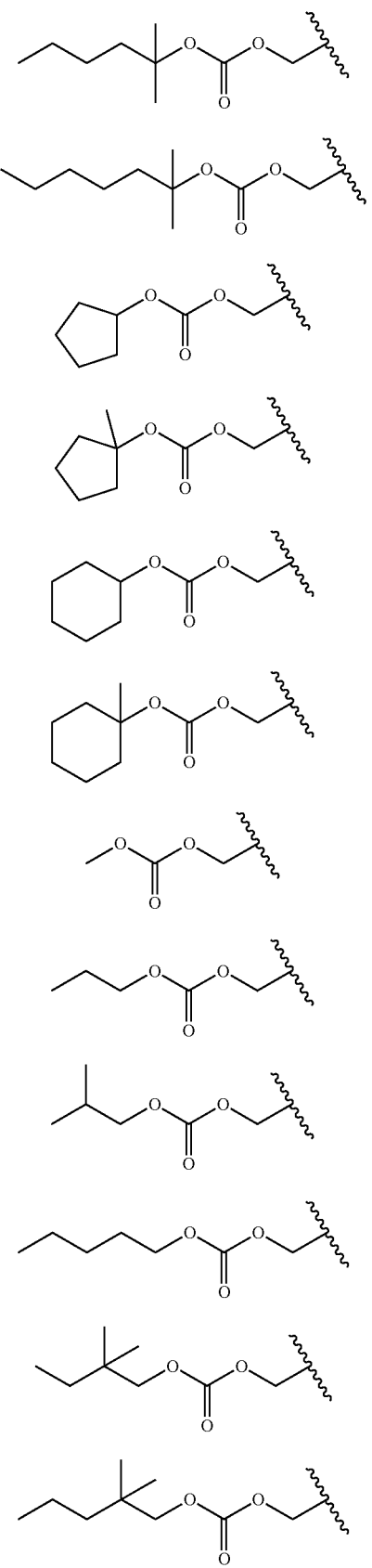
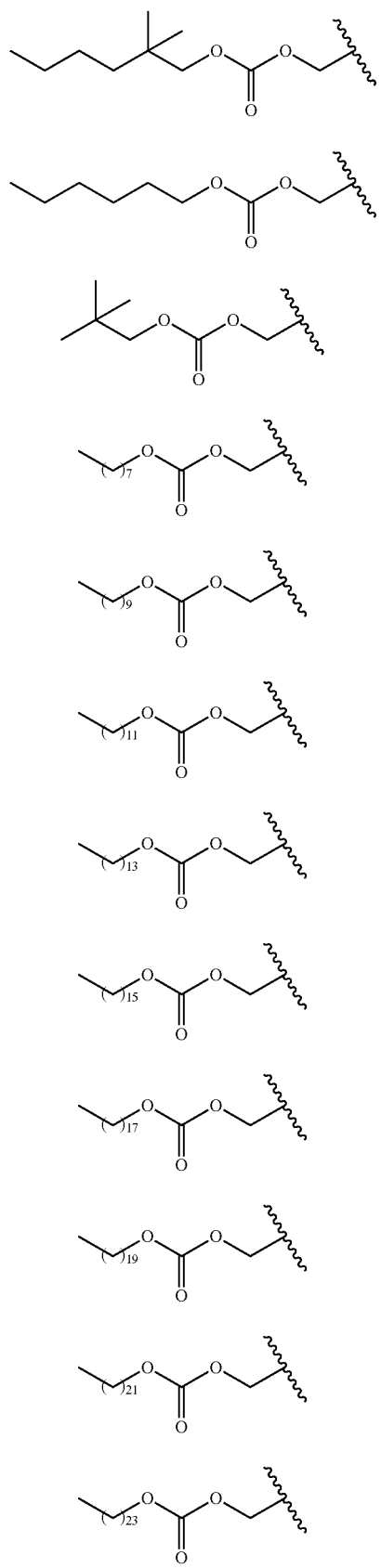

TABLE 1-continued
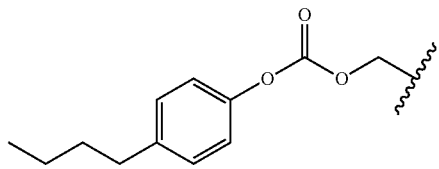 [SMILES: *COC(=O)Oc1ccc(CCCC)cc1]
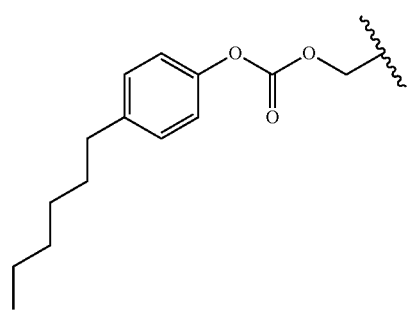 [SMILES: *COC(=O)Oc1ccc(CCCCCC)cc1]
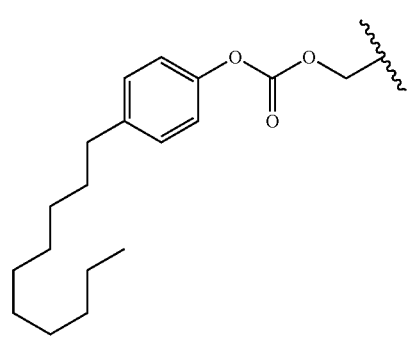 [SMILES: *COC(=O)Oc1ccc(CCCCCCCCCC)cc1]
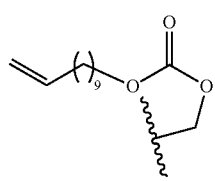
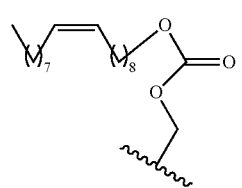
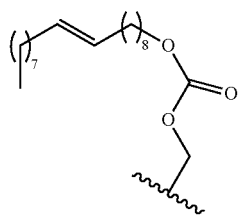
TABLE 1-continued
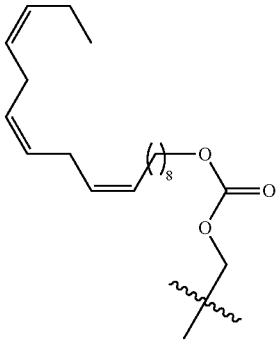
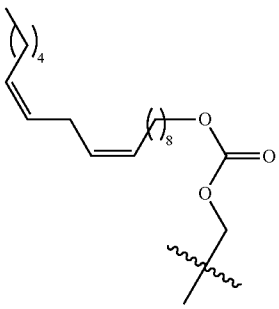
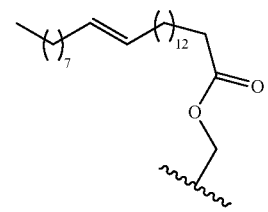
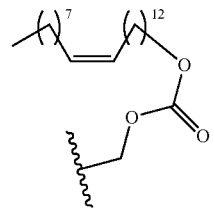
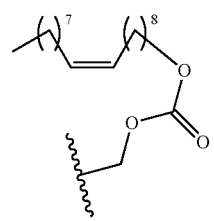
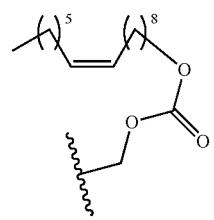

TABLE 1-continued
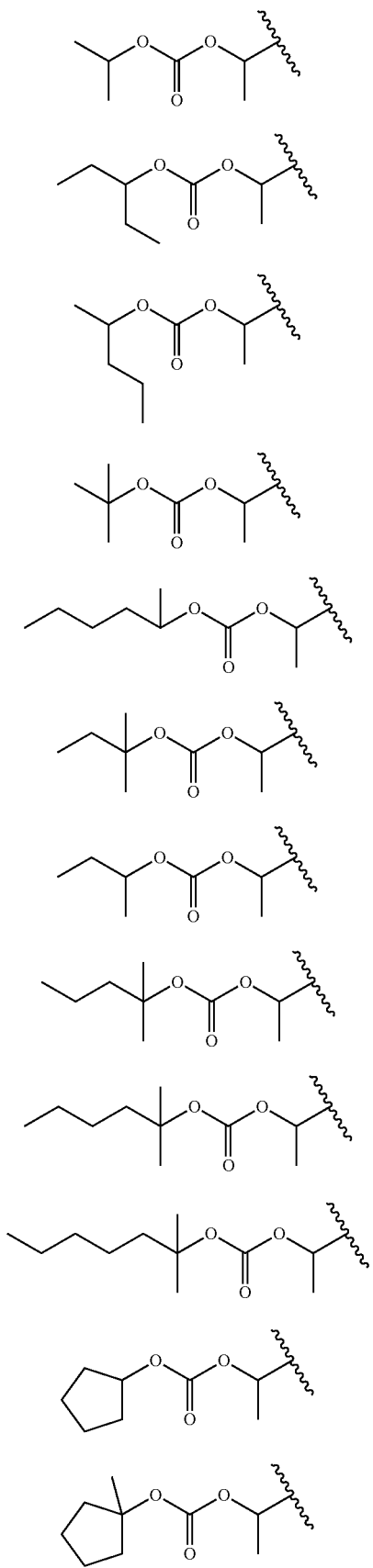
TABLE 1-continued
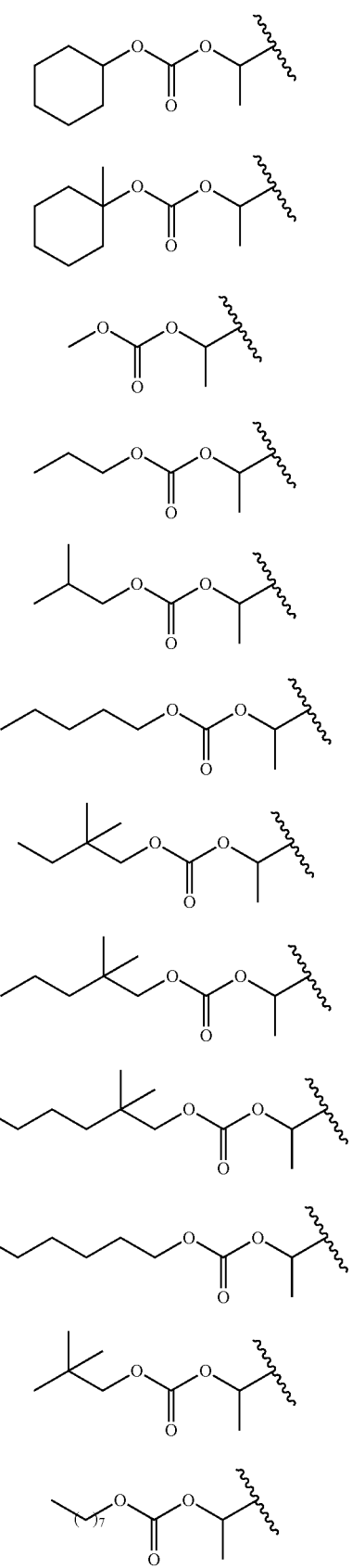

TABLE 1-continued
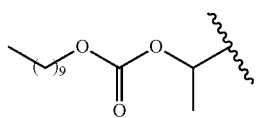
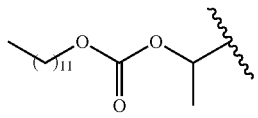
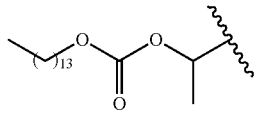
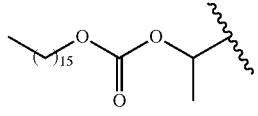
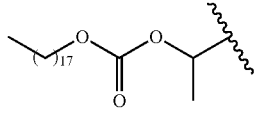
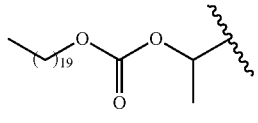
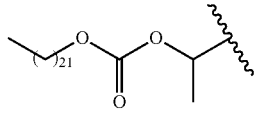
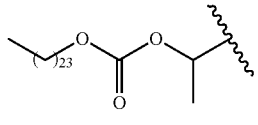
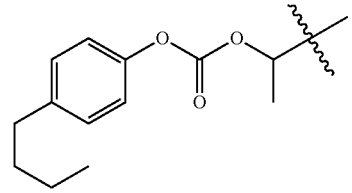 [SMILES: *C(C)OC(=O)Oc1ccc(CCCC)cc1]
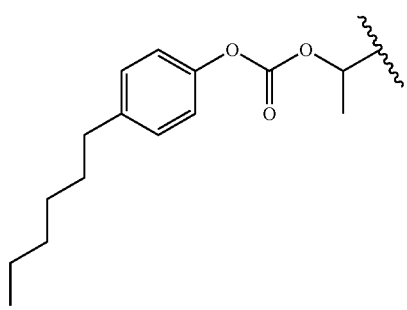 [SMILES: *C(C)OC(=O)Oc1ccc(CCCCCC)cc1]
TABLE 1-continued
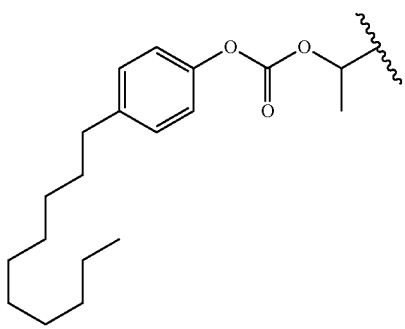 [SMILES: *C(C)OC(=O)Oc1ccc(CCCCCCCCCC)cc1]
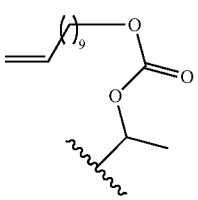
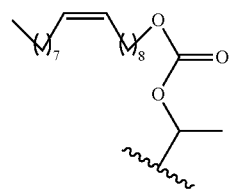
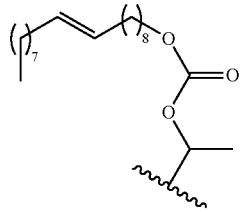
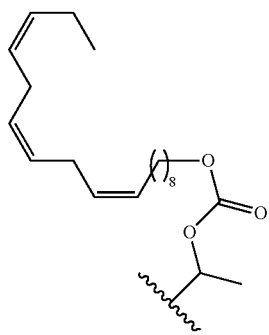
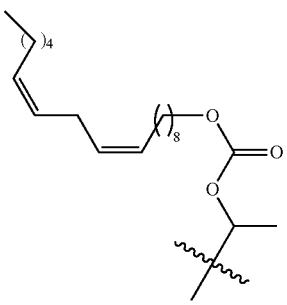

TABLE 1-continued
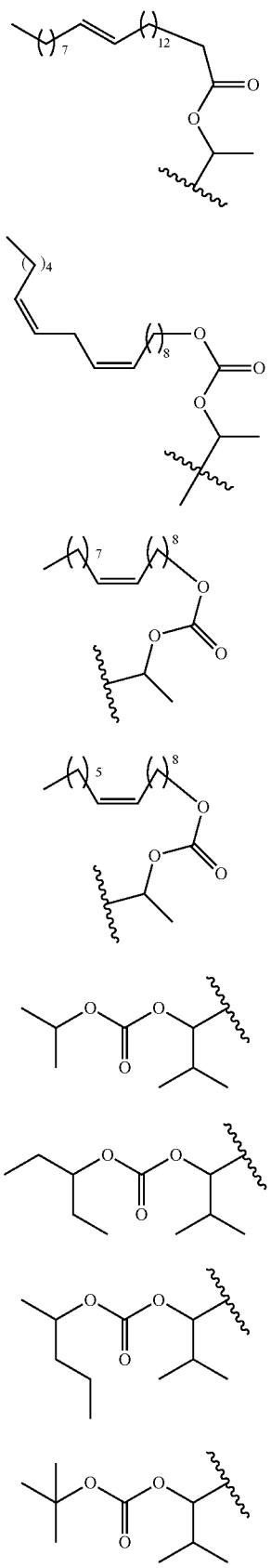
TABLE 1-continued
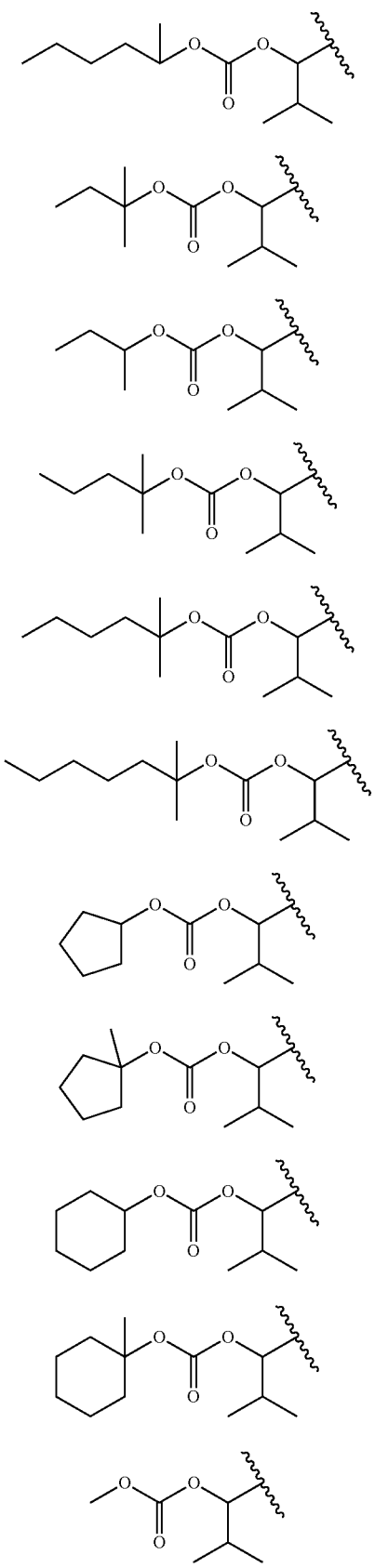

TABLE 1-continued
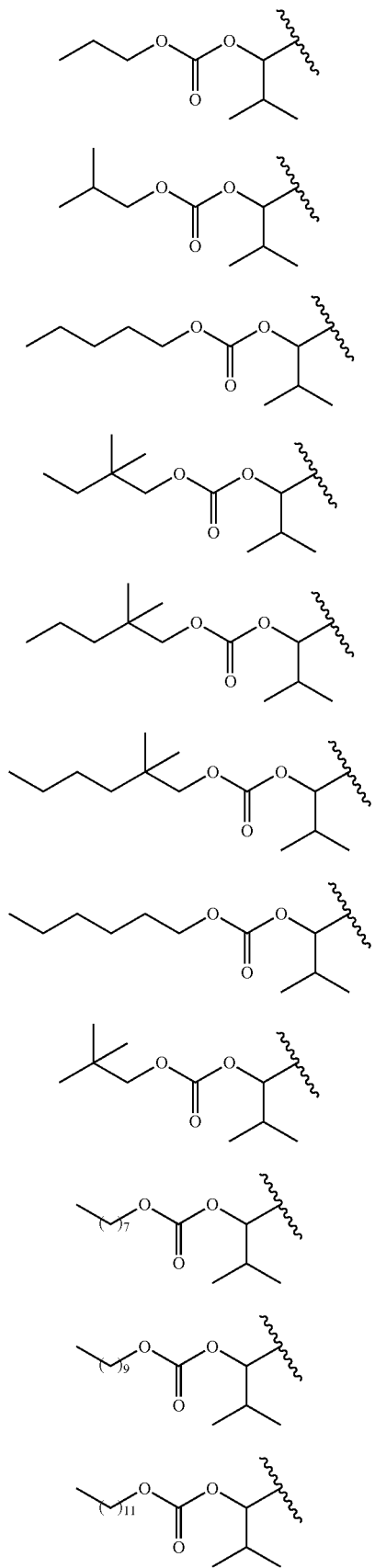
TABLE 1-continued
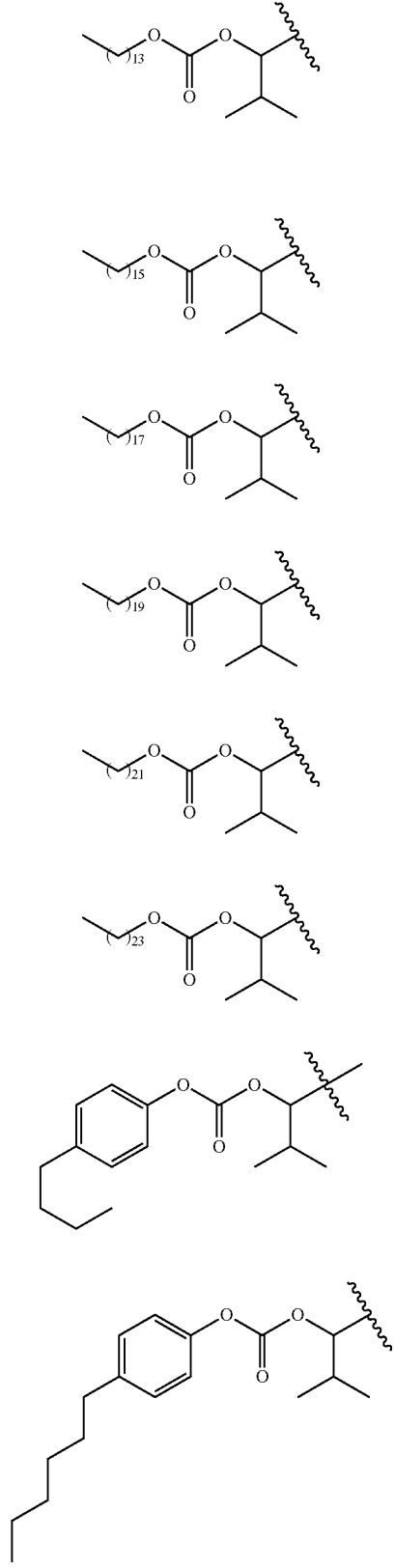

TABLE 1-continued
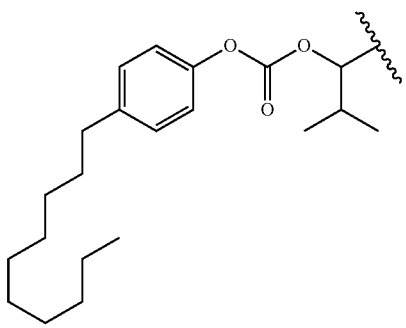 [SMILES: *C(OC(=O)Oc1ccc(CCCCCCCCCC)cc1)C(C)C]
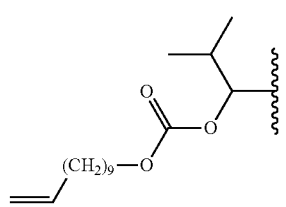
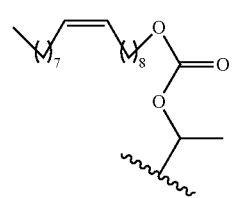
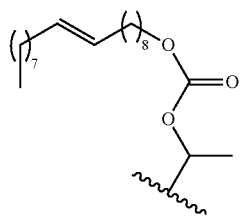
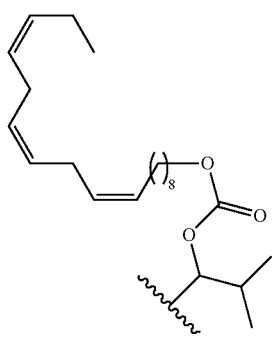
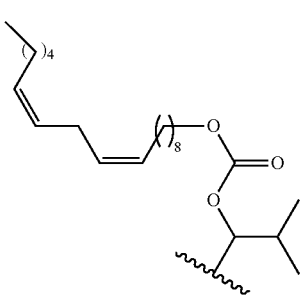
TABLE 1-continued
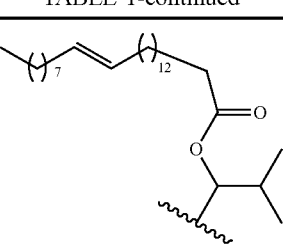
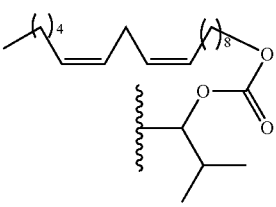
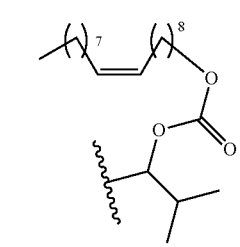
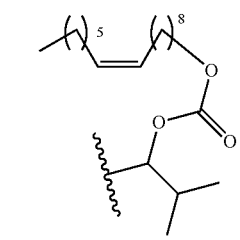
In a more preferred embodiment, $R_5$ is selected from Table 2:
TABLE 2
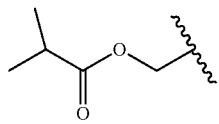 [SMILES: *COC(=O)C(C)C]
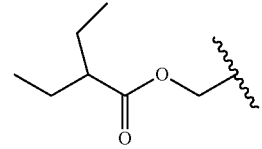 [SMILES: *COC(=O)C(CC)CC]
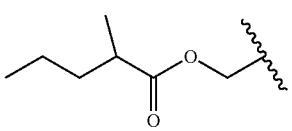 [SMILES: *COC(=O)C(C)CCC]
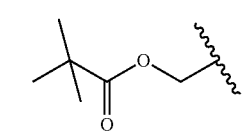 [SMILES: *COC(=O)C(C)(C)C]

TABLE 2-continued
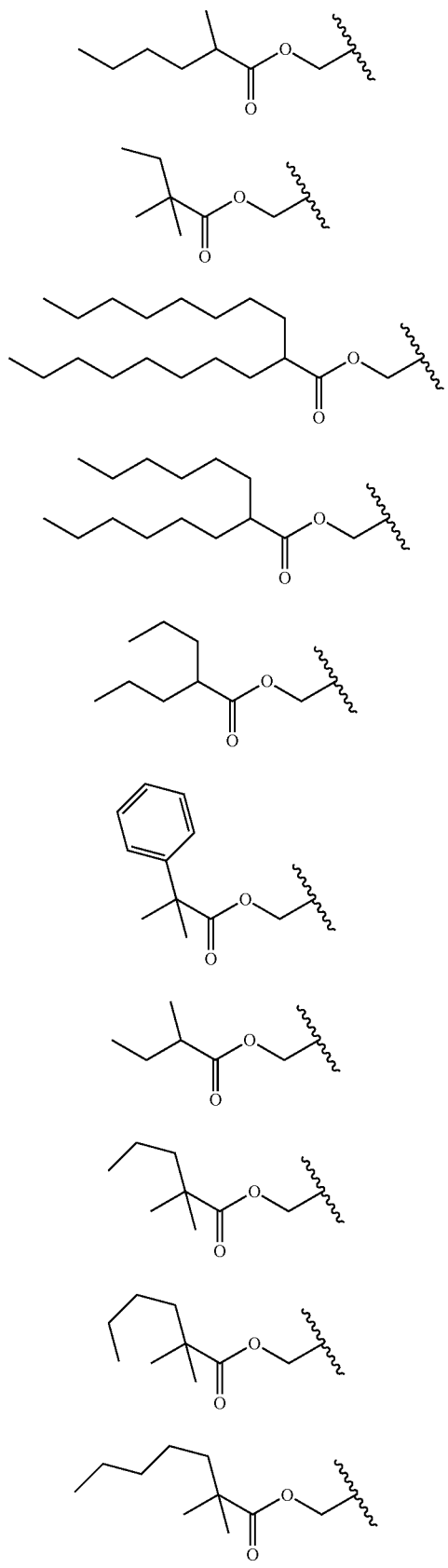
TABLE 2-continued
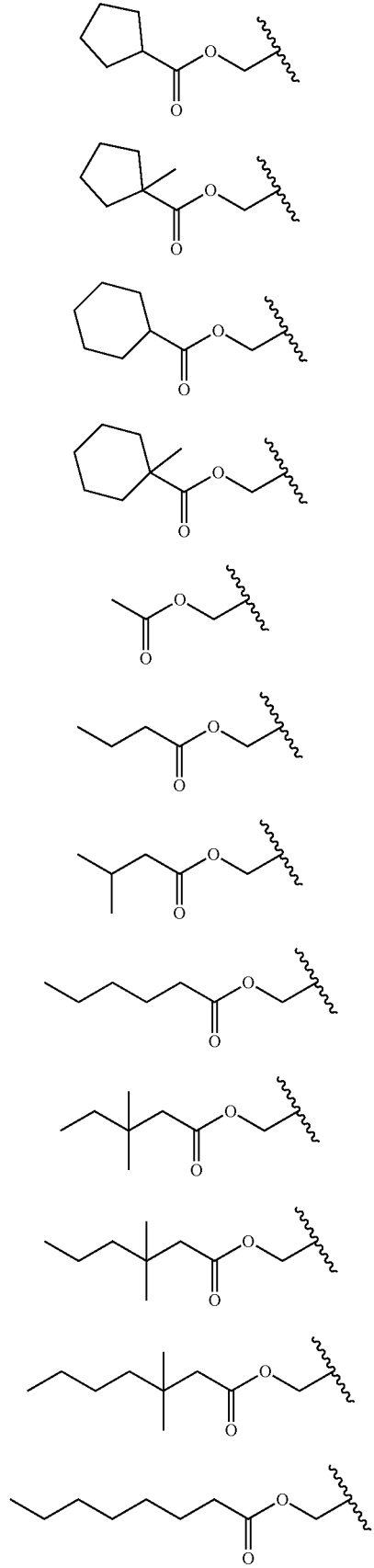

TABLE 2-continued
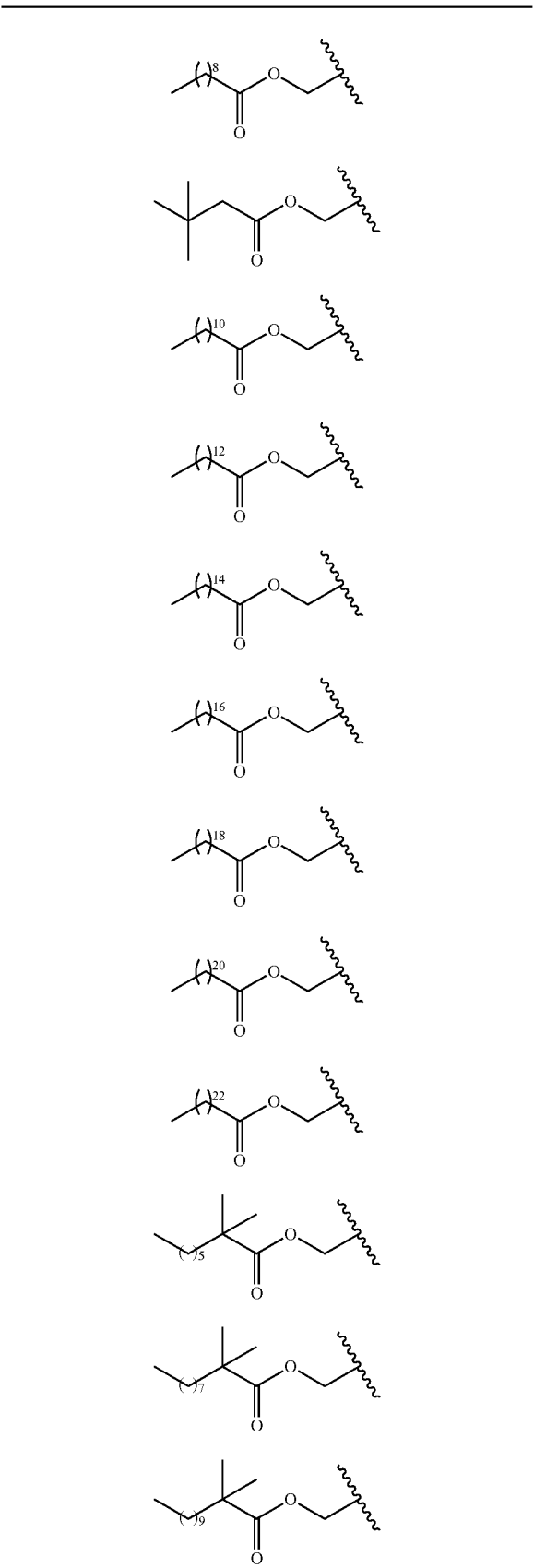
TABLE 2-continued
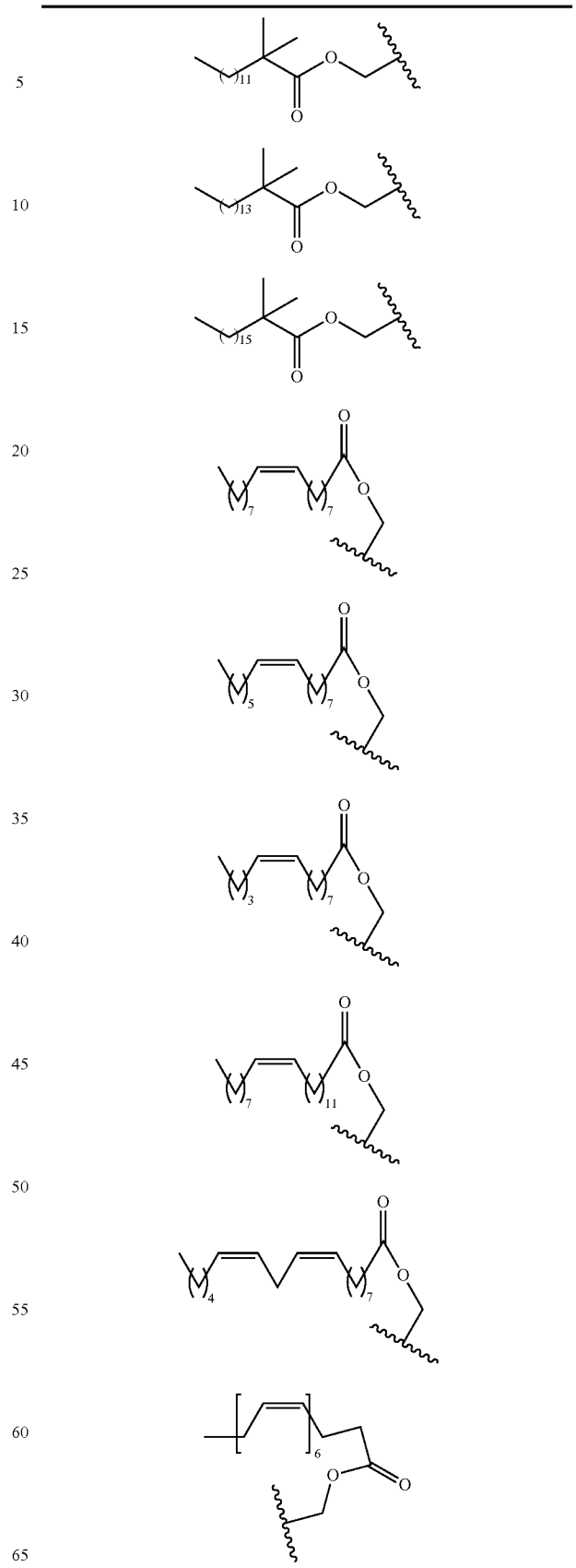

TABLE 2-continued
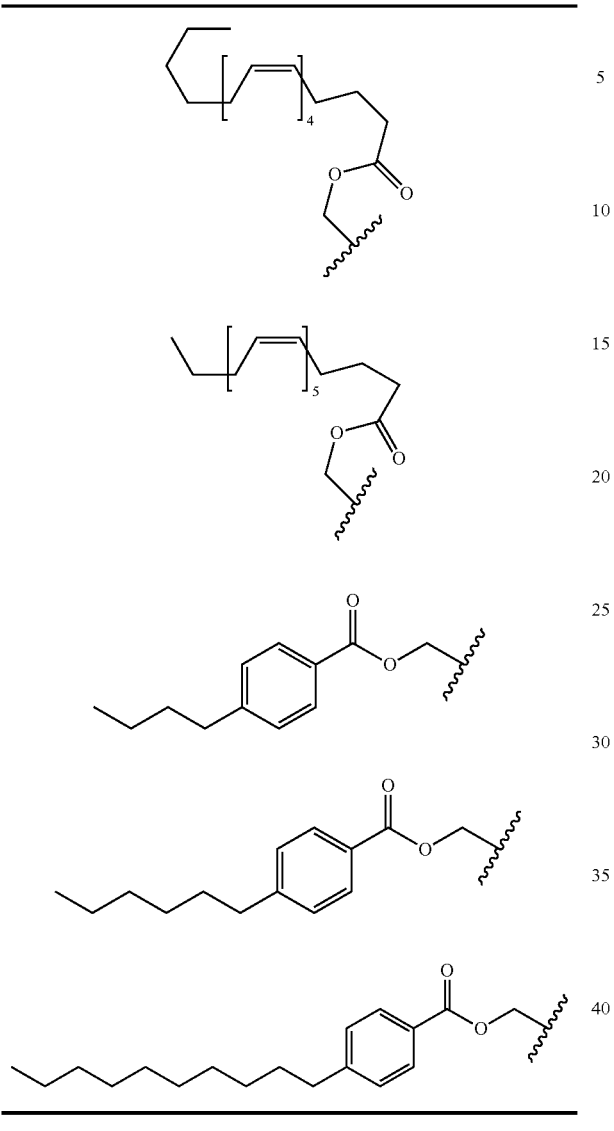
In a more preferred embodiment, $R_5$ is selected from Table 3:
TABLE 3
TABLE 3-continued
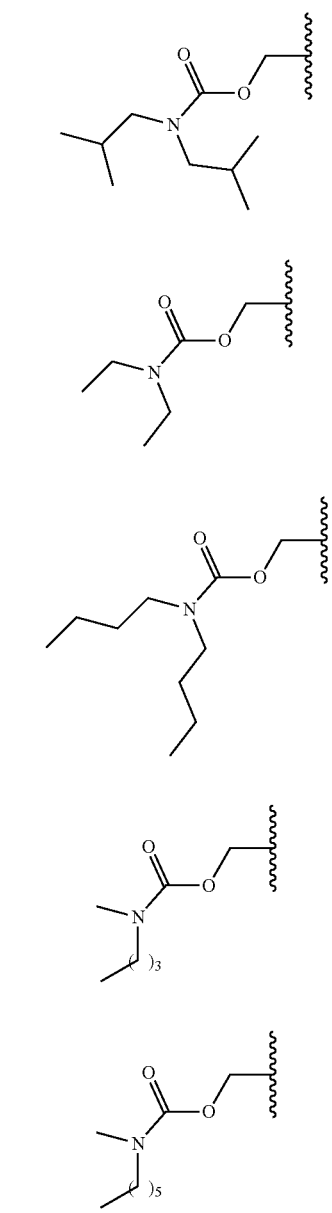
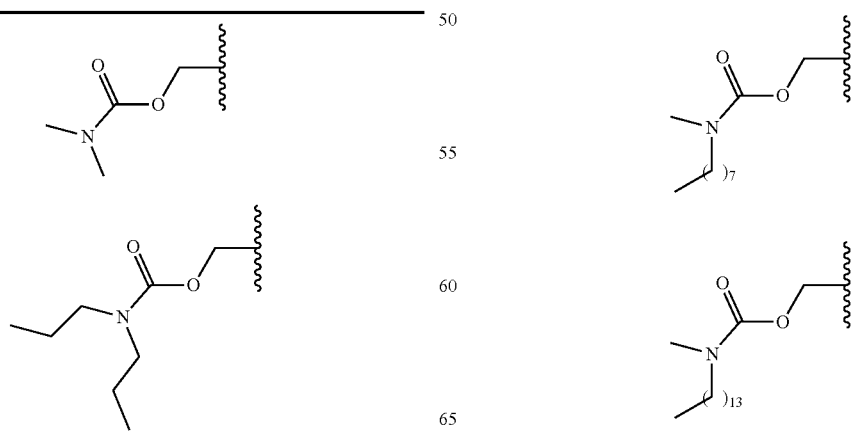

TABLE 3-continued
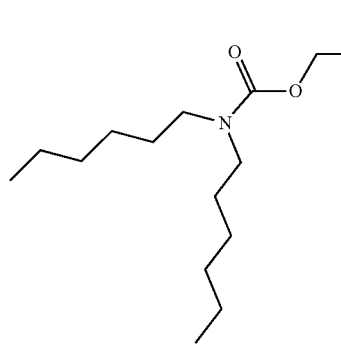
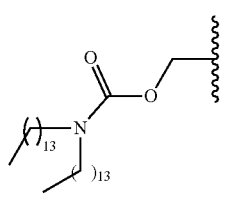
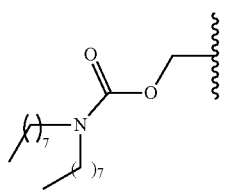
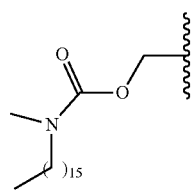
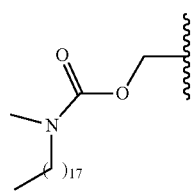
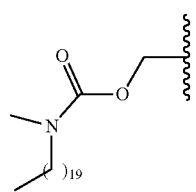
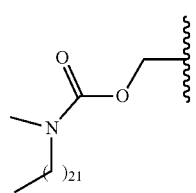
TABLE 3-continued
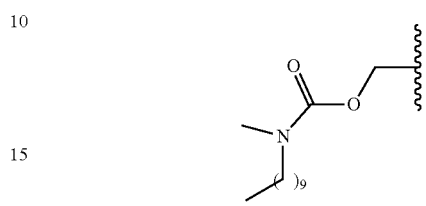
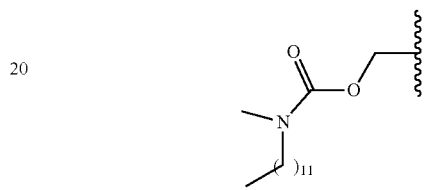
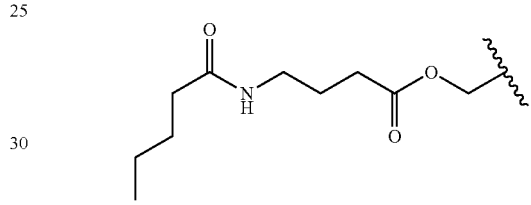
In a more preferred embodiment, $R_5$ is selected from Table 4:
TABLE 4
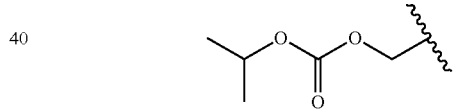
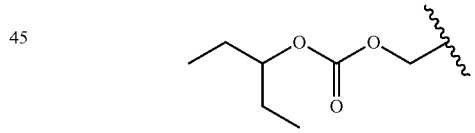
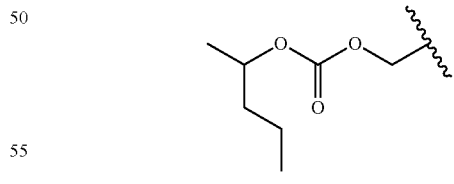
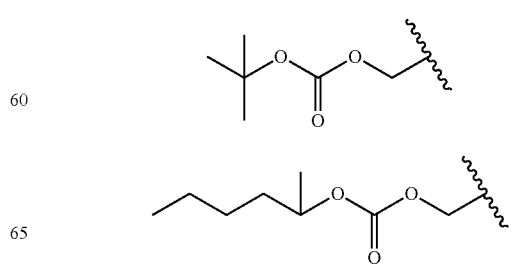

TABLE 4-continued
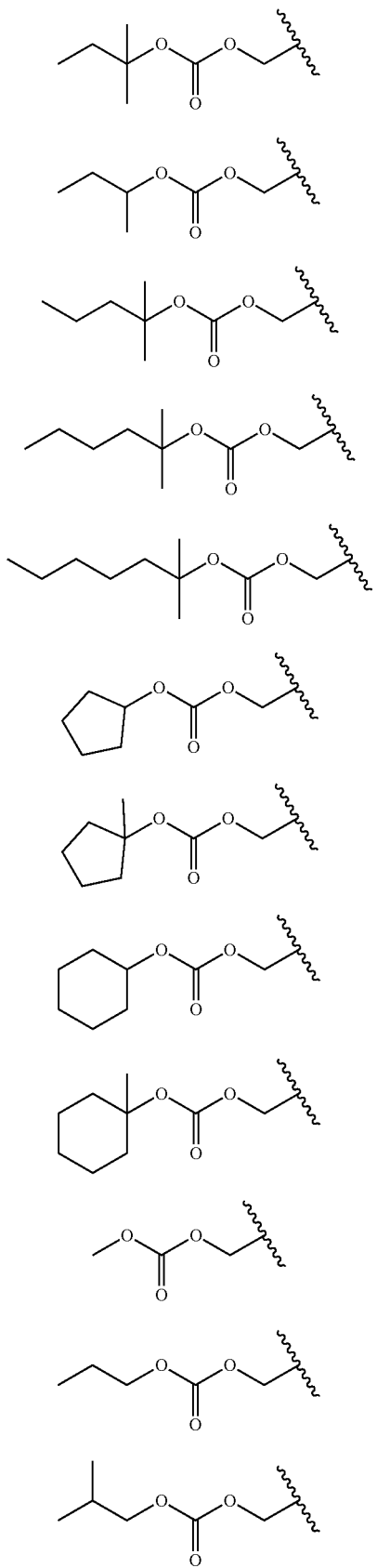
TABLE 4-continued
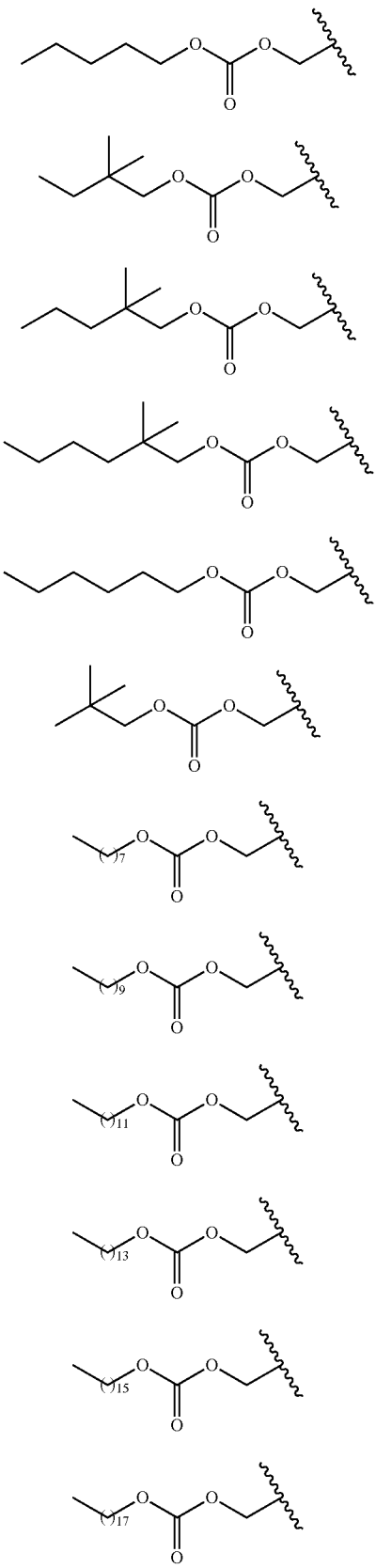

TABLE 4-continued
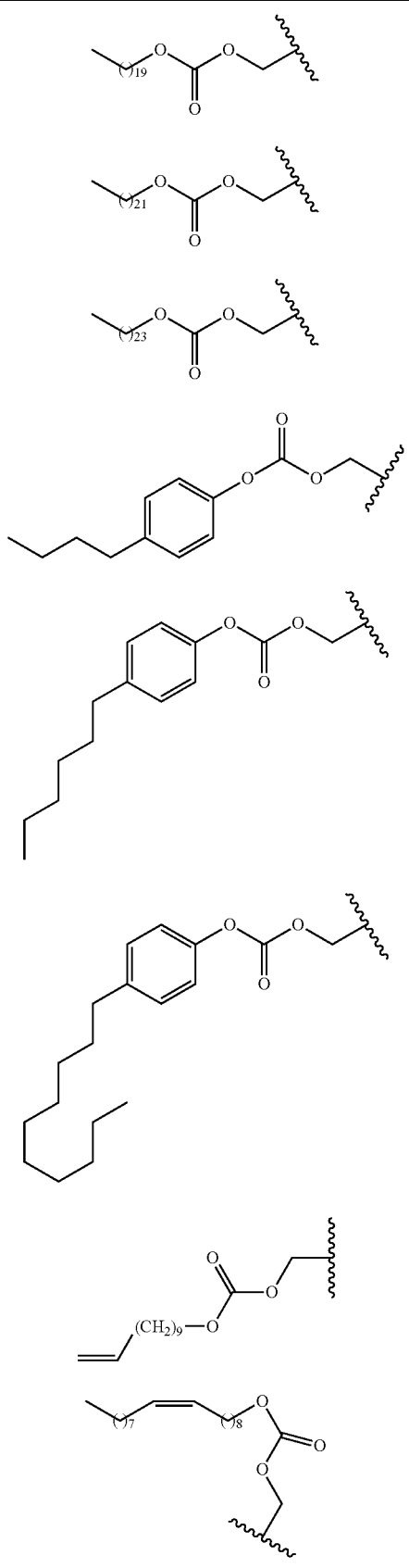
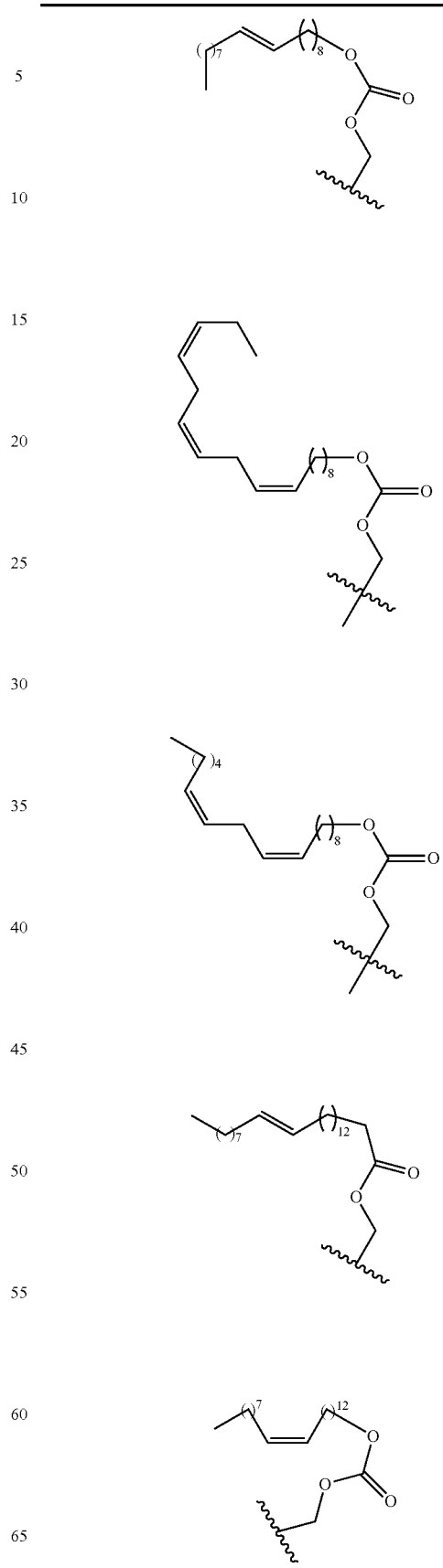

TABLE 4-continued

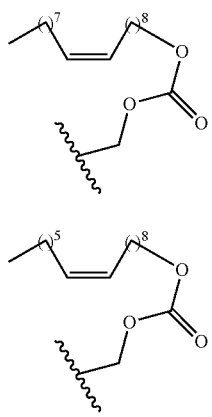

In a preferred embodiment, a compound having Formula XIX is provided:

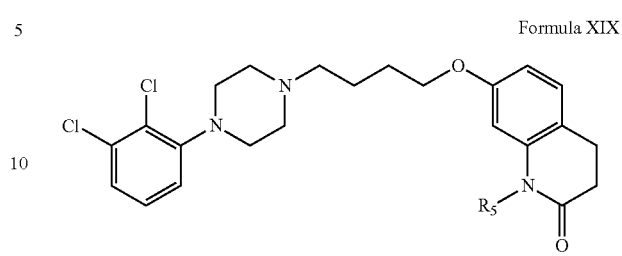

Formula XIX wherein $R_5$ is selected from Table 1. A more preferred compound is where $R_5$ is selected from Tables 2-4.

Representative compounds according to the invention are those selected from the Table A below or its geometric isomers, enantiomers, diastereomers, racemates, pharmaceutically acceptable salts and solvates thereof:

TABLE A

| No | Structure |
|---|---|
| 1 | 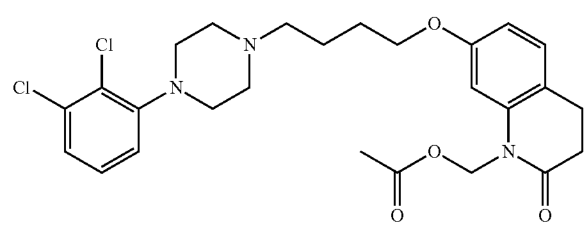 [SMILES: CC(=O)OCN1C(=O)CCc2ccc(OCCCCN3CCN(c4cccc(Cl)c4Cl)CC3)cc21] |
| 2 | 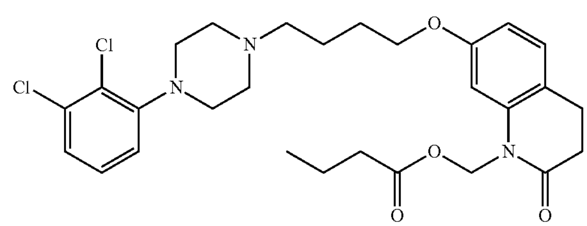 [SMILES: CCCC(=O)OCN1C(=O)CCc2ccc(OCCCCN3CCN(c4cccc(Cl)c4Cl)CC3)cc21] |
| 3 | 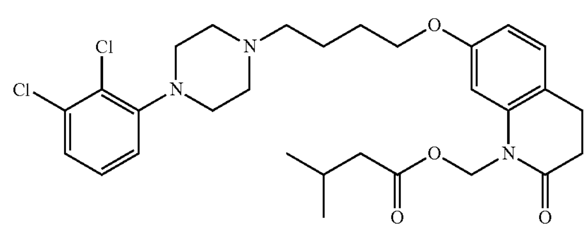 |
| 4 | 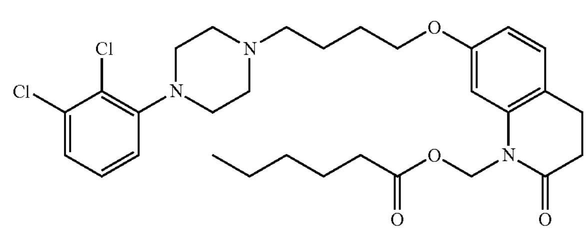 |

TABLE A-continued

| No | Structure |
|---|---|
| 5 | (structure: 1-(2,3-dichlorophenyl)piperazine linked via butoxy to 7-position of 3,4-dihydroquinolin-2(1H)-one; N-CH2-O-C(=O)-heptyl ester) |
| 6 | (same core; N-CH2-O-C(=O)-(CH2)8-CH3) |
| 7 | (same core; N-CH2-O-C(=O)-(CH2)10-CH3) |
| 8 | (same core; N-CH2-O-C(=O)-(CH2)12-CH3) |
| 9 | (same core; N-CH2-O-C(=O)-(CH2)13-CH3) |
| 10 | (same core; N-CH2-O-C(=O)-(CH2)14-CH3) |
| 11 | (same core; N-CH2-O-C(=O)-(CH2)16-CH3) |

TABLE A-continued
| No | Structure |
|---|---|
| 12 | 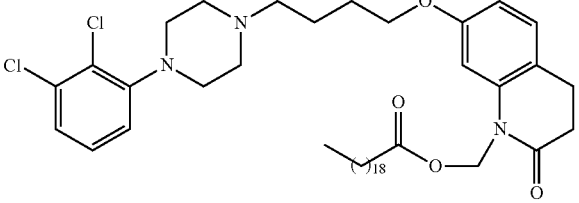 |
| 13 | 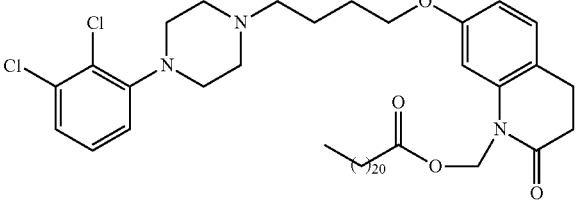 |
| 14 | 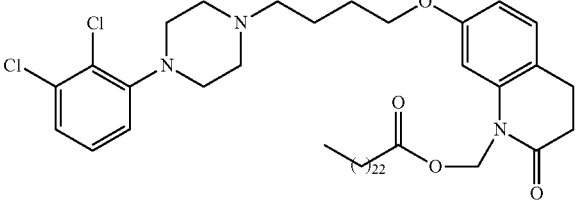 |
| 15 | 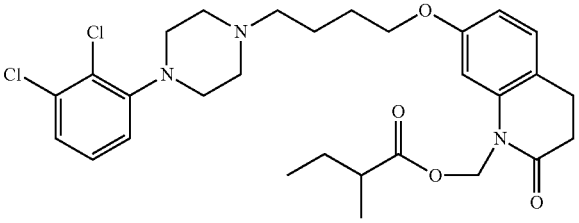 [SMILES: CCC(C)C(=O)OCN1C(=O)CCc2ccc(OCCCCN3CCN(c4cccc(Cl)c4Cl)CC3)cc21] |
| 16 | 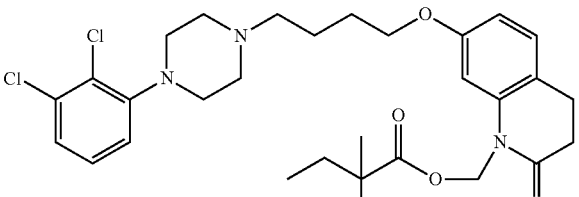 |
| 17 | 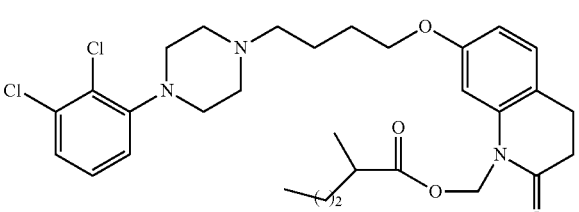 |
| 18 | 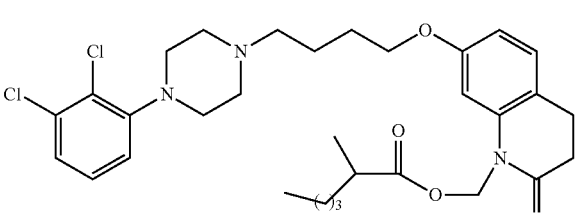 |

TABLE A-continued
| No | Structure |
|---|---|
| 19 | 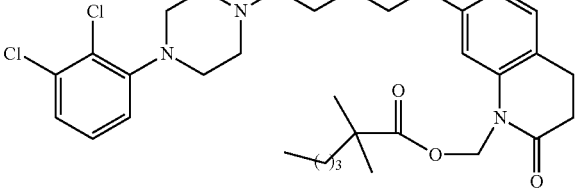 |
| 20 | 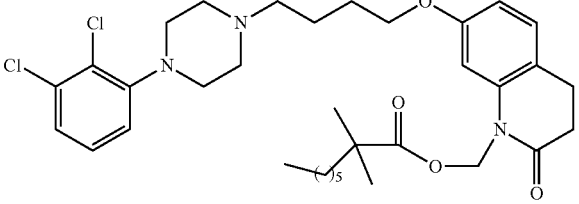 |
| 21 | 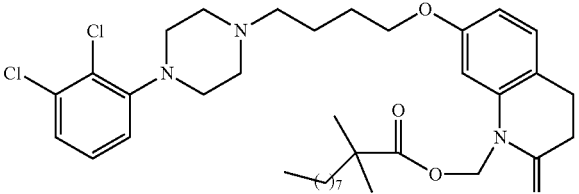 |
| 22 | 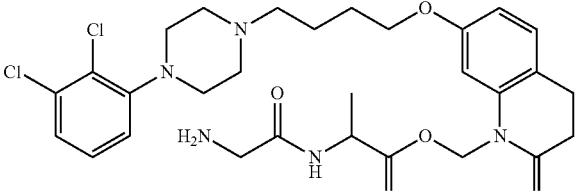 |
| 23 | 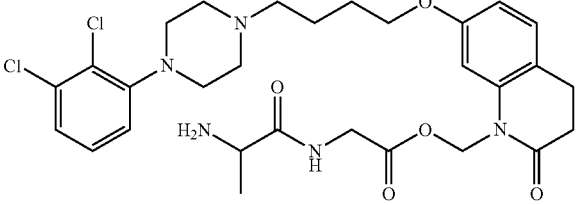 |
| 24 | 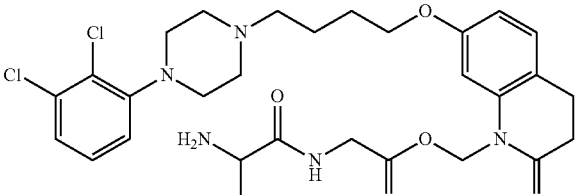 |

TABLE A-continued

| No | Structure |
|---|---|
| 25 | 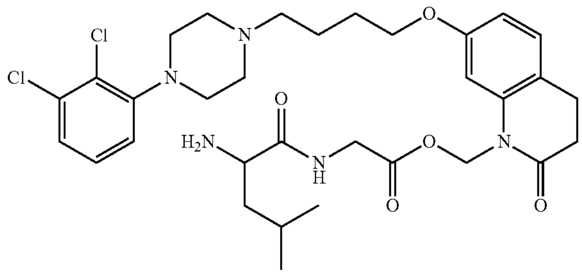 [SMILES: CC(C)CC(N)C(=O)NCC(=O)OCN1C(=O)CCc2ccc(OCCCCN3CCN(c4cccc(Cl)c4Cl)CC3)cc21] |
| 26 | 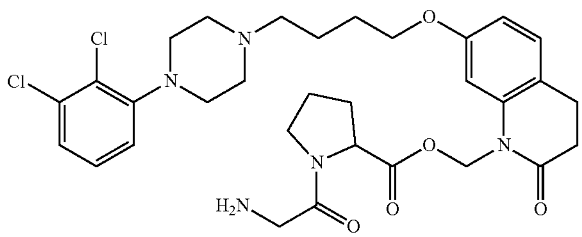 [SMILES: NCC(=O)N1CCCC1C(=O)OCN1C(=O)CCc2ccc(OCCCCN3CCN(c4cccc(Cl)c4Cl)CC3)cc21] |
| 27 | 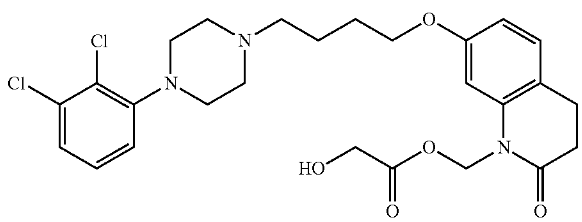 [SMILES: O=C(CO)OCN1C(=O)CCc2ccc(OCCCCN3CCN(c4cccc(Cl)c4Cl)CC3)cc21] |
| 28 | 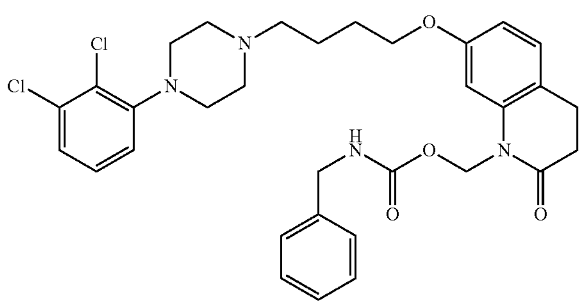 [SMILES: O=C(NCc1ccccc1)OCN1C(=O)CCc2ccc(OCCCCN3CCN(c4cccc(Cl)c4Cl)CC3)cc21] |
| 29 | 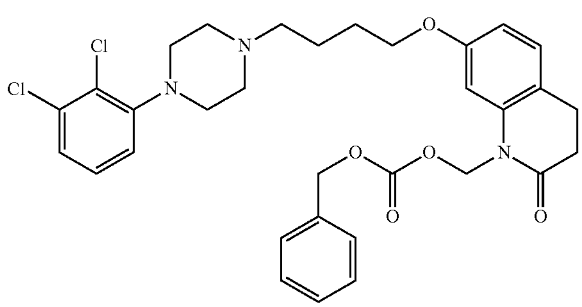 [SMILES: O=C(OCc1ccccc1)OCN1C(=O)CCc2ccc(OCCCCN3CCN(c4cccc(Cl)c4Cl)CC3)cc21] |

TABLE A-continued
| No | Structure |
|---|---|
| 30 | 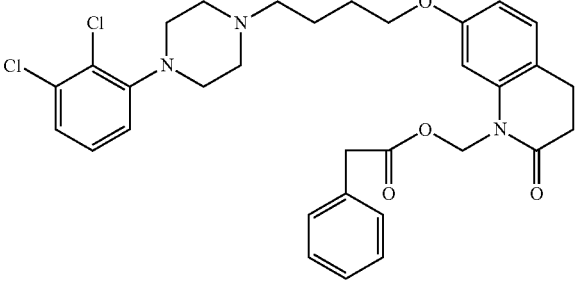 |
| 31 | 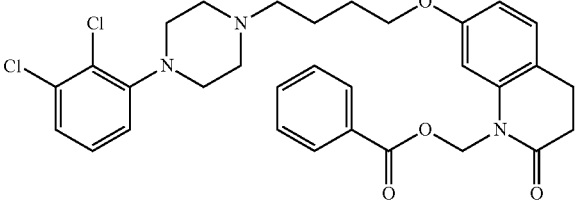 |
| 32 | 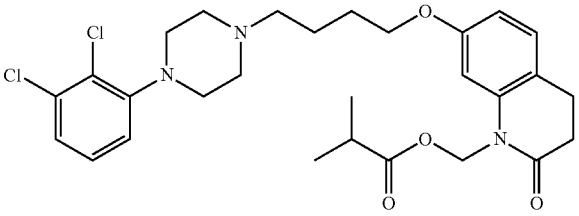 [SMILES: CC(C)C(=O)OCN1C(=O)CCc2ccc(OCCCCN3CCN(c4cccc(Cl)c4Cl)CC3)cc21] |
| 33 | 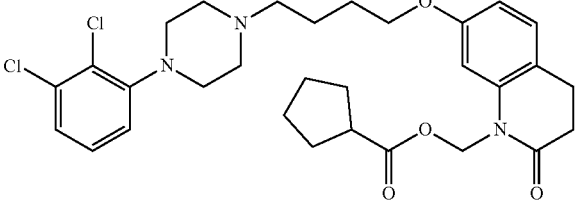 |
| 34 | 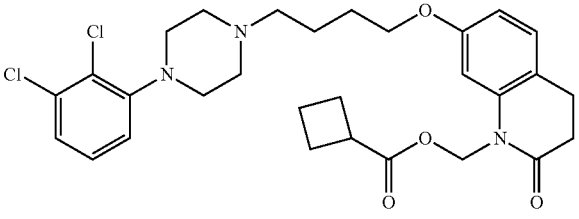 [SMILES: O=C(OCN1C(=O)CCc2ccc(OCCCCN3CCN(c4cccc(Cl)c4Cl)CC3)cc21)C1CCC1] |
| 35 | 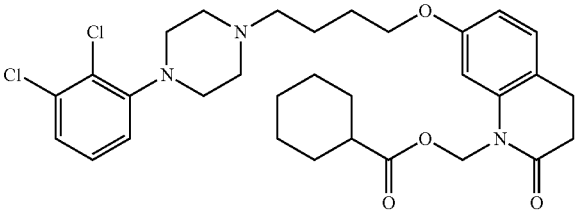 |

TABLE A-continued
| No | Structure |
|----|-----------|
| 36 | 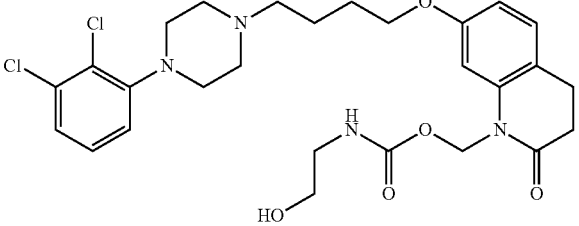 |
| 37 | 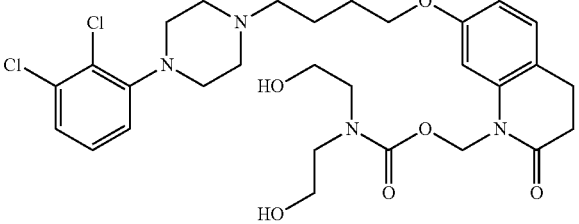 |
| 38 | 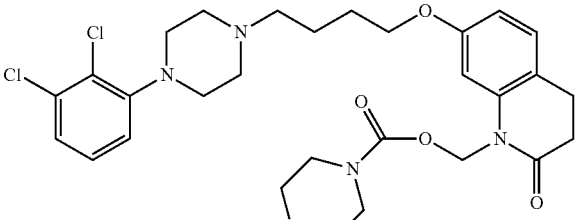 |
| 39 | 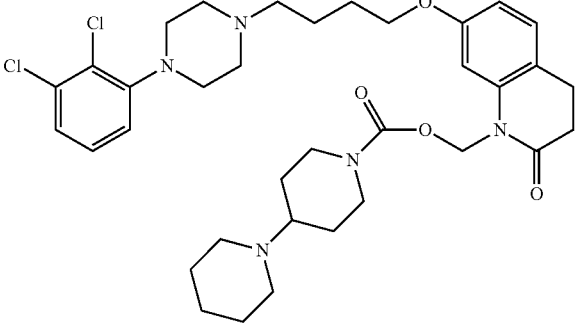 |
| 40 | 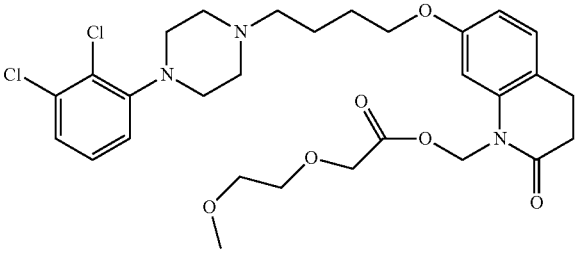 [SMILES: COCCOCC(=O)OCN1C(=O)CCc2ccc(OCCCCN3CCN(c4cccc(Cl)c4Cl)CC3)cc21] |

TABLE A-continued

| No | Structure |
|---|---|
| 41 | 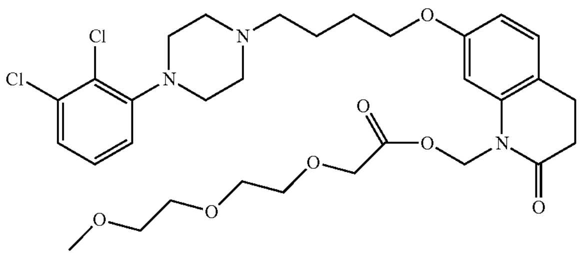 [SMILES: COCCOCCOCC(=O)OCN1C(=O)CCc2ccc(OCCCCN3CCN(c4cccc(Cl)c4Cl)CC3)cc21] |
| 42 | 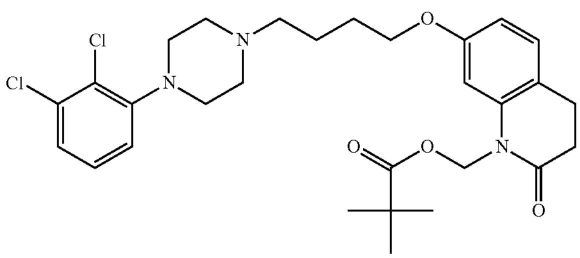 [SMILES: CC(C)(C)C(=O)OCN1C(=O)CCc2ccc(OCCCCN3CCN(c4cccc(Cl)c4Cl)CC3)cc21] |
| 43 | 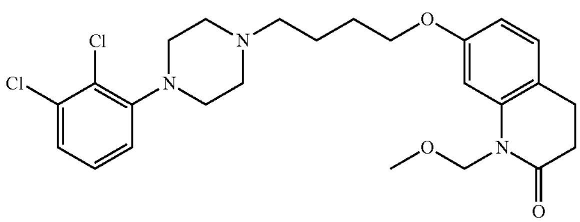 [SMILES: COCN1C(=O)CCc2ccc(OCCCCN3CCN(c4cccc(Cl)c4Cl)CC3)cc21] |
| 44 | 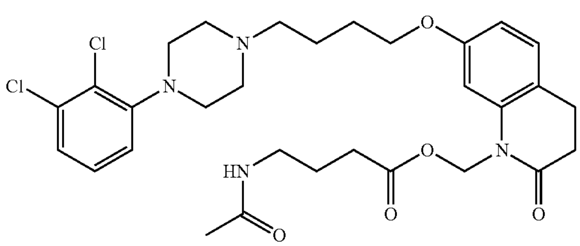 [SMILES: CC(=O)NCCCC(=O)OCN1C(=O)CCc2ccc(OCCCCN3CCN(c4cccc(Cl)c4Cl)CC3)cc21] |
| 45 | 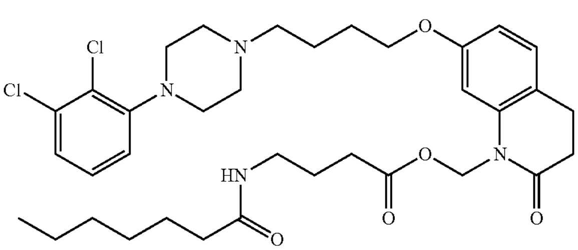 [SMILES: CCCCCCC(=O)NCCCC(=O)OCN1C(=O)CCc2ccc(OCCCCN3CCN(c4cccc(Cl)c4Cl)CC3)cc21] |
| 46 | 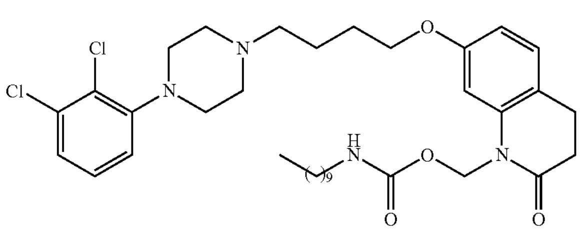 |

TABLE A-continued

| No | Structure |
|---|---|
| 47 | 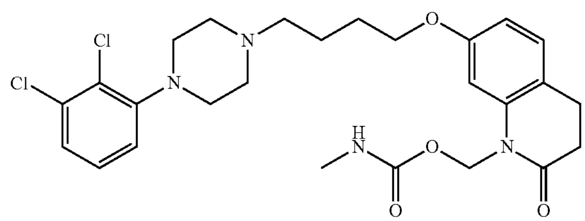 [SMILES: CNC(=O)OCN1C(=O)CCc2ccc(OCCCCN3CCN(c4cccc(Cl)c4Cl)CC3)cc21] |
| 48 | 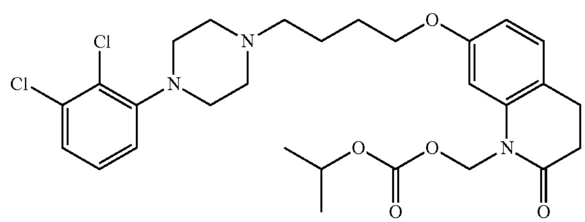 [SMILES: CC(C)OC(=O)OCN1C(=O)CCc2ccc(OCCCCN3CCN(c4cccc(Cl)c4Cl)CC3)cc21] |
| 49 | 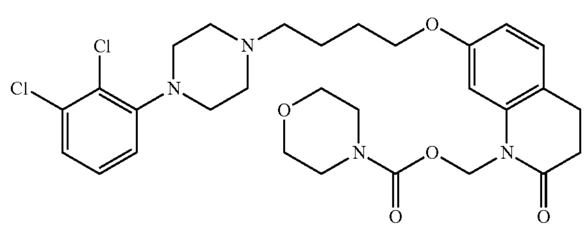 [SMILES: O=C(OCN1C(=O)CCc2ccc(OCCCCN3CCN(c4cccc(Cl)c4Cl)CC3)cc21)N1CCOCC1] |
| 50 | 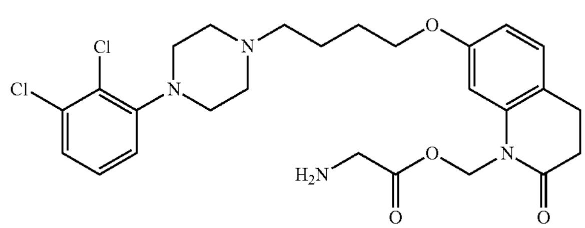 [SMILES: NCC(=O)OCN1C(=O)CCc2ccc(OCCCCN3CCN(c4cccc(Cl)c4Cl)CC3)cc21] |
| 51 | 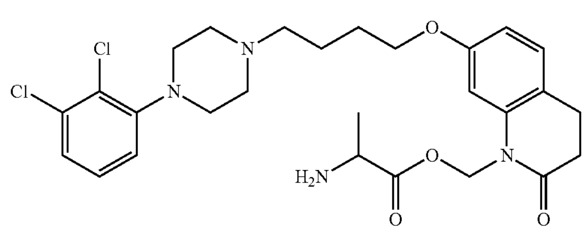 [SMILES: CC(N)C(=O)OCN1C(=O)CCc2ccc(OCCCCN3CCN(c4cccc(Cl)c4Cl)CC3)cc21] |
| 52 | 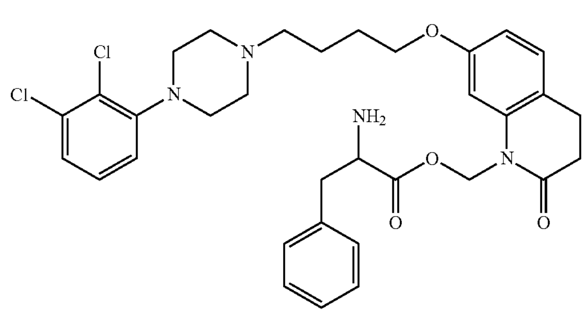 [SMILES: NC(Cc1ccccc1)C(=O)OCN1C(=O)CCc2ccc(OCCCCN3CCN(c4cccc(Cl)c4Cl)CC3)cc21] |

TABLE A-continued
| No | Structure |
|---|---|
| 53 | 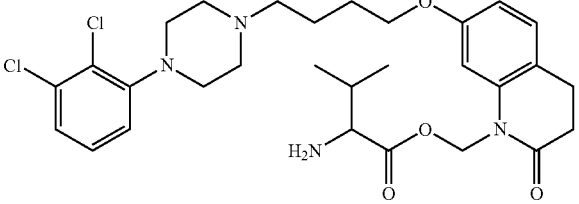 |
| 54 | 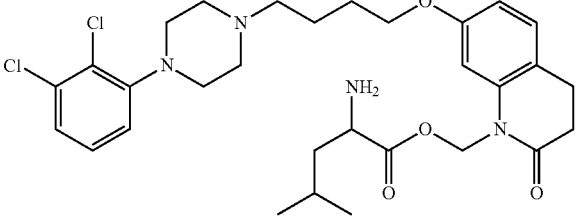 |
| 55 | 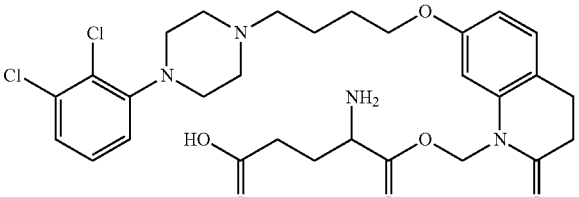 |
| 56 | 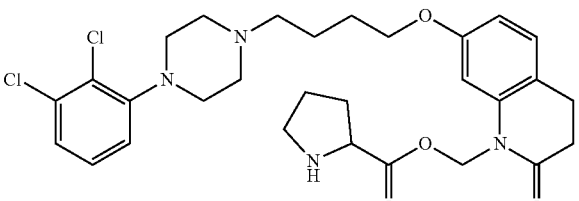 |
| 57 | 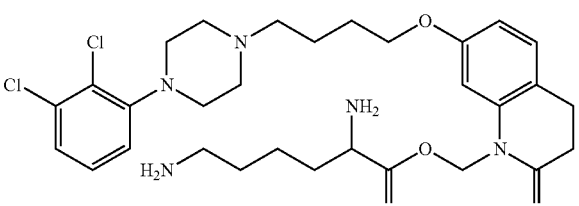 |
| 58 | 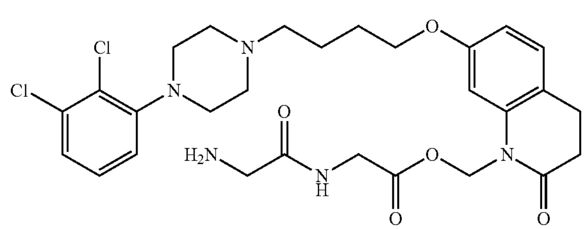 [SMILES: NCC(=O)NCC(=O)OCN1C(=O)CCc2ccc(OCCCCN3CCN(c4cccc(Cl)c4Cl)CC3)cc21] |
| 59 | 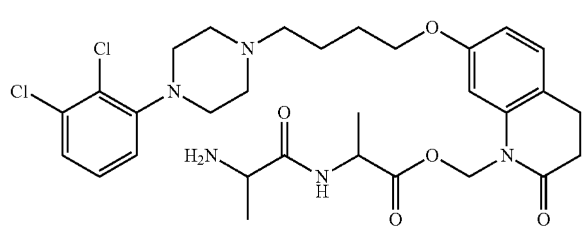 [SMILES: CC(N)C(=O)NC(C)C(=O)OCN1C(=O)CCc2ccc(OCCCCN3CCN(c4cccc(Cl)c4Cl)CC3)cc21] |

TABLE A-continued

| No | Structure |
|---|---|
| 60 | 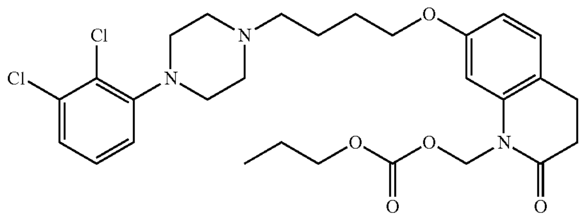 [SMILES: CCCOC(=O)OCN1C(=O)CCc2ccc(OCCCCN3CCN(c4cccc(Cl)c4Cl)CC3)cc21] |
| 61 | 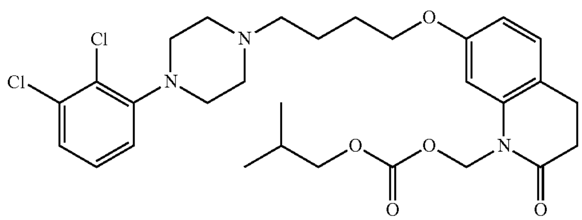 |
| 62 | 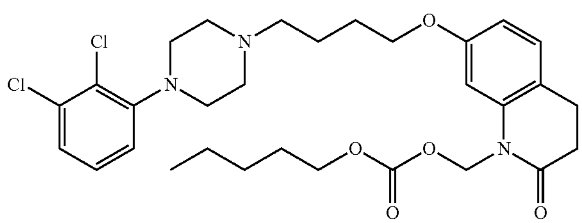 [SMILES: CCCCCOC(=O)OCN1C(=O)CCc2ccc(OCCCCN3CCN(c4cccc(Cl)c4Cl)CC3)cc21] |
| 63 | 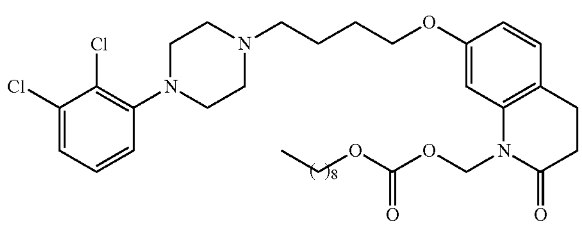 |
| 64 | 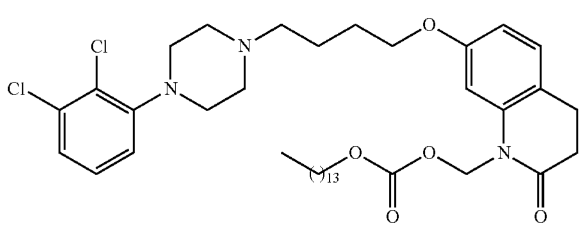 [SMILES: CCOC(=O)OCN1C(=O)CCc2ccc(OCCCCN3CCN(c4cccc(Cl)c4Cl)CC3)cc21] |
| 65 | 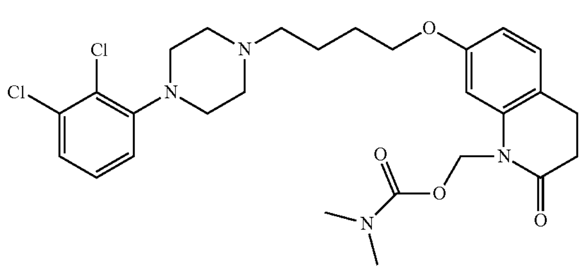 [SMILES: CN(C)C(=O)OCN1C(=O)CCc2ccc(OCCCCN3CCN(c4cccc(Cl)c4Cl)CC3)cc21] |

TABLE A-continued
| No | Structure |
|---|---|
| 66 | 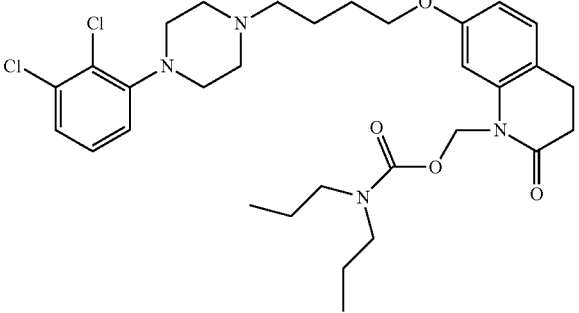 |
| 67 | 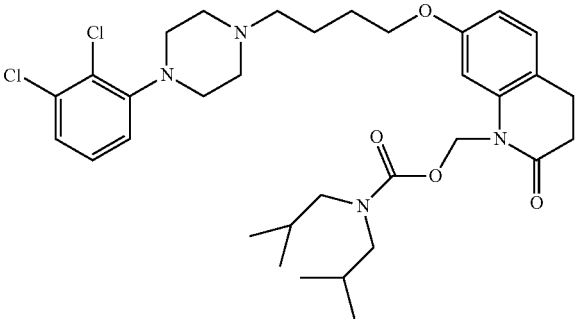 [SMILES: CC(C)CN(CC(C)C)C(=O)OCN1C(=O)CCc2ccc(OCCCCN3CCN(c4cccc(Cl)c4Cl)CC3)cc21] |
| 68 | 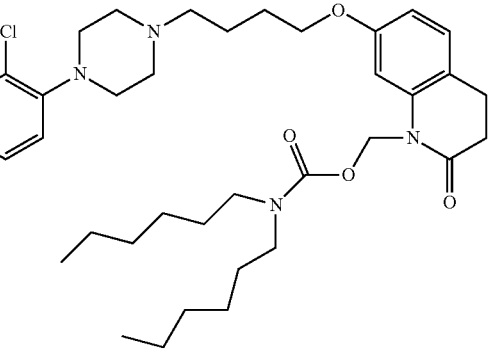 |
| 69 | 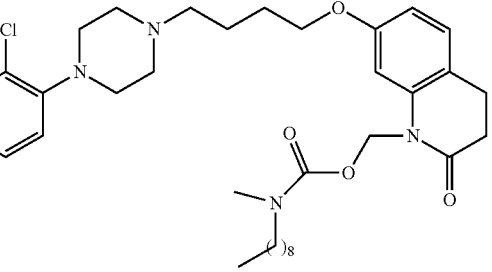 |
| 70 | 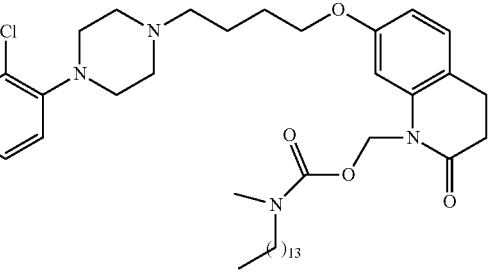 |

TABLE A-continued
| No | Structure |
|---|---|
| 71 | 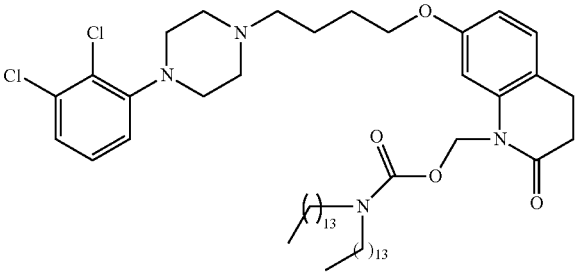 |
| 72 | 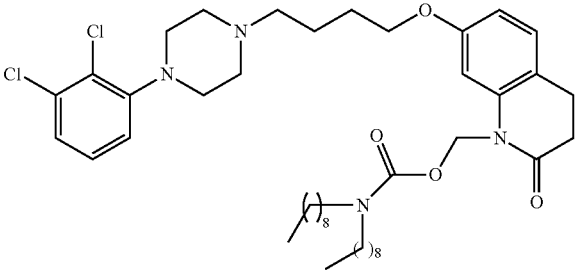 |
| 73 | 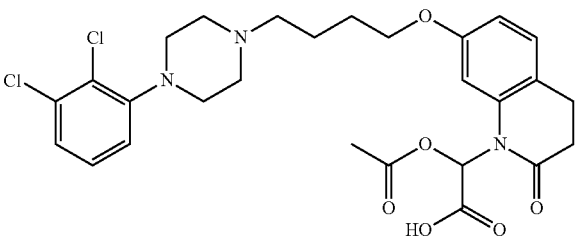 [SMILES: CC(=O)OC(C(=O)O)N1C(=O)CCc2ccc(OCCCCN3CCN(c4cccc(Cl)c4Cl)CC3)cc21] |
| 74 | 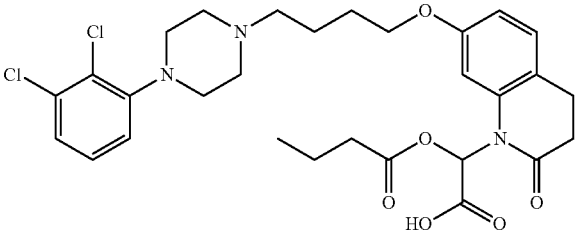 [SMILES: CCCC(=O)OC(C(=O)O)N1C(=O)CCc2ccc(OCCCCN3CCN(c4cccc(Cl)c4Cl)CC3)cc21] |
| 75 | 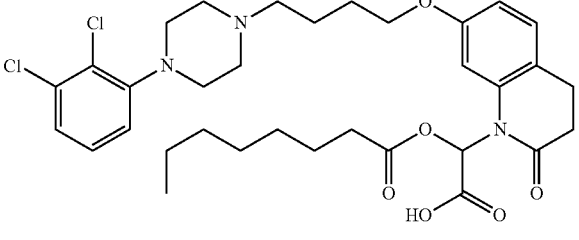 |
| 76 | 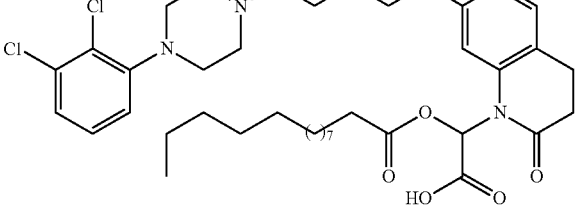 |

TABLE A-continued
| No | Structure |
|---|---|
| 77 | 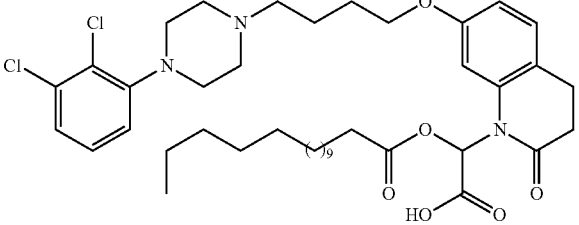 |
| 78 | 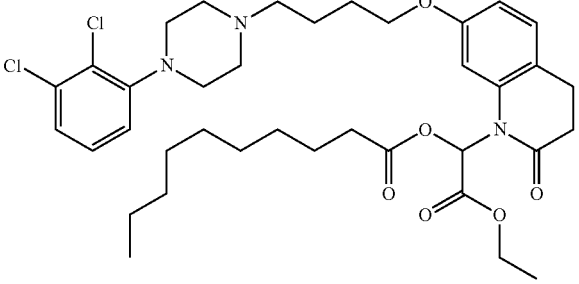 |
| 79 | 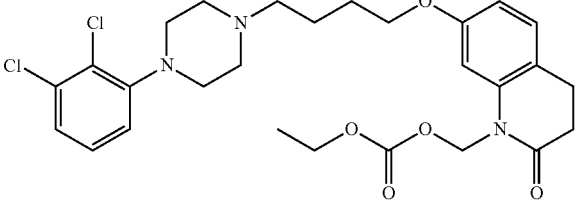 |
| 80 | 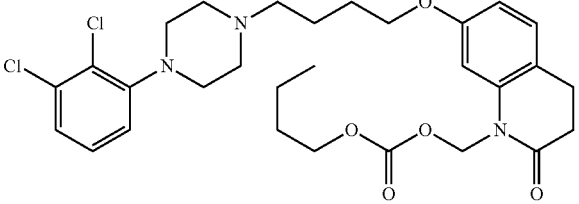 |
| 81 | 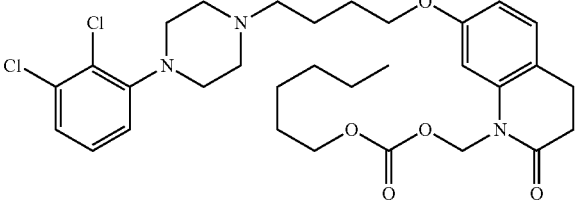 |
| 82 | 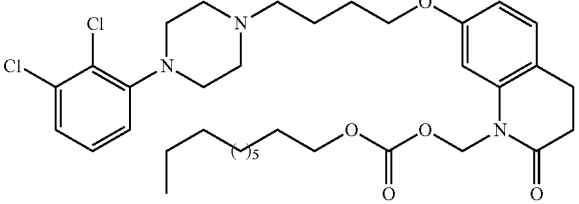 |

TABLE A-continued
| No | Structure |
|---|---|
| 83 | 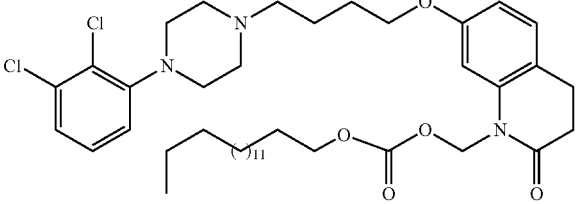 |
| 84 | 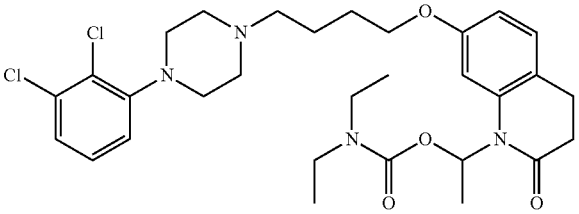 [SMILES: CCN(CC)C(=O)OC(C)N1C(=O)CCc2ccc(OCCCCN3CCN(c4cccc(Cl)c4Cl)CC3)cc21] |
| 85 | 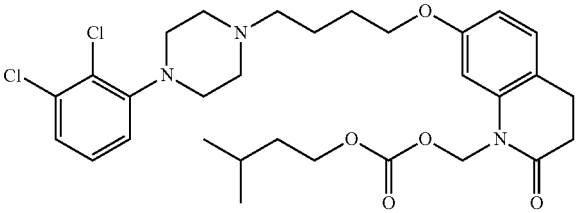 [SMILES: CC(C)CCOC(=O)OCN1C(=O)CCc2ccc(OCCCCN3CCN(c4cccc(Cl)c4Cl)CC3)cc21] |
| 86 | 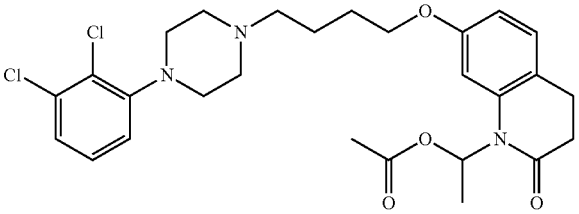 [SMILES: CC(=O)OC(C)N1C(=O)CCc2ccc(OCCCCN3CCN(c4cccc(Cl)c4Cl)CC3)cc21] |
| 87 | 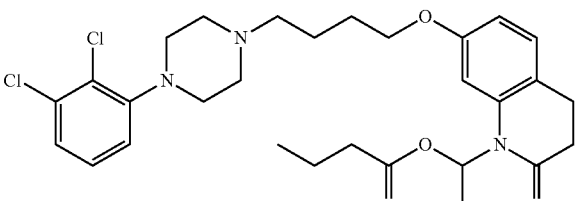 |
| 88 | 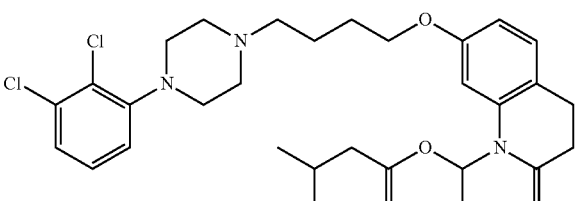 |
| 89 | 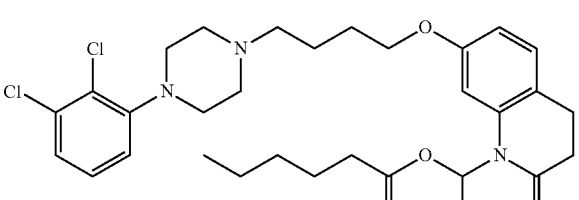 |

TABLE A-continued

| No | Structure |
|---|---|
| 90 | 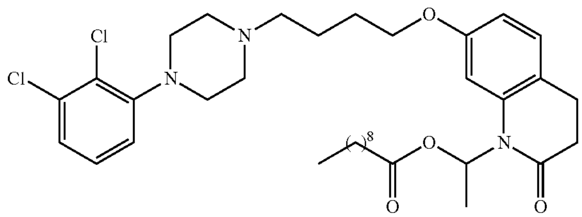 |
| 91 | 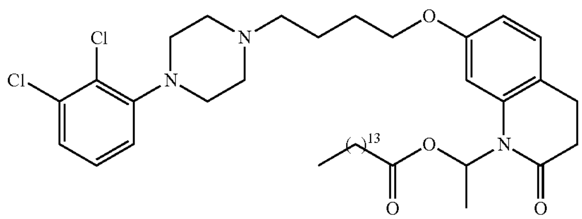 |
| 92 | 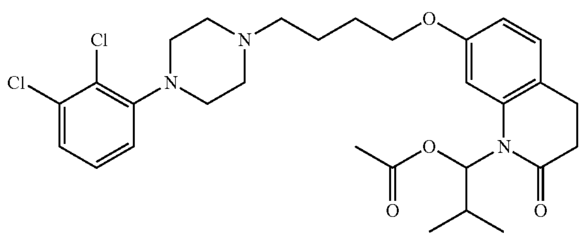 [SMILES: CC(=O)OC(C(C)C)N1C(=O)CCc2ccc(OCCCCN3CCN(c4cccc(Cl)c4Cl)CC3)cc21] |
| 93 | 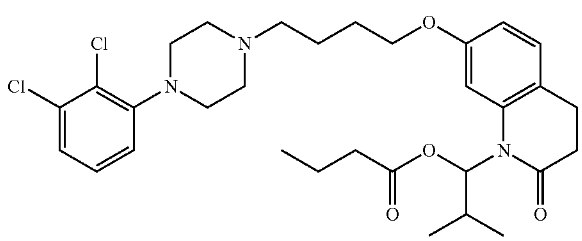 [SMILES: CCCC(=O)OC(C(C)C)N1C(=O)CCc2ccc(OCCCCN3CCN(c4cccc(Cl)c4Cl)CC3)cc21] |
| 94 | 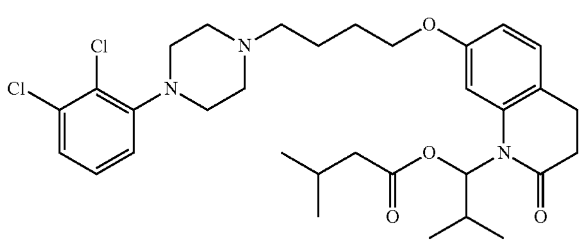 [SMILES: CC(C)CC(=O)OC(C(C)C)N1C(=O)CCc2ccc(OCCCCN3CCN(c4cccc(Cl)c4Cl)CC3)cc21] |
| 95 | 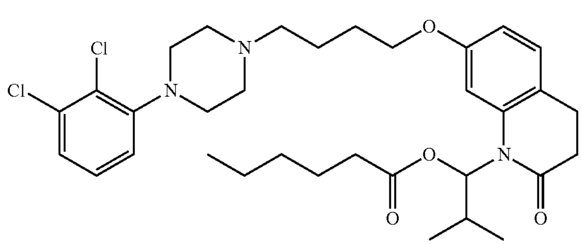 [SMILES: CCCCCC(=O)OC(C(C)C)N1C(=O)CCc2ccc(OCCCCN3CCN(c4cccc(Cl)c4Cl)CC3)cc21] |

TABLE A-continued
| No | Structure |
|---|---|
| 96 | 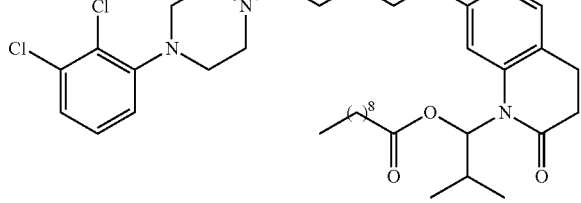 |
| 97 | 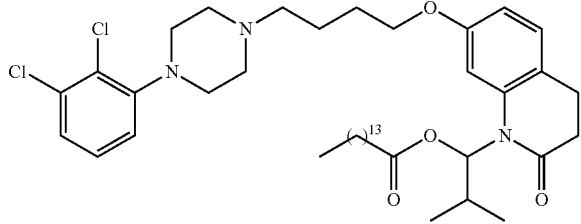 |
| 98 | 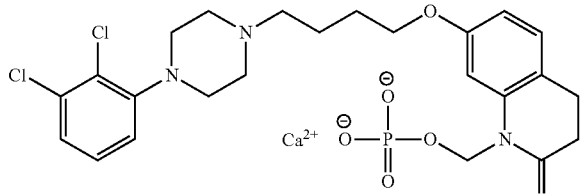 |
| 99 | 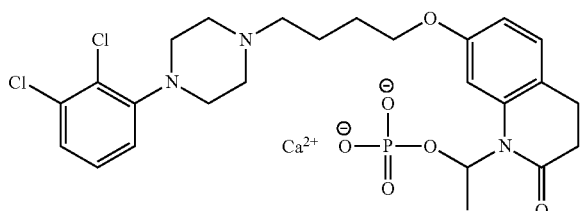 |
| 100 | 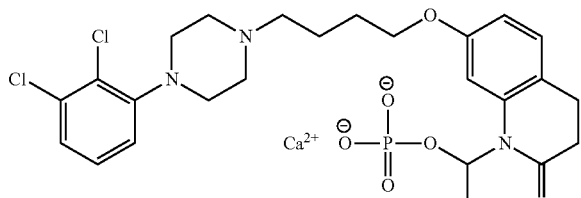 |
| 101 | 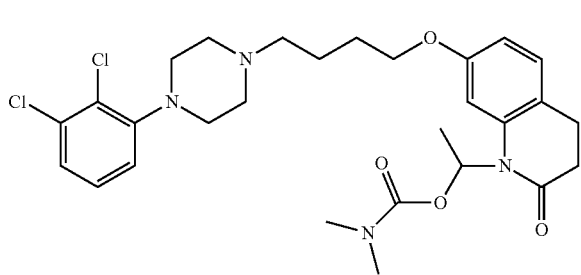 [SMILES: CC(OC(=O)N(C)C)N1C(=O)CCc2ccc(OCCCCN3CCN(c4cccc(Cl)c4Cl)CC3)cc21] |

TABLE A-continued
| No | Structure |
|---|---|
| 102 | 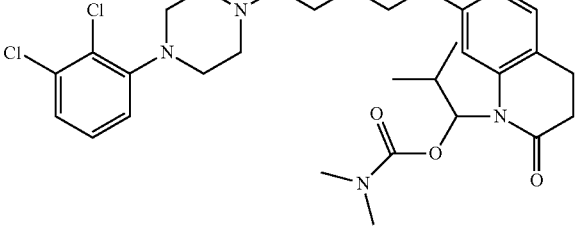 |
| 103 | 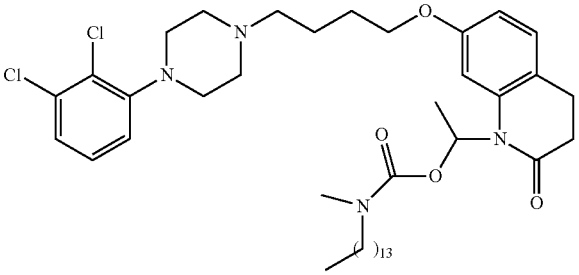 |
| 104 | 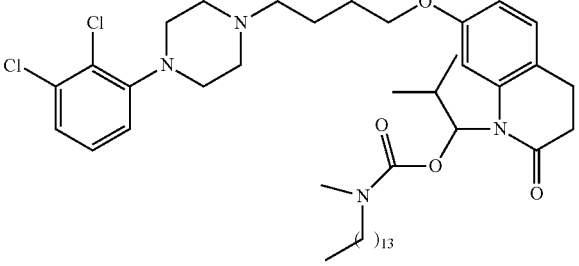 |
| 105 | 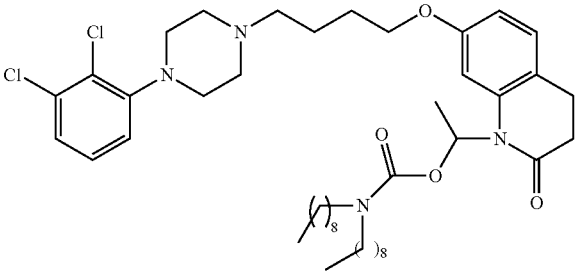 |
| 106 | 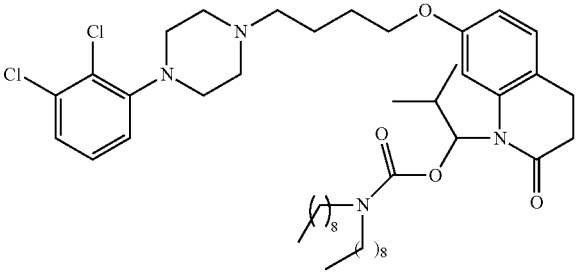 |

TABLE A-continued
| No | Structure |
|---|---|
| 107 | 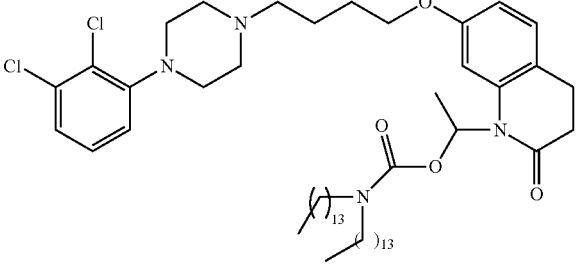 |
| 108 | 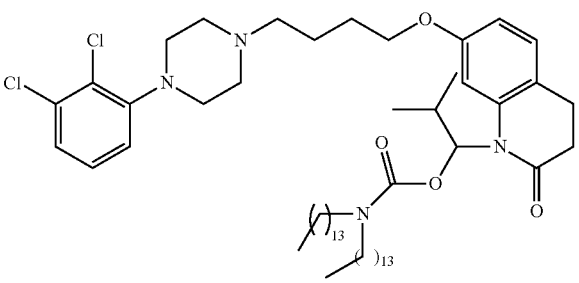 |
| 109 | 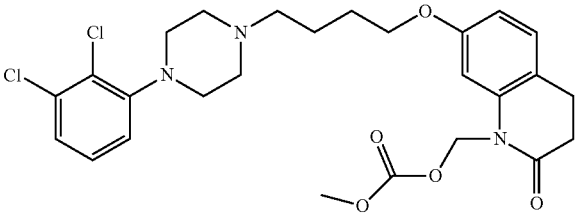 [SMILES: COC(=O)OCN1C(=O)CCc2ccc(OCCCCN3CCN(c4cccc(Cl)c4Cl)CC3)cc21] |
| 110 | 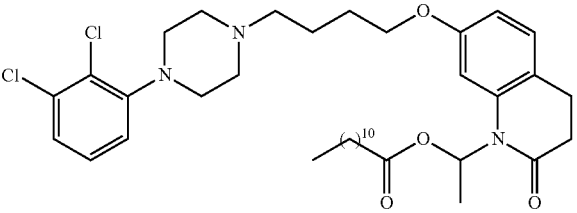 |
| 111 | 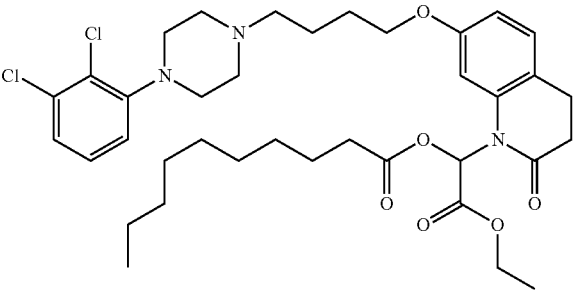 [SMILES: CCCCCCCCCC(=O)OC(C(=O)OCC)N1C(=O)CCc2ccc(OCCCCN3CCN(c4cccc(Cl)c4Cl)CC3)cc21] |

TABLE A-continued

| No | Structure |
|---|---|
| 112 | 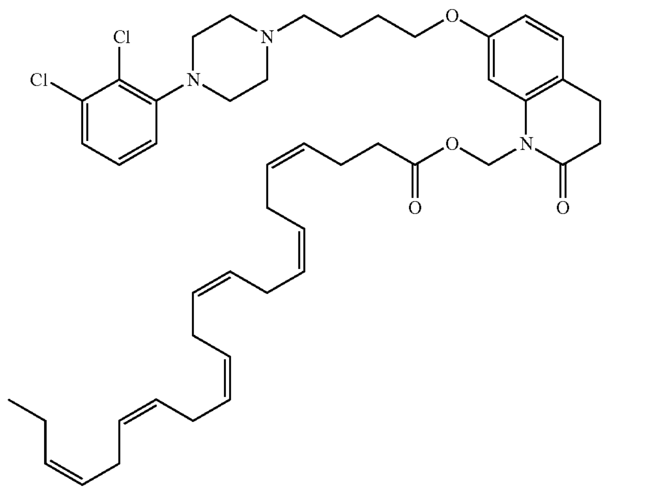 |
| 113 | 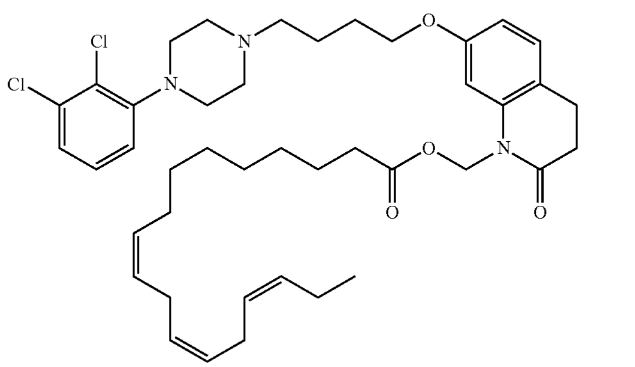 [SMILES: CC/C=C\C/C=C\C/C=C\CCCCCCCC(=O)OCN1C(=O)CCc2ccc(OCCCCN3CCN(c4cccc(Cl)c4Cl)CC3)cc21] |
| 114 | 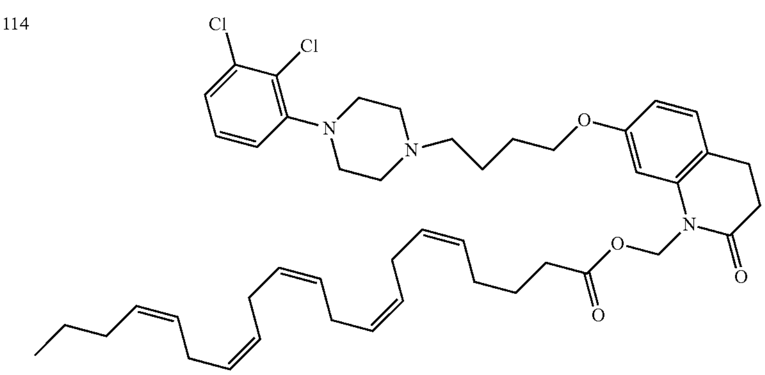 |
| 115 | 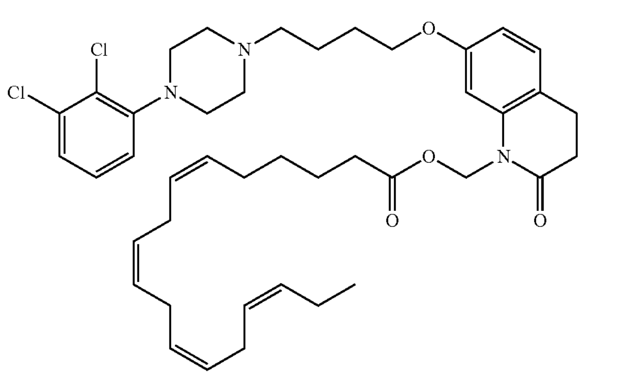 [SMILES: CC/C=C\C/C=C\C/C=C\C/C=C\CCCCC(=O)OCN1C(=O)CCc2ccc(OCCCCN3CCN(c4cccc(Cl)c4Cl)CC3)cc21] |

TABLE A-continued
| No | Structure |
|---|---|
| 116 | 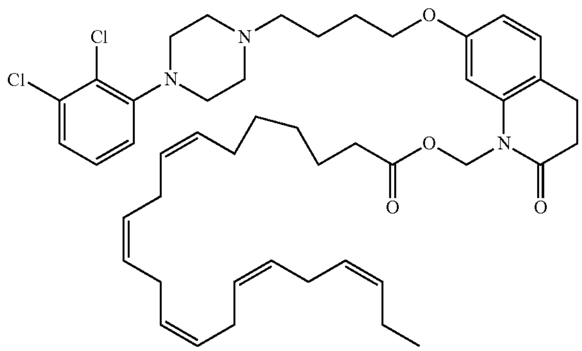 [SMILES: CC/C=C\C/C=C\C/C=C\C/C=C\C/C=C\CCCCCC(=O)OCN1C(=O)CCc2ccc(OCCCCN3CCN(c4cccc(Cl)c4Cl)CC3)cc21] |
| 117 | 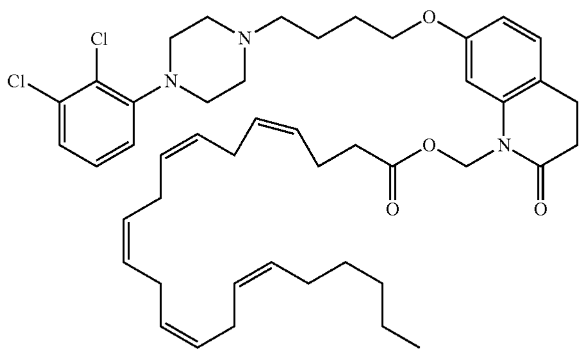 [SMILES: CCCCC/C=C\C/C=C\C/C=C\C/C=C\C/C=C\CCC(=O)OCN1C(=O)CCc2ccc(OCCCCN3CCN(c4cccc(Cl)c4Cl)CC3)cc21] |
| 118 | 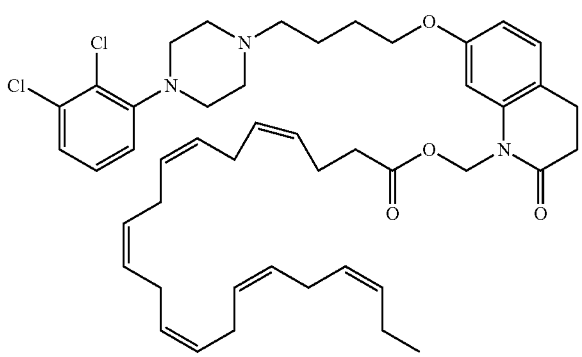 [SMILES: CC/C=C\C/C=C\C/C=C\C/C=C\C/C=C\C/C=C\CCC(=O)OCN1C(=O)CCc2ccc(OCCCCN3CCN(c4cccc(Cl)c4Cl)CC3)cc21] |
In a preferred embodiment, a compound having Formula XX is provided:
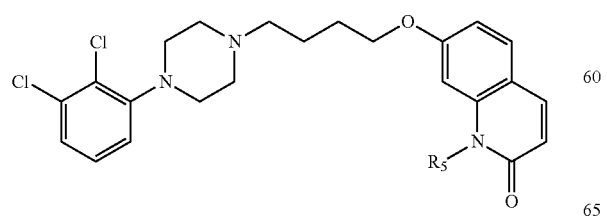
Formula XX
wherein $R_5$ is selected from Table 1.

Representative compounds according to the invention are those selected from the Table B below or its geometric isomers, enantiomers, diastereomers, racemates, pharmaceutically acceptable salts and solvates thereof:
TABLE B
| No | Structure |
|---|---|
| 150 | 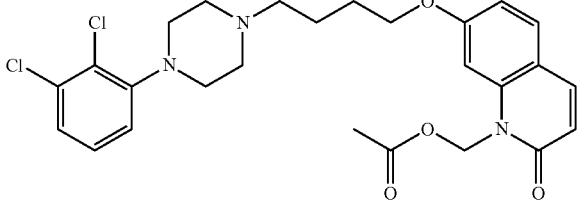 |
| 151 | 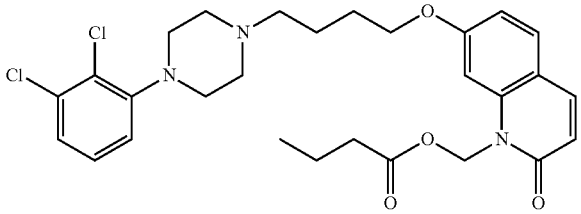 [SMILES: CCCC(=O)OCn1c(=O)ccc2ccc(OCCCCN3CCN(c4cccc(Cl)c4Cl)CC3)cc21] |
| 152 | 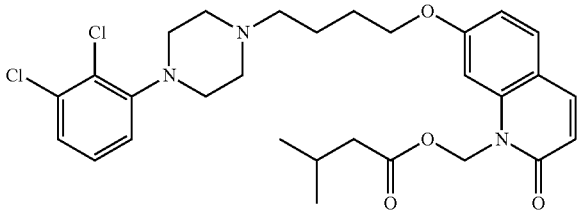 |
| 153 | 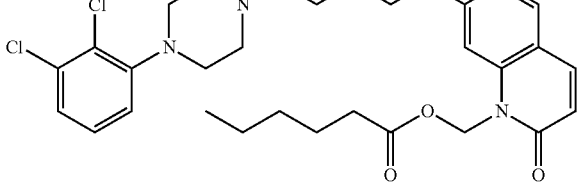 |
| 154 | 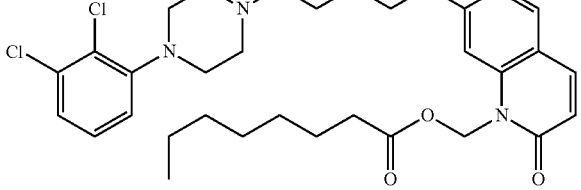 |
| 155 | 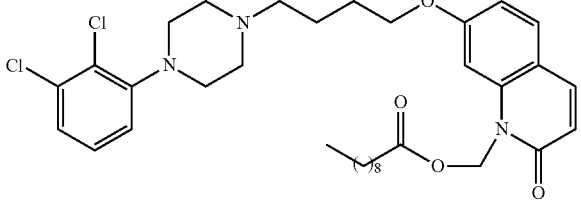 |

TABLE B-continued

| No | Structure |
|---|---|
| 156 | 2,3-dichlorophenyl-piperazine-(CH₂)₄-O-quinolin-2(1H)-one, N-CH₂-O-C(=O)-(CH₂)₁₀-CH₃ |
| 157 | 2,3-dichlorophenyl-piperazine-(CH₂)₄-O-quinolin-2(1H)-one, N-CH₂-O-C(=O)-(CH₂)₁₂-CH₃ |
| 158 | 2,3-dichlorophenyl-piperazine-(CH₂)₄-O-quinolin-2(1H)-one, N-CH₂-O-C(=O)-(CH₂)₁₃-CH₃ |
| 159 | 2,3-dichlorophenyl-piperazine-(CH₂)₄-O-quinolin-2(1H)-one, N-CH₂-O-C(=O)-(CH₂)₁₄-CH₃ |
| 160 | 2,3-dichlorophenyl-piperazine-(CH₂)₄-O-quinolin-2(1H)-one, N-CH₂-O-C(=O)-(CH₂)₁₆-CH₃ |
| 161 | 2,3-dichlorophenyl-piperazine-(CH₂)₄-O-quinolin-2(1H)-one, N-CH₂-O-C(=O)-(CH₂)₁₈-CH₃ |
| 162 | 2,3-dichlorophenyl-piperazine-(CH₂)₄-O-quinolin-2(1H)-one, N-CH₂-O-C(=O)-(CH₂)₂₀-CH₃ |

TABLE B-continued

| No | Structure |
|---|---|
| 163 | 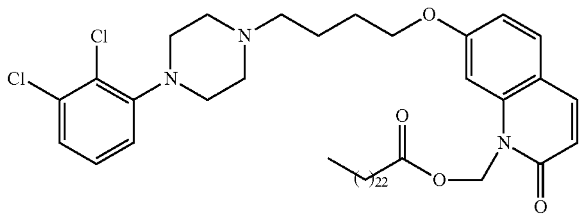 |
| 164 | 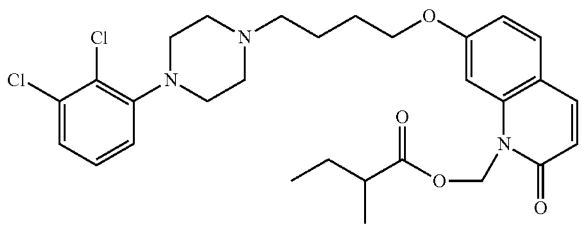 [SMILES: CCC(C)C(=O)OCn1c(=O)ccc2ccc(OCCCCN3CCN(c4cccc(Cl)c4Cl)CC3)cc21] |
| 165 | 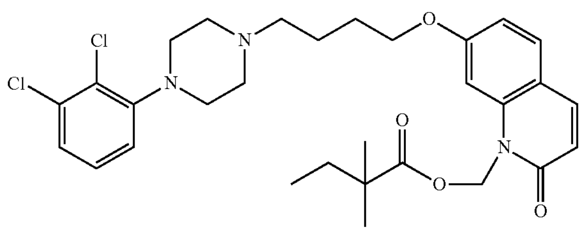 |
| 166 | 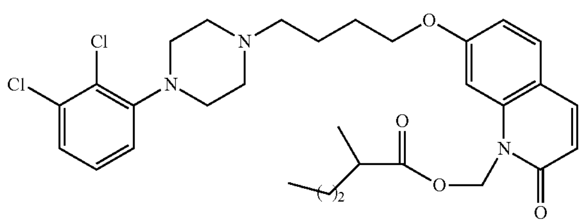 |
| 167 | 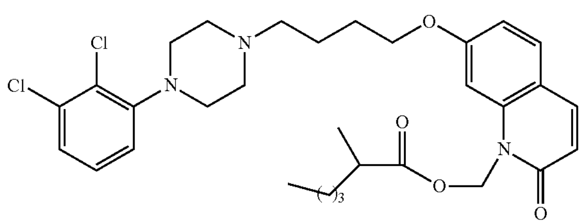 |
| 168 | 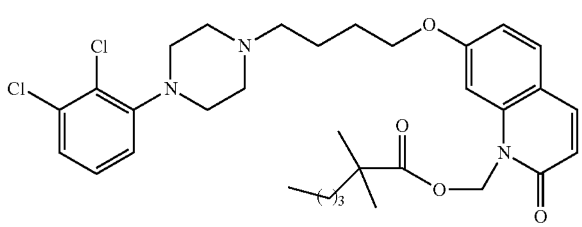 |
| 169 | 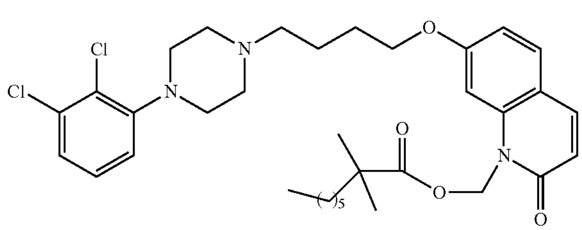 |

TABLE B-continued
| No | Structure |
|---|---|
| 170 | 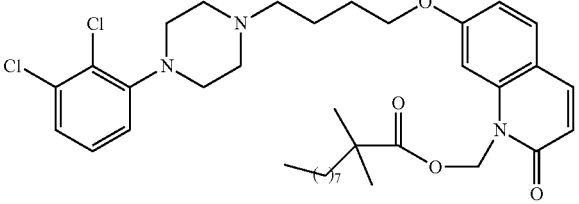 |
| 171 | 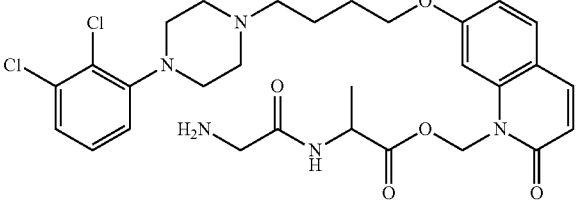 |
| 172 | 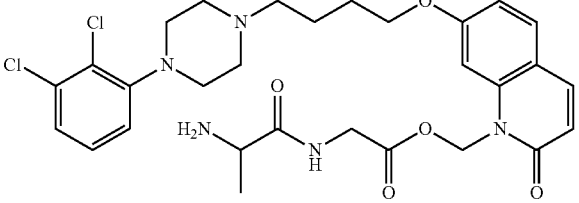 |
| 173 | 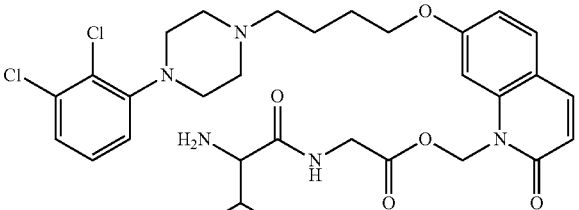 |
| 174 | 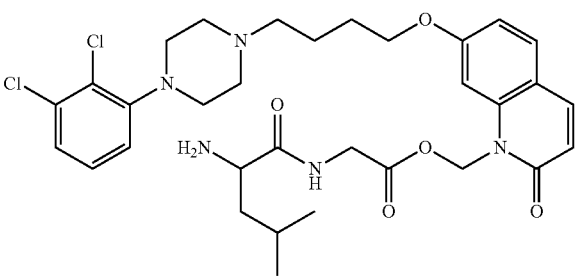 |
| 175 | 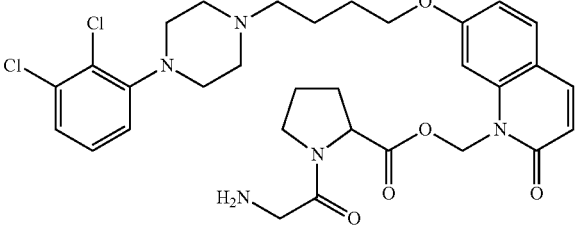 |

TABLE B-continued
| No | Structure |
|---|---|
| 176 | 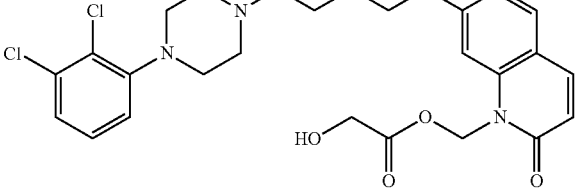 |
| 177 | 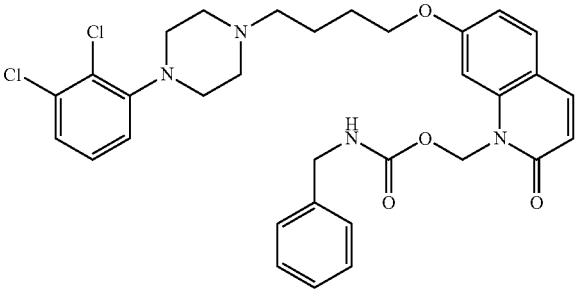 |
| 178 | 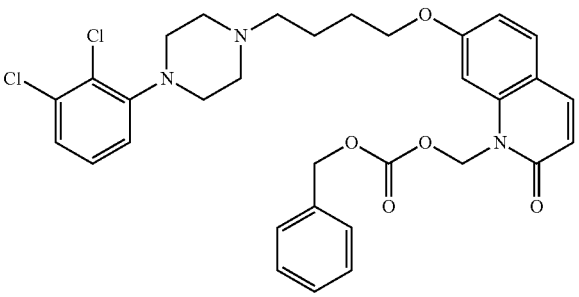 |
| 179 | 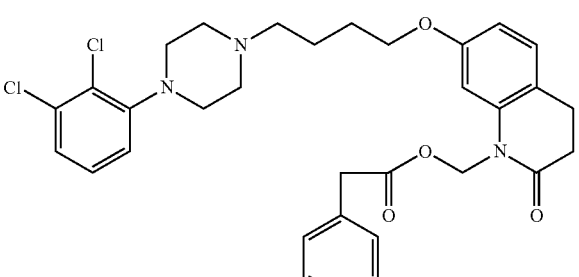 |
| 180 | 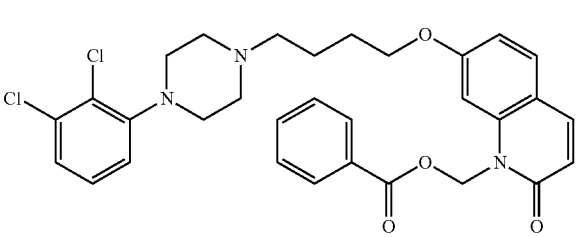 |
| 181 | 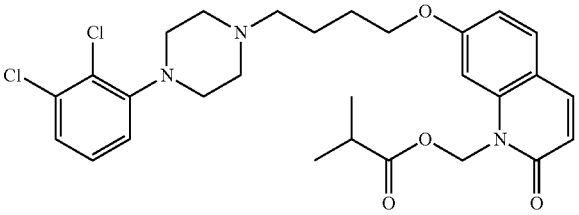 |

TABLE B-continued
| No | Structure |
|---|---|
| 182 | 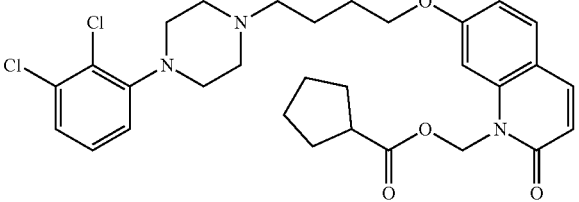 |
| 183 | 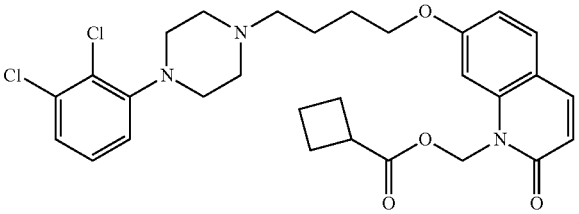 |
| 184 | 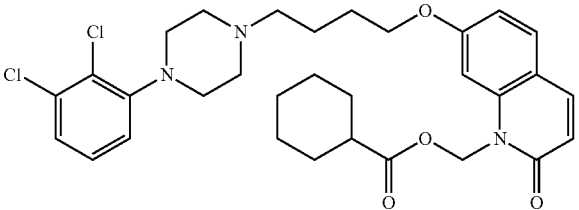 |
| 185 | 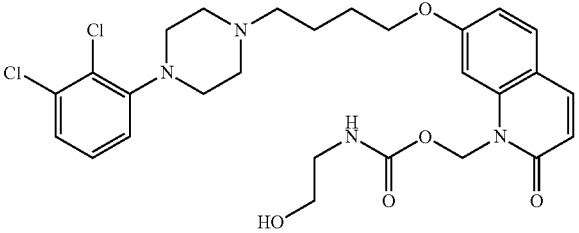 |
| 186 | 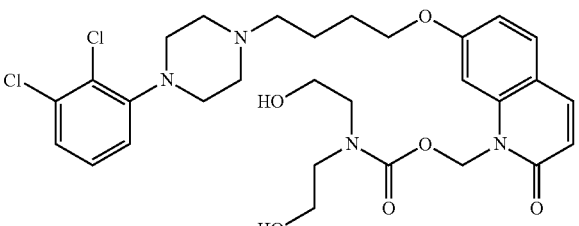 |
| 187 | 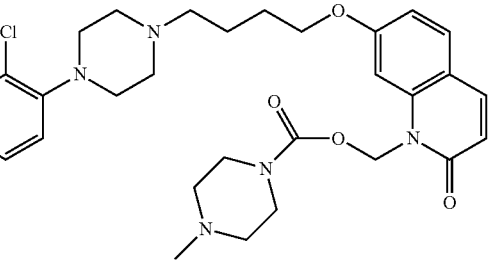 |

TABLE B-continued
| No | Structure |
|---|---|
| 188 | 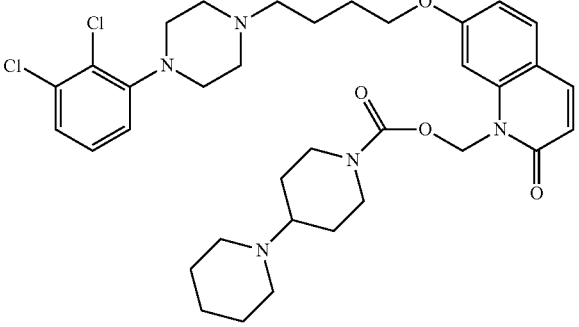 |
| 189 | 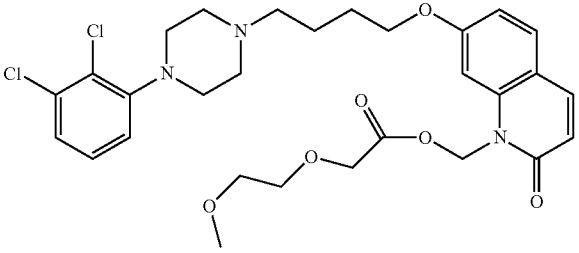 |
| 190 | 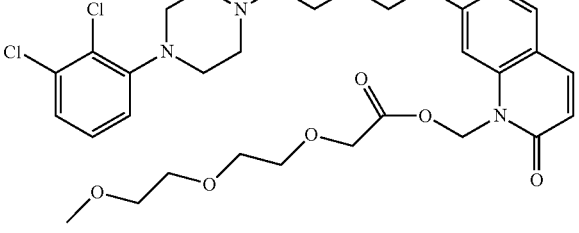 |
| 191 | 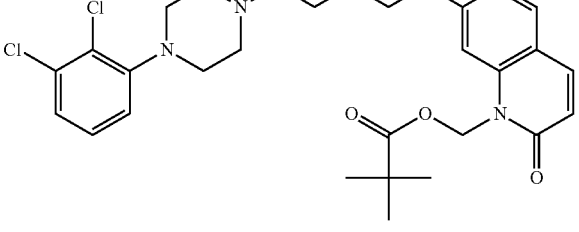 |
| 192 | 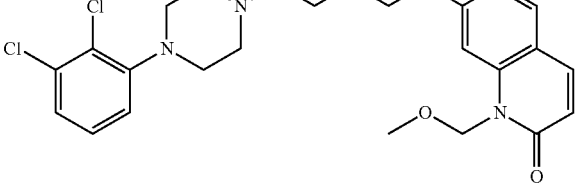 |
| 193 | 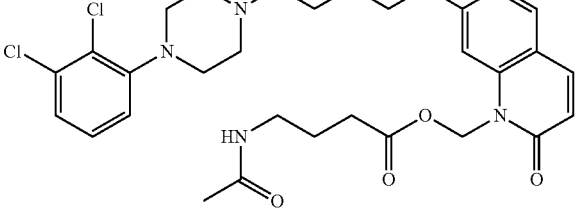 |

TABLE B-continued

| No | Structure |
|---|---|
| 194 | 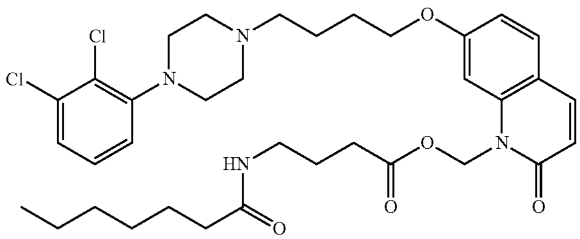 |
| 195 | 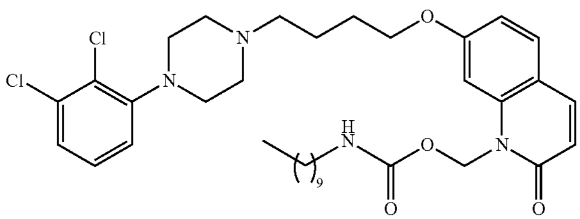 |
| 196 | 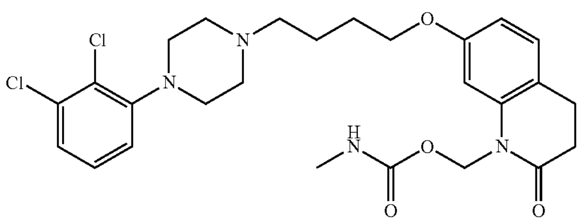 [SMILES: CNC(=O)OCN1C(=O)CCc2ccc(OCCCCN3CCN(c4cccc(Cl)c4Cl)CC3)cc21] |
| 197 | 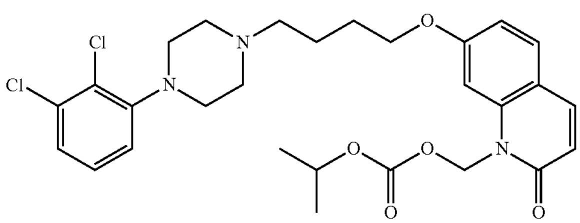 |
| 198 | 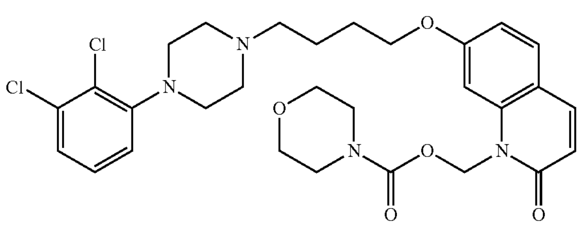 [SMILES: O=C(OCn1c(=O)ccc2ccc(OCCCCN3CCN(c4cccc(Cl)c4Cl)CC3)cc21)N1CCOCC1] |
| 199 | 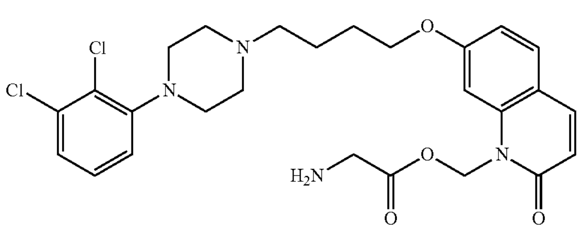 [SMILES: NCC(=O)OCn1c(=O)ccc2ccc(OCCCCN3CCN(c4cccc(Cl)c4Cl)CC3)cc21] |
| 200 | 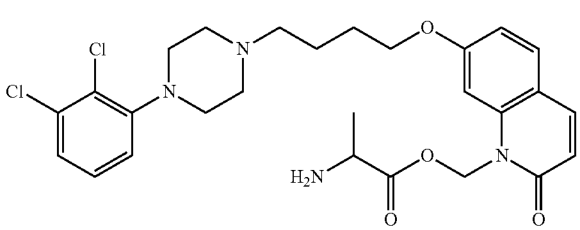 [SMILES: CC(N)C(=O)OCn1c(=O)ccc2ccc(OCCCCN3CCN(c4cccc(Cl)c4Cl)CC3)cc21] |

TABLE B-continued
| No | Structure |
|---|---|
| 201 | 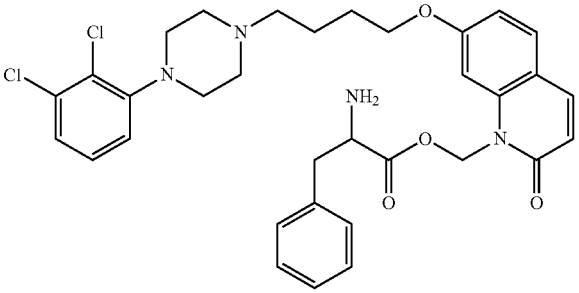 |
| 202 | 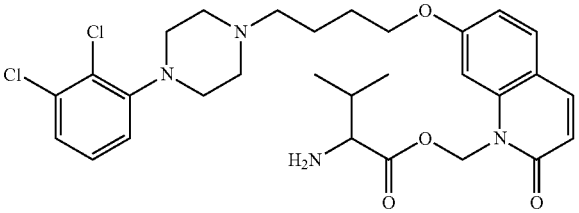 |
| 203 | 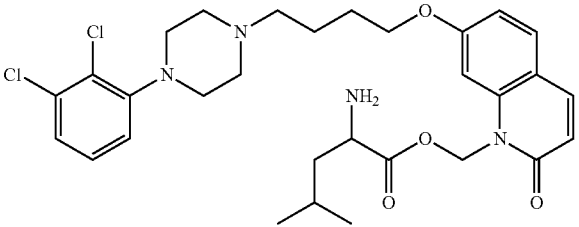 |
| 204 | 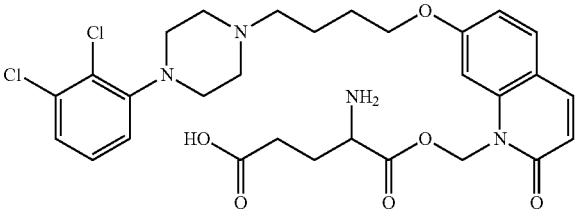 |
| 205 | 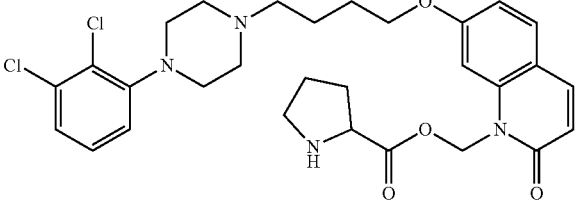 |
| 206 | 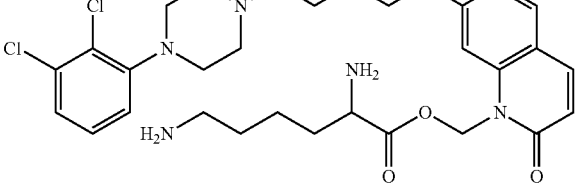 |

TABLE B-continued
| No | Structure |
|---|---|
| 207 | 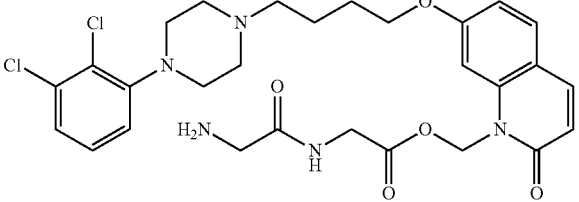 |
| 208 | 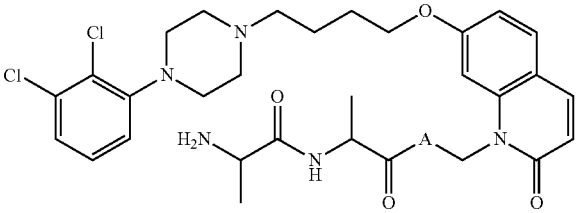 |
| 209 | 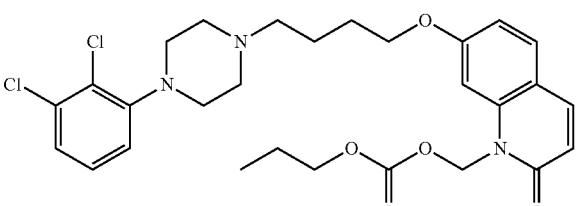 |
| 210 | 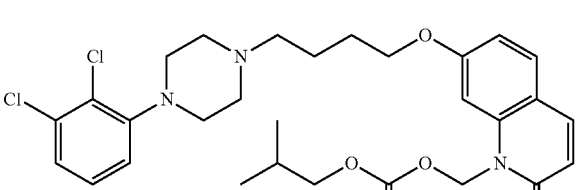 |
| 211 | 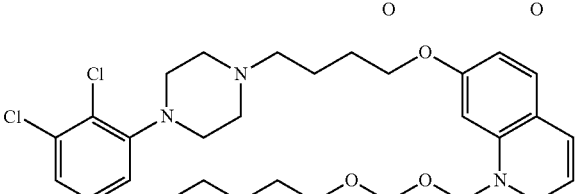 |
| 212 | 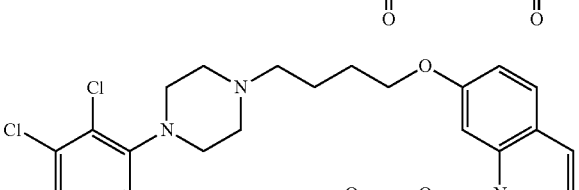 |
| 213 | 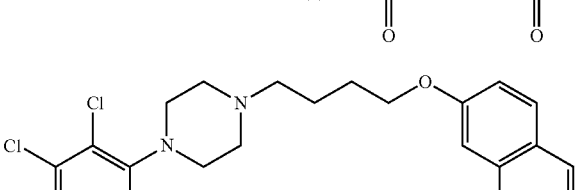 |

TABLE B-continued

| No | Structure |
|----|-----------|
| 214 | 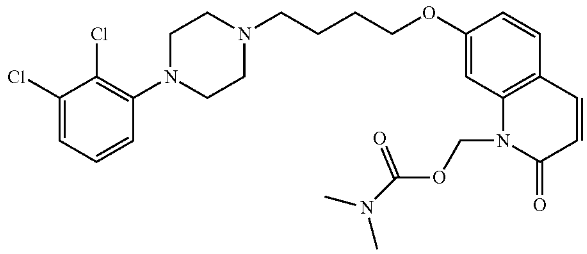 [SMILES: CN(C)C(=O)OCn1c(=O)ccc2ccc(OCCCCN3CCN(c4cccc(Cl)c4Cl)CC3)cc21] |
| 215 | 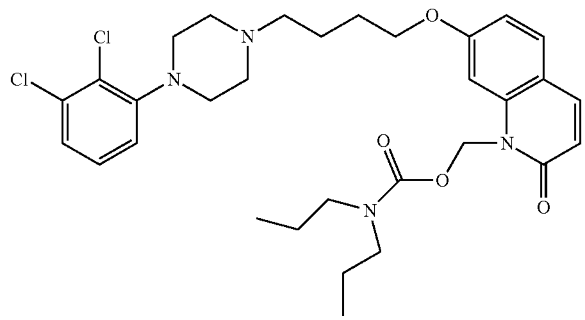 [SMILES: CCCN(CCC)C(=O)OCn1c(=O)ccc2ccc(OCCCCN3CCN(c4cccc(Cl)c4Cl)CC3)cc21] |
| 216 | 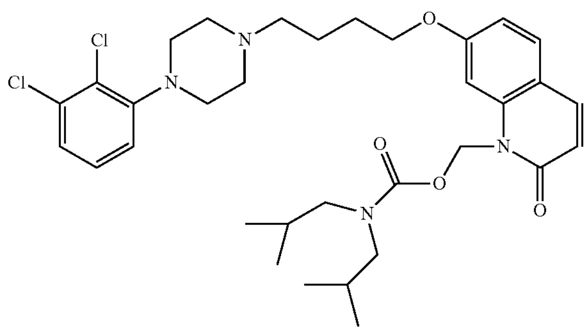 [SMILES: CC(C)CN(CC(C)C)C(=O)OCn1c(=O)ccc2ccc(OCCCCN3CCN(c4cccc(Cl)c4Cl)CC3)cc21] |
| 217 | 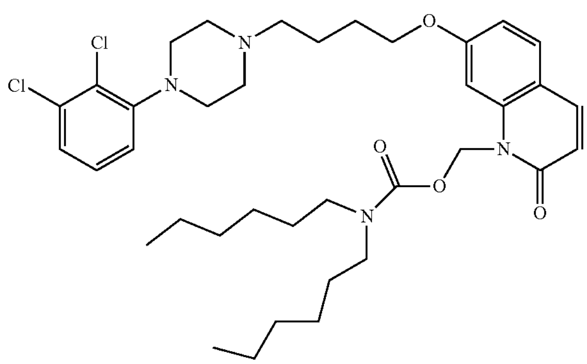 [SMILES: CCCCCCN(CCCCCC)C(=O)OCn1c(=O)ccc2ccc(OCCCCN3CCN(c4cccc(Cl)c4Cl)CC3)cc21] |
| 218 | 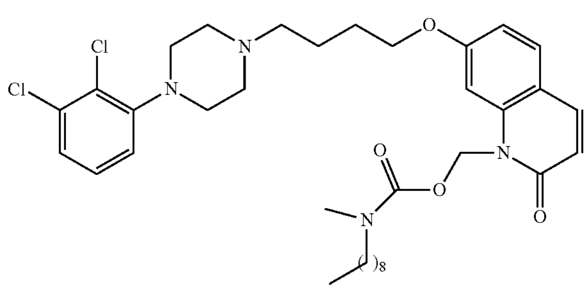 |

TABLE B-continued
| No | Structure |
|---|---|
| 219 | 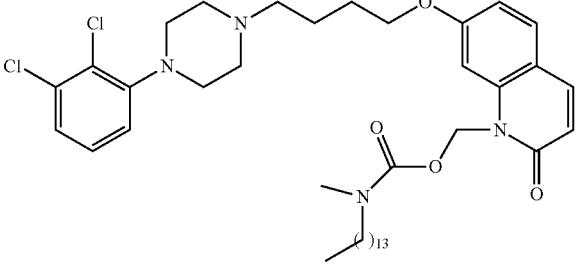 |
| 220 | 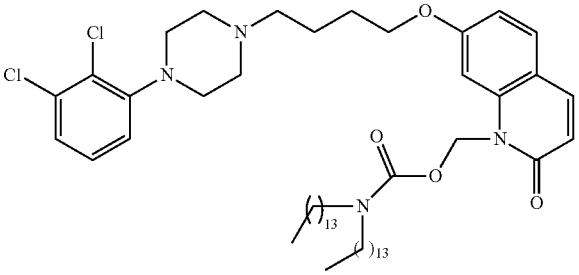 |
| 221 | 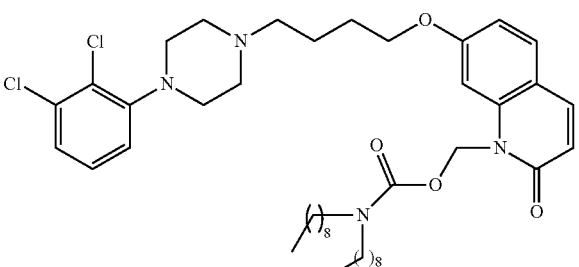 |
| 222 | 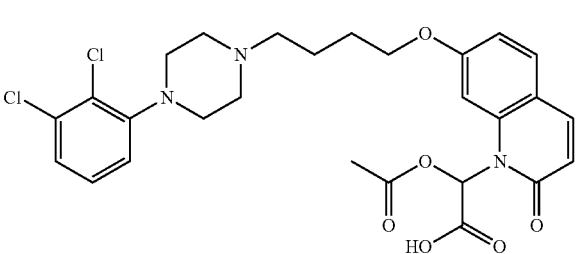 [SMILES: CC(=O)OC(C(=O)O)n1c(=O)ccc2ccc(OCCCCN3CCN(c4cccc(Cl)c4Cl)CC3)cc21] |
| 223 | 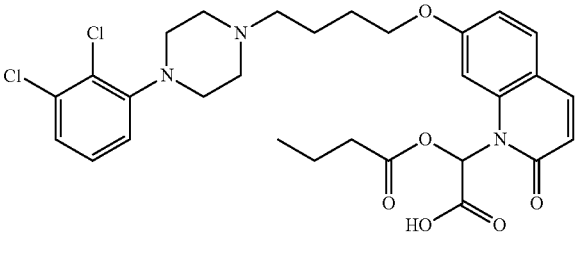 |
| 224 | 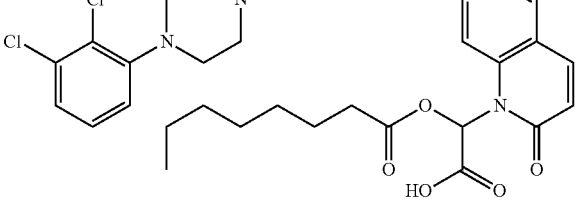 |

TABLE B-continued

| No | Structure |
|---|---|
| 225 | 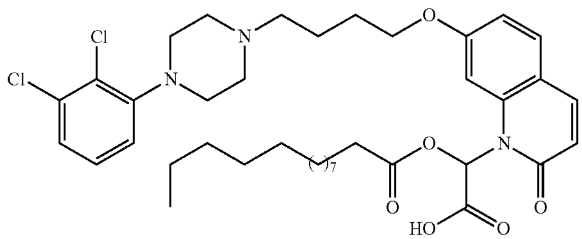 |
| 226 | 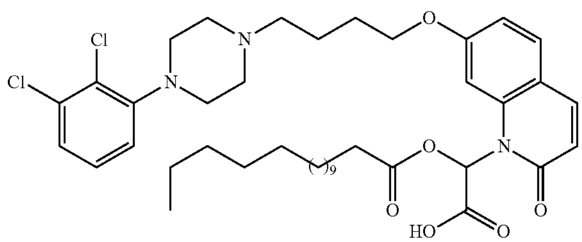 |
| 227 | 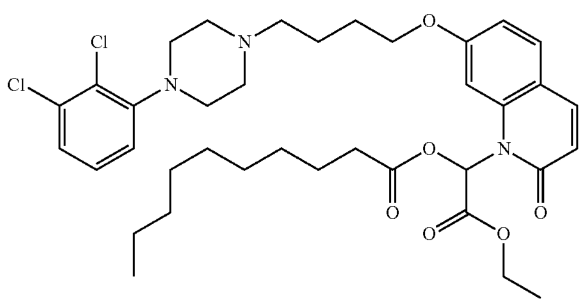 [SMILES: CCCCCCCCCC(=O)OC(C(=O)OCC)n1c(=O)ccc2ccc(OCCCCN3CCN(c4cccc(Cl)c4Cl)CC3)cc21] |
| 228 | 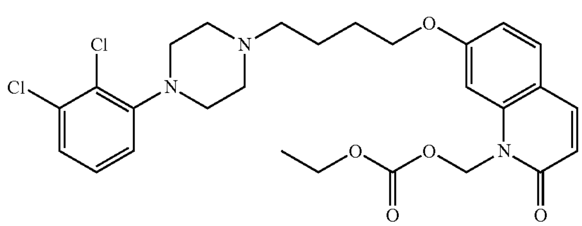 |
| 229 | 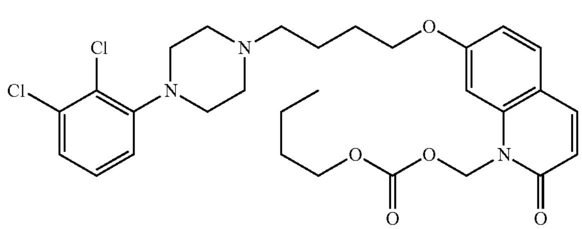 [SMILES: CCCCOC(=O)OCn1c(=O)ccc2ccc(OCCCCN3CCN(c4cccc(Cl)c4Cl)CC3)cc21] |
| 230 | 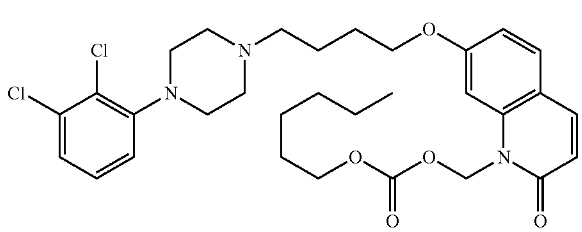 |

TABLE B-continued

| No | Structure |
|---|---|
| 231 | (structure) |
| 232 | (structure) |
| 233 | (structure) |
| 234 | (structure) |
| 235 | (structure) |
| 236 | (structure) |
| 237 | (structure) |

TABLE B-continued
| No | Structure |
|---|---|
| 238 | 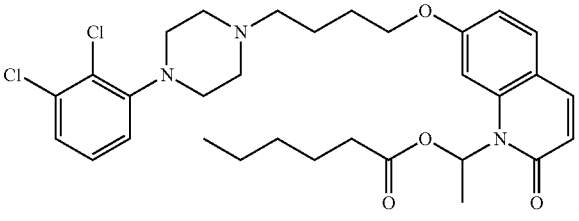 |
| 239 | 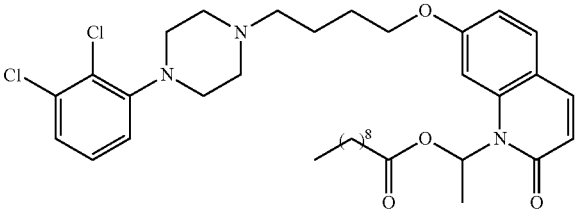 |
| 240 | 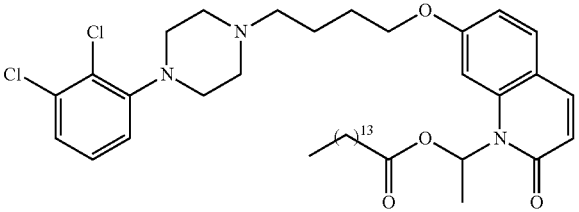 |
| 241 | 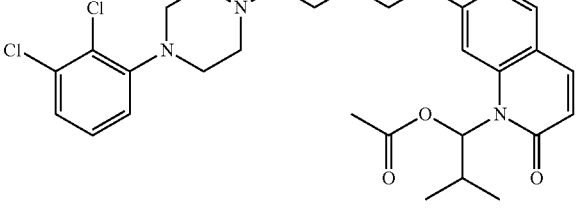 |
| 242 | 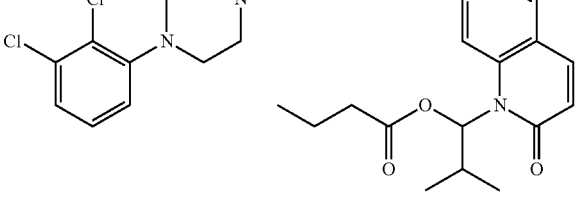 |
| 243 | 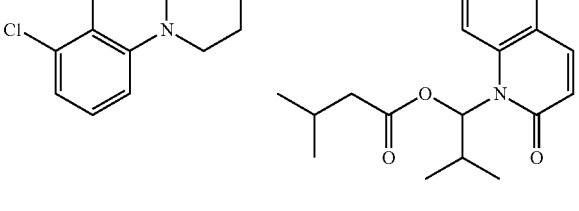 |

TABLE B-continued
| No | Structure |
|---|---|
| 244 | 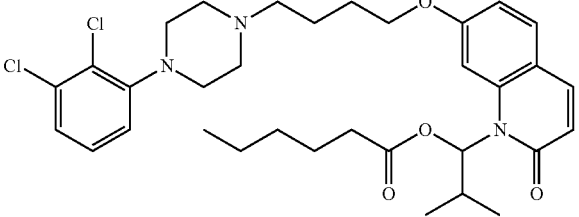 |
| 245 | 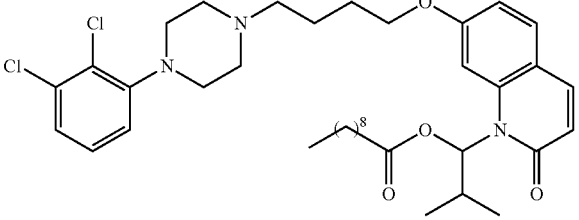 |
| 246 | 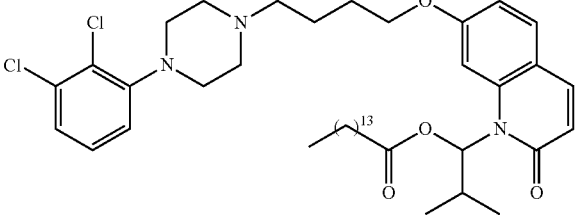 |
| 247 | 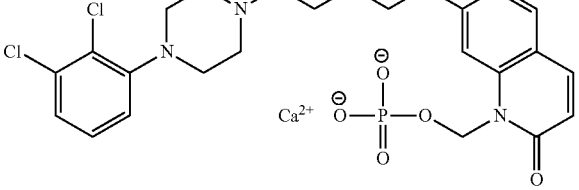 |
| 248 | 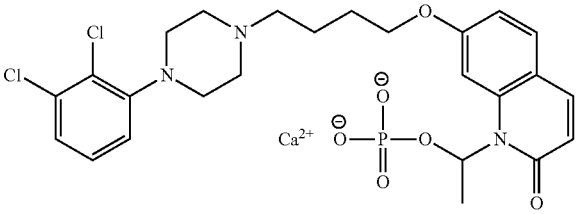 |
| 249 | 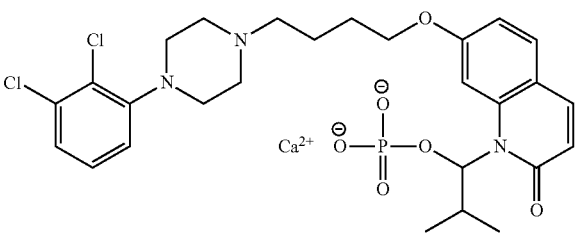 |

TABLE B-continued
| No | Structure |
|---|---|
| 250 | 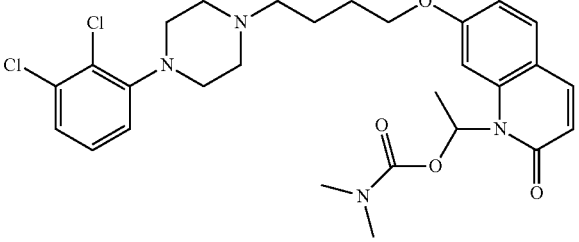 |
| 251 | 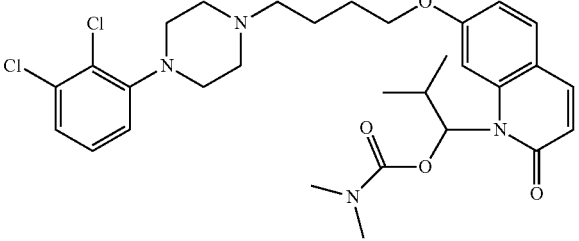 |
| 252 | 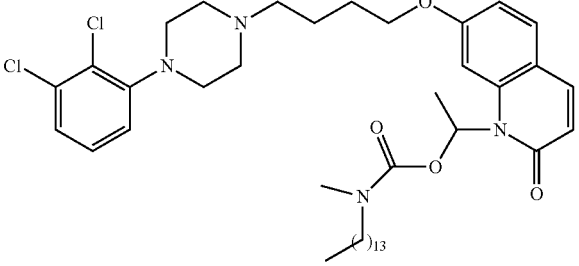 |
| 253 | 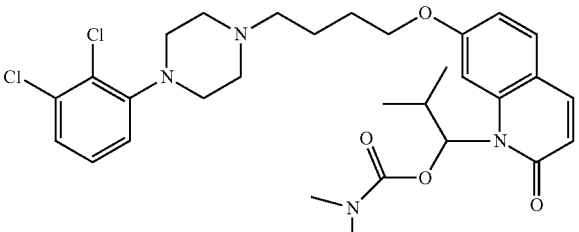 |
| 254 | 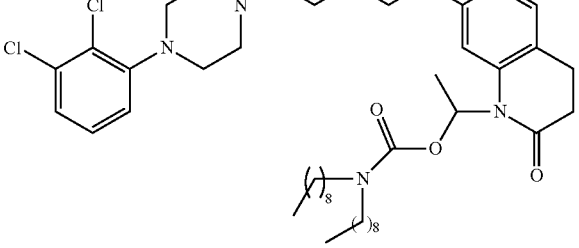 |

TABLE B-continued

| No | Structure |
|---|---|
| 255 | 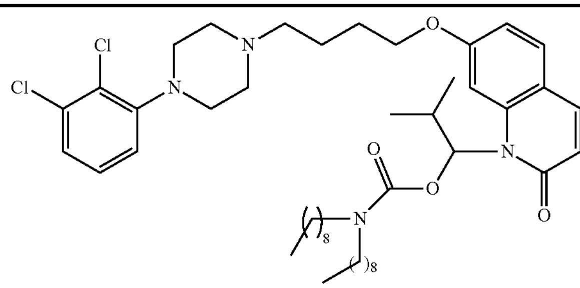 |
| 256 | 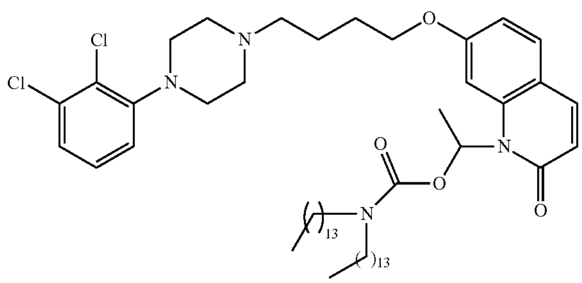 |
| 257 | 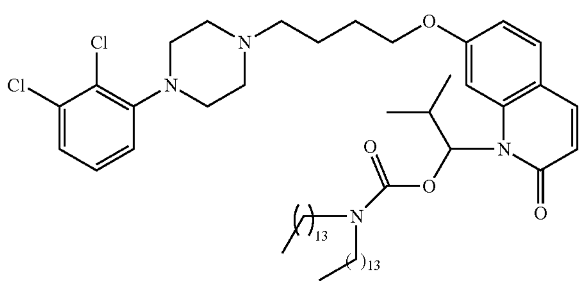 |
| 258 | 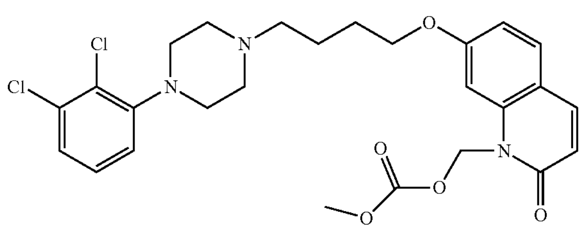 |
| 259 | 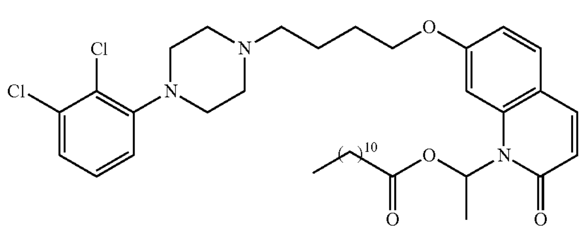 |
| 260 | 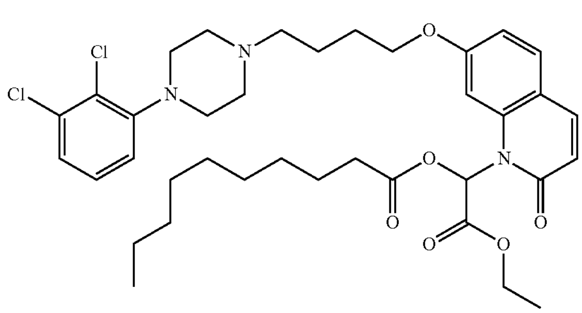 |

TABLE B-continued

| No | Structure |
|---|---|
| 261 | 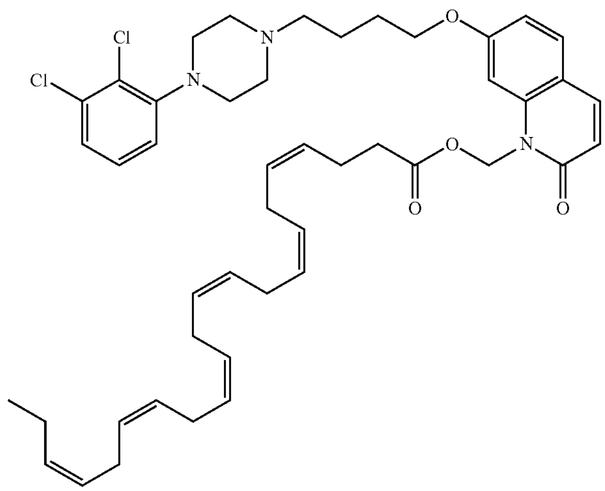 [SMILES: CC/C=C\C/C=C\C/C=C\C/C=C\C/C=C\C/C=C\CCC(=O)OCn1c(=O)ccc2ccc(OCCCCN3CCN(c4cccc(Cl)c4Cl)CC3)cc21] |
| 262 | 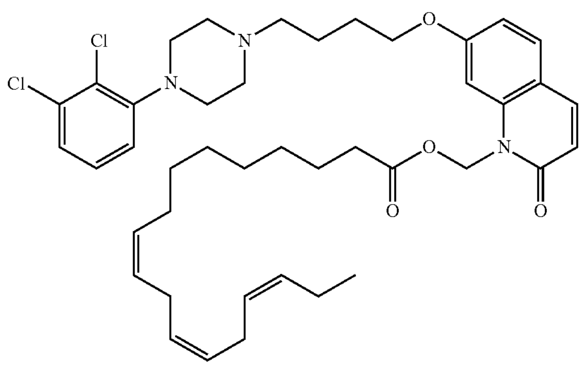 |
| 263 | 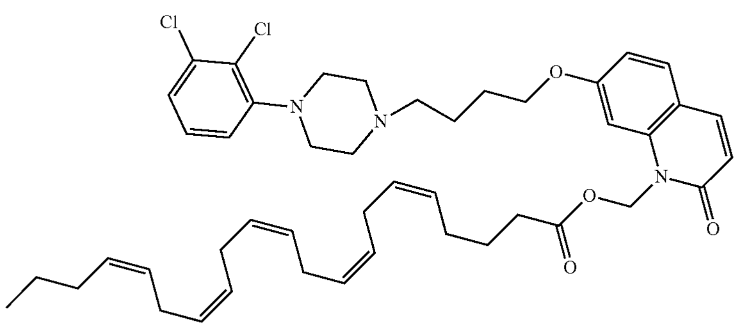 [SMILES: CCC/C=C\C/C=C\C/C=C\C/C=C\C/C=C\CCCC(=O)OCn1c(=O)ccc2ccc(OCCCCN3CCN(c4cccc(Cl)c4Cl)CC3)cc21] |
| 264 | 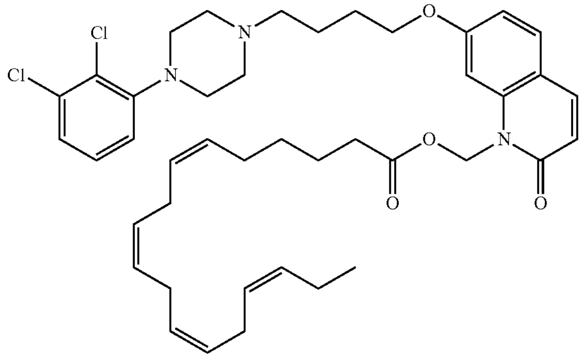 |

TABLE B-continued
| No | Structure |
|---|---|
| 265 | 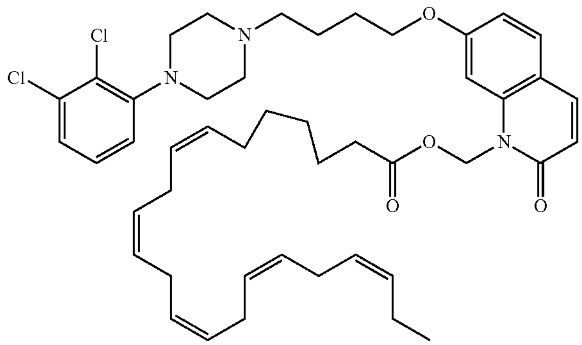 [SMILES: CC/C=C\C/C=C\C/C=C\C/C=C\C/C=C\CCCCCC(=O)OCn1c(=O)ccc2ccc(OCCCCN3CCN(c4cccc(Cl)c4Cl)CC3)cc21] |
| 266 | 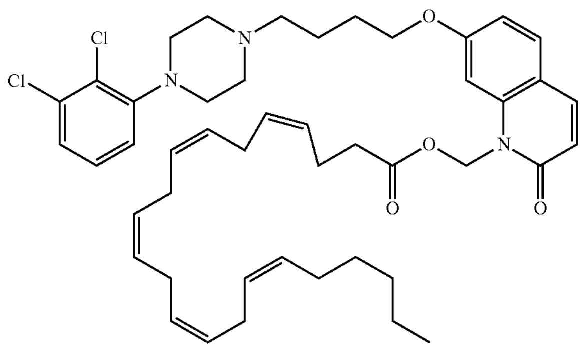 [SMILES: CCCCC/C=C\C/C=C\C/C=C\C/C=C\C/C=C\CCC(=O)OCn1c(=O)ccc2ccc(OCCCCN3CCN(c4cccc(Cl)c4Cl)CC3)cc21] |
| 267 | 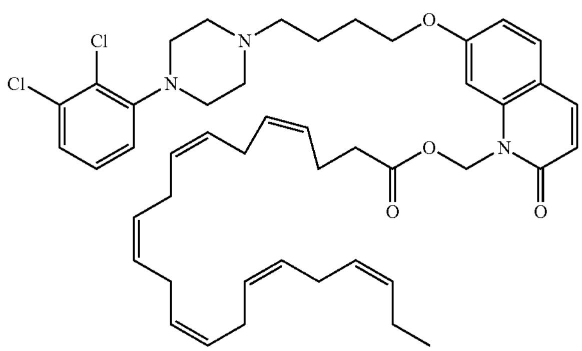 [SMILES: CC/C=C\C/C=C\C/C=C\C/C=C\C/C=C\C/C=C\CCC(=O)OCn1c(=O)ccc2ccc(OCCCCN3CCN(c4cccc(Cl)c4Cl)CC3)cc21] |
In a preferred embodiment, a compound having Formula XXI is provided:
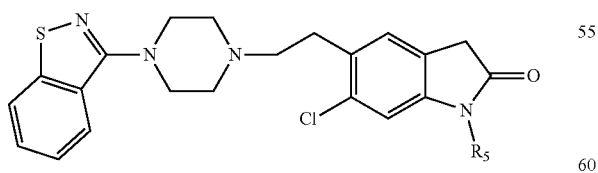
Formula XXI
wherein $R_5$ is selected from Table-1. In a more preferred compound $R_5$ is selected from Tables 2-4.

Representative compounds according to the invention are those selected from the Table C below or its geometric isomers, enantiomers, diastereomers, racemates, pharmaceutically acceptable salts, prodrugs and solvates thereof:

TABLE C

| No. | Structure |
|---|---|
| 300 | 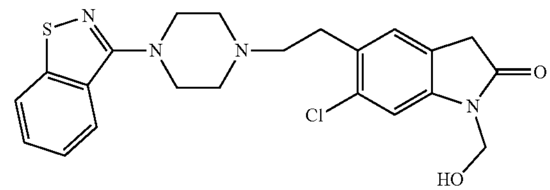 [SMILES: O=C1Cc2cc(CCN3CCN(c4nsc5ccccc45)CC3)c(Cl)cc2N1CO] |
| 301 | 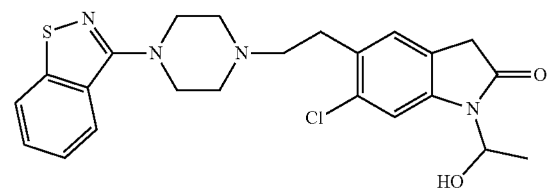 [SMILES: CC(O)N1C(=O)Cc2cc(CCN3CCN(c4nsc5ccccc45)CC3)c(Cl)cc21] |
| 302 | 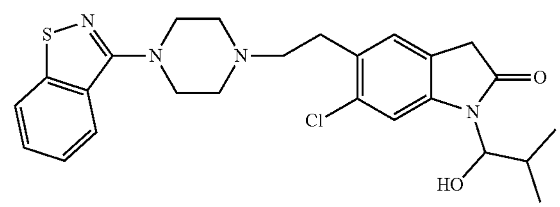 [SMILES: CC(C)C(O)N1C(=O)Cc2cc(CCN3CCN(c4nsc5ccccc45)CC3)c(Cl)cc21] |
| 303 | 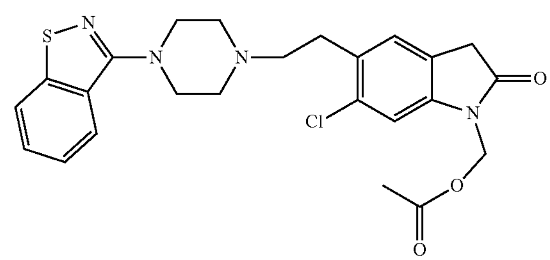 [SMILES: CC(=O)OCN1C(=O)Cc2cc(CCN3CCN(c4nsc5ccccc45)CC3)c(Cl)cc21] |
| 304 | 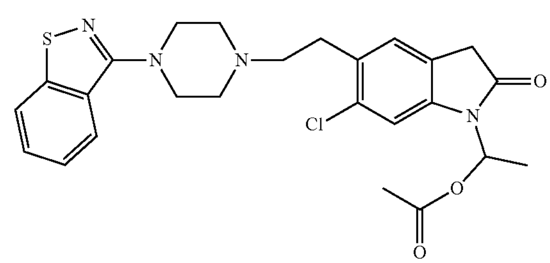 [SMILES: CC(=O)OC(C)N1C(=O)Cc2cc(CCN3CCN(c4nsc5ccccc45)CC3)c(Cl)cc21] |
| 305 | 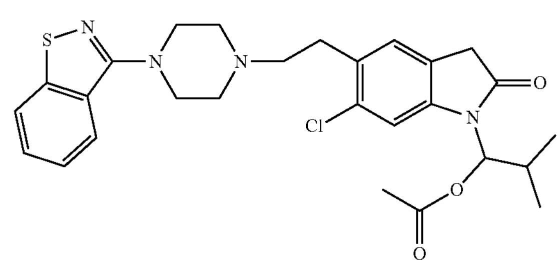 [SMILES: CC(=O)OC(C(C)C)N1C(=O)Cc2cc(CCN3CCN(c4nsc5ccccc45)CC3)c(Cl)cc21] |

TABLE C-continued

| No. | Structure |
|---|---|
| 306 | 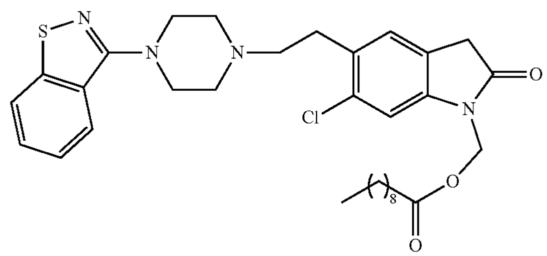 |
| 307 | 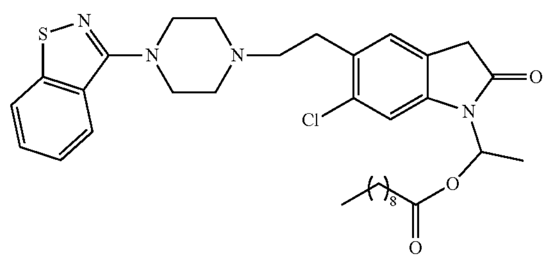 |
| 308 | 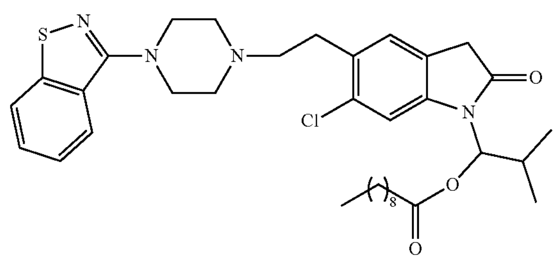 |
| 309 | 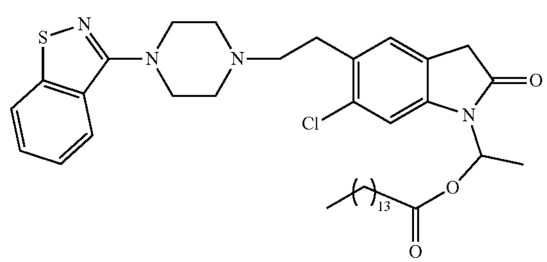 |
| 310 | 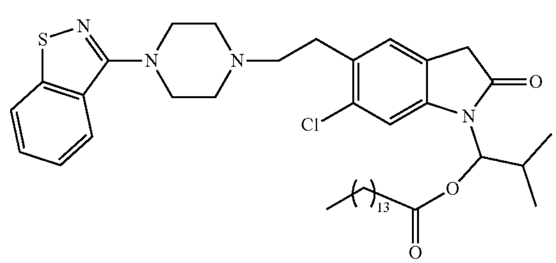 |
| 311 | 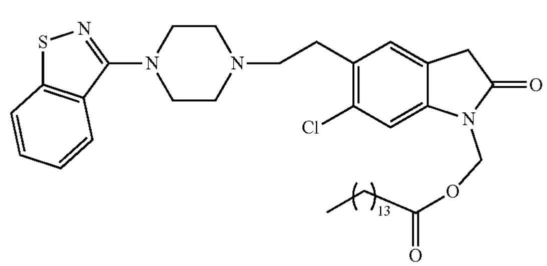 |

TABLE C-continued
| No. | Structure |
|---|---|
| 312 | 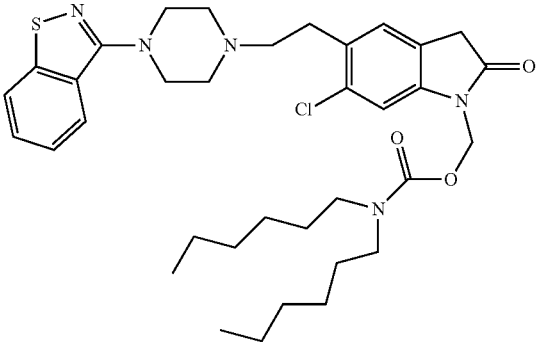 [SMILES: CCCCCCN(CCCCCC)C(=O)OCN1C(=O)Cc2cc(CCN3CCN(c4nsc5ccccc45)CC3)c(Cl)cc21] |
| 313 | 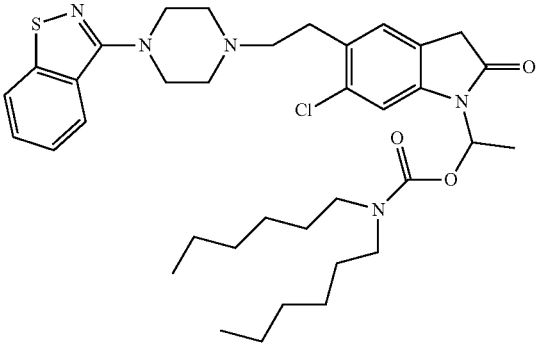 [SMILES: CCCCCCN(CCCCCC)C(=O)OC(C)N1C(=O)Cc2cc(CCN3CCN(c4nsc5ccccc45)CC3)c(Cl)cc21] |
| 314 | 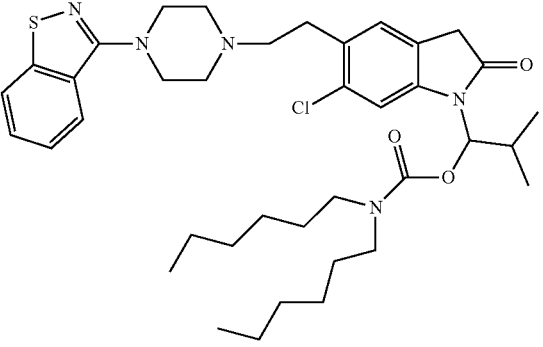 [SMILES: CCCCCCN(CCCCCC)C(=O)OC(C(C)C)N1C(=O)Cc2cc(CCN3CCN(c4nsc5ccccc45)CC3)c(Cl)cc21] |
| 315 | 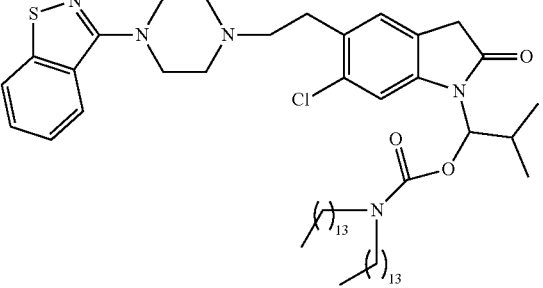 |

TABLE C-continued
| No. | Structure |
|---|---|
| 316 | 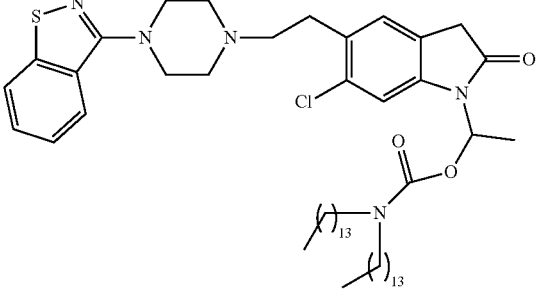 |
| 317 | 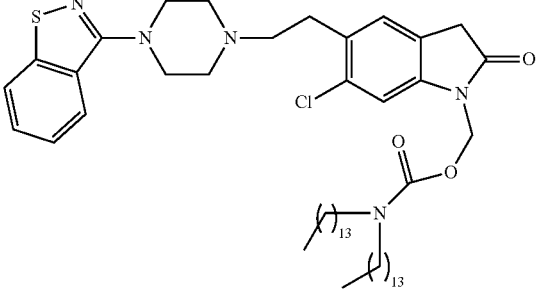 |
| 318 | 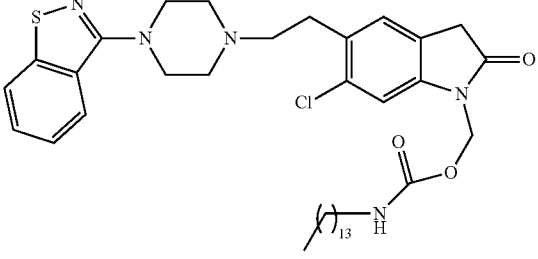 |
| 319 | 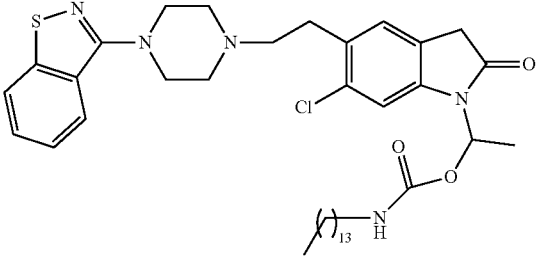 |
| 320 | 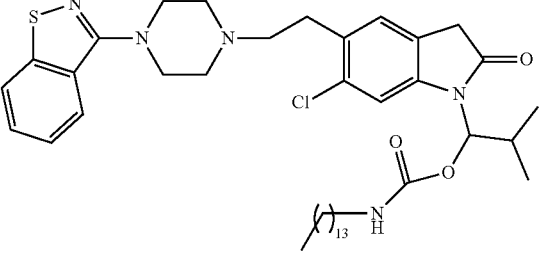 |

TABLE C-continued
| No. | Structure |
|---|---|
| 321 | 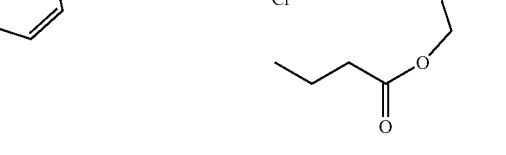 |
| 322 | 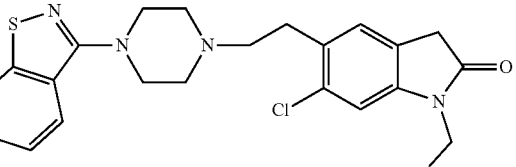 |
| 323 | 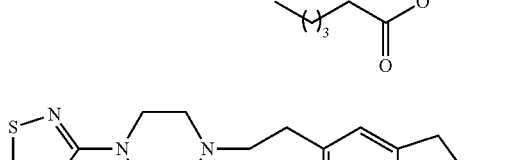 |
| 324 | 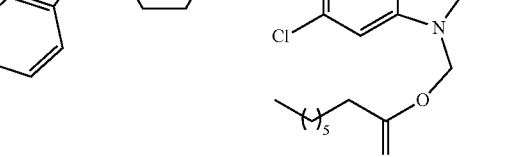 |
| 325 | 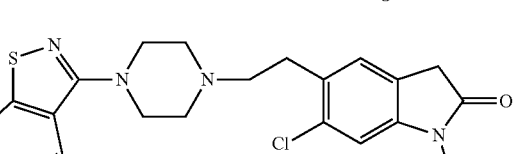 |
| 326 | 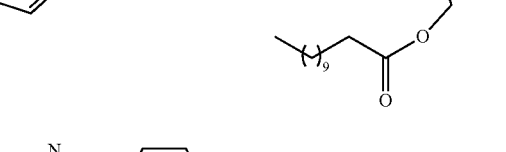 |

TABLE C-continued

| No. | Structure |
|---|---|
| 327 | 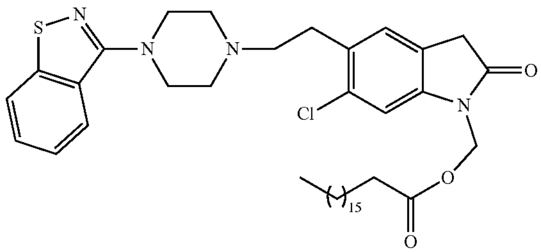 |
| 328 | 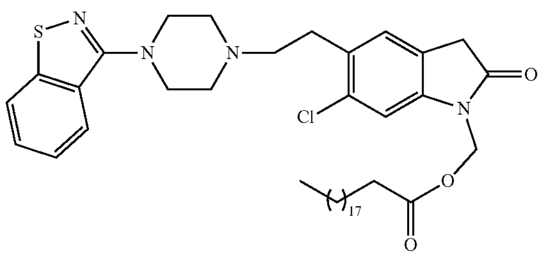 |
| 329 | 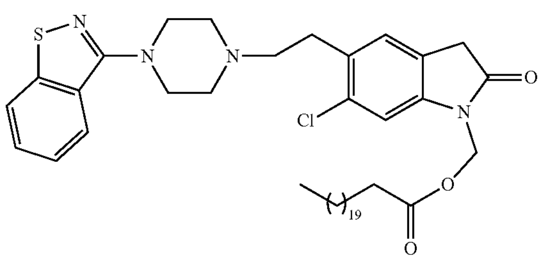 |
| 330 | 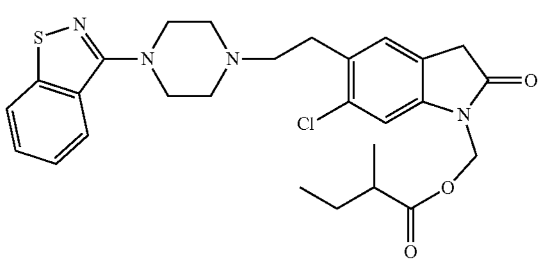 [SMILES: CCC(C)C(=O)OCN1C(=O)Cc2cc(CCN3CCN(c4nsc5ccccc45)CC3)c(Cl)cc21] |
| 331 | 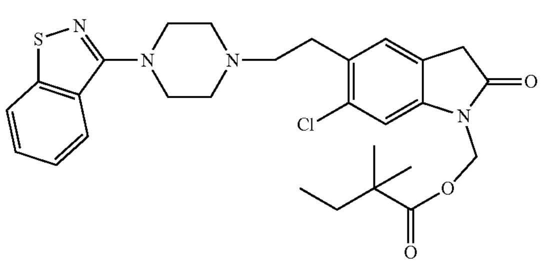 [SMILES: CCC(C)(C)C(=O)OCN1C(=O)Cc2cc(CCN3CCN(c4nsc5ccccc45)CC3)c(Cl)cc21] |

TABLE C-continued

| No. | Structure |
|---|---|
| 332 | 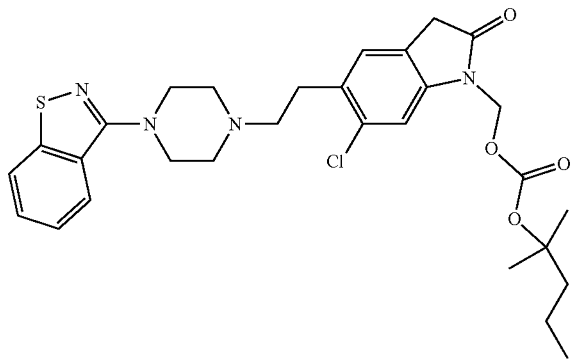 [SMILES: CCCC(C)(C)OC(=O)OCN1C(=O)Cc2cc(CCN3CCN(c4nsc5ccccc45)CC3)c(Cl)cc21] |
| 333 | 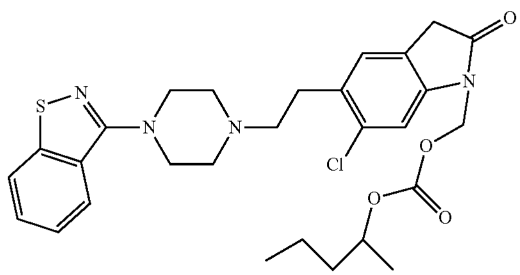 [SMILES: CCCC(C)OC(=O)OCN1C(=O)Cc2cc(CCN3CCN(c4nsc5ccccc45)CC3)c(Cl)cc21] |
| 334 | 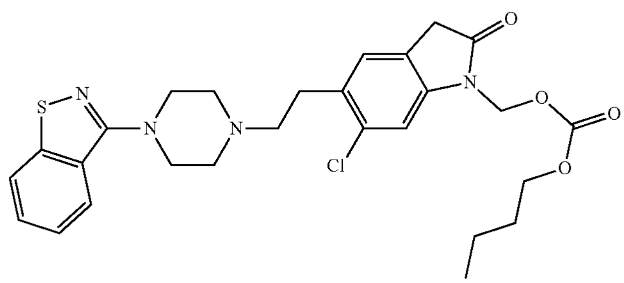 [SMILES: CCCCOC(=O)OCN1C(=O)Cc2cc(CCN3CCN(c4nsc5ccccc45)CC3)c(Cl)cc21] |
| 335 | 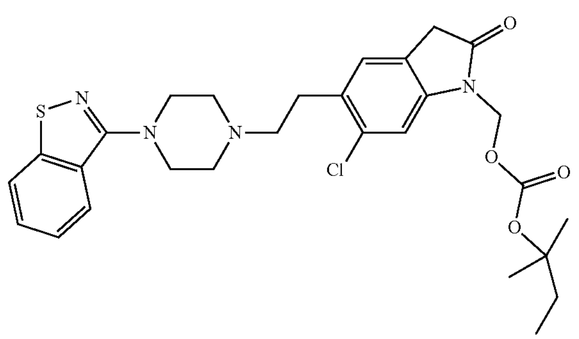 [SMILES: CCC(C)(C)OC(=O)OCN1C(=O)Cc2cc(CCN3CCN(c4nsc5ccccc45)CC3)c(Cl)cc21] |
| 336 | 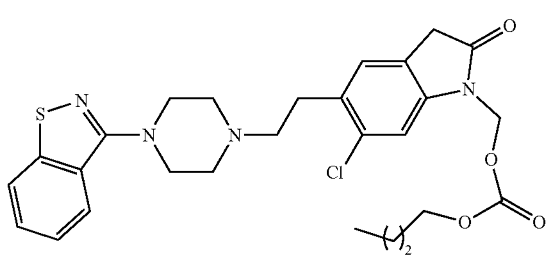 |

TABLE C-continued

| No. | Structure |
|---|---|
| 337 | (structure) |
| 338 | (structure) |
| 339 | (structure) |
| 340 | (structure) |
| 341 | (structure) |
| 342 | (structure) |

TABLE C-continued
| No. | Structure |
|---|---|
| 343 | 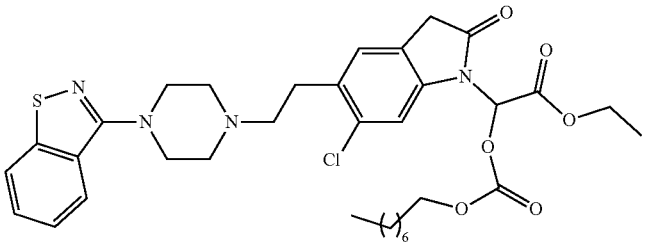 |
| 344 | 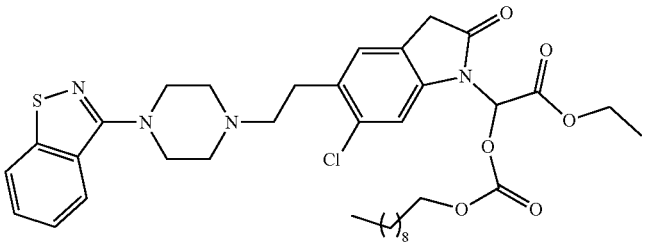 |
| 345 | 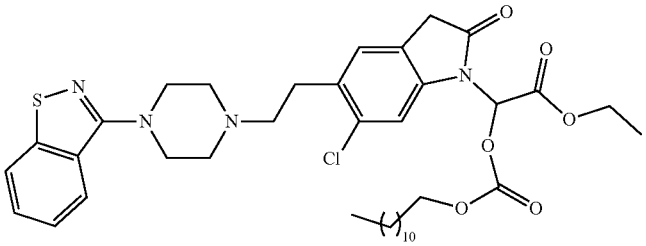 |
| 346 | 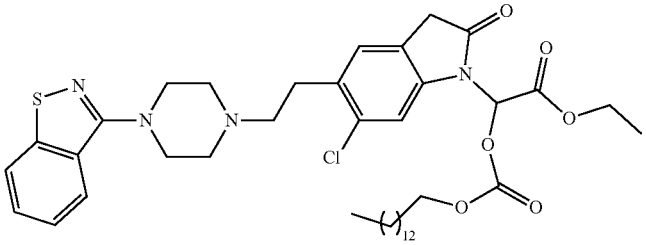 |
| 347 | 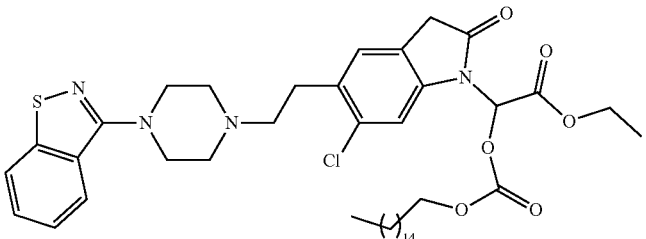 |
| 348 | 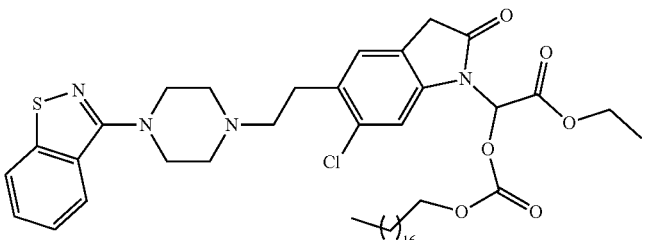 |

TABLE C-continued
| No. | Structure |
|---|---|
| 349 | 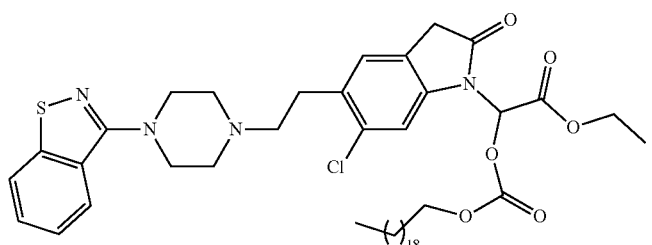 |
| 350 | 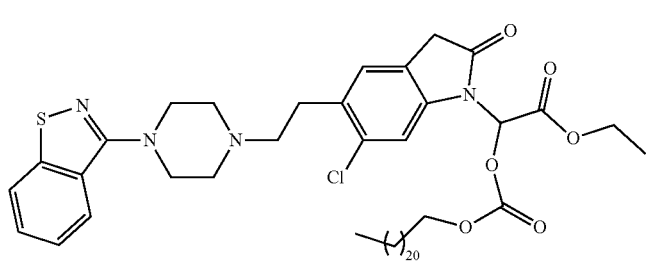 |
| 351 | 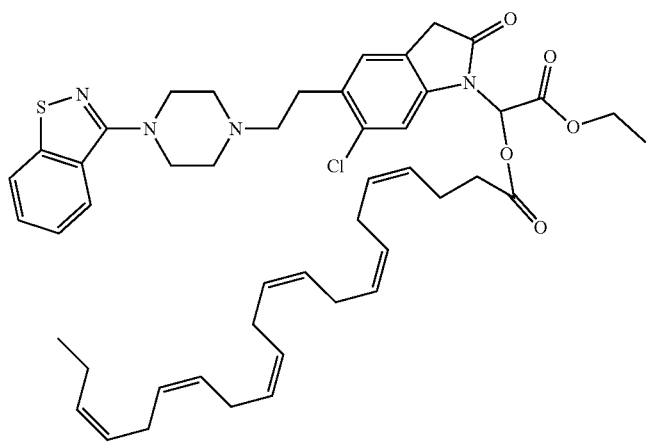 [SMILES: CC/C=C\C/C=C\C/C=C\C/C=C\C/C=C\C/C=C\CCC(=O)OC(C(=O)OCC)N1C(=O)Cc2cc(CCN3CCN(c4nsc5ccccc45)CC3)c(Cl)cc21] |
| 352 | 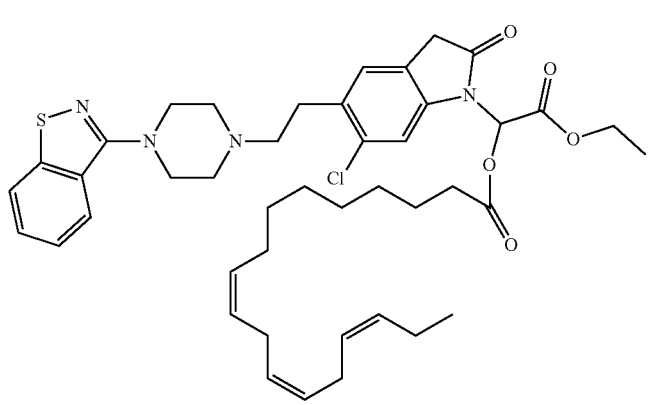 [SMILES: CC/C=C\C/C=C\C/C=C\CCCCCCCC(=O)OC(C(=O)OCC)N1C(=O)Cc2cc(CCN3CCN(c4nsc5ccccc45)CC3)c(Cl)cc21] |

TABLE C-continued

| No. | Structure |
|---|---|
| 353 | 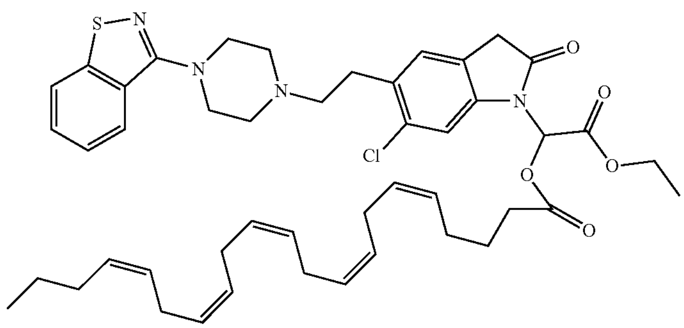 [SMILES: CCC/C=C\C/C=C\C/C=C\C/C=C\C/C=C\CCCC(=O)OC(C(=O)OCC)N1C(=O)Cc2cc(CCN3CCN(c4nsc5ccccc45)CC3)c(Cl)cc21] |
| 354 | 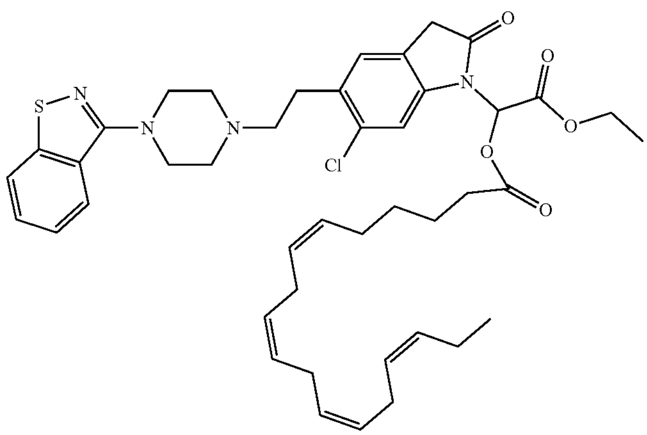 [SMILES: CC/C=C\C/C=C\C/C=C\C/C=C\CCCCC(=O)OC(C(=O)OCC)N1C(=O)Cc2cc(CCN3CCN(c4nsc5ccccc45)CC3)c(Cl)cc21] |
| 355 | 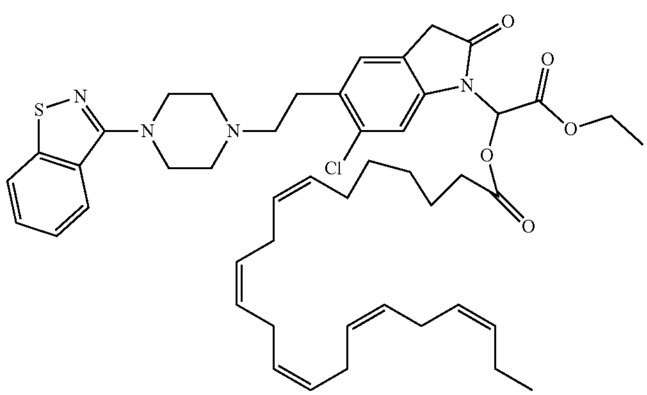 [SMILES: CC/C=C\C/C=C\C/C=C\C/C=C\C/C=C\CCCCCC(=O)OC(C(=O)OCC)N1C(=O)Cc2cc(CCN3CCN(c4nsc5ccccc45)CC3)c(Cl)cc21] |
| 356 | 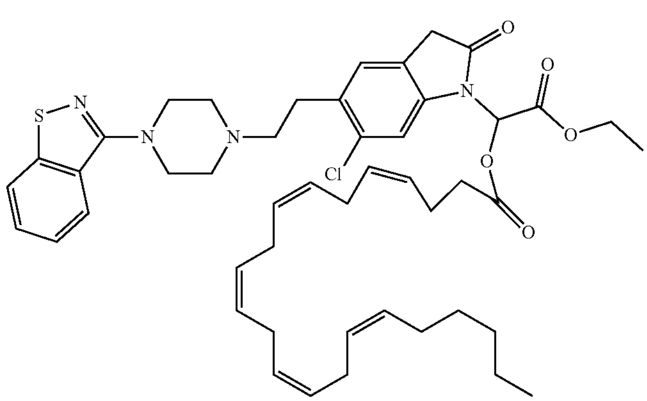 [SMILES: CCCCC/C=C\C/C=C\C/C=C\C/C=C\C/C=C\CCC(=O)OC(C(=O)OCC)N1C(=O)Cc2cc(CCN3CCN(c4nsc5ccccc45)CC3)c(Cl)cc21] |

TABLE C-continued

| No. | Structure |
|---|---|
| 357 | (structure shown) |

In a preferred embodiment, a compound having Formula XXII is provided:

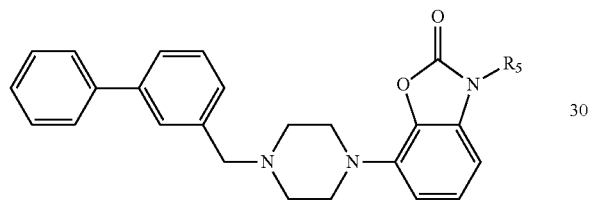

Formula XXII wherein $R_5$ is selected from Table 1. In a more preferred compound $R_5$ is selected from Tables 2-4.

Representative compounds according to the invention are those selected from the Table D below or its geometric isomers, enantiomers, diastereomers, racemates, pharmaceutically acceptable salts and solvates thereof:

TABLE D

| No. | Structure |
|---|---|
| 400 | (structure shown) |
| 401 | (structure shown) |

TABLE D-continued
| No. | Structure |
|---|---|
| 402 | 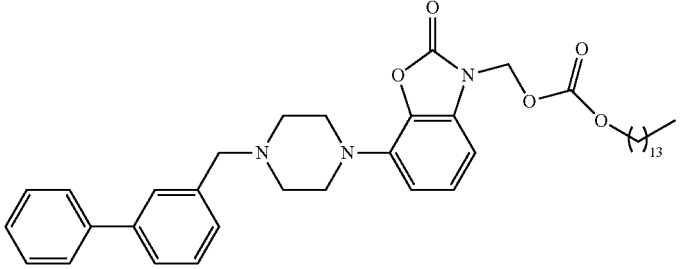 |
| 403 | 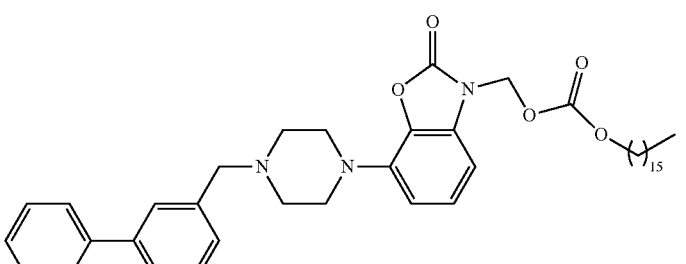 |
| 404 | 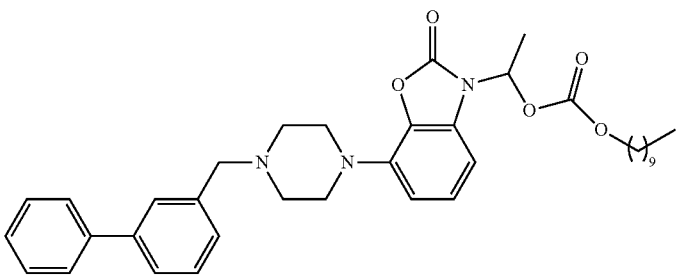 |
| 405 | 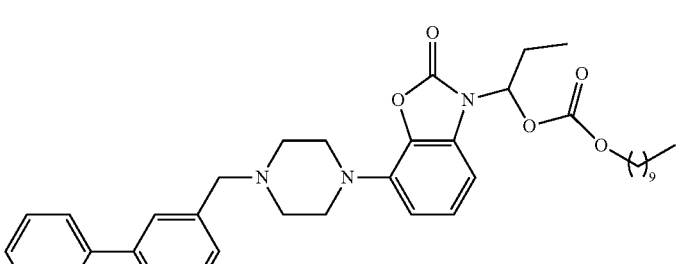 |
| 406 | 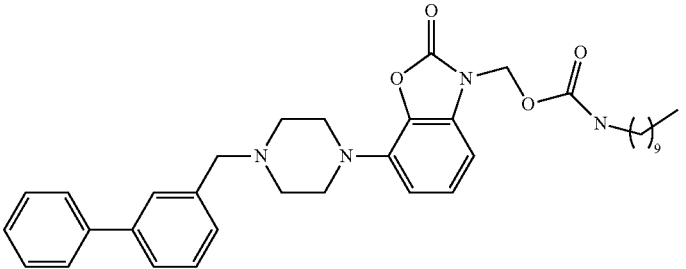 |

TABLE D-continued
| No. | Structure |
|---|---|
| 407 | 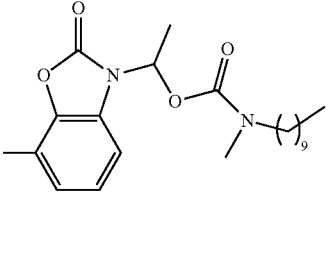 |
| 408 | 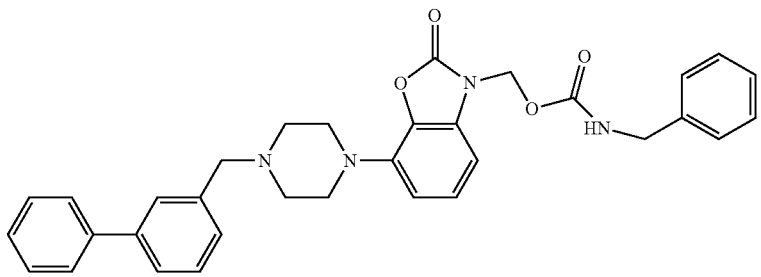 [SMILES: O=C(NCc1ccccc1)OCn1c(=O)oc2c(N3CCN(Cc4cccc(-c5ccccc5)c4)CC3)cccc21] |
| 409 | 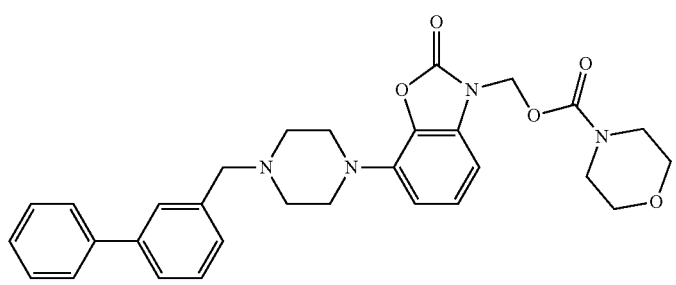 [SMILES: O=C(OCn1c(=O)oc2c(N3CCN(Cc4cccc(-c5ccccc5)c4)CC3)cccc21)N1CCOCC1] |
| 410 | 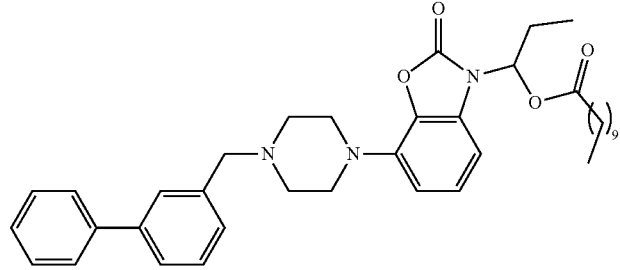 |
| 411 | 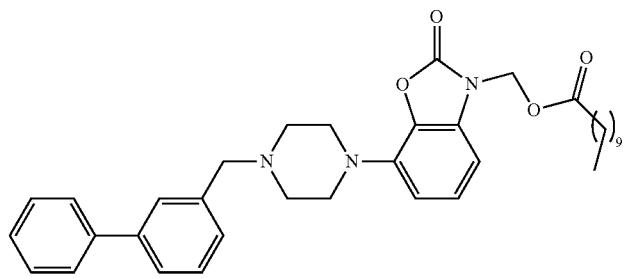 |
| 412 | 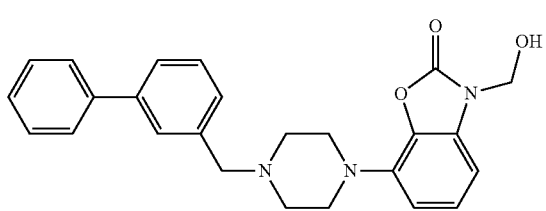 [SMILES: O=c1oc2c(N3CCN(Cc4cccc(-c5ccccc5)c4)CC3)cccc2n1CO] |

TABLE D-continued

| No. | Structure |
|---|---|
| 413 | 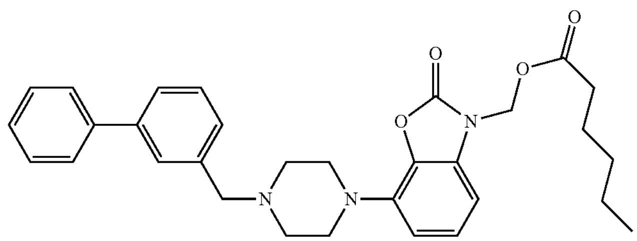 [SMILES: CCCCCC(=O)OCn1c(=O)oc2c(N3CCN(Cc4cccc(-c5ccccc5)c4)CC3)cccc21] |
| 414 | 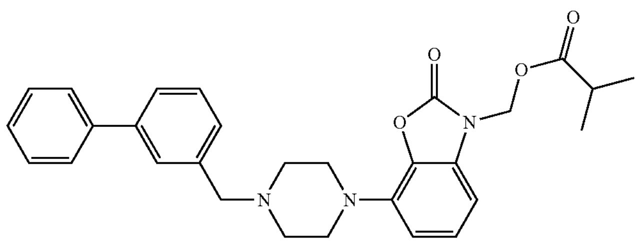 [SMILES: CC(C)C(=O)OCn1c(=O)oc2c(N3CCN(Cc4cccc(-c5ccccc5)c4)CC3)cccc21] |
| 415 | 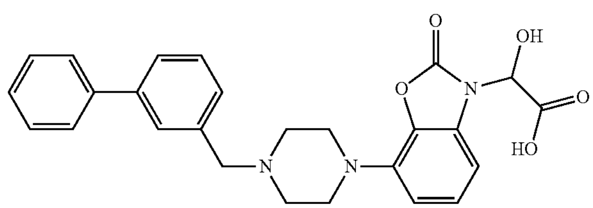 [SMILES: O=C(O)C(O)n1c(=O)oc2c(N3CCN(Cc4cccc(-c5ccccc5)c4)CC3)cccc21] |
| 416 | 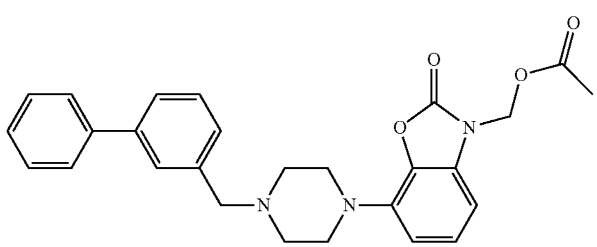 [SMILES: CC(=O)OCn1c(=O)oc2c(N3CCN(Cc4cccc(-c5ccccc5)c4)CC3)cccc21] |
| 417 | 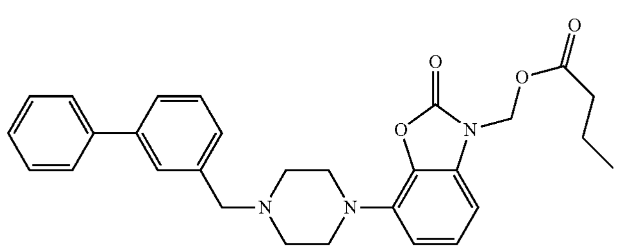 [SMILES: CCCC(=O)OCn1c(=O)oc2c(N3CCN(Cc4cccc(-c5ccccc5)c4)CC3)cccc21] |
| 418 | 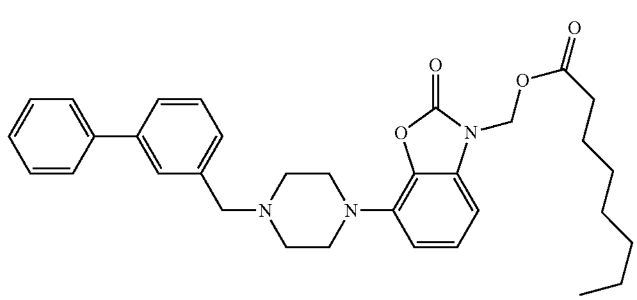 [SMILES: CCCCCCCC(=O)OCn1c(=O)oc2c(N3CCN(Cc4cccc(-c5ccccc5)c4)CC3)cccc21] |

TABLE D-continued
| No. | Structure |
|---|---|
| 419 | 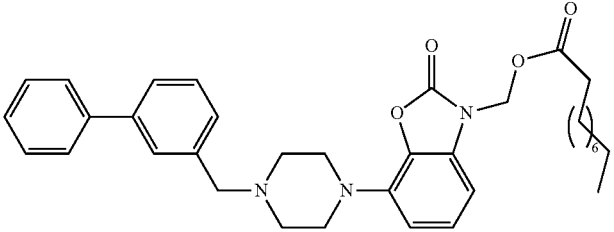 |
| 420 | 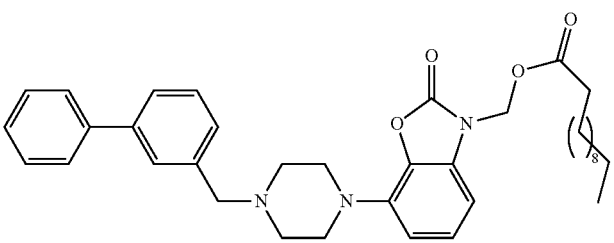 |
| 421 | 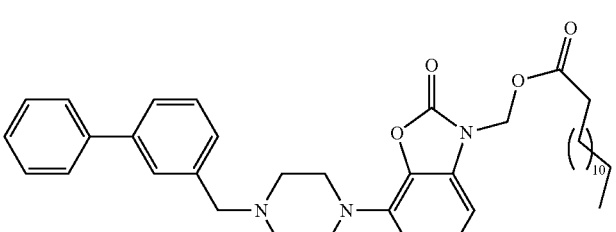 |
| 422 | 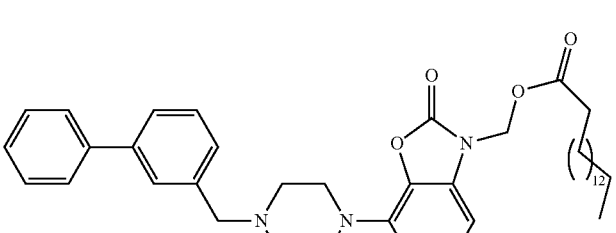 |
| 423 | 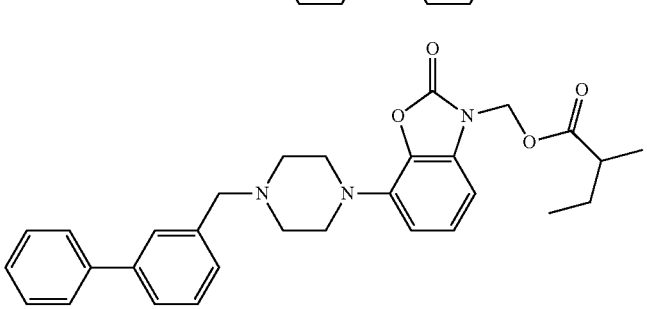 |
| 424 | 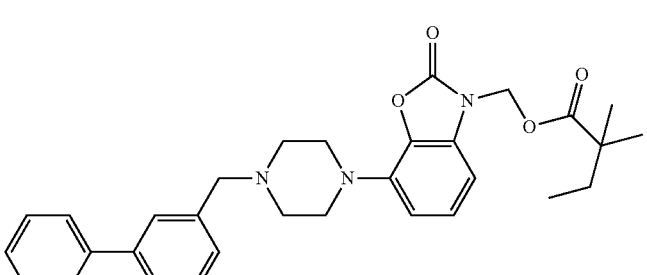 |

TABLE D-continued
| No. | Structure |
|---|---|
| 425 | 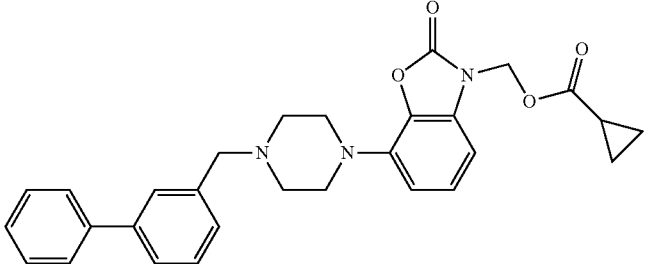 [SMILES: O=C(OCn1c(=O)oc2c(N3CCN(Cc4cccc(-c5ccccc5)c4)CC3)cccc21)C1CC1] |
| 426 | 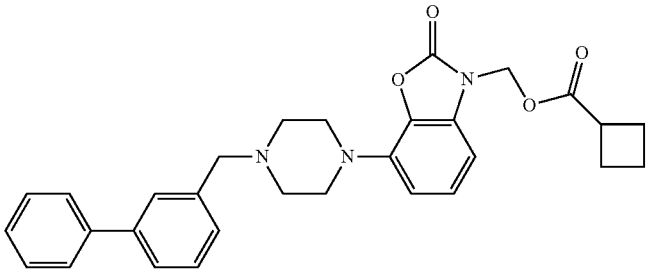 [SMILES: O=C(OCn1c(=O)oc2c(N3CCN(Cc4cccc(-c5ccccc5)c4)CC3)cccc21)C1CCC1] |
| 427 | 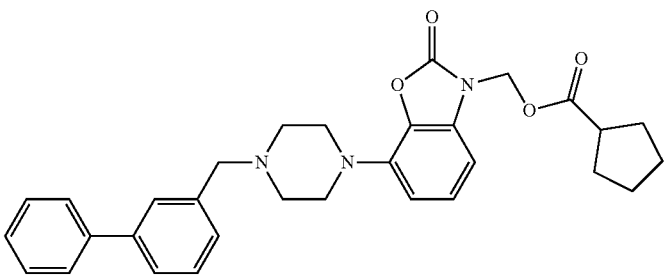 [SMILES: O=C(OCn1c(=O)oc2c(N3CCN(Cc4cccc(-c5ccccc5)c4)CC3)cccc21)C1CCCC1] |
| 428 | 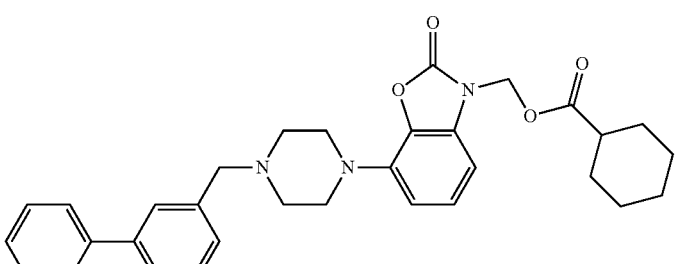 |
| 429 | 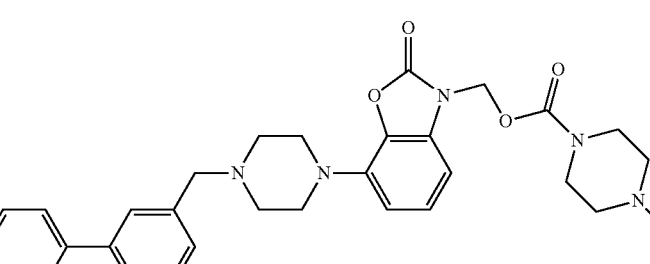 |

TABLE D-continued
| No. | Structure |
|---|---|
| 430 | 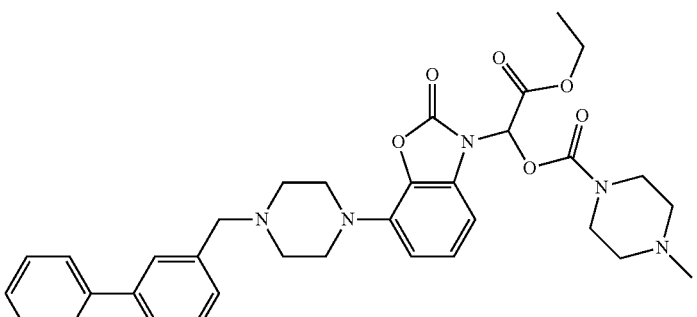 |
| 431 | 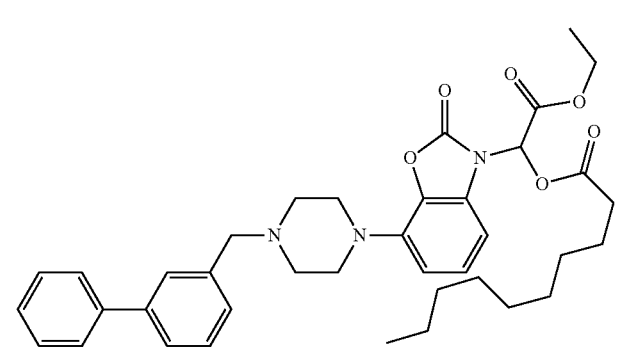 [SMILES: CCCCCCCCCC(=O)OC(C(=O)OCC)n1c(=O)oc2c(N3CCN(Cc4cccc(-c5ccccc5)c4)CC3)cccc21] |
| 432 | 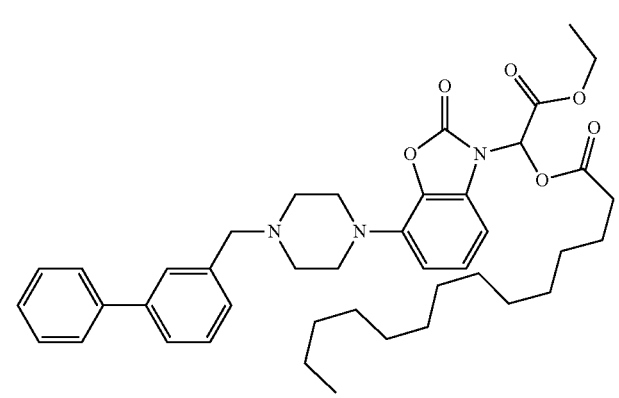 [SMILES: CCCCCCCCCCCCCC(=O)OC(C(=O)OCC)n1c(=O)oc2c(N3CCN(Cc4cccc(-c5ccccc5)c4)CC3)cccc21] |
| 433 | 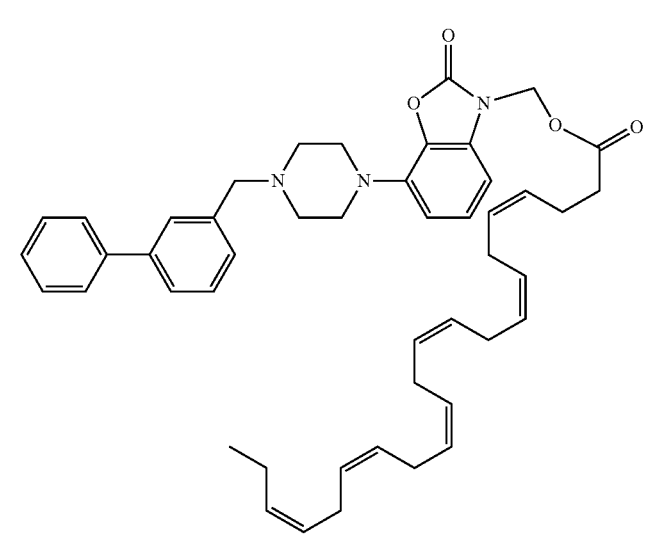 [SMILES: CC/C=C\C/C=C\C/C=C\C/C=C\C/C=C\C/C=C\CCC(=O)OCn1c(=O)oc2c(N3CCN(Cc4cccc(-c5ccccc5)c4)CC3)cccc21] |

TABLE D-continued
| No. | Structure |
|---|---|
| 434 | 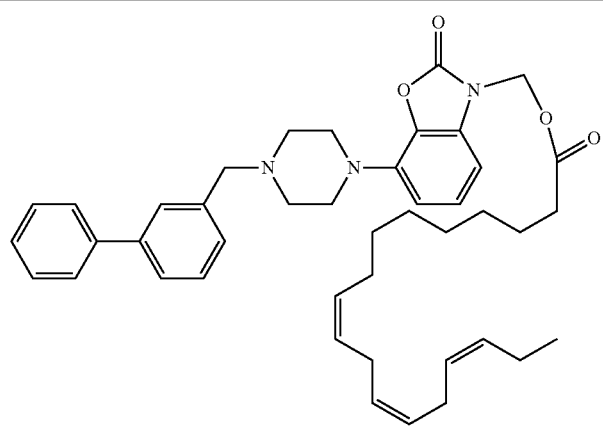 [SMILES: CC/C=C\C/C=C\C/C=C\CCCCCCCC(=O)OCn1c(=O)oc2c(N3CCN(Cc4cccc(-c5ccccc5)c4)CC3)cccc21] |
| 435 | 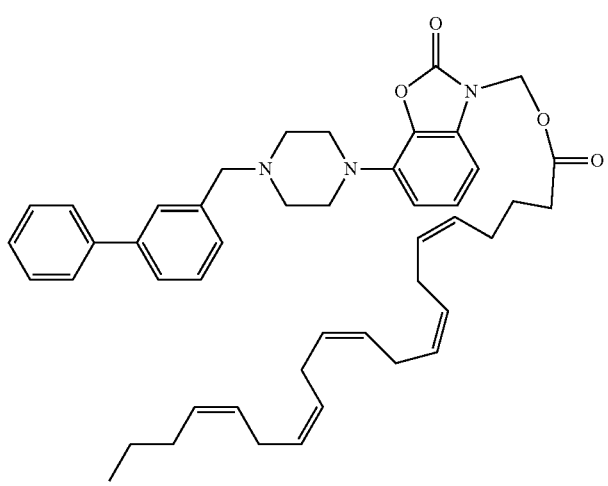 [SMILES: CCC/C=C\C/C=C\C/C=C\C/C=C\C/C=C\CCCC(=O)OCn1c(=O)oc2c(N3CCN(Cc4cccc(-c5ccccc5)c4)CC3)cccc21] |
| 436 | 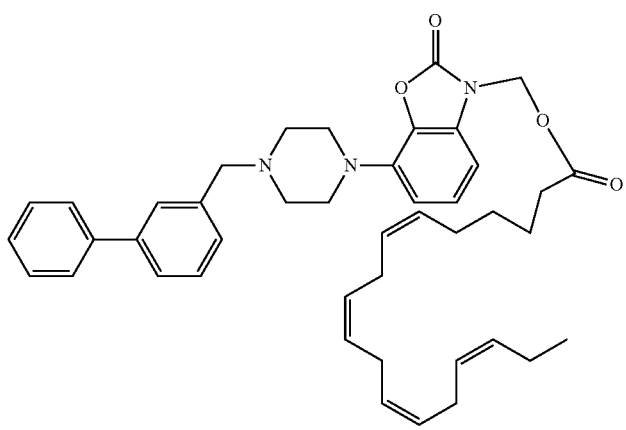 [SMILES: CC/C=C\C/C=C\C/C=C\C/C=C\CCCCC(=O)OCn1c(=O)oc2c(N3CCN(Cc4cccc(-c5ccccc5)c4)CC3)cccc21] |

TABLE D-continued

| No. | Structure |
|---|---|
| 437 | 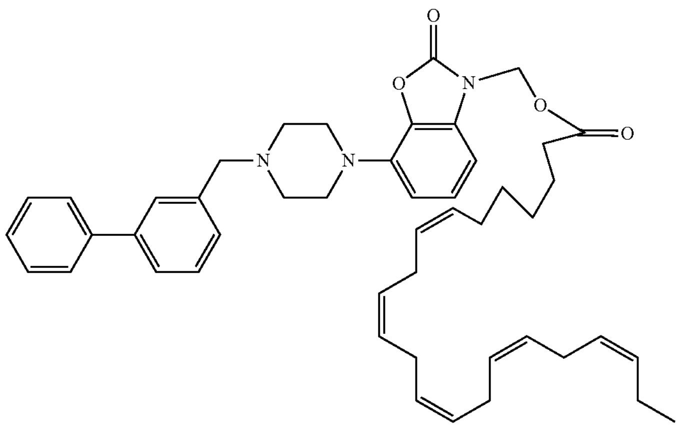 [SMILES: CC/C=C\C/C=C\C/C=C\C/C=C\C/C=C\CCCCCC(=O)OCn1c(=O)oc2c(N3CCN(Cc4cccc(-c5ccccc5)c4)CC3)cccc21] |

In a preferred embodiment a compound of Formula XXII is provided:

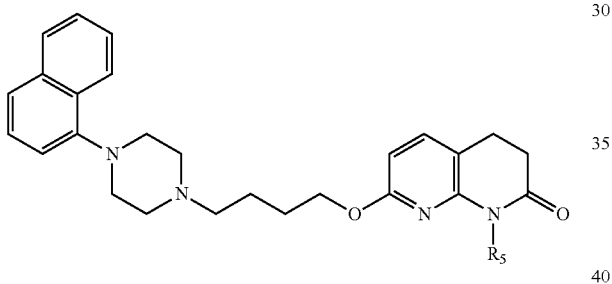

Formula XXII wherein $R_5$ is selected from Table 1. In a more preferred compound $R_5$ is selected from Tables 2-4.

Representative compounds according to the invention are those selected from the Table E below or its geometric isomers, enantiomers, diastereomers, racemates, pharmaceutically acceptable salts and solvates thereof:

TABLE E

| No. | Structure |
|---|---|
| 501 | 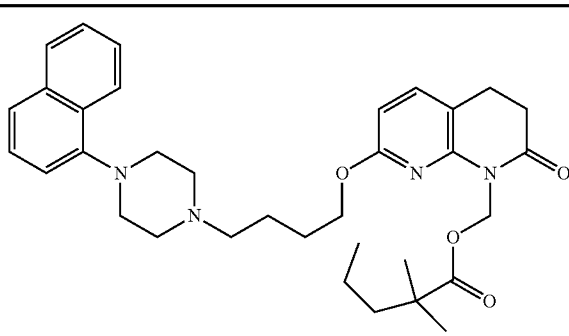 |

TABLE E-continued
| No. | Structure |
|---|---|
| 502 | 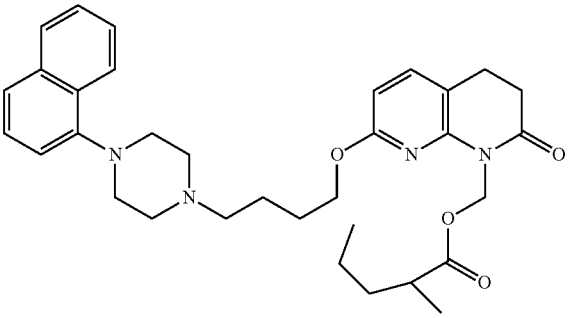 [SMILES: CCCC(C)C(=O)OCN1C(=O)CCc2ccc(OCCCCN3CCN(c4cccc5ccccc45)CC3)nc21] |
| 503 | 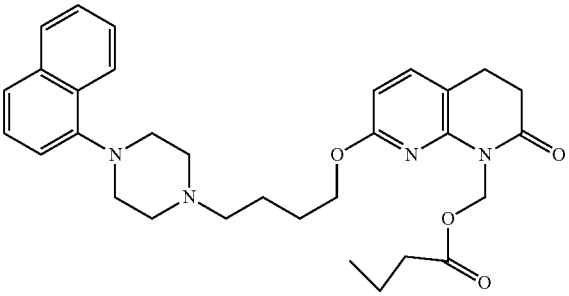 [SMILES: CCCC(=O)OCN1C(=O)CCc2ccc(OCCCCN3CCN(c4cccc5ccccc45)CC3)nc21] |
| 504 | 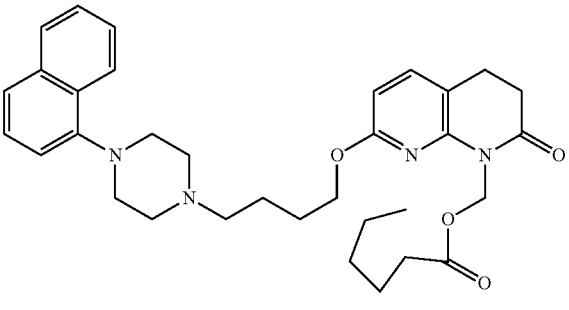 [SMILES: CCCCCC(=O)OCN1C(=O)CCc2ccc(OCCCCN3CCN(c4cccc5ccccc45)CC3)nc21] |
| 505 | 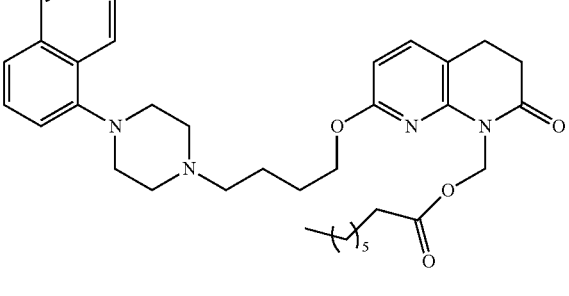 |
| 506 | 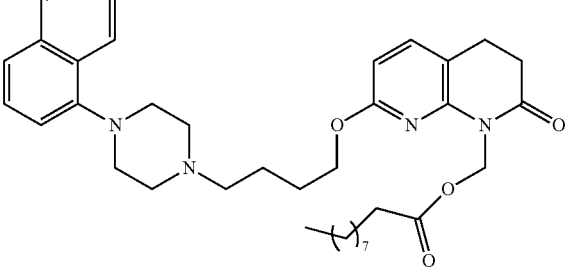 |

TABLE E-continued

| No. | Structure |
|-----|-----------|
| 507 | 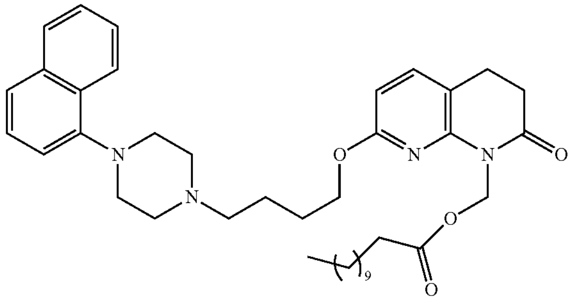 |
| 508 | 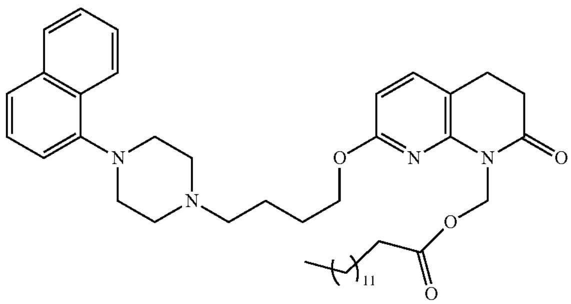 |
| 509 | 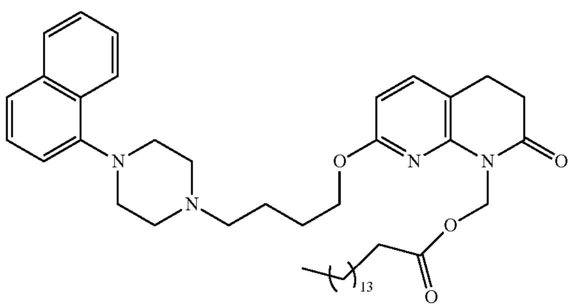 |
| 510 | 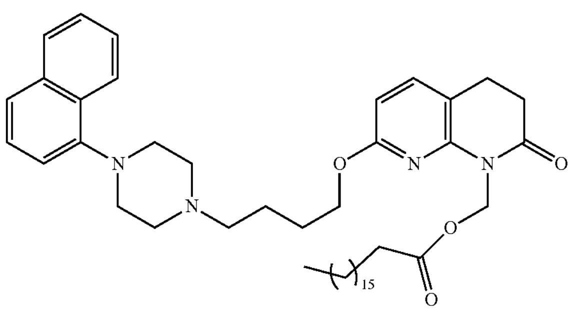 |
| 511 | 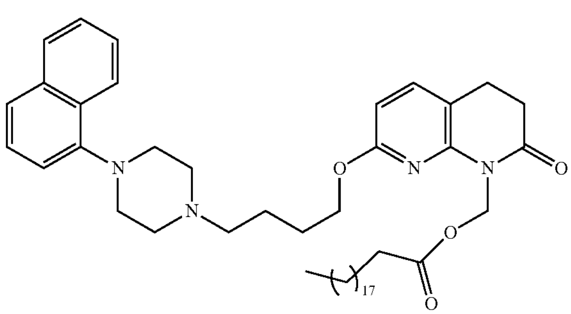 |

TABLE E-continued
| No. | Structure |
|---|---|
| 512 | 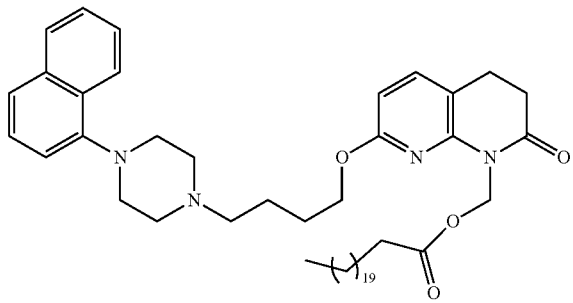 |
| 513 | 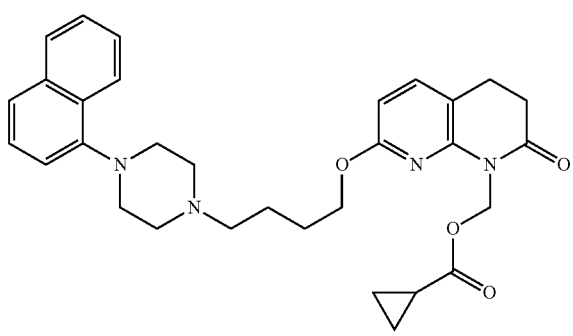 [SMILES: O=C(OCN1C(=O)CCc2ccc(OCCCCN3CCN(c4cccc5ccccc45)CC3)nc21)C1CC1] |
| 514 | 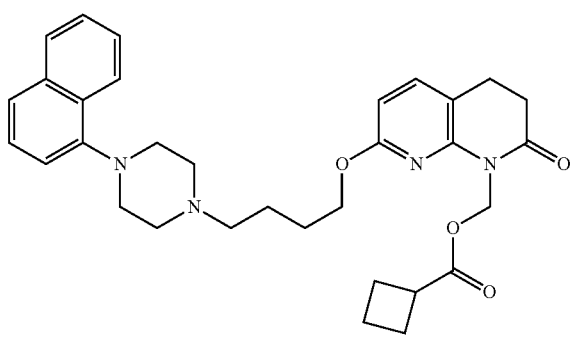 [SMILES: O=C(OCN1C(=O)CCc2ccc(OCCCCN3CCN(c4cccc5ccccc45)CC3)nc21)C1CCC1] |
| 515 | 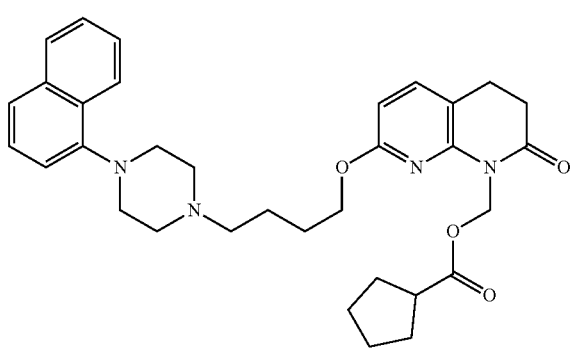 [SMILES: O=C(OCN1C(=O)CCc2ccc(OCCCCN3CCN(c4cccc5ccccc45)CC3)nc21)C1CCCC1] |

TABLE E-continued

| No. | Structure |
|---|---|
| 516 | 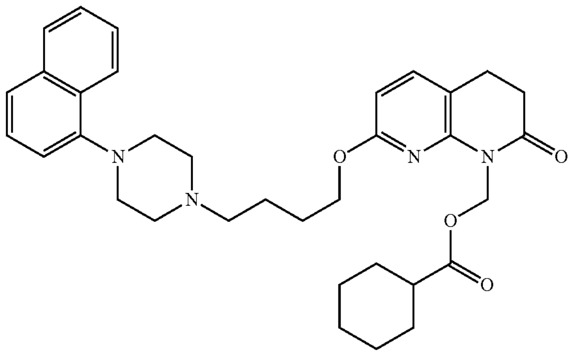 [SMILES: O=C(OCN1C(=O)CCc2ccc(OCCCCN3CCN(c4cccc5ccccc45)CC3)nc21)C1CCCCC1] |
| 517 | 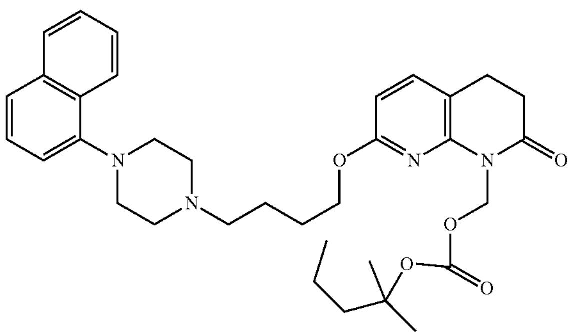 [SMILES: CCCC(C)(C)OC(=O)OCN1C(=O)CCc2ccc(OCCCCN3CCN(c4cccc5ccccc45)CC3)nc21] |
| 518 | 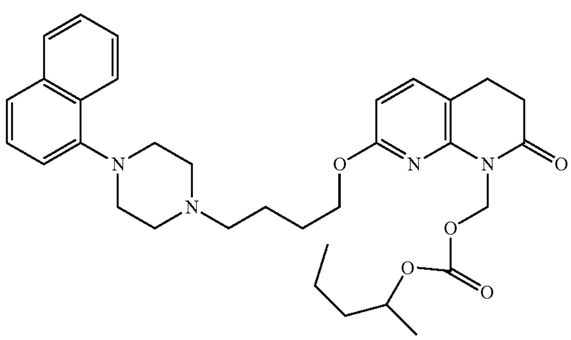 [SMILES: CCCC(C)OC(=O)OCN1C(=O)CCc2ccc(OCCCCN3CCN(c4cccc5ccccc45)CC3)nc21] |
| 519 | 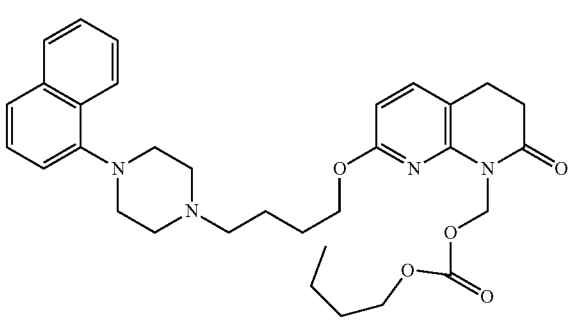 [SMILES: CCCCOC(=O)OCN1C(=O)CCc2ccc(OCCCCN3CCN(c4cccc5ccccc45)CC3)nc21] |

TABLE E-continued
| No. | Structure |
|---|---|
| 520 | 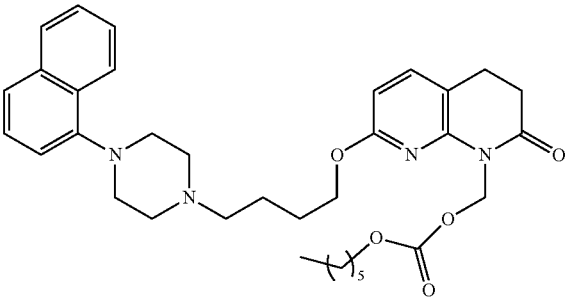 |
| 521 | 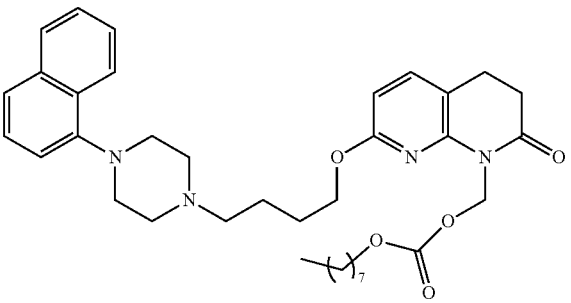 |
| 522 | 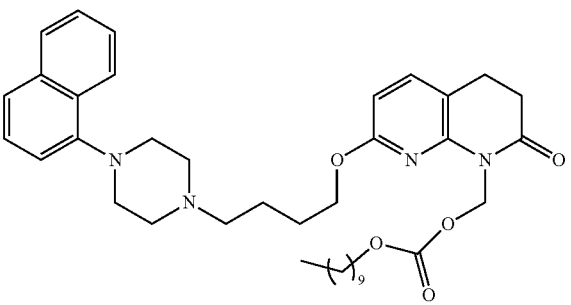 |
| 523 | 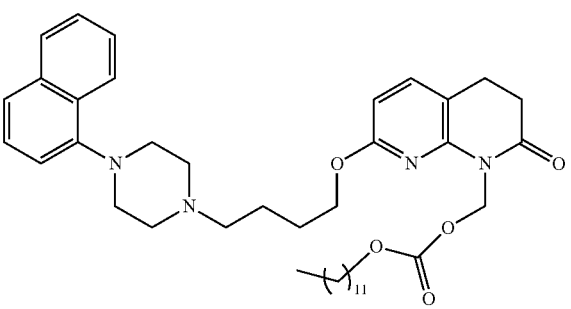 |
| 524 | 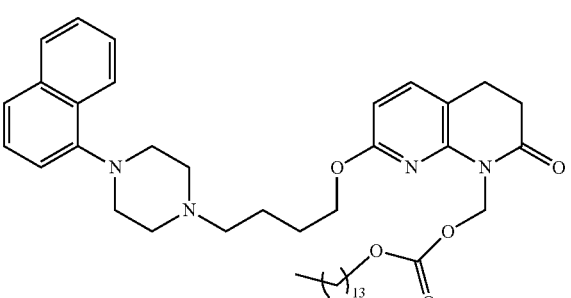 |

TABLE E-continued

| No. | Structure |
|---|---|
| 525 | 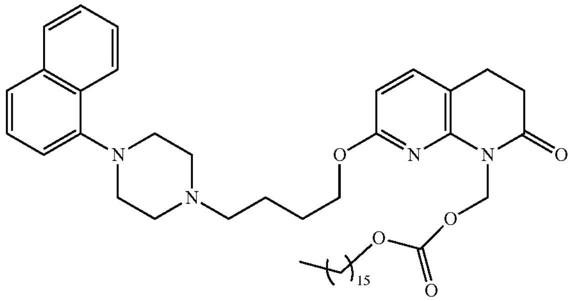 |
| 526 | 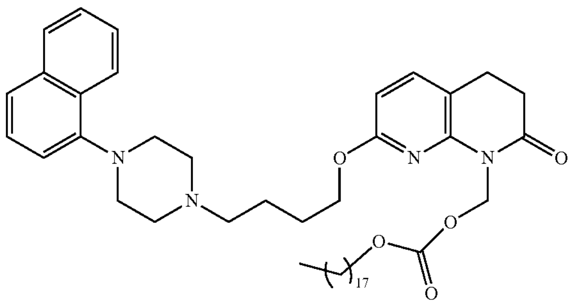 |
| 527 | 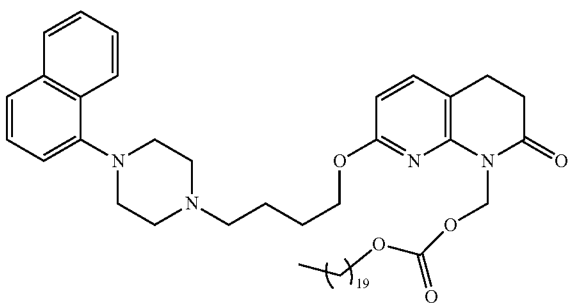 |
| 528 | 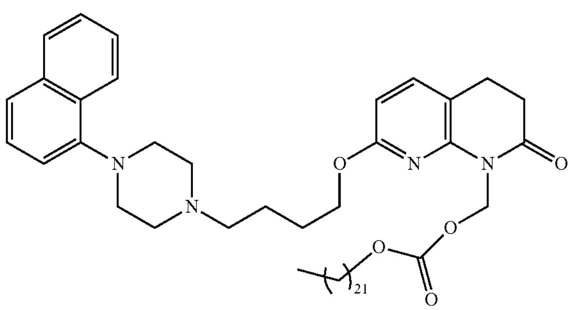 |
| 529 | 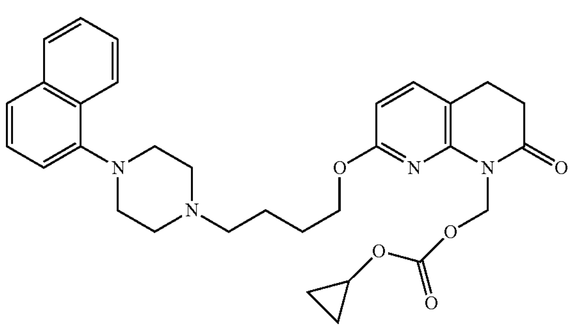 [SMILES: O=C(OCN1C(=O)CCc2ccc(OCCCCN3CCN(c4cccc5ccccc45)CC3)nc21)OC1CC1] |

TABLE E-continued
| No. | Structure |
|---|---|
| 530 | 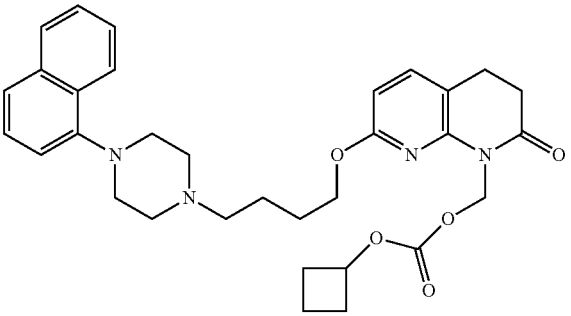 [SMILES: O=C(OCN1C(=O)CCc2ccc(OCCCCN3CCN(c4cccc5ccccc45)CC3)nc21)OC1CCC1] |
| 531 | 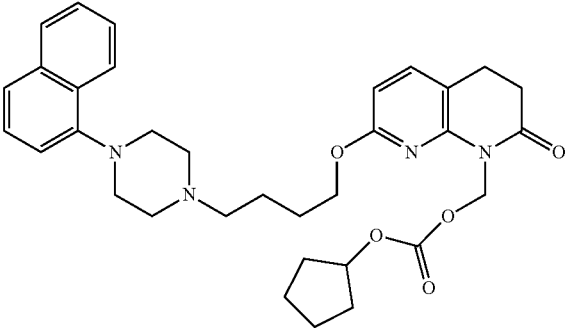 [SMILES: O=C(OCN1C(=O)CCc2ccc(OCCCCN3CCN(c4cccc5ccccc45)CC3)nc21)OC1CCCC1] |
| 532 | 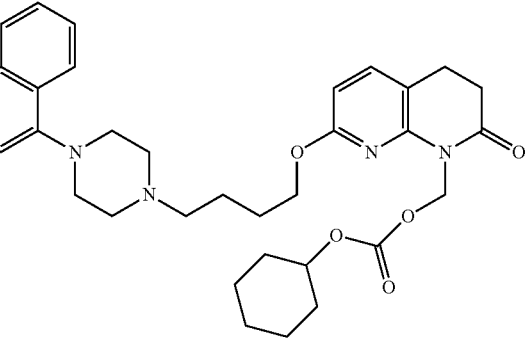 |
| 533 | 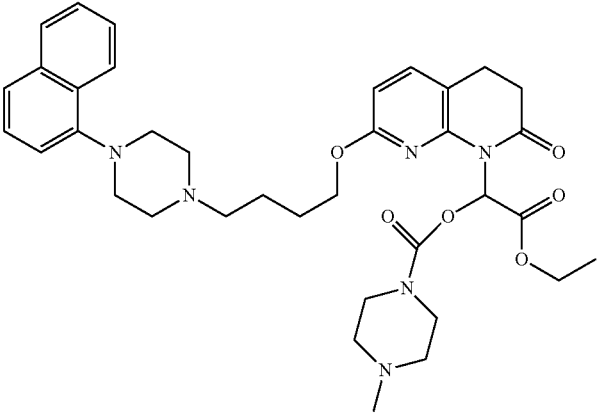 [SMILES: CCOC(=O)C(OC(=O)N1CCN(C)CC1)N1C(=O)CCc2ccc(OCCCCN3CCN(c4cccc5ccccc45)CC3)nc21] |

TABLE E-continued
| No. | Structure |
|---|---|
| 534 | 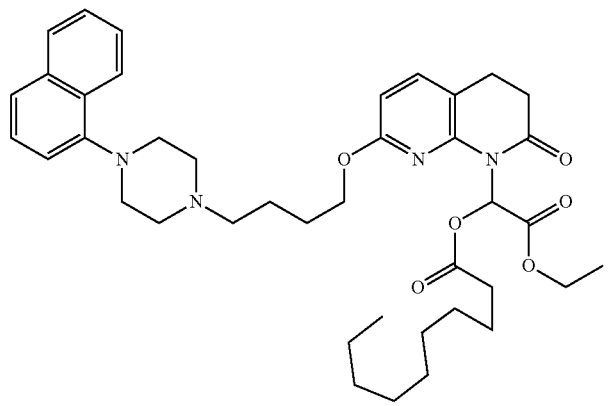 [SMILES: CCCCCCCCCC(=O)OC(C(=O)OCC)N1C(=O)CCc2ccc(OCCCCN3CCN(c4cccc5ccccc45)CC3)nc21] |
| 535 | 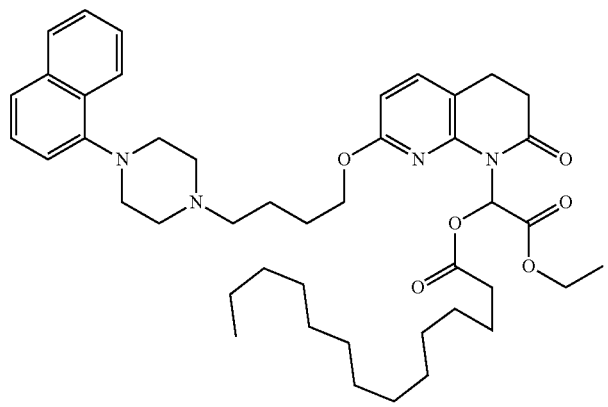 [SMILES: CCCCCCCCCCCCCC(=O)OC(C(=O)OCC)N1C(=O)CCc2ccc(OCCCCN3CCN(c4cccc5ccccc45)CC3)nc21] |
| 536 | 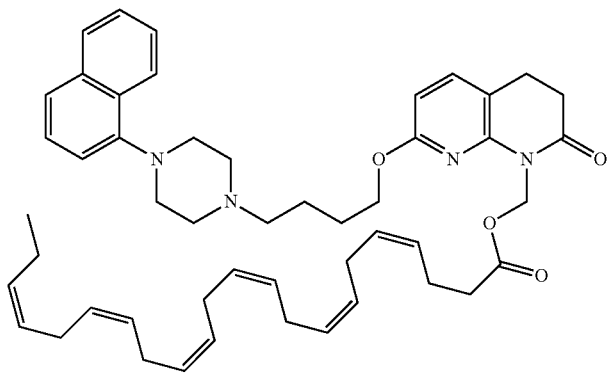 [SMILES: CC/C=C\C/C=C\C/C=C\C/C=C\C/C=C\C/C=C\CCC(=O)OCN1C(=O)CCc2ccc(OCCCCN3CCN(c4cccc5ccccc45)CC3)nc21] |

TABLE E-continued
| No. | Structure |
|---|---|
| 537 | 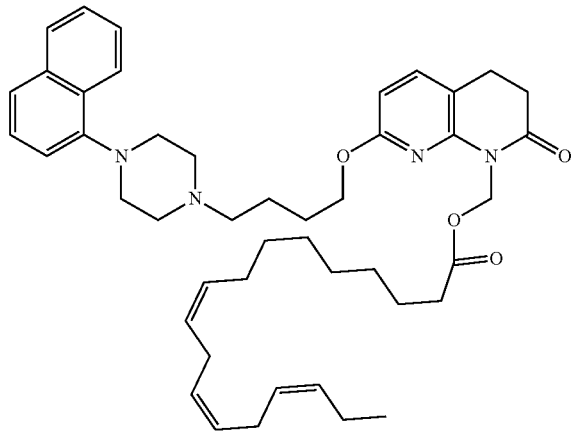 [SMILES: CC/C=C\C/C=C\C/C=C\CCCCCCCC(=O)OCN1C(=O)CCc2ccc(OCCCCN3CCN(c4cccc5ccccc45)CC3)nc21] |
| 538 | 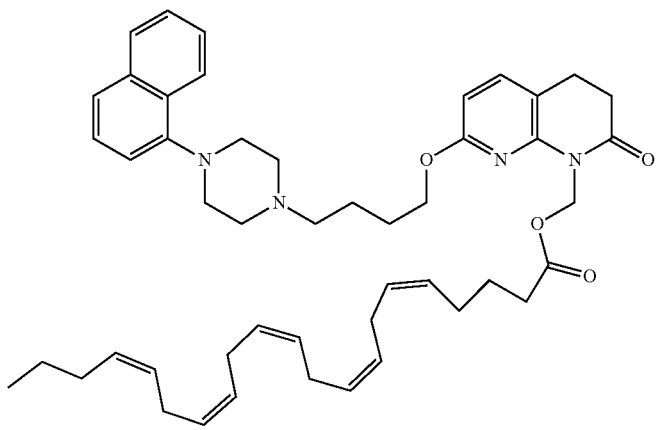 [SMILES: CCC/C=C\C/C=C\C/C=C\C/C=C\C/C=C\CCCC(=O)OCN1C(=O)CCc2ccc(OCCCCN3CCN(c4cccc5ccccc45)CC3)nc21] |
| 539 | 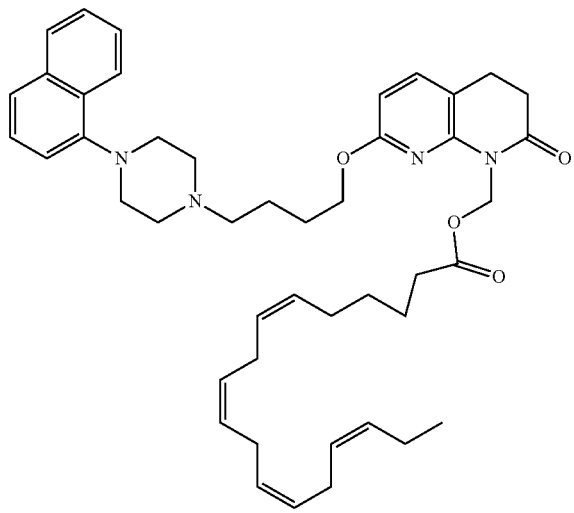 [SMILES: CC/C=C\C/C=C\C/C=C\C/C=C\CCCCC(=O)OCN1C(=O)CCc2ccc(OCCCCN3CCN(c4cccc5ccccc45)CC3)nc21] |

TABLE E-continued

| No. | Structure |
|---|---|
| 540 | 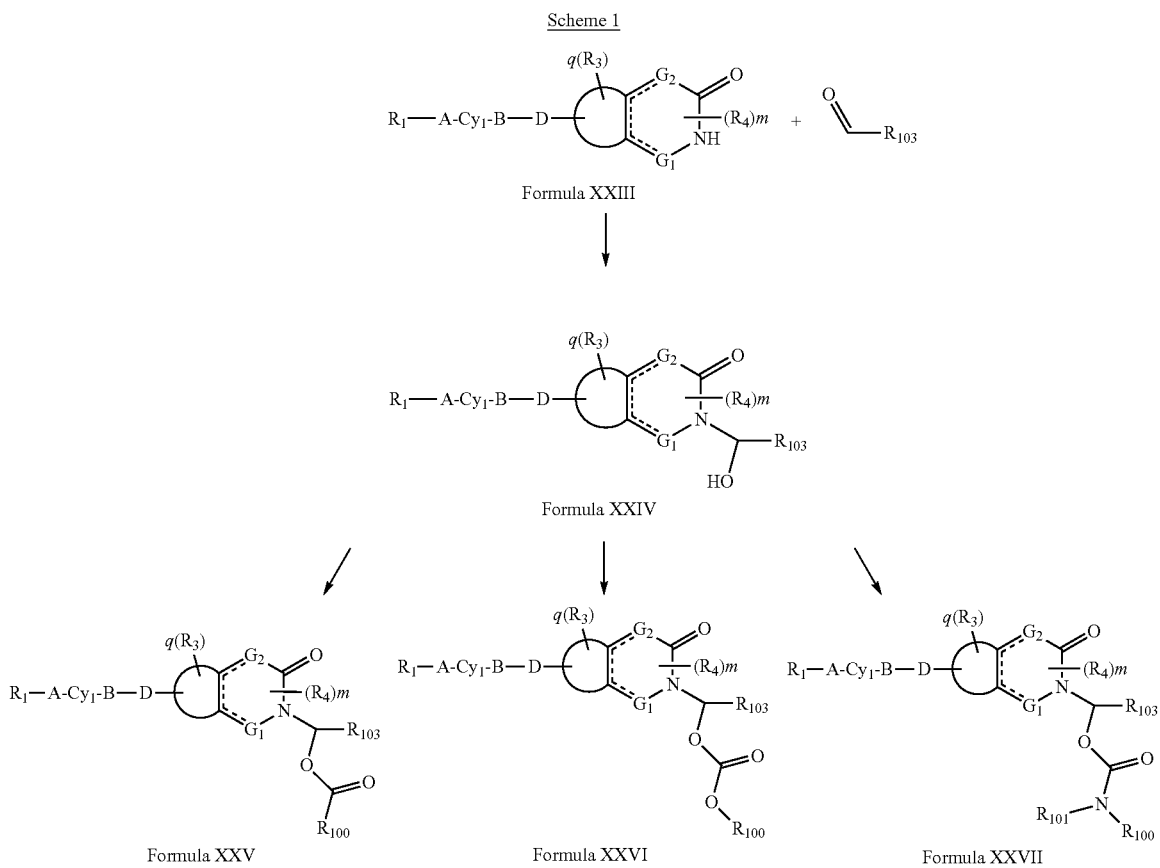 |

In another aspect of the invention a general method to convert lactam compounds of Formula XXIII with secondary amides to substituted tertiary amides is provided (Scheme 1).

In addition to the reaction of an aldehyde or ketone to compounds of formula XXIII, other process for converting secondary lactam groups can be used. For example, alkylation followed by addition of sodium in inert solvents, or addition of potassium hydroxide or sodium hydroxide followed by alkyl halide addition can be used. Microwave based synthetic procedures can also be used to convert secondary lactams to substituted tertiary lactam compounds of the instant application. (For a general review see March J. *Advanced Organic Chemistry*, Wiley, 1992; Inoue et al., *Bull. Chem. Soc. Jpn.*, 58, 2721-2722, 1985; Mijin et al., *J. Serb. Chem. Soc.*, 73(10) 945-950, 2008; Bogdal et al. *Molecules*, 1999, 4, 333-337; U.S. Pat. No. 5,041,659).

The invention further relates the sustained delivery of a compound of Formula XXIII by the administration of a compound of Formula I. Upon administration of a compound of Formula I, the labile $R_5$ moiety may be cleaved off enzymatically, chemically or through first phase metabolism giving a compound of Formula XXIII Without being bound to any theory, it is postulated that for some of the compounds of Formula I, the release of a compound of Formula XXIII upon cleavage of the $R_5$ moiety results in a therapeutically active agent. For example, such active ingredient can be aripiprazole, ziprasadone or bifeprunox. In one embodiment, the sustained release comprises a therapeutically effective amount of a compound of Formula XXIII in the blood stream of the patient for a period of at least about 36 hours after administration of the compound of Formula I. In a preferred embodiment, a compound of the invention provides sustained delivery of the parent drug (Formula XXIII) over hours, days, weeks or months when administered parenterally to a subject. For example, the compounds can provide sustained delivery of the parent drug for up to 7, 15, 30, 60, 75 or 90 days or longer. Without being bound by theory, it is believed that the compounds of the invention form an insoluble depot upon parenteral administration, for example subcutaneous, intramuscular or intraperitoneal injection.

Definitions

Listed below are definitions of various terms used to describe this invention. These definitions apply to the terms as they are used throughout this specification and claims, unless otherwise limited in specific instances, either individually or as part of a larger group.

An "aliphatic group" or "aliphatic" is non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted.

An aliphatic group, when used as a linker, preferably contains between about 1 and about 24 atoms, more preferably between about 4 to about 24 atoms, more preferably between about 4 to about 12 atoms, more typically between about 4 and about 8 atoms. An aliphatic group, when used as a substituent, preferably contains between about 1 and about 24 atoms, more preferably between about 1 to about 10 atoms, more preferably between about 1 to about 8 atoms, more typically between about 1 and about 6 atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl groups described herein.

The term "substituted carbonyl" includes compounds and moieties which contain a carbon connected with a double bond to an oxygen atom, and tautomeric forms thereof.

Examples of moieties that contain a substituted carbonyl include aldehydes, ketones, carboxylic acids, amides, esters, anhydrides, etc. The term "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide).

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as $(C_1-C_6)$alkanoyl (e.g., formyl, acetyl, propionyl, butyryl, valeryl, caproyl, t-butyl acetyl, etc.), $(C_3-C_6)$cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to about eight carbon atoms.

Examples of alkynyl radicals include propargyl, 1-propynyl, 2-propynyl, 1-butyne, 2-butynyl and 1-pentynyl.

The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkoxy" embraces linear or branched oxy-containing radicals each having alkyl portions of one to about twenty carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" embrace saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" embraces heterocyclo-substituted alkyl radicals. More preferred heterocycloalkyl radicals are "lower heterocycloalkyl" radicals having one to six carbon atoms in the heterocyclo radicals.

The term "alkylthio" embraces radicals containing a linear or branched alkyl radical, of one to about ten carbon atoms attached to a divalent sulfur atom. Preferred alkylthio radicals have alkyl radicals of one to about twenty carbon atoms or, preferably, one to about twelve carbon atoms. More preferred alkylthio radicals have alkyl radicals are "lower alkylthio" radicals having one to about ten carbon atoms. Most preferred are alkylthio radicals having lower alkyl radicals of one to about eight carbon atoms. Examples of such lower alkylthio radicals are methylthio, ethylthio, propylthio, butylthio and hexylthio.

The terms "aralkyl" or "arylalkyl" embrace aryl-substituted alkyl radicals such as benzyl, diphenylmethyl, triphenylmethyl, phenylethyl, and diphenylethyl.

The term "aryloxy" embraces aryl radicals attached through an oxygen atom to other radicals.

The terms "aralkoxy" or "arylalkoxy" embrace aralkyl radicals attached through an oxygen atom to other radicals.

The term "aminoalkyl" embraces alkyl radicals substituted with amino radicals. Preferred aminoalkyl radicals have alkyl radicals having about one to about twenty carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "linker" means an organic moiety that connects two parts of a compound. Linkers typically comprise a direct bond or an atom such as oxygen or sulfur, a unit such as $NR_8$, C(O), C(O)NH, SO, $SO_2$, $SO_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkyl aryl alkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N($R_8$), C(O), substituted or unsubstituted aryl, substituted or unsubstituted heteroaryl, substituted or unsubstituted heterocyclic; where $R_8$ is hydrogen, acyl, aliphatic or substituted aliphatic. In one embodiment, the linker B is between one to about twenty-four atoms, preferably one to about twelve atoms, preferably between about one to about eight atoms, more preferably one to about six atoms, and most preferably about four to about six atoms. In some embodiments, the linker is a C(O)NH(alkyl) chain or an alkoxy chain.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkyl sulfonyl, alkylsulfonylalkyl, arylsulfonylalkyl, alkoxy, aryloxy, aralkoxy, aminocarbonyl, alkylaminocarbonyl, aryl aminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The term "compound" is defined herein to include pharmaceutically acceptable salts, solvates, hydrates, polymorphs, enantiomers, diastereoisomers, racemates and the like of the compounds having a formula as set forth herein.

The term "sugar" includes aldose, ketoaldose, alditols, ketoses, aldonic acids, ketoaldonic acids, aldaric acids, ketoaldaric acids, amino sugars, keto-amino sugars, uronic acids, ketouronic acids, lactones and keto-lactones. A sugar moiety can be a triosyl, tetraosyl, pentosyl, hexosyl, heptosyl, octosyl and nonosyl radicals. Hexosyl sugars include allose, altrose, glucose, mannose, gulose, idose, galactose, talose, fructose, ribo-hexulose, arabino-hexulose and lyxo-hexulose. Pentosyl sugars include ribose, arabinose, xylose, lyxose, ribulose and xylulose.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of neurological and psychiatric disorders to clinically acceptable standards.

The neurological and psychiatric disorders include, but are not limited to, disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, and conduct disorder.

The term "treatment" refers to any process, action, application, therapy, or the like, wherein a mammal, including a human being, is subject to medical aid with the object of improving the mammal's condition, directly or indirectly.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical *Sciences,* 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein may contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

The terms "sustained release", "sustained delivery" and "extended release" are used interchangeably herein to indicate that compounds of Formula I-XXII, where a labile $R_5$ moiety is present, provides for the release of a compound by any mechanism including slow first order kinetics of absorption or zero order kinetics of absorption, such that the resulting compounds without the $R_5$ moiety is present in the patient, in effective amounts, for a period of time that is longer than the period of time that results from administering the corresponding drug without the $R_5$ moiety alone (i.e. not as a prodrug of the invention). The mechanism for timed release may be due to several factors including, but not limited to, decreasing the solubility upon conjugation of $R_5$, resulting in more gradual dissolution and slower release of the $R_5$ conjugated compounds (Formula I-XXII) by the action of serum enzymes or chemical hydrolysis.

In one embodiment, compounds of Formula I-XXII of the present invention provide an extended period during which an active agent is absorbed thereby providing a longer duration of action per dose than is currently expected. This leads to an overall improvement of dosing parameters such as, for example taking an active agent twice a day where it has previously required four times a day dosing. Alternatively, many active agents presently given at a once a day dosing frequency, lack the pharmacokinetic properties suitable for dosing intervals of exactly twelve or twenty-four hours. The need for an extended period of active agent adsorption for the current single dose active agent still exists and would be beneficial as well. "Effective amounts" or a "therapeutically effective amount" of a prodrug of the invention is based on that amount of the parent drug which is deemed to provide clinically beneficial therapy to the patient. However, the prodrug of the invention provides an effective amount for a longer period of time per dose than that of the parent drug per the same dose when delivered alone.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha- ($\alpha$), beta- ($\beta$) and gamma- ($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, according to the requirements of the particular drug. The methods herein contemplate administration of an effective amount of compound or compound composition to achieve the desired or stated effect. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. General methodology for the preparation of lactam compounds can be found in the following publications: U.S. Pat. Nos. 7,160,888; 5,462,934; 4,914,094; 4,234,584; 4,514,401; 5,462,934; 4,468,402; WO 2006/090273 A2; WO 2008/150848 A1; WO 2006/112464 A1; WO 2008/132600 A1.

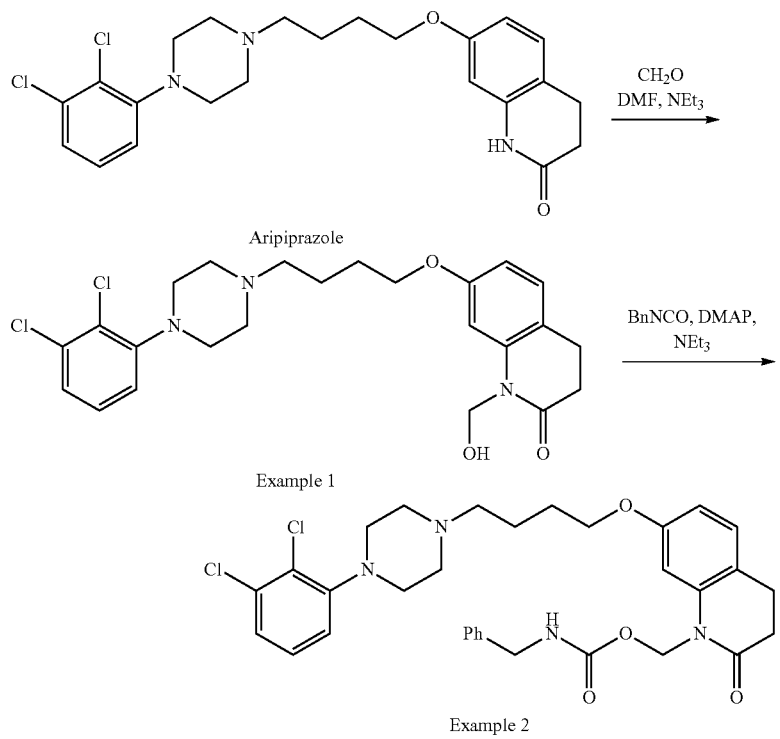

Aripiprazole

Example 1

Example 2

Preparation of 7-(4-(4-(2,3-dichlorophenyl)piperazin-1-yl)butoxy)-1-(hydroxymethyl)-3,4-dihydroquinolin-2(1H)-one (Example 1: Compound A1)

A mixture of Aripiprazole (20 g, 45 mmol), triethylamine (1 mL, 7.1 mmol), formaldehyde (37% aqueous solution, 70 mL) and dimethylformamide (200 mL) was heated to 80° C. for 20 h. The reaction mixture was cooled, diluted with ethyl acetate (400 mL) and washed with water/brine (1:1, 3×500 mL). The organic phase was dried over MgSO$_4$, filtered and evaporated to dryness under vacuum to give hemi-aminal A1 as a white solid (18.6 g, containing 25% Aripiprazole, 65% yield based on A1).

$^1$-EINNIR (CDCl$_3$, 300 MHz) complex mixture of signals due to contamination with Aripiprazole, main signal δ 5.34 (s, 2H, OHCH$_2$N); m/z (M$^+$H) 478 and 480.

(7-(4-(4-(2,3-dichlorophenyl)piperazin-1-yl)butoxy)-2-oxo-3,4-dihydroquinolin-1(2H)-yl)methyl benzylcarbamate (Example 2: Compound 28)

To a solution of hemi-aminal A1 from Example 1 (4 g, 8.4 mmol), 4-dimethylaminopyridine (0.15 g, 1.3 mmol) and triethylamine (1.1 mL, 7.5 mmol) in dichloromethane (30 mL) was added benzylisocyanate (1.03 mL, 8.3 mmol) and the reaction mixture stirred for 24 hours. The reaction mixture was then heated at 35° C. for 20 hours, cooled and washed with water/brine (1:1, 50 mL). The organic phase was dried over MgSO$_4$, filtered and evaporated under vacuum. The residue was further purified by chromatography on silica eluting with ethyl acetate/dichloromethane/methanol (1:1:0.1) to give the desired product as an off white foam (530 mg, 14% yield). $^1$H NMR (CDCl$_3$, 300 MHz) δ 1.58-1.88 (m, 4H), 2.48 (t, 2H), 2.60-2.72 (m, 6H), 2.85 (m, 2H), 300-3.12 (m, 4H), 3.96 (t, 2H), 4.40 (d, 2H), 5.13 (NH), 5.96 (s, 2H), 6.58 (dd, 1H), 6.79 (d, 1H), 6.92-6.98 (m, 1H), 7.04 (d, 1H), 7.12-7.16 (m, 1H), 7.23-7.35 (m, 6H); m/z (M$^+$H) 611.12 and 613.10.

The following compounds were prepared in an analogous fashion to Example 2.

(7-(4-(4-(2,3-dichlorophenyl)piperazin-1-yl)butoxy)-2-oxo-3,4-dihydroquinolin-1(2H)-yl)methyl ethyl carbonate (Example 3: Compound 79) The desired product was isolated as a yellow oil (830 mg, 24% yield). $^1$H NMR (d$_6$-DMSO, 300 MHz) δ 1.78 (t, 3H), 1.52-1.61 (m, 2H), 1.63-1.76 (m, 2H), 2.31-2.40 (m, 2H), 2.40-2.60 (m, 6H), 2.73-2.80 (m, 2H), 2.91-2.99 (m, 4H), 3.96 (t, 3H), 4.11 (q, 2H), 5.87(s, 2H), 6.60-6.70 (m, 2H), 7.07-7.12 (m, 2H), 7.24-7.30 (m, 2H); m/z (M$^+$H) 550.48 and 552.40.

butyl (7-(4-(4-(2,3-dichlorophenyl)piperazin-1-yl)butoxy)-2-oxo-3,4-dihydroquinolin-1(2H)-yl)methyl carbonate (Example 4: Compound 80) The desired product was isolated as a yellow oil (750 mg, 21% yield). $^1$H NMR (CDCl$_3$, 300 MHz) δ 0.92 (t, 3H), 1.33-1.45 (m, 2H), 1.59-1.80 (m, 4H), 1.80-1.92 (m, 2H), 2.49 (t, 2H), 2.58-2.75 (m, 6H), 2.85 (t, 2H), 3.00-3.13 (m, 4H), 3.98 (t, 2H), 4.18 (t, 2H), 5.92 (s, 2H), 6.58 (dd, 1H), 6.67 (d, 1H), 6.92-6.99 (m, 1H), 7.03 (dd, 1H), 7.10-7.20 (m, 2H); m/z (M$^+$H) 578.10 and 580.08.

(7-(4-(4-(2,3-dichlorophenyl)piperazin-1-yl)butoxy)-2-oxo-3,4-dihydroquinolin-1(2H)-yl)methyl hexyl carbonate (Example 5: Compound 81) The desired product was isolated as a yellow oil (1.77 g, 62% yield). $^1$H NMR (d$_6$-DMSO, 300 MHz) δ 0.80 (t, 3H), 1.15-1.30 (m, 6H), 1.50-1.60 (m, 4H), 1.65-1.73 (m, 2H), 2.35 (t, 2H), 2.41-2.60 (m, 6H), 2.78 (t, 2H), 2.88-3.00 (m, 4H), 3.95 (t, 2H), 4.06 (t, 2H), 5.86 (s, 2H), 6.60-6.70 (m, 2H), 7.05-7.15 (m, 2H), 7.22-7.28 (m 2H); m/z (M$^+$H) 606.15 and 608.15.

decyl (7-(4-(4-(2,3-dichlorophenyl)piperazin-1-yl)butoxy)-2-oxo-3,4-dihydroquinolin-1(2H)-yl)methyl carbonate (Example 6: Compound 82) The desired product was isolated as a yellow oil (1.42 g, 46% yield). $^1$H NMR (d$_6$-DMSO, 300 MHz) δ 0.79 (m, 3H), 1.13-1.30 (m, 14H), 1.48-1.60 (m, 4H), 1.65-1.75 (m, 2H), 2.33 (t, 2H), 2.41-2.60 (m, 6H), 2.72-2.80 (m, 2H), 2.89-2.98 (m, 4H), 3.95 (t, 2H), 4.05 (t, 2H), 5.86 (s, 2H), 6.60-6.70 (m, 2H), 7.05-7.13 (m, 2H), 7.22-7.28 (m, 2H); m/z (M$^+$H) 662.56 and 664.54.

(7-(4-(4-(2,3-dichlorophenyl)piperazin-1-yl)butoxy)-2-oxo-3,4-dihydroquinolin-1(2H)-yl)methyl hexadecyl carbonate (Example 7: Compound 83) The desired product was isolated as a yellow oil (1.55 g, 44% yield). $^1$H NMR (d$_6$-DMSO, 300 MHz) δ 0.80 (t, 3H), 1.10-1.29 (m, 26H), 1.49-1.60 (m, 4H), 1.65-1.75 (m, 2H), 2.33 (t, 2H), 2.43-2.55 (m, 6H), 2.78 (t, 2H), 2.90-2.95 (m, 4H), 3.95 (t, 2H), 4.05 (t, 2H), 5.84 (s, 2H), 6.60-6.68 (m, 2H), 7.05-7.12 (m, 2H), 7.24-7.29 (m, 2H); m/z (M–C$_{10}$H$_{20}$))$^+$ 606.52 and 608.54.

(7-(4-(4-(2,3-dichlorophenyl)piperazin-1-yl)butoxy)-2-oxo-3,4-dihydroquinolin-1(2H)-yl)methyl morpholine-4-carboxylate (Example 8: Compound 49) The desired product was isolated as a yellow oil (1.52 g, 55% yield). $^1$H NMR (d$_6$-DMSO, 300 MHz) δ 1.50-1.75 (m, 4H), 2.35 (t, 2H), 2.42-2.61 (m, 6H), 2.70-2.82 (m, 2H), 2.88-3.00 (m, 4H), 3.26-3.40 (m, 4H), 3.40-3.60 (m, 4H), 3.94 (t, 2H), 5.81 (s, 2H), 6.61 (dd, 1H), 6.68 (d, 1H), 7.05-7.13 (m, 2H), 7.20-7.30 (m, 2H); m/z (M$^+$H) 591.11 and 593.15.

(7-(4-(4-(2,3-dichlorophenyl)piperazin-1-yl)butoxy)-2-oxo-3,4-dihydroquinolin-1(2H)-yl)methyl diethylcarbamate (Example 9: Compound 84) The desired product was isolated as a yellow oil (0.83 g, 31% yield). $^1$H NMR (CDCl$_3$, 300 MHz) δ 1.00-1.20 (m, 6H), 1.65-1.88 (m, 4H), 2.45-2.52 (m, 2H), 2.58-2.83 (m, 6H), 2.82-2.90 (m, 2H), 3.00-3.12 (m, 4H), 3.18-3.38 (m, 4H), 3.97 (t, 2H), 5.91 (s, 2H), 6.58 (dd, 1H), 6.77 (d, 1H), 6.94-6.98 (m, 1H), 7.06 (d, 1H), 7.15-7.20 (m, 2H); m/z (M$^+$H) 577.48 and 579.46.

(7-(4-(4-(2,3-dichlorophenyl)piperazin-1-yl)butoxy)-2-oxo-3,4-dihydroquinolin-1(2H)-yl)methyl isopentyl carbonate (Example 10: Compound 84) To a solution of phosgene (20% in toluene, 54 mL, 110 mmol) in tetrahydrofuran (100 mL) was added a solution of 3-methyl-1-butanol (1.7 mL, 15.7 mmol) in tetrahydrofuran (50 mL) over 1 hour. After 4 hours the volatiles were removed under vacuum and the residue added to a solution of the hemi-aminal A1 (3 g, 4.7 mmol), 4-dimethylaminopyridine (0.3 g, 1.9 mmol), pyridine (10 mL) and triethylamine (1.3 mL, 9.4 mmol) in dichloromethane (30 mL). After being stirred for 72 hours, the reaction mixture was diluted with ethyl acetate (100 mL) and washed with 5% aqueous NaHCO$_3$/brine (1:1, 100 mL). The organic phase was dried over MgSO$_4$, filtered and evaporated under vacuum. The residue was further purified by chromatography on silica eluting with ethyl acetate/dichloromethane/methanol (1:1:0.1) to give the desired product as a yellow oil (1.54 g, 55% yield). $^1$H NMR (CDCl$_3$, 300 MHz) δ 1.90-1.95 (m, 6H), 1.50-1.60 (m, 4H), 1.65-1.79 (m, 2H), 1.79-1.89 (m, 2H), 2.50 (t, 2H), 2.60-2.72 (m, 6H), 2.82-2.90 (m, 2H), 3.02-3.11 (m, 4H), 3.98 (t, 2H), 4.21 (t, 2H), 5.92 (s, 2H), 6.56 (dd, 1H), 6.67 (d, 1H), 6.95-7.00 (m, 1H), 7.05 (d, 1H), 7.13-7.19 (m, 2H); m/z (M$^+$H) 592.48 and 594.46.

(7-(4-(4-(2,3-dichlorophenyl)piperazin-1-yl)butoxy)-2-oxo-3,4-dihydroquinolin-1(2H)-yl)methyl acetate (Example 11: Compound 1)

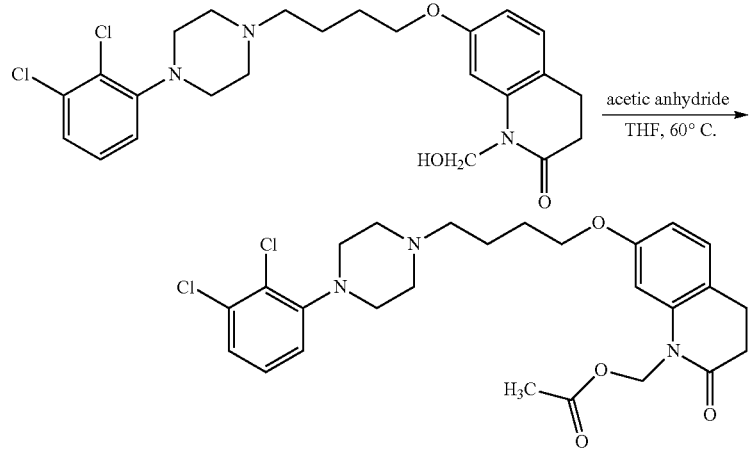

A solution of Compound-A1 from Example-1, (50.63 g, 0.105 mol) in anhydrous tetrahydrofuran (THF, 80 mL) was treated with acetic anhydride (15.3 mL, 0.16 mol) and heated for 2.0 hours at 60° C. (oil-bath). To the above solution, triethylamine (2.0 mL, 0.014 mol) was added and stirred for 16 hours at 60° C. The solvent was removed using a rotator evaporator. To the resulting crude mixture, ethyl acetate (150 mL) and heptane (50 mL) was added. The solution was washed with NaHCO$_3$ (5% aqueous solution, 250 mL,). After separation of the two layers, pH of the aqueous layer was adjusted to above 7. The aqueous layer was further extracted using the organic mixture. The organic layer was separated and washed with 5% NaHCO$_3$ solution, followed by deionized water, and brine. The solution was dried using anhydrous MgSO$_4$, filtered and evaporated under vacuum. The resulting product was purified using silica gel column chromatography using ethanol: ethyl acetate (5:95) as the eluent. Fractions containing the desired product were combined and d-tartaric acid (12.5 g dissolved in 60:5 ethanol: water) was added, resulting in the precipitation of the desired product (48.78 g, 89% yield). $^1$H NMR (CDCl$_3$, 300 MHz) δ 1.73 (m, 2H), 1.84 (m, 2H), 2.12 (s, 3H), 2.50 (t, 2H), 2.68 (m, 6H), 2.87 (dd, 2H), 3.08 (m, 4H), 3.98 (t, 2H), 5.91 (s, 2H), 6.59 (m, 2H), 6.96 (dd, 1H), 7.08 (dd, 1H), 7.15 (m, 2H).

The following compounds were prepared in an analogous fashion to Example 11.

(7-(4-(4-(2,3-dichlorophenyl)piperazin-1-yl)butoxy)-2-oxo-3,4-dihydroquinolin-1(2H)-yl)methyl dodecanoate (Example 12: Compound 7) The desired product was isolated as a crystalline solid (0.3 g, 21% yield). The molecular weight was confirmed by mass spectrometer analysis. FIG. 2-6 shows the PXRD, IR, Raman, TGA spectrum of the desired product. $^1$H NMR (CDCl$_3$, 300 MHz) δ 0.87 (t, 3H), 1.24 (m, 16H), 1.62 (m, 2H), 1.83 (m, 2H), 1.86 (m, 2H), 2.36 (t, 2H), 2.49 (t, 2H), 2.68 (m, 6H), 2.86 (dd, 2H), 3.08 (m, 4H), 3.97 (t, 2H), 5.91 (s, 2H), 6.59 (m, 2H), 6.96 (dd, 1H), 7.07 (dd, 1H), 7.14 (m, 2H).

(7-(4-(4-(2,3-dichlorophenyl)piperazin-1-yl)butoxy)-2-oxo-3,4-dihydroquinolin-1(2H)-yl)methyl palmitate (Example 13: Compound 10)

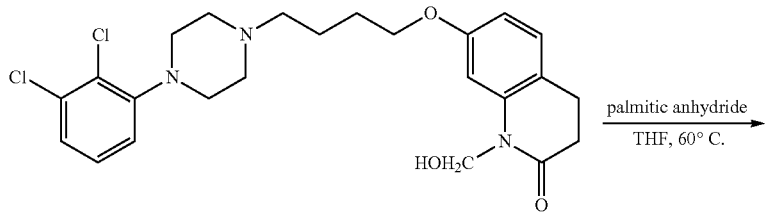

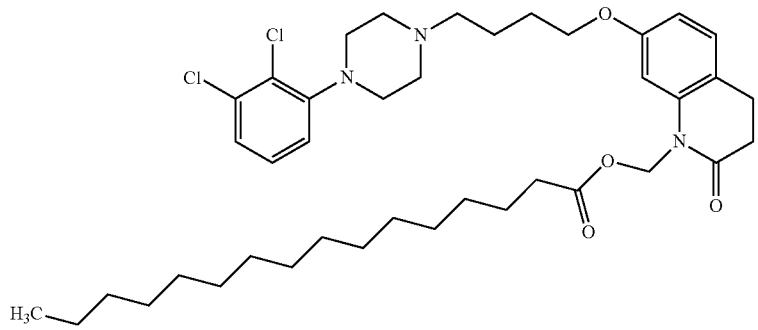

The desired product was isolated as a crystalline solid (4.2 g, 70% yield). The molecular weight (716.6) was confirmed by mass spectrometer analysis. $^1$H NMR (CDCl$_3$, 300 MHz) δ 0.88 (t, 3H), 1.25 (m, 24 H), 1.64 (m, 2H), 1.72 (m, 2H), 1.84 (m, 2H), 2.36 (t, 2H), 2.49 (t, 2H), 2.68 (m, 6H), 2.86 (dd, 2H), 3.08 (m, 4H), 3.97 (t, 2H), 5.92 (br s, 2H), 6.59 (dd, 1H), 6.60 (s, 1H), 6.96 (dd, 1H), 7.07 (d, 1H), 7.14 (m, 2H).

(7-(4-(4-(2,3-dichlorophenyl)piperazin-1-yl)butoxy)-2-oxo-3,4-dihydroquinolin-1(2H)-yl)methyl decanoate (Example 14: Compound 6)

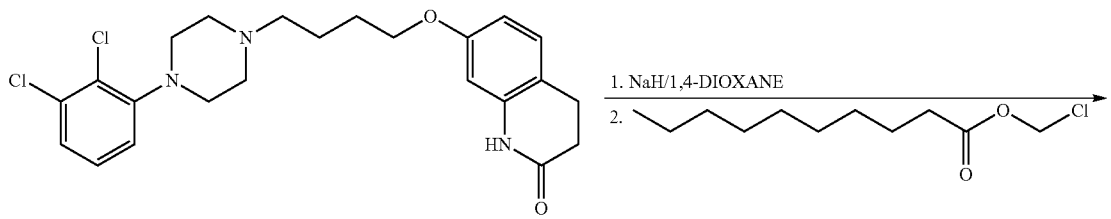

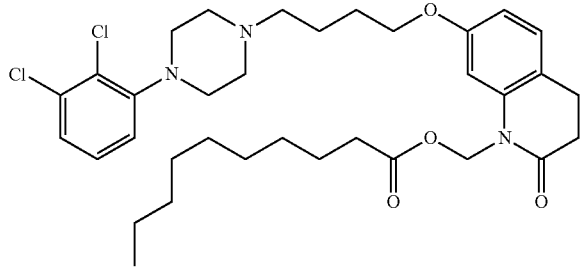

The chloromethyl ester above is dried over 4 Å molecular sieves. A solution of aripiprazole (45 grams, 0.1 mol) in 1,4-dioxane (800 mL) was sonicated to dissolve the aripiprazole completely, and then treated with NaH (38 g, 0.95 mol, 60% dispersion) in one portion. After stirring this reaction mixture for 15 minutes at room temperature, the reaction mixture was treated dropwise with chloromethyl ester (0.3 mol.) and a catalytic amount of sodium iodide (0.05 mol.). The resultant cloudy mixture was heated to 90° C. for 2 hours, cooled to ambient temperature and poured into water. The product was extracted with ethyl acetate, and the combined ethyl acetate layers washed with brine, dried over sodium sulfate, filtered and concentrated under reduced pressure. Column chromatography over silica gel provided the desired product (12.5 gram, 70% yield). $^1$H NMR (CDCl3, 300 MHz) δ 0.87 (t, 3H), 1.20 (m, 12H), 1.63 (m, 2H), 1.70 (m, 2H), 1.83 (m, 2H), 2.35 (t, 2H), 2.50 (t, 2H), 2.68 (m, 6H), 2.86 (t, 2H), 3.08 (m, 4H), 3.97 (t, 2H), 5.92 (s, 2H), 6.58 (dd, 1H), 6.61 (d, 1H), 6.94 (dd, 1H), 7.06 (d, 1H), 7.14-7.17 (m, 2H); m/z (M$^+$H) 632.88.

The following compounds (Examples 15-29) were prepared in an analogous fashion to Example 2:

(7-(4-(4-(2,3-dichlorophenyl)piperazin-1-yl)butoxy)-2-oxo-3,4-dihydroquinolin-1(2H)-yl)methyl benzoate (Example 15, Compound 31) The desired product was isolated as a yellow oil.

$^1$H NMR (CDCl$_3$, 300 MHz) δ 1.60-1.85 (m, 4H), 2.45 (t, 2H), 2.55-2.70 (m, 4H), 2.70-2.78 (m, 2H), 2.85-2.92 (m, 2H), 3.00-3.10 (m, 4H), 3.94 (t, 2H), 6.16 (s, 2H), 6.60 (d, 1H), 6.72 (dd, 1H), 6.90-6.95 (m, 1H), 7.05-7.18 (m, 2H), 7.35-7.42 (m, 2H), 7.52-7.60 (m, 1H), 8.00-8.08 (m, 2H). m/z (M$^+$H) 582.3.

(7-(4-(4-(2,3-dichlorophenyl)piperazin-1-yl)butoxy)-2-oxo-3,4-dihydroquinolin-1(2H)-yl)methyl butyrate (Example 16, Compound 2) The desired product was isolated by chromatography on silica eluting with ethyl acetate/dichloromethane/methanol (1:1:0.1) to give a yellow oil (2.0 g, 87% yield). $^1$H NMR (CDCl$_3$, 300 MHz) δ 0.94 (t, 3H), 1.60-1.90 (m, 6H), 2.34 (t, 2H), 2.51 (t, 2H), 2.61-2.73 (m, 6H), 2.82-2.90 (m, 2H), 3.02-3.12 (m, 4H), 3.96 (t, 2H), 5.91 (s, 1H), 6.55-6.61 (m, 2H), 6.93-6.98 (m, 1H), 7.05 (d, 1H), 7.11-7.18 (m, 2H). m/z (M$^+$H) 548.2 and 550.2.

(7-(4-(4-(2,3-dichlorophenyl)piperazin-1-yl)butoxy)-2-oxo-3,4-dihydroquinolin-1(2H)-yl)methyl hexanoate (Example 17, Compound 4) The desired product was isolated as a yellow solid (3.69 g, 87% yield). $^1$H NMR (CDCl$_3$, 300 MHz) δ 0.78 (t, 3H), 1.11-1.28 (m, 4H), 1.40-1.78 (m, 6H), 2.20-2.40 (m, 4H), 2.40-2.60 (m, 6H), 2.73-2.81 (m, 2H), 2.85-3.00 (m, 4H), 3.88-4.00 (m, 2H), 5.75-5.83 (m, 2H), 6.55-6.62 (m, 2H), 7.03-7.12 (m, 2H), 7.20-7.26 (m, 2H). m/z (M$^+$H) 576.4 and 578.4.

(7-(4-(4-(2,3-dichlorophenyl)piperazin-1-yl)butoxy)-2-oxo-3,4-dihydroquinolin-1(2H)-yl)methyl tetradecanoate (Example 18, Compound 8) The desired product was isolated as a pale yellow solid (5.3 g, 74% yield). $^1$H NMR (CDCl$_3$, 300 MHz) δ 0.87 (t, 3H), 1.07-1.37 (m, 22H), 1.55-1.70 (m, 2H), 1.70-1.90 (m, 4H), 2.34 (t, 2H), 2.53 (t, 2H), 2.65-2.78 (m, 6H), 2.82-2.90 (m, 2H), 3.02-3.12 (m, 4H), 3.96 (t, 2H), 5.91 (s, 2H), 6.55-6.62 (m, 2H), 6.92-6.98 (m, 1H), 7.05 (d, 1H), 7.11-7.18 (m, 2H). m/z (M$^+$H) 688.4 and 690.4.

(7-(4-(4-(2,3-dichlorophenyl)piperazin-1-yl)butoxy)-2-oxo-3,4-dihydroquinolin-1(2H)-yl)methyl octanoate (Example 19, Compound 5) The desired product was isolated as a yellow oil (2.2 g, 87% yield). $^1$H NMR (CDCl$_3$, 300 MHz) δ 0.82 (t, 3H), 1.15-1.35 (m, 10H), 1.55-1.87 (m, 6H), 2.34 (t, 2H), 2.53 (t, 2H), 2.65-2.73 (m, 4H), 2.85 (dd, 2H), 3.01-3.11 (m, 4H), 3.95 (t, 2H), 5.85-5.92 (m, 2H), 2.53-2.60 (m, 2H), 6.91-6.97 (m, 1H), 7.05 (d, 1H), 7.10-7.16 (m, 2H). m/z (M$^+$H) 604.3 and 606.3.

(7-(4-(4-(2,3-dichlorophenyl)piperazin-1-yl)butoxy)-2-oxo-3,4-dihydroquinolin-1(2H)-yl)methyl isopropyl carbonate (Example 20, Compound 48) The desired product was isolated as an orange oil (2.4 g, 68% yield). $^1$H NMR (CDCl$_3$, 300 MHz) δ 1.31 (d, 6H), 1.62-1.77 (m, 2H), 1.77-1.89 (m, 2H), 2.48 (t, 2H), 2.60-2.71 (m, 6H), 2.81-2.90 (m, 2H), 3.01-3.11 (m, 4H), 3.98 (t, 2H), 4.89-4.97 (m, 1H), 5.92 (s, 2H), 6.57 (d, 1H), 6.68 (d, 1H), 6.91-7.00 (m, 1H), 7.05 (dd, 1H), 7.11-7.18 (m, 2H). m/z (M$^+$H) 564.3 and 566.3.

(7-(4-(4-(2,3-dichlorophenyl)piperazin-1-yl)butoxy)-2-oxo-3,4-dihydroquinolin-1(2H)-yl)methyl methylcarbamate (Example 21, Compound 47) The desired product was isolated as a yellow solid (1.3 g, 52% yield). $^1$H NMR (CDCl$_3$, 300 MHz) δ 1.68-1.88 (m, 4H), 2.49 (dd, 2H), 2.60-2.73 (m, 6H), 2.80-2.90 (m, 5H), 3.02-3.12 (m, 4H), 3.95-4.02 (m, 2H), 5.90 (s, 2H), 6.57 (d, 1H), 6.77 (d, 1H), 6.93-6.70 (m, 1H), 7.05 (d, 1H), 7.10-7.19 (m, 2H). m/z (M$^+$H) 535.5 and 537.5.

(7-(4-(4-(2,3-dichlorophenyl)piperazin-1-yl)butoxy)-2-oxo-3,4-dihydroquinolin-1(2H)-yl)methyl decylcarbamate (Example 22, Compound 46) The desired product was isolated as a yellow solid (0.50 g, 14% yield). $^1$H NMR (CDCl$_3$, 300 MHz) δ 0.86 (t, 3H), 1.18-1.35 (m, 16H), 1.42-1.53 (m, 2H), 1.67-1.79 (m, 2H), 1.79-1.87 (m, 2H), 2.48 (t, 2H), 2.58-2.72 (m, 4H), 2.80-2.90 (m, 2H), 3.01-3.12 (m, 4H), 3.15-3.22 (m, 2H), 3.98 (t, 2H), 4.78 (NH), 5.90 (s, 2H), 6.58 (d, 1H), 6.78 (d, 1H), 6.93-7.00 (m, 1H), 7.04 (d, 1H), 7.10-7.16 (m, 2H). m/z (M$^+$H) 661.6 and 663.6.

(7-(4-(4-(2,3-dichlorophenyl)piperazin-1-yl)butoxy)-2-oxo-3,4-dihydroquinolin-1(2H)-yl)methyl isobutyrate (Example 23, Compound 32)

$^1$H NMR (CDCl$_3$, 300 MHz) δ 1.18 (d, 6H), 1.68-1.88 (m, 4H), 2.45-2.73 (m, 9H), 2.87 (dd, 2H), 3.03-3.12 (m, 2H), 3.95 (t, 2H), 5.91 (s, 2H), 6.55-6.60 (m, 2H), 6.93-6.97 (m, 1H), 7.04-7.09 (m, 1H), 7.12-7.19 (m, 2H). m/z (M+H) 548.15.

(7-(4-(4-(2,3-dichlorophenyl)piperazin-1-yl)butoxy)-2-oxo-3,4-dihydroquinolin-1(2H)-yl)methyl cyclopentanecarboxylate (Example 24, Compound 33)

$^1$H NMR (CDCl$_3$, 300 MHz) δ 1.47-1.93 (m, 13H), 2.50-2.60 (m, 2H), 2.60-2.90 (m, 8H), 3.02-3.15 (m, 4H), 3.95 (t, 2H), 5.89 (s, 2H), 6.50-6.60 (m, 2H), 6.90-6.95 (m, 1H), 7.02-7.07 (m, 1H), 7.10-7.19 (m, 2H). m/z (M+H) 574.15.

(7-(4-(4-(2,3-dichlorophenyl)piperazin-1-yl)butoxy)-2-oxo-3,4-dihydroquinolin-1(2H)-yl)methyl cyclobutanecarboxylate (Example 25, Compound 34)

$^1$H NMR (CDCl$_3$, 300 MHz) δ 1.82-1.91 (m, 3H), 1.22-1.30 (m, 2H), 1.75-2.05 (m, 6H), 2.05-2.40 (m, 6H), 2.68-2.73 (m, 2H), 2.84-2.90 (m, 2H), 3.06-3.22 (m, 4H), 3.96 (t, 2H), 5.91 (s, 2H), 6.55-6.59 (m, 2H), 6.97 (dd, 1H), 7.07 (d, 1H), 7.12-7.18 (m, 2H). m/z (M+H) 560.19.

(7-(4-(4-(2,3-dichlorophenyl)piperazin-1-yl)butoxy)-2-oxo-3,4-dihydroquinolin-1(2H)-yl)methyl cyclohexanecarboxylate (Example 26, Compound 35)

$^1$H NMR (CDCl$_3$, 300 MHz) δ 1.15-1.35 (m, 3H), 1.35-1.55 (m, 2H), 1.55-1.95 (m, 10H), 2.21-2.40 (m, 1H), 2.52-2.60 (m, 1H), 2.62-3.00 (m, 8H), 3.02-3.12 (m, 4H), 3.95 (t, 2H), 5.89 (s, 2H), 6.50-6.60 (m, 2H), 6.93-6.97 (m, 1H), 7.02-7.06 (m, 1H), 7.10-7.15 (m, 2H). m/z (M+H) 588.24.

(7-(4-(4-(2,3-dichlorophenyl)piperazin-1-yl)butoxy)-2-oxo-3,4-dihydroquinolin-1(2H)-yl)methyl 2-(2-methoxyethoxy)acetate (Example 27, Compound 40)

$^1$H NMR (CDCl$_3$, 300 MHz) δ 1.56-1.90 (m, 6H), 2.43-2.55 (m, 2H), 2.55-2.80 (m, 4H), 2.81-2.90 (m, 2H), 3.37 (s, 3H), 3.55-3.61 (m, 2H), 3.72-3.79 (m, 2H), 4.20 (s, 2H), 5.97 (s, 2H), 6.55-6.59 (m, 2H), 6.91-6.98 (m, 1H), 7.09 (d, 1H), 7.11-7.15 (m, 2H). m/z (M+H) 594.17.

(7-(4-(4-(2,3-dichlorophenyl)piperazin-1-yl)butoxy)-2-oxo-3,4-dihydroquinolin-1(2H)-yl)methyl 2-(2-(2-methoxyethoxy)ethoxy)acetate (Example 28, Compound 41)

$^1$H NMR (CDCl$_3$, 300 MHz) δ 1.65-1.93 (m, 6H), 2.49-2.60 (m, 2H), 2.61-2.77 (m, 4H), 2.81-2.90 (m, 2H), 3.02-3.20 (m, 4H), 3.36 (s, 3H), 3.51-3.57 (m, 2H), 3.60-3.70 (m, 4H), 3.72-3.78 (m, 2H), 3.92-3.99 (m, 2H), 4.20 (s, 2H), 5.97 (s, 2H), 6.55-6.59 (m, 2H), 6.95-6.99 (m, 1H), 7.05-7.09 (m, 1H), 7.11-7.18 (m, 2H). m/z (M+H) 638.30.

(7-(4-(4-(2,3-dichlorophenyl)piperazin-1-yl)butoxy)-2-oxo-3,4-dihydroquinolin-1(2H)-yl)methyl pivalate (Example 29, Compound 42)

$^1$H NMR (CDCl$_3$, 300 MHz) δ 1.21 (s, 9H), 1.65-1.88 (m, 4H), 2.45-2.55 (m, 2H), 2.60-2.73 (m, 6H), 2.82-2.91 (m, 2H), 3.02-3.13 (m, 4H), 3.95 (t, 2H), 5.89 (s, 2H), 6.54-6.60 (m, 2H), 6.92-6.99 (m, 1H), 7.06 (d, 1H), 7.13-7.17 (m, 2H); m/z (M+H) 562.39.

(7-(4-(4-(2,3-dichlorophenyl)piperazin-1-yl)butoxy)-2-oxo-3,4-dihydroquinolin-1(2H)-yl)methyl 2-hydroxyethylcarbamate (Example 30, Compound 36)

2-(((7-(4-(4-(2,3-dichlorophenyl)piperazin-1-yl)butoxy)-2-oxo-3,4-dihydroquinolin-1(2H)-yl)methoxy)carbonylamino)ethyl methacrylate (2.0 g) was synthesised in a similar manner to Example 2. This was reacted with 16% NH$_3$/MeOH at room temperature for 18 hours and then concentrated at 40° C. The residue was purified by silica chromatography eluting with 1:1:0.1 to 1:1:0.2 DCM/EtOAc/MeOH. The resulting yellow oil was re-crystallised from EtOAc/heptane to give the title compound as a white solid (1.2 g, 67%).

$^1$H NMR (CDCl$_3$, 300 MHz) δ 1.60-1.88 (m, 4H), 2.40-2.50 (m, 2H), 2.50-2.75 (m, 6H), 2.75-2.89 (m, 2H), 2.95-3.15 (m, 4H), 3.20-3.40 (m, 2H), 2.58-3.78 (m, 2H), 3.89-4.05 (m, 2H), 5.30-5.45 (m, NH), 5.91 (s, 2H), 6.55 (dd, 1H), 6.73 (d, 1H), 6.91-6.96 (m, 1H), 6.98-7.03 (m, 1H), 7.04-7.18 (m, 2H). m/z (M+H) 565.16.

(7-(4-(4-(2,3-dichlorophenyl)piperazin-1-yl)butoxy)-2-oxo-3,4-dihydroquinolin-1(2H)-yl)methyl bis(2-hydroxyethyl)carbamate (Example 31, Compound 37)

To a solution of hemiaminal A1 (2 g, 0.0042 mol) in dichloromethane (30 mL) at room temperature was added pyridine (0.68 mL), followed by p-nitrophenylchloroformate (1.27 g, 0.0063 mol). After 90 minutes diethanolamine (3.5 g, 0.0334 mol) and triethylamine (1.2 mL, 0.084 mol) were added. After 3 h the reaction was diluted with dichloromethane and washed with sat. NaHCO$_3$, dried over MgSO$_4$ and evaporated. The residue was purified on silica eluting with 1:1:0.1 to 1:1:0.2 DCM/EtOAc/MeOH to give the title compound as a colourless gum (0.83 g, 33%).

$^1$H NMR (CDCl$_3$, 300 MHz) δ 1.70-1.82 (m, 4H), 2.42-2.52 (m, 2H), 2.59-2.79 (m, 6H), 2.80-2.90 (m, 2H), 3.00-3.12 (m, 4H), 3.40-3.48 (m, 2H), 3.50-3.58 (m, 2H), 3.61-3.70 (m, 2H), 3.85-3.90 (m, 2H), 3.99-4.06 (m, 2H), 5.90 (m, 2H), 6.57 (d, 1H), 6.70 (dd, 1H), 6.92-6.98 (m, 1H), 7.07 (d, 1H), 7.10-7.20 (m, 2H). m/z (M+H) 609.21.

(7-(4-(4-(2,3-dichlorophenyl)piperazin-1-yl)butoxy)-2-oxo-3,4-dihydroquinolin-1(2H)-yl)methyl 4-methylpiperazine-1-carboxylate (Example 32, Compound 38)

Compound 141 was synthesised in a similar manner to Example 28.

$^1$H NMR (CDCl$_3$, 300 MHz) δ 1.68-1.88 (m, 4H), 2.25-2.42 (m, 7H), 2.45-2.55 (m, 2H), 2.61-2.76 (m, 6H), 2.85 (dd, 2H), 3.02-3.16 (m, 4H), 3.40-3.60 (m, 4H), 3.97 (t, 2H), 5.92 (s, 2H), 6.59 (d, 1H), 6.74 (d, 1H), 6.92-6.98 (m, 1H), 7.02-7.07 (m, 1H), 7.10-7.16 (m, 2H). m/z (M+H) 604.24.

(7-(4-(4-(2,3-dichlorophenyl)piperazin-1-yl)butoxy)-2-oxo-3,4-dihydroquinolin-1(2H)-yl)methyl 1,4'-bipiperidine-1'-carboxylate (Example 33, Compound 39)

Compound 142 was synthesised in a similar manner to Example 28.

$^1$H NMR (CDCl$_3$, 300 MHz) δ 1.26-2.06 (m, 14H), 2.31-2.91 (m, 17H), 2.95-3.18 (m, 4H), 3.97 (t, 2H), 4.0-4.37 (m, 2H), 5.91 (s, 2H), 6.58 (dd, 1H), 6.74 (d, 1H), 6.90-6.99 (m, 1H), 7.05 (d, 1H), 7.11-7.18 (m, 2H); m/z (M+H) 672.25.

7-(4-(4-(2,3-dichlorophenyl)piperazin-1-yl)butoxy)-1-(methoxymethyl)-3,4-dihydroquinolin-2(1H)-one (Example 34, Compound 100)

To a mixture of hemiaminal A1 (2.0 g, 4.2 mmol) in dichloromethane (20 mL) was added thionyl chloride (1.5 mL, 12.6 mmol) and stirred for 2 h at room temperature. To the reaction mixture was added methanol (10 mL) and stirred a further 2 h. The reaction poured into NaHCO$_3$ (aq)

and extracted with dichloromethane. The organic phase dried over MgSO$_4$, evaporated and the residue purified on silica eluting with 1:1:0.1 dichloromethane/ethyl acetate/methanol to give the title compound as a cream solid (1.3 g, 63%).

$^1$H NMR (CDCl$_3$, 300 MHz) δ 1.65-1.83 (m, 4H), 2.47 (t, 2H), 2.58-2.70 (m, 6H), 2.82 (dd, 2H), 2.99-3.01 (m, 4H), 3.38 (s, 3H), 3.96 (t, 2H), 5.27 (s, 2H), 6.55 (dd, 1H), 6.88 (dd, 1H), 6.91-6.96 (m, 1H), 7.03 (d, 1H), 7.08-7.15 (m, 2H). m/z (M$^+$H) 492.05.

1-(7-(4-(4-(2,3-dichlorophenyl)piperazin-1-yl)butoxy)-2-oxo-3,4-dihydroquinolin-1(2H)-yl)-2-ethoxy-2-oxoethyl decanoate (Example 35, Compound 111)

A mixture of Aripiprazole (2.0 g, 4.5 mmol), ethyl glyoxylate (50% soln. in toluene, 2.7 mL), K$_2$CO$_3$ (0.49 g, 3.6 mmol), tetrabutylammonium bromide (0.57 g, 1.8 mmol) and dichloromethane (20 mL) was heated at reflux for 4 h. The reaction mixture was cooled and quickly washed with water, dried over MgSO$_4$ and filtered. The resulting solution was treated with pyridine (1.8 mL, 22.2 mmol) and then decanoylchloride (4.6 mL, 22.2 mmol). After being stirred for 3 h, methanol (1 mL) was added and stirred a further 10 min. The reaction mixture was washed with sat.NaHCO$_3$ (aq), dried over MgSO$_4$ and evaporated. The residue was purified on silica eluting with 1:1:0.1 dichloromethane/ethyl acetate/methanol to give the title compound as a yellow oil (1.2 g, 38%).

$^1$H NMR (CDCl$_3$, 300 MHz) δ 0.86 (t, 3H), 1.11 (t, 3H), 1.05-1.40 (m, 12H), 1.59-1.75 (m, 2H), 1.75-1.98 (m, 4H), 2.40-2.54 (m, 2H), 2.60-3.07 (m, 10H), 3.15-3.32 (m, 4H), 3.89-3.99 (m, 2H), 4.09-4.21 (m, 2H), 6.57 (dd, 1H), 6.67 (d, 1H), 6.95-7.00 (m, 1H), 7.08 (dd, 1H), 7.12-7.20 (m, 2H), 7.27-7.32 (m, 1H). m/z (M$^+$H) 704.38.

(7-(4-(4-(2,3-dichlorophenyl)piperazin-1-yl)butoxy)-2-oxo-3,4-dihydroquinolin-1(2H)-yl)methyl 4-acetamidobutanoate (Example 36, Compound 44)

To a suspension of hemiaminal A1 (2.6 g, 5.5 mmol) in dichloromethane (30 mL) was added triethylamine (2.3 mL, 16.4 mmol), followed by addition of methanesulfonyl chloride (0.47 g, 6.0 mmol) over 3 min. The reaction mixture was stirred for 25 min and then N-acetyl-4-aminobutyric acid (1.6 g, 10.1 mmol) added. The reaction mixture was then heated at reflux for 18 h, cooled and washed with sat. NaHCO$_3$ (aq). The organic phase was dried over MgSO$_4$, filtered and evaporated. The residue was further purified on silica eluting with 1:1:0.1 to 1:1:0.2 dichloromethane/ethyl acetate/methanol to give the title compound as an off white solid (1.1 g, 34%).

$^1$H NMR (CDCl$_3$, 300 MHz) δ 1.70-1.80 (m, 2H), 1.80-1.90 (m, 4H), 1.97 (s, 3H), 2.41 (t, 2H), 2.50-2.57 (m, 2H), 2.60-2.75 (m, 6H), 2.83-2.88 (m, 2H), 3.03-3.12 (m, 4H), 3.24-3.32 (m, 2H), 3.95-4.00 (m, 2H), 5.85-5.92 (m, 3H), 6.58 (d, 2H), 6.92-6.96 (m, 1H), 7.05 (d, 1H), 7.12-7.16 (m, 2H).). m/z (M$^+$H) 605.08.

(7-(4-(4-(2,3-dichlorophenyl)piperazin-1-yl)butoxy)-2-oxo-3,4-dihydroquinolin-1(2H)-yl)methyl 4-octanamidobutanoate (Example 37, Compound 45)

Compound 149 (1.4 g) was synthesized in a similar manner to Compound 148.

$^1$H NMR (d$_6$-DMSO, 300 MHz) δ 0.79 (t, 3H), 1.10-1.28 (m, 8H), 1.38-1.48 (m, 2H), 1.50-1.77 (m, 6H), 1.93-2.00 (m, 2H), 2.25-2.40 (m, 4H), 2.40-2.60 (m, 6H), 2.72-2.81 (m, 2H), 2.87-3.02 (m, 6H), 3.90-4.00 (m, 2H), 5.82 (s, 2H), 6.58-6.63 (m, 2H), 7.04-7.02 (m, 2H), 7.20-7.30 (m, 2H). m/z (M$^+$H) 689.47.

(5-(2-(4-(benzo[d]isothiazol-3-yl)piperazin-1-yl)ethyl)-6-chloro-2-oxoindolin-1-yl)methyl hexanoate (Example 38, Compound 322)

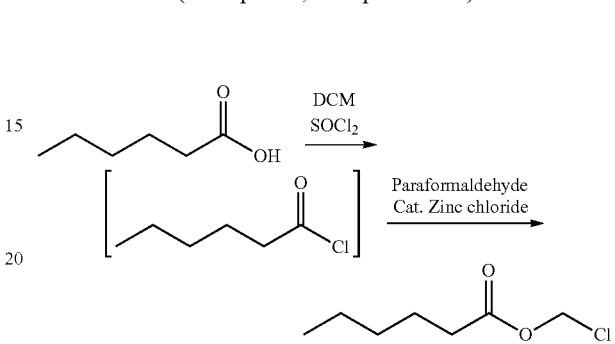

STEP 1: Thionyl chloride (12.31 g, 103 mmol) followed by catalytic amount of N,N-dimethyl formamide (DMF, 0.1 mL) was added to a solution of Hexanoic acid (10 g, 86 mmol) in dichloromethane (DCM, 100 mL) at 25-30° C. The reaction solution was stirred at same temperature for 2 hours under nitrogen atmosphere, upon completion of the starting material by TLC analysis. The volatiles were evaporated under reduced pressure below 40° C., which provided a viscous liquid material, hexanoyl chloride (about 10.5 g).

STEP 2: To the above hexanoyl chloride, para formaldehyde (3.8 g, 128 mmol) and anhydrous ZnCl$_2$ (0.232 g, 17 mmol) were added at 25-30° C. under inert atmosphere and then heated to 90° C. The thick mass was stirred at 90-95° C. for 5 hours, which after cooling provided crude product, chloromethyl hexanoate which was purified by silica gel column chromatography.

$^1$H-NMR (CDCl3, 500 MHz): δ 5.70 (s, 2H), 2.39-2.33 (m, 2H), 1.69-1.61 (m, 2H), 1.33-1.28 (m, 4H), 0.90-0.88 (t, J=7, 3H).

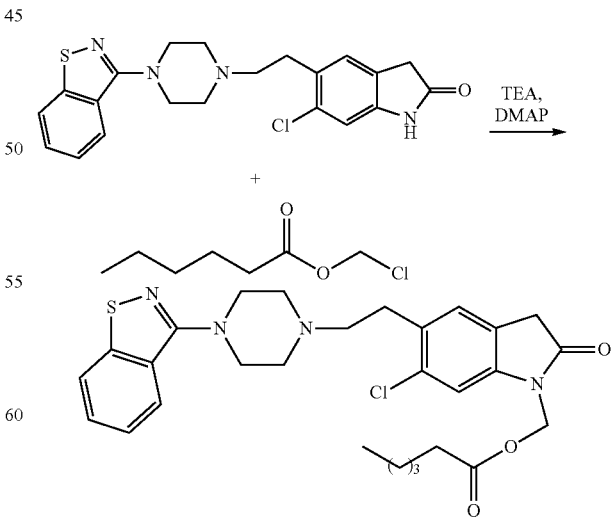

STEP 3: Chloromethyl hexanoate (3.18 g, 19.0 mmol) in dichloromethane (6 mL) was added to a suspension of Ziprasidone free base (4.0 g, 9.6 mmol), triethyl amine (4.0 mL, 27 mmol) and 4-dimethylamino pyridine (DMAP, 0.708 g, 5 mmol) in dichloride methane (240 mL) at 25-30° C. The reaction solution was stirred for 24 h at same temperature. The crude mixture was washed with water (100 mL) followed by brine solution (100 mL), upon solvent evaporation under vacuum below 40° C. provided crude title product, Compound 322, which was further purified by silica gel column chromatography. (1.4 g, 27% yield).

$^1$H-NMR(CDCl3, 500 MHz): δ 7.92-7.90 (d, J=7.5, 1H), 7.82-7.80 (d, J=7.5, 1H), 7.48-7.45 (t, J=7.5, 1H), 7.37-7.34 (t, J=7.5, 1H), 7.17 (s, 1H), 7.05 (s, 1H), 5.72 (s, 2H), 3.60-3.55 (m, 6H), 2.98-2.95 (t, J=7.5, 2H), 2.79-2.78 (m, 4H), 2.68-2.65 (t, J=8.5, 2H), 2.35-2.32 (t, J=7.5, 2H), 1.64-1.61 (t, J=7.5, 2H), 1.29-1.25 (m, 4H), 0.88-0.85 (t, J=7, 3H).

Mass (m/z)=541 [M$^+$+1].

(5-(2-(4-(benzo[d]isothiazol-3-yl)piperazin-1-yl)ethyl)-6-chloro-2-oxoindolin-1-yl)methyl dodecanoate (Example 39, Compound 324)

Compound 324 was synthesized in a similar manner to Compound 322, Example 38.

$^1$H-NMR(CDCl3, 500 MHz): δ 7.92-7.90 (d, J=7.5, 1H), 7.82-7.80 (d, J=7.5, 1H), 7.48-7.45 (t, J=7.5, 1H), 7.37-7.34 (t, J=7.5, 1H), 7.17 (s, 1H), 7.05 (s, 1H), 5.72 (s, 2H), 3.60-3.55 (m, 6H), 2.98-2.95 (t, J=8, 2H), 2.79-2.77 (m, 4H), 2.68-2.65 (t, J=8, 2H), 2.34-2.31 (t, J=7, 2H), 1.63-1.60 (m, 2H), 1.24 (s, 16H), 0.89-0.86 (t, J=7, 3H).

Mass (m/z)=625.5 [M$^+$+1].

(5-(2-(4-(benzo[d]isothiazol-3-yl)piperazin-1-yl)ethyl)-6-chloro-2-oxoindolin-1-yl)methyl palmitate (Example 40, Compound 326)

$^1$H-NMR (CDCl3, 500 MHz): δ 7.92-7.90 (d, J=7.5, 1H), 7.82-7.80 (d, J=7.5, 1H), 7.48-7.45 (t, J=7.5, 1H), 7.37-7.34 (t, J=7.5, 1H), 7.17 (s, 1H), 7.05 (s, 1H), 5.72 (s, 2H), 3.60-3.55 (m, 6H), 2.98-2.95 (t, J=8, 2H), 2.79-2.77 (m, 4H), 2.68-2.65 (t, J=8, 2H), 2.34-2.31 (t, J=8, 2H), 1.63-1.56 (m, 2H), 1.25-1.23 (m, 24H), 0.88-0.86 (t, J=7, 2H).

Mass (m/z)=681.5 [M$^+$+1].

(7-[(4-biphenyl-3yl methyl)piperazin-1-yl]-2-oxobenzo[d]oxazol-3(2H)-yl)methyl acetate (Example 41, Compound 416)

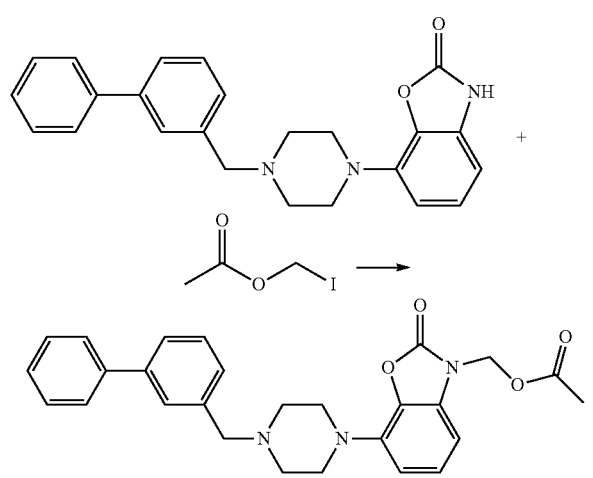

Step 1. Synthesis of chloromethyl acetate: Acetyl chloride (5 g, 0.06 mol) was added dropwise to a mixture of paraformaldhyde (8.5 g, 0.06 mol) and anhydrous zinc chloride (0.175 g, 0.02 mol) at 0° C. under Argon. The reaction mixture was warmed to room temperature and stirred for 1 hour, then heated to 90° C. for 18 hours. The solid was filtered off washed with dichloromethane, and the filtrate was concentrated under vacuum at 37° C. to provide the desired product (6.6 g, 94% yield). The product was used directly (without purification) in to next step and stored with activated molecular sieves (4° A).

Step 2. Synthesis of iodomethyl acetate: Sodium iodide (27.6 g, 0.18 mol) was added to a solution of chloromethyl acetate (6.6 g, 0.06 mol) in acetonitrile (66 mL). The reaction flask was covered in aluminum foil to exclude light and stirred at ambient temperature for 15 hours. The reaction mixture was partition between dichloromethane and water, and the aqueous layer was extracted with dichloromethane. The combine organics were washed with aqueous saturated NaHCO$_3$, 10% aqueous sodium sulfite solution, and brine then dried with sodium sulphate and concentrated to give the product (1.13 g, 12% yield) as a yellow oil.

Step 3. n-Butyl lithium (1.6 M in hexane; 3.8 mL, 0.007 mol) was added drop wise from a syringe to a stirred solution of bifeprunox (1.46 g, 0.003 mol) in tetrahydrofuran at −78° C. After 1 hour a solution of iodomethyl acetate (1.13 g, 0.005 mol) was added drop-wise at −70° C. The reaction mixture was stirred for 15 hours. The reaction mixture was dumped in a saturated aqueous solution of ammonium chloride and extracted with ethyl acetate. The combined organic layers were washed with 1N solution of NaOH and brine, then dried with sodium sulphate and concentrated under vacuum. Purification by flash chromatography provided compound 416. (0.25 g, 14% yield). $^1$H NMR (DMSO, 400 MHz) δ 2.034 (s, 3H), 2.565 (s, 4H), 3.183 (s, 4H), 3.597 (s, 2H), 5.765 (s, 2H), 6.696-6.717 (d, 1H), 6.882-6.901 (d, 1H), 7.091-7.182 (t, 1H), 7.315-7.370 (q, 2H), 7.404-7.473 (m, 3H), 7.515-7.555 (d, 1H), 7.59 (d, 1H), 7.639-7.657 (d, 2H). m/z (M+H) 457.

(7-[(4-biphenyl-3yl methyl)piperazin-1-yl]-2-oxobenzo[d]oxazol-3(2H)-yl)methyl butyrate (Example 42, Compound 417)

Compound 417 was prepared in a similar manner to Example 41 using butanoyl chloride. Purification by flash chromatography provided the desired product (1.25 g, 45% yield). 1H NMR (DMSO, 400 MHz) δ 1.065 (t, 3H), 1.448-1.54 (m, 2H), 2.284-2.320 (t, 2H), 2.564 (s, 4H), 3.184 (s, 4H), 3.597 (s, 2H), 5.787 (s, 2H), 6.694-6.713 (d, 1H), 6.878-6.896 (d, 1H), 7.092-7.133 (t, 1H), 7.315-7.370 (q, 2H), 7.422-7.533 (m, 3H), 7.535-7.555 (d, 1H), 7.639 (d, 1H), 7.657-7.660 (d, 2H). m/z (M+H)485.

(7-[(4-biphenyl-3yl methyl)piperazin-1-yl]-2-oxobenzo[d]oxazol-3(2H)-yl)methyl hexanoate (Example 43, Compound 413)

Compound 413 was prepared in a similar manner to Example 41 using hexanoyl chloride. Purification by flash chromatography provided the desired product (0.6 g, 60% yield). 1H NMR (DMSO, 400 MHz) δ 0.774 (t, 3H), 1.114-1.187 (m, 4H), 1.433-1.506 (m, 2H), 2.291-2.328 (t, 2H), 2.564 (s, 4H), 3.182 (s, 4H), 3.597 (s, 2H), 5.783 (s, 2H), 6.693-6.713 (d, 1H), 6.870-6.890 (d, 1H), 7.090-7.130

(t, 1H), 7.314-7.351 (q, 2H), 7.422-7.472 (m, 3H), 7.535-7.554 (d, 1H), 7.589 (d, 1H), 7.638-7.656 (d, 2H). m/z (M+H)513.

(7-[(4-biphenyl-3yl methyl)piperazin-1-yl]-2-oxobenzo[d]oxazol-3(2H)-yl)methyl palmitate (Example 44, Compound 422)

Compound 422 was prepared in a similar manner to Example 41 using palmitoyl chloride. Purification by flash chromatography provided the desired product (0.5 g, 47% yield). 1H NMR (DMSO, 400 MHz) δ 0.819 (t, 3H), 1.127-1.302 (m, 22H), 1.437-1.454 (t, 2H), 2.287-2.305 (t, 2H), 2.564 (s, 4H), 3.182 (s, 4H), 3.596 (s, 2H), 5.784 (s, 2H), 6.688-6.708 (d, 1H), 6.863-6.882 (d, 1H), 7.083-7.124 (t, 1H), 7.331-7.368 (q, 2H), 7.400-7.470 (m, 3H), 7.534-7.553 (d, 1H), 7.587 (d, 1H), 7.635-7.653 (d, 2H). m/z (M+H)653.

(7-[(4-biphenyl-3yl methyl)piperazin-1-yl]-2-oxobenzo[d]oxazol-3(2H)-yl)methyl decanoate (Example 45, Compound 419)

Compound 419 was prepared in a similar manner to Example 41 using decanoyl chloride. Purification by flash chromatography provided the desired product (0.8 g, 77% yield). 1H NMR (DMSO, 400 MHz) δ 0.795-0.829 (t, 3H), 1.140-1.211 (m, 12H), 1.438-1.471 (t, 2H), 2.288-2.324 (t, 2H), 2.562 (s, 4H), 3.181 (s, 4H), 3.595 (s, 2H), 5.783 (s, 2H), 6.689-6.709 (d, 1H), 6.856-6.884 (d, 1H), 7.083-7.124 (t, 1H), 7.311-7.367 (q, 2H), 7.400-7.470 (m, 3H), 7.533-7.552 (d, 1H), 7.587 (d, 1H), 7.635-7.653 (d, 2H). m/z (M+H)569.

(7-[(4-biphenyl-3yl methyl)piperazin-1-yl]-2-oxobenzo[d]oxazol-3(2H)-yl)methyl isobutyrate (Example 46, Compound 414)

Compound 414 was prepared in a similar manner to Example 41 using isobutyryl chloride. Purification by flash chromatography provided the desired product (0.3 g, 15% yield). 1H NMR (DMSO, 400 MHz) δ 1.027-1.044 (d, 6H), 2.478-2.553 (m, 1H), 2.562 (s, 4H), 3.185 (s, 4H), 3.597 (s, 2H), 5.785 (s, 2H), 6.692-6.713 (d, 1H), 6.873-6.892 (d, 1H), 7.093-7.134 (t, 1H), 7.315-7.369 (q, 2H), 7.403-7.472 (m, 3H), 7.533-7.555 (d, 1H), 7.590 (d, 1H), 7.657-7.660 (d, 2H). m/z (M+H)485.

(7-(4-(4-(2,3-dichlorophenyl)piperazin-1-yl)butoxy)-2-oxoquinolin-1(2H)-yl)methyl butyrate (Example 47, Compound 151)

(7-(4-(4-(2,3-dichlorophenyl)piperazin-1-yl)butoxy)-2-oxo-3,4-dihydroquinolin-1(2H)-yl)methyl butyrate (Compound 2) was prepared as described in Example 16, supra.

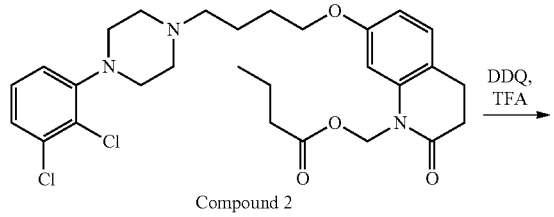
Compound 2 → DDQ, TFA →

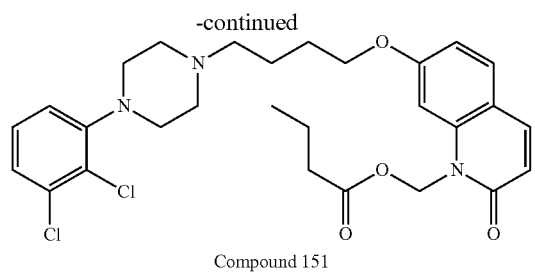
Compound 151

To a stirred solution of (7-(4-(4-(2,3-dichlorophenyl)piperazin-1-yl)butoxy)-2-oxo-3,4-dihydroquinolin-1(2H)-yl) methyl butyrate (3.26 g, 5.94 mmol) in THF (100 mL) was added TFA (2.74 mL, 35.63 mmol) followed by 2,3-dichloro-5,6-dicyanobenzoquinone (DDQ; 7.01 g, 30.88 mmol) in THF (40 mL). The reaction was stirred at room temperature over the weekend. The reaction was quenched with water (100 mL) and then poured into water (600 mL) and dichloromethane (100 mL). Solid NaHCO$_3$ (100 g) was added and the mixture stirred for approximately 30 minutes. Dichloromethane (200 mL) was added and the mixture filtered. The collected filtrate was transferred to a separating funnel and the layers separated. The aqueous layer was extracted with dichloromethane (2×100 mL) and the combined organics washed with water (3×100 mL, brine (100 mL) and dried over MgSO$_4$. After filtration, the volatiles were removed. The crude material was purified by silica chromatography eluting 0-4% Methanol/(1:1 ethyl acetate/dichloromethane). The oil was recrystallized from methanol to give Compound 151. (2.03 g, 3.72 mmol, 63% yield).

$^1$H-NMR (300 MHz, CDCl$_3$) δ 7.63 (1H, d), 7.45 (1H, d), 7.19-7.06 (2H, m), 6.99-6.90 (1H, m), 6.88-6.78 (2H, m), 6.52 (1H, d), 6.33 (2H, s), 4.06 (2H, t), 3.17-2.99 (4H, bs), 2.74-2.43 (6H, m), 2.35 (2H, t), 1.94-1.54 (6H, m), 0.93 (3H, t).

The following compounds were synthesized in a similar manner to Example 47 from their corresponding 3,4 dihydro precursors:

(7-(4-(4-(2,3-dichlorophenyl)piperazin-1-yl)butoxy)-2-oxoquinolin-1(2H)-yl)methyl palmitate (Example 48, Compound 159)

Compound 159 was synthesized in a similar manner to Example 47 from Compound 10.

2.04 g. $^1$H-NMR (400 MHz, CDCl$_3$) δ 7.62 (1H, d), 7.44 (1H, d), 7.18-7.10 (2H, m), 6.98-6.91 (1H, m), 6.87-6.80 (2H, m), 6.52 (1H, d), 6.32 (2H, s), 4.05 (2H, t), 3.15-2.99 (4H, bs), 2.74-2.44 (6H, m), 2.35 (2H, t), 1.92-1.83 (2H, m), 1.80-1.68 (2H, m) 1.66-1.55 (2H, m), 1.32-1.14 (24H, m), 0.87 (3H, t).

(7-(4-(4-(2,3-dichlorophenyl)piperazin-1-yl)butoxy)-2-oxoquinolin-1(2H)-yl)methyl laurate (Example 49, Compound 156)

Compound 156 was synthesized in a similar manner to Example 47 from Compound 7.

1.37 g. $^1$H-NMR (400 MHz, CDCl$_3$) δ 7.62 (1H, d), 7.43 (1H, d), 7.17-7.10 (2H, m), 6.96-6.92 (1H, m), 6.87-6.80 (2H, m), 6.51 (1H, d), 6.33 (2H, s), 4.06 (2H, t), 3.12-3.01 (4H, bs), 2.71-2.59 (4H, bs), 2.50 (2H, t), 2.35 (2H, t), 1.92-1.83 (2H, m), 1.78-1.69 (2H, m) 1.66-1.55 (2H, m), 1.32-1.16 (16H, m), 0.86 (3H, t).

(7-(4-(4-(2,3-dichlorophenyl)piperazin-1-yl)butoxy)-2-oxoquinolin-1(2H)-yl)methyl stearate (Example 50, Compound 160)

Compound 160 was synthesized in a similar manner to Example 47 from Compound 11.

1.38 g $^1$H-NMR (400 MHz, CDCl$_3$) δ 7.62 (1H, d), 7.44 (1H, d), 7.17-7.11 (2H, m), 6.97-6.92 (1H, m), 6.87-6.79 (2H, m), 6.51 (1H, d), 6.32 (2H, s), 4.05 (2H, t), 3.13-3.00 (4H, bs), 2.73-2.58 (4H, bs), 2.50 (2H, t), 2.35 (2H, t), 1.92-1.83 (2H, m), 1.79-1.69 (2H, m) 1.66-1.55 (2H, m), 1.32-1.14 (28H, m), 0.87 (3H, t).

(7-(4-(4-(2,3-dichlorophenyl)piperazin-1-yl)butoxy)-2-oxoquinolin-1(2H)-yl)methyl acetate (Example 51, Compound 150)

Compound 150 was synthesized in a similar manner to Example 47 from Compound 1.

1.61 g $^1$H-NMR (300 MHz, CDCl$_3$) δ 7.63 (1H, d), 7.45 (1H, d), 7.18-7.11 (2H, m), 6.98-6.92 (1H, m), 6.90-6.80 (2H, m), 6.52 (1H, d), 6.32 (2H, s), 4.07 (2H, t), 3.14-3.01 (4H, bs), 2.73-2.59 (4H, bs), 2.51 (2H, t), 2.12 (3H, s), 1.95-1.82 (2H, m), 1.82-1.68 (2H, m).

(7-(4-(4-(2,3-dichlorophenyl)piperazin-1-yl)butoxy)-2-oxoquinolin-1(2H)-yl)methyl 2,2-dimethylbutanoate (Example 52, Compound 165)

Compound 165 was synthesized in a similar manner to Example 47 from Compound 16.

1.02 g $^1$H-NMR (400 MHz, CDCl$_3$) δ 7.61 (1H, d), 7.43 (1H, d), 7.17-7.10 (2H, m), 6.97-6.92 (1H, m), 6.83-6.79 (2H, m), 6.51 (1H, d), 6.31 (2H, s), 4.05 (2H, t), 3.12-3.02 (4H, bs), 2.71-2.60 (4H, bs), 2.50 (2H, t), 1.92-1.83 (2H, m), 1.78-1.68 (2H, m) 1.55 (2H, q), 1.15 (6H, s), 0.81 (3H, t).

Pharmacokinetic Evaluation in Rats

Pharmakokinetic Evaluation of Prodrugs in Rats Following Intramuscular Injection Animals: Male Sprague-Dawley rats (Charles River Laboratories, Wilmington, MA) were obtained. Approximately 24 rats were used in each study. Rats were approximately 350-375 g at time of arrival. Rats were housed 2 per cage with ad libitum chow and water. Environmental conditions in the housing room: 64-67° F., 30% to 70% relative humidity, and 12:12-h light:dark cycle. All experiments were approved by the institutional animal care and use committee.

Pharmacokinetics study: Rats were dosed IM by means of a 25 gauge, ⅝ in. needle with 1 cc syringe 0.3 mL suspension was withdrawn from the vial containing the test compound (see Table E). The mouse was injected in the muscles of the hind limb after anesthesia with isoflourane. Blood samples were collected via a lateral tail vein after brief anesthesia with Isoflurane. A 27½ G needle and lcc syringe without an anticoagulant was used for the blood collection. Approximately 350 μL of whole blood was collected at each sampling time-point of 6 hours, 24 hours and 2, 5, 7, 9, 12, 14, 21, 28, 35 days after administration. Once collected, whole blood was immediately transferred to tubes containing K2 EDTA, inverted 10-15 times and immediately placed on ice. The tubes were centrifuged for 2 minutes at >14,000 g's (11500 RPMs using Eppendorf Centrifuge 5417C, F45-30-11 rotor) at room temperature to separate plasma. Plasma samples were transferred to labeled plain tubes (MICRO-TAINER®; MFG #BD5962) and stored frozen at <−70° C.

Data Analysis: Drug concentrations in plasma samples were analyzed by liquid chromatography-mass spectroscopy using appropriate parameters for each compound. Half-life, volume of distribution, clearance, maximal concentration, and AUC were calculated by using WinNonlin Version 5.2 software.

Results and Discussion: The Results are shown in Table E. As shown in Table E, each of the compounds tested provides a plasma concentration that is extended as compared to the parent drug when administered alone.

TABLE E

| API Form used (Compound No.) | Excipients | Dose **(mg/kg) | AUC$_{0-14}$ (ng * day/mL) | AUC$_{0-T}$ (ng * day/mL) |
|---|---|---|---|---|
| 82 | solution in ethyl oleate | 57 | 204 | NC |
| 2 | Recrystallized crystalline suspension in 1% HPMC in PBS + 0.2% Tween 20 | 67 | 1016.9 | 1139.8 |
| 81 | solution in ethyl oleate | 56 | 584 | NC |
| 48 | Milled crystalline suspension in 1% HPMC in PBS + 0.2% Tween 20. Measured and diluted to correct concentration* | 70.00 | 2238 | 2264.6 |
| 5 | Ethyl oleate emulsion in water with DPPC, Glycerol and NCOH | 67 | 1728.6 | 1742 |
| 6 | solution in ethyl oleate | 67 | 67 | 327 |
| 6 | Oil emulsion in water with DPPC and Glycerol | 67 | 1490.3 | 1678.1 |
| 47 | Milled crystalline suspension in 1% HPMC | 100.0 | 113 | 176 |
| 85 | Milled crystalline suspension in 1% HPMC in PBS + 0.2% Tween 20. Measured and diluted to correct concentration | 67 | 1233.9 | 1348 |
| 1 | Crystalline material suspended in 1% HPMC | 56.7 | 1673 | 1938 |
| 7 | Recrystallized crystalline suspention in 1% HPMC in PBS + 0.2% Tween 20 | 67 | 512.0 | 1169.5 |
| 32 | Milled crystalline suspension in 1% HPMC in PBS + 0.2% Tween 20. Measured and diluted to correct concentration* | 67 | 1334.4 | 1486 |

TABLE E-continued

| API Form used (Compound No.) | Excipients | Dose **(mg/kg) | AUC$_{0-14}$ (ng * day/mL) | AUC$_{0-T}$ (ng * day/mL) |
|---|---|---|---|---|
| 8 | Milled crystalline suspension in 1% HPMC in PBS + 0.2% Tween 20 | 24 | 580.3 | 666.1 |
| 49 | Milled crystalline suspension in 1% HPMC | 73.3 | 152 | 199.7 |
| 34 | Milled crystalline suspension in 1% HPMC in PBS + 0.2% Tween 20. Measured and diluted to correct concentration* | 43.33 | 2050 | 2095.8 |
| 79 | Prodrug solution in ethyl oleate | 67 | 954 | NC |
| 79 | Recrystallized crystalline suspention in 1% HPMC in PBS + 0.2% Tween 20 | 67 | 907.4 | 940 |
| 31 | Recrystallized crystalline suspention in 1% HPMC in PBS + 0.2% Tween 20 | 67 | 819.0 | 997 |
| 10 | Recrystallized crystalline suspention in 1% HPMC in PBS + 0.2% Tween 20 | 67 | 302 | 786.6 |
| 4 | Recrystallized crystalline suspention in 1% HPMC in PBS + 0.2% Tween 20 | 67 | 1455.4 | 1678 |

Example 53

Pharmacodynamic Studies Using an Amphetamine-Induced Locomotion Model

Introduction: Prodrugs of the invention useful in the treatment of schizophrenia and bipolar disorder show predictive validity in rodent models of hyperlocomotion. D-Amphetamine-induced locomotion is postulated to mimic the dopaminergic hyperactivity which forms the basis for the "dopamine hypothesis" of schizophrenia. The AMPH-induced hyperactivity model provides a simple, initial screen of antipsychotic compound efficacy. See, Fell et al., *Journal of Pharmacology and Experimental Therapeutics*, (2008) 326:209-217. Amphetamine induced hyperactivity was used to screen various doses of orally administered (PO) prodrug formulations of aripiprazole to measure pharmacodynamic efficacy in an acute hyperlocomotion paradigm. The hypothesis of the study is that PO administration of aripiprazole prodrug formulations, which result in plasma concentrations of ~100-200 ng/ml, will produce a significant attenuation of AMPH-induced locomotion.

General behavior and activity can be measured in experimental animals (typically rats and mice) in order to assess psychomotor stimulant properties, anxiogenic/anxiolytic or sedative properties of a drug. As such, open-field studies can provide insight into the behavioral effects of test compounds. Certain prodrugs of the present invention are useful in the treatment of schizophrenia and bipolar disorder. Aripiprazole is a parent lactam containing drug from which some of the prodrugs of the invention are derived that is useful in the treatment of schizophrenia and bipolar disorder. Such aripiprazole prodrugs of the invention show predictive validity in rodent models of hyperlocomotion. D-Amphetamine-induced locomotion is postulated to mimic the dopaminergic hyperactivity which forms the basis for the "dopamine hypothesis" of schizophrenia. Likewise, glutamate NMDA receptor antagonist (MK-801, PCP, etc.) induced locomotion is postulated to mimic the NMDA hypoactivity hypothesis of schizophrenia (Fell et al., supraa). These tests of drug-induced hyperactivity provide simple, initial screens of antipsychotic compound efficacy. Amphetamine induced hyperactivity will be used to screen various prodrugs of aripiprazole, administered PO in oil solutions, to measure pharmacodynamic efficacy. The results of the D-AMPH induced locomotion done in this study will be compared to the historical results of subcutaneous (S.C.) aripiprazole administration on D-AMPH. The hypothesis of the study is that PO exposure to aripiprazole prodrugs, which results in aripiprazole concentrations of 100-200 ng/ml at locomotor testing, will display efficacy in in-vivo measures of antipsychotic efficacy.

Materials: Experimental animals: 12, Sprague Dawley rats were purchased from Charles River Laboratory. The rats were approximately 90 days old, and weighed in the range of 350-275 grams upon receipt from the supplier. One rat was placed in a cage and allowed to acclimate for about 1 week. The rats were provided with food and water ad libitum.

Dosing solution of D-Amphetamine (D-AMPH): D-AMPH was purchased from Sigma Aldrich. D-amphetamine HCl was prepared in 0.9% saline to a concentration of 1.5 mg/ml. D-Amphetamine was given I.P. per body weight at a dose of 1 ml/kg (=1.5 mg/kg). Salt form correction was not used in accordance with historical literature. D-Amphetamine was prepared fresh from solid form 30 min. prior to each test period.

Dosing Solutions of Prodrug Derivatives of Aripiprazole:

TABLE F

| Study Group | Formulation (Route) | Dose mg/rat | Dose volume mL | N |
|---|---|---|---|---|
| A | Arp-laurate oral oil Solution (PO) | 7.5 | 1.5 | 4 |
| B | Arp-Hexanoate oral oil Solution (PO) | 20 | 1.5 | 4 |
| C | Arp-Hexanoate oral oil Solution (PO) | 10 | 1.5 | 4 |
| D | Arp-laurate oral oil Solution (PO) | 10 | 1.5 | 4 |
| E | Arp-Hexanoate oral oil Solution (PO) | 0.66 | 1.5 | 4 |
| F | Arp-Laurate oral oil Solution (PO) | 20 | 1.5 | 4 |

TABLE F-continued

| Study Group | Formulation (Route) | Dose mg/rat | Dose volume mL | N |
|---|---|---|---|---|
| G | Saline (PO) | 0 | 1.5 | 4 |
| | | | | 4 |

Behavior Box: The behavior chambers were purchased from Med Associates, Inc. of St. Albans, VT, Model ENV-515. Software for measuring animal movement is provided with the behavior chamber by the supplier.

Methods: Following 1 week habituation to the animal facility, the activity assessments commenced. The animals were initially acclimated to the behavior box for about 15 minutes before they were removed from the box and injected PO with 1.5 ml of an aripiprazole prodrug compound of the invention, at concentrations which produce PK levels of 100-200 ng/ml approximately 1 hour after administration. After an additional 15 minutes the animals were placed back in the behavior box for an additional 30 minute drug-baseline test session. The mice were then administered by IP injection, D-AMPH (1.5 mg/kg) followed by a 60 minute experimental behavorial measurement period. The parameters that were measured were a) total distance measured (primary measure), b) total number of ambulatory moves (secondary measure), c) total number of vertical moves (secondary measure) and d) time spent immobile (secondary measure).

Blood Sampling: Tail vein blood was taken on experiment days immediately following locomotor activity measurements (2-hours post-prodrug administration) and again the following day a time-point corresponding to 22 hours post-prodrug administration. Blood samples were collected via a lateral tail vein after anesthesia with Isoflurane. A 27½ G syringe without an anticoagulant was used for the blood collection, and the whole blood transferred to pre-chilled (wet ice) tubes containing K2 EDTA. 0.5 ml of blood per animal was collected per time point. The tubes were inverted 15-20 times and immediately returned to the wet ice until being centrifuged for 2 minutes≥14,000 g to separate plasma. The plasma samples prepared in this manner were transferred to labeled plain tubes (MICROTAINER®; MFG #BD5962) and stored frozen at <−70° C.

Behavioral Data Acquisition: Behavioral data was captured electronically by the software package associated with the behavior chambers. Data was transformed and analyzed via GraphPad PRISM® 5 software (GraphPad Software, Inc., La Jolla, CA). The data was analyzed using a 2-way repeated measures ANOVA.

Figure 6:
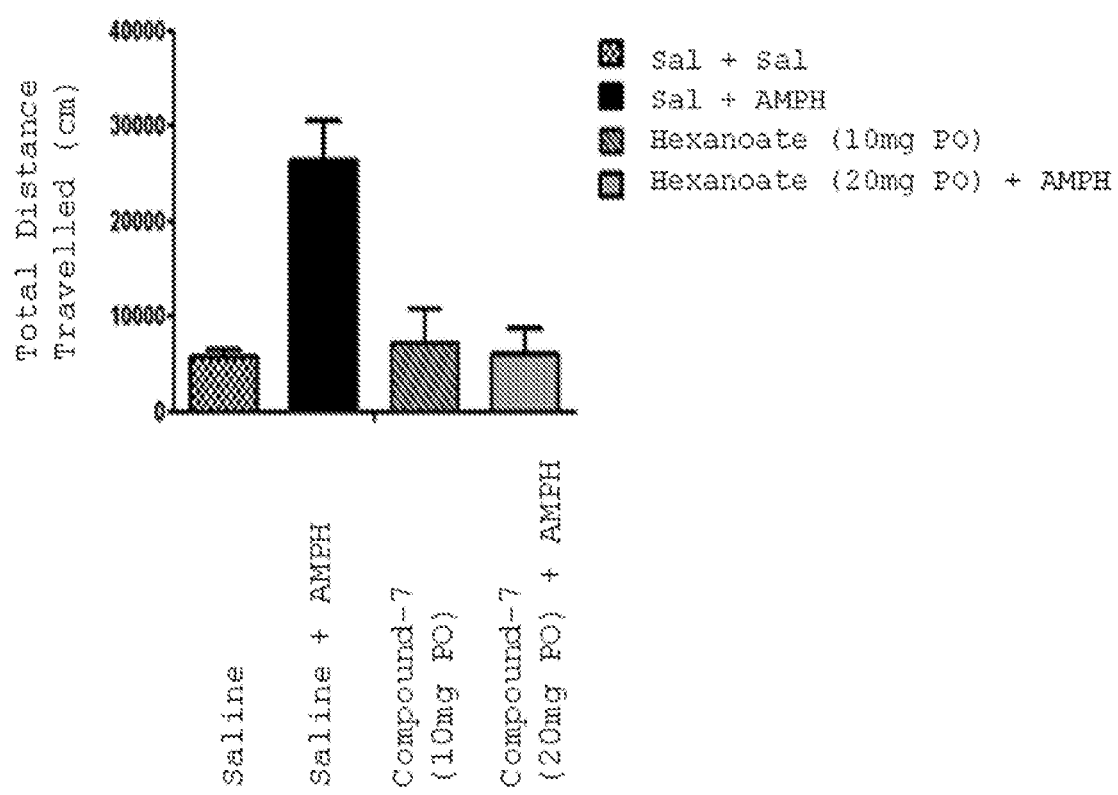
FIG. 6: Pharmacodynamic (PD) study of compound-4 in AMPH induced locomotion model.
Figure 7:
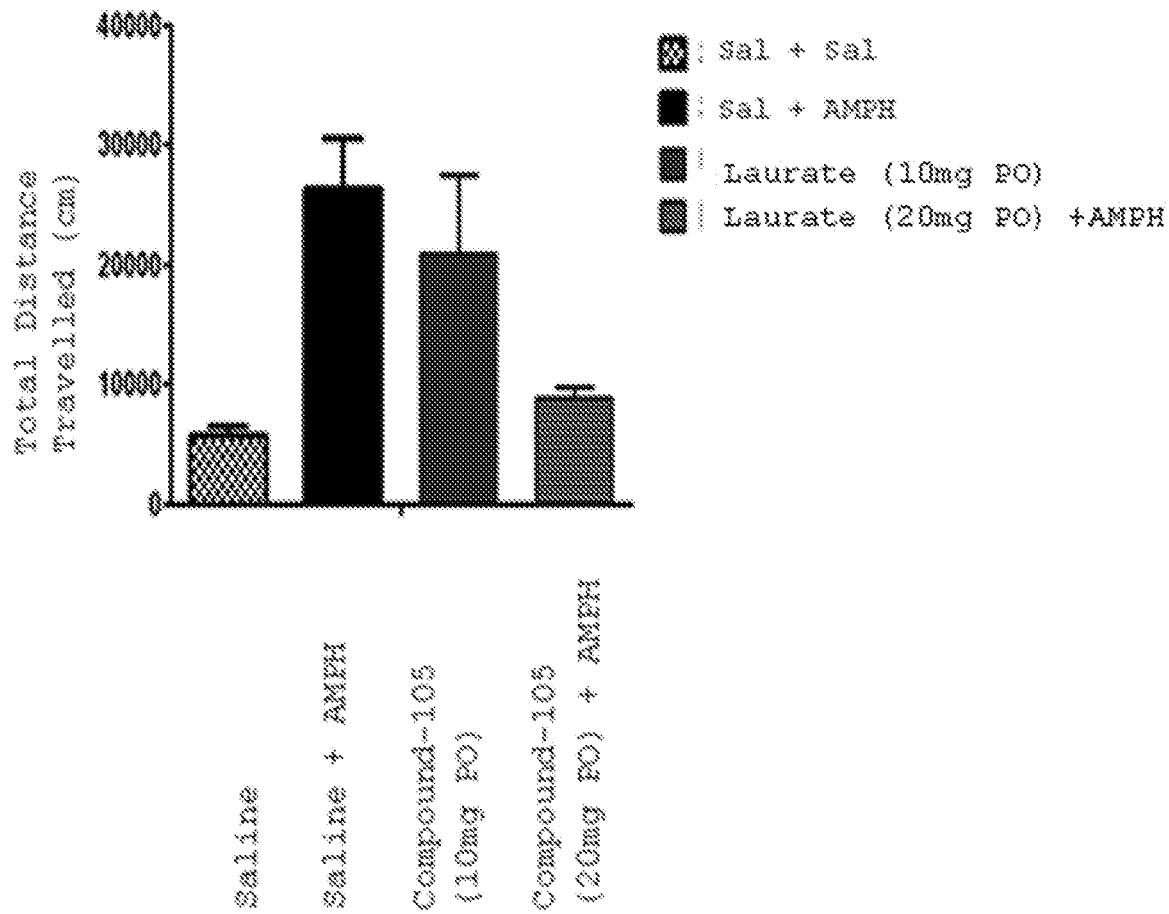
FIG. 7 Pharmacodynamic (PD) study of compound-7 in AMPH induced locomotion model.
Figure 8:
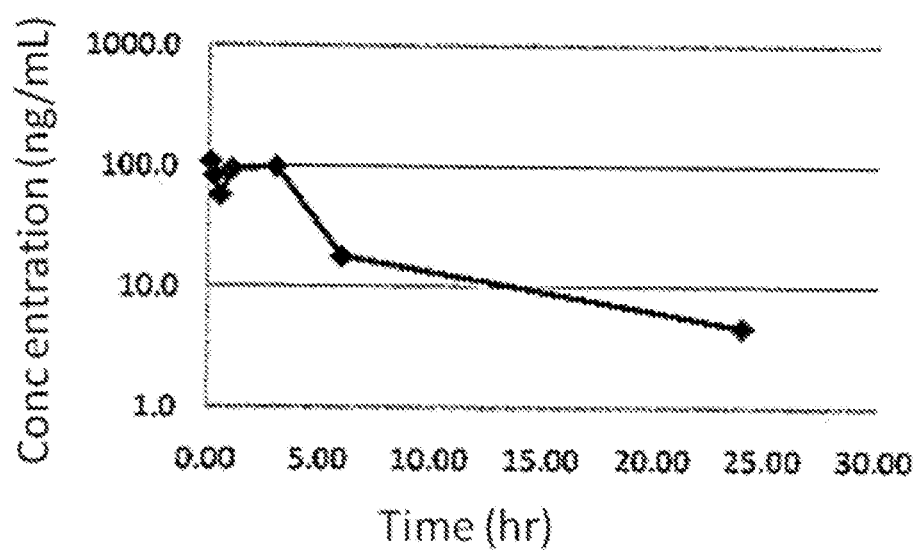
FIG. 8: Plasma concentration of aripiprazole after intravenous administration of (0.5 mg/Kg) compound 7 to rats.
Figure 9:
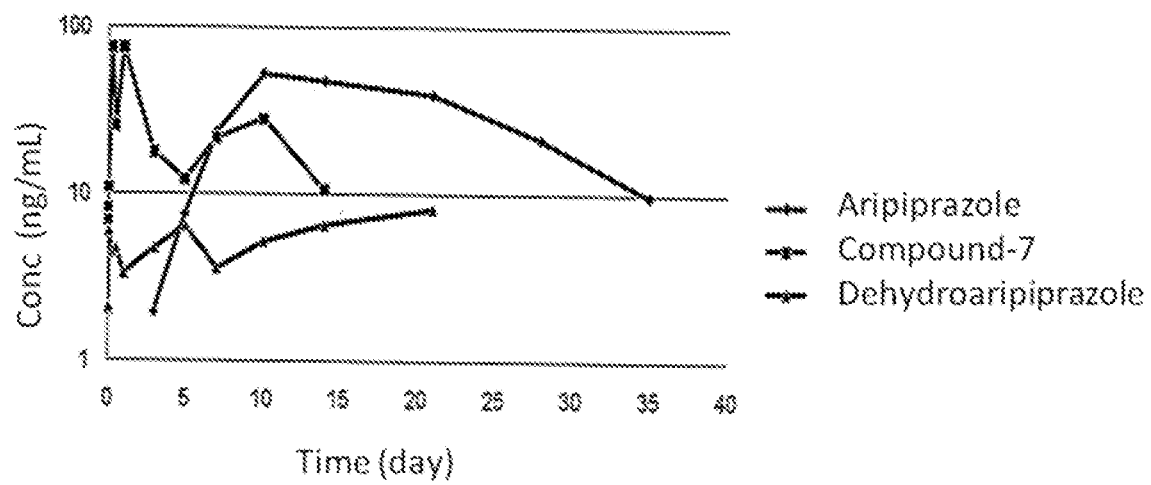
FIG. 9: Plasma concentration of aripiprazole, dehydroaripiprazole and compound 7 after intramuscular administration of 30 mg/Kg of compound 7 to dogs.

Results and Discussion: The results are shown in FIGS. 6 and 7. The results indicate that orally administered D-AMPH caused a significant increase in the total distance traveled by the mice as compared to mice who were administered only saline. The results also indicate that aripiprazole prodrug compound 4 of the invention significantly inhibited the increases in distance traveled caused by D-AMPH. The inhibition of distance travelled by compound 4 did not appear to be dose dependent. Likewise, aripiprazole prodrug compounds 7 and 47 did appear to significantly inhibit increases in distance traveled caused by D-AMPH at the higher dose of 20 mg. This data indicates that in accordance with the invention, the prodrug compounds are cleaved in vivo to release the parent tertiary amine-containing drug (aripiprazole in this example) to provide the expected pharmacological effects on the animal.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:
1. A compound of Formula V:

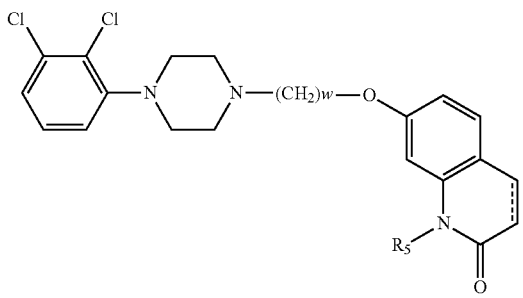

Formula V or a pharmaceutically acceptable salt thereof:
wherein
╌╌╌╌ represents a single or double bond;
$R_5$ is —CH($R_{10}$)–$OR_{20}$ or —CH($R_{10}$)–OC(O)$R_{20}$;
w is 4;
$R_{10}$ is hydrogen; and
$R_{20}$ is hydrogen.
2. The compound of claim 1, wherein
╌╌╌╌ represents a single bond.
3. The compound of claim 1, wherein $R_5$ is —CH($R_{10}$)—$OR_{20}$.
4. The compound of claim 1, wherein $R_5$ is —CH($R_{10}$)—OC(O)$R_{20}$.
5. The compound of claim 1 that is

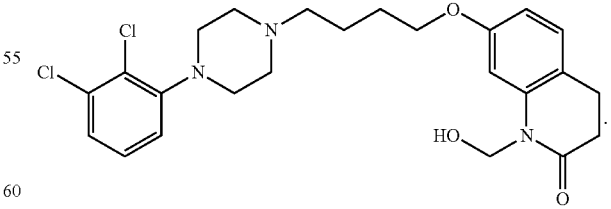

* * * * *